United States Patent
Müller et al.

[11] Patent Number: 5,922,710
[45] Date of Patent: Jul. 13, 1999

[54] IMINOOXYBENZYLCROTONATE ESTERS, THEIR PREPARATION AND THEIR USE

[75] Inventors: Bernd Müller, Frankenthal; Wassilios Grammenos, Ludwigshafen; Hubert Sauter, Mannheim; Franz Röhl, Schifferstadt; Eberhard Ammermann, Heppenheim; Gisela Lorenz, Hambach; Norbert Götz, Worms, all of Germany

[73] Assignee: BASF Aktiengesellschaft, Ludwigshafen, Germany

[21] Appl. No.: 08/836,853

[22] PCT Filed: Nov. 20, 1995

[86] PCT No.: PCT/EP95/04555

§ 371 Date: May 22, 1997

§ 102(e) Date: May 22, 1997

[87] PCT Pub. No.: WO96/16943

PCT Pub. Date: Jun. 6, 1996

[30] Foreign Application Priority Data

Nov. 30, 1994 [DE] Germany ................ 44 42 560

[51] Int. Cl.[6] ............ C07D 239/26; C07D 239/34; A01N 43/40; A01N 43/54
[52] U.S. Cl. .......... 514/247; 514/255; 514/256; 514/344; 514/357; 544/180; 544/182; 544/217; 544/218; 544/219; 544/224; 544/239; 544/242; 544/319; 544/335; 544/336; 544/406; 544/408; 544/409; 546/290; 546/298; 546/301; 546/328; 546/334
[58] Field of Search ................... 514/247, 255, 514/256, 344, 357; 544/224, 243, 333, 334, 335, 336, 405, 409, 239, 319, 406, 180, 182, 217, 218, 219; 546/286, 287, 329, 330, 334, 290, 298, 301, 328

[56] References Cited

U.S. PATENT DOCUMENTS

| 4,937,372 | 6/1990 | Wenderoth et al. ........... 560/55 |
| 5,221,762 | 6/1993 | Wingert et al. ............... 560/35 |
| 5,298,527 | 3/1994 | Grammenos et al. ......... 514/539 |
| 5,387,607 | 2/1995 | Brand et al. .................. 514/513 |
| 5,563,168 | 10/1996 | Brand et al. ................. 514/357 |

FOREIGN PATENT DOCUMENTS

| 280 185 | 8/1988 | European Pat. Off. . |
| 460575 | 12/1991 | European Pat. Off. . |
| 463 488 | 1/1992 | European Pat. Off. . |
| 493 711 | 7/1992 | European Pat. Off. . |
| 41 16 090 | 11/1992 | Germany . |
| 92/13830 | 8/1992 | WIPO . |
| 92/18487 | 10/1992 | WIPO . |
| 94/08968 | 4/1994 | WIPO . |

*Primary Examiner*—Mukund J. Shah
*Assistant Examiner*—Deepak Rao
*Attorney, Agent, or Firm*—Keil & Weinkauf

[57] ABSTRACT

Iminooxybenzylcrotonate esters of the formula I

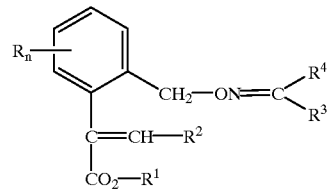

where the index and the substituents have the following meanings:

n is 0, 1, 2, 3 or 4;

R is nitro, cyano, halogen,
  unsubst. or subst. alkyl, alkenyl, alkynyl, alkoxy, alkenyloxy, alkynyloxy or
  in the case where n is 2, additionally an unsubst. or subst. bridge bonded to two adjacent ring atoms;

$R^1$ is $C_1$–$C_4$-alkyl;

$R^2$ is hydrogen or $C_1$–$C_4$-alkyl;

$R^3$ is hydrogen, cyano, halogen, alkyl, haloalkyl, alkoxy, haloalkoxy, alkylthio, haloalkylthio or cycloalkyl;

$R^4$ is a 5 to 10-membered mono- or bicyclic, substituted heteroaromatic ring system, processes for their preparation and their use are described.

20 Claims, No Drawings

IMINOOXYBENZYLCROTONATE ESTERS, THEIR PREPARATION AND THEIR USE

The present invention relates to iminooxybenzylcrotonate esters of the formula I

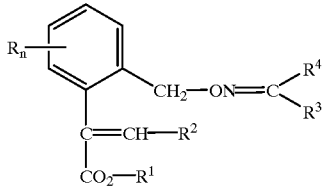

where the index and the substituents have the following meanings:

n is 0, 1, 2, 3 or 4, it being possible for the substituents R to be different if n is greater than 1;

R is nitro, cyano, halogen,
  unsubst. or subst. alkyl, alkenyl, alkynyl, alkoxy, alkenyloxy, alkynyloxy or
  in the case where n is 2, additionally an unsubst. or subst. bridge bonded to two adjacent ring atoms, which contains three to four members from the group consisting of 3 or 4 carbon atoms, 2 or 3 carbon atoms and 1 or 2 nitrogen, oxygen and/or sulfur atoms, it being possible for this bridge, together with the ring to which it is bonded, to form a partially unsaturated or aromatic radical;

$R^1$ is $C_1$–$C_4$-alkyl;

$R^2$ is hydrogen or $C_1$–$C_4$-alkyl;

$R^3$ is hydrogen, cyano, halogen, alkyl, haloalkyl, alkoxy, haloalkoxy, alkylthio, haloalkylthio or cycloalkyl;

$R^4$ is a 5 to 10-membered mono- or bicyclic, heteroaromatic ring system which is substituted by customary groups, and processes for their preparation and their use.

2-Phenylcrotonic acids having fungicidal activity are disclosed in the literature (EP-A 280 185; EP-A 463 488; DE-A 41 16 090).

It is an object of the present invention to provide active compounds having improved activity.

We have found that this object is achieved by the compounds I defined at the beginning. Processes for their preparation, compositions containing them and methods for their use, in particular for controlling animal pests and harmful fungi, have additionally been found.

The compounds I are obtainable by various methods. They are particularly advantageously obtained by reacting a benzyl derivative of the formula II with an oxime of the formula III or its salt.

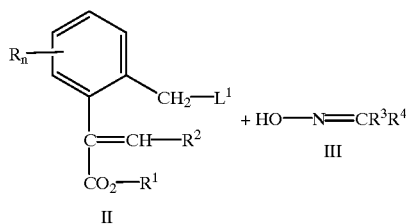

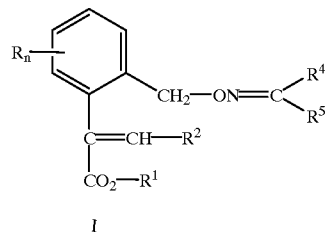

$L^1$ in the formula II is a leaving group, ie. a nucleophilically replaceable group such as halogen (eg. chlorine, bromine or iodine), or an alkyl- or arylsulfonate (methylsulfonate, trifluoromethylsulfonate, phenylsulfonate or 4-methylphenylsulfonate).

The oximes III can also be used in the form of their salts, eg. with inorganic acids, such as hydrochlorides, hydrobromides, hydrosulfates and hydrophosphonates.

The reaction of the compounds II and III is customarily carried out at from 0° C. to 80° C., preferably 20° C. to 60° C., in an inert solvent in the presence of a base.

Suitable solvents are aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, i-propanol, n-butanol and tert-butanol, ketones such as acetone and methyl ethyl ketone, and also dimethyl sulfoxide, dimethylformamide, dimethylacetamide, 1,3-dimethylimidazolidin-2-one and 1,2-dimethyltetrahydro-2(1H)-pyrimidine, preferably methylene chloride, acetone, toluene, tert-butyl methyl ether and dimethylformamide. Mixtures of the solvents mentioned can also be used.

Suitable bases are generally inorganic compounds such as alkali metal and alkaline earth metal hydroxides (eg. lithium hydroxide, sodium hydroxide, potassium hydroxide and calcium hydroxide), alkali metal and alkaline earth metal oxides (eg. lithium oxide, sodium oxide, calcium oxide and magnesium oxide), alkali metal and alkaline earth metal hydrides (eg. lithium hydride, sodium hydride, potassium hydride and calcium hydride), alkali metal amides (eg. lithium amide, sodium amide and potassium amide), alkali metal and alkaline earth metal carbonates (eg. lithium carbonate and calcium carbonate) and also alkali metal hydrogen carbonates (eg. sodium hydrogen carbonate), organometallic compounds, in particular alkali metal alkyls (eg. such as methyllithium, butyllithium and phenyllithium), alkylmagnesium halides (eg. methylmagnesium chloride) and also alkali metal and alkaline earth metal alkoxides (eg. sodium methoxide, sodium ethoxide, potassium ethoxide, potassium tert-butoxide and dimethoxymagnesium), additionally organic bases, eg. tertiary amines such as trimethylamine, triethylamine, triisopropylethylamine and N-methylpiperidine. Pyridine, substituted pyridines such as collidine, lutidine and 4-dimethylaminopyridine and also bicyclic amines. Sodium hydroxide, potassium carbonate and potassium tert-butoxide are particularly preferred. The bases are in general used in an equimolar amount, in an excess or if appropriate as solvents.

It can be advantageous for the reaction to add a catalytic amount of a crown ether (eg. 18-crown-6 or 15-crown-5).

The reaction can also be carried out in two-phase systems consisting of a solution of alkali metal or alkaline earth metal hydroxides or carbonates in water and an organic phase (eg. aromatic and/or halogenated hydrocarbons). Suitable phase-transfer catalysts here ate, for example, ammonium halides and tetrafluoroborates (eg. benzyltriethylammonium chloride, benzyltributylammonium bromide, tetrabutylammonium chloride, hexadecyltrimethylammonium bromide or tetrabutylammonium tetrafluoroborate) and also phosphonium halides(eg. tetrabutylphosphonium chloride and tetraphenylphosphonium bromide).

The starting substances II needed for the preparation of the compounds I are disclosed in EP-A 463 488 or can be prepared by the methods described there.

The oximes III and their salts are disclosed in the literature (WO-A 92/13,830, WO-A 92/18,487 and WO-A 94/08, 968) or can be prepared by the methods described there.

It can be advantageous for the reaction first to convert the oxime III or its salt, using the base, to the corresponding base, which is then reacted with the benzyl derivative II.

In addition, the compounds I are obtained by reaction of α-ketoesters IV in the sense of a Wittig reaction.

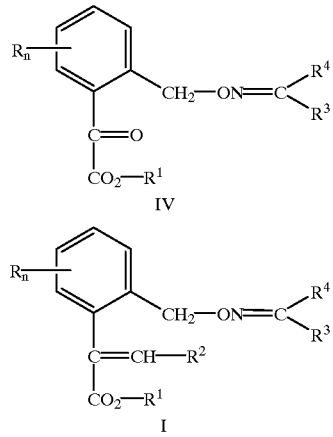

The α-ketoesters IV are obtainable by known methods [eg. EP-A 493 711; Synthetic Commun. 11 (1981), 943].

The compounds I can contain acidic or basic centers and accordingly form acid addition products or base addition products or salts.

Acids for acid addition products are, inter alia, mineral acids (eg. hydrohalic acids such as hydrochloric and hydrobromic acid, phosphoric acid, sulfuric acid, nitric acid), organic acids (eg. formic acid, acetic acid, oxalic acid, malonic acid, lactic acid, malic acid, succinic acid, tartaric acid, citric acid, salicylic acid, p-toluenesulfonic acid, dodecylbenzenesulfonic acid) or other proton-acidic compounds (eg. saccharin).

Bases for base addition products are, inter alia, oxides, hydroxides, carbonates or hydrogen carbonates of alkali metals or alkaline earth metals (eg. potassium or sodium hydroxide or carbonate) or ammonium compounds (eg. ammonium hydroxide).

On account of their double bonds, the compounds I can be formed and used in various spatial forms (isomers).

According to present knowledge, with respect to use those compounds I are particularly preferred where the crotonic ester double bond has the E-configuration and/or where $R^3$ and the oxygen are on the same side of the C=N double bond.

In the case of the definitions of the symbols indicated in the above formulae, in some cases collective terms were used which are generally representative of the following substituents:

halogen: fluorine, chlorine, bromine and iodine;

alkyl: saturated, straight-chain or branched hydrocarbon radicals preferably having 1 to 10 carbon atoms, eg. methyl, ethyl, propyl, 1-methylethyl, butyl, 1-methylpropyl, 2-methylpropyl and 1,1-dimethylethyl;

haloalkyl: straight-chain or branched alkyl groups preferably having 1 to 4 carbon atoms (as mentioned above), it being possible in these groups for the hydrogen atoms to be replaced partly or completely by halogen atoms as mentioned above, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups preferably having 1 to 10 carbon atoms (as mentioned above), which are bonded to the structure via an oxygen atom (—O—);

haloalkoxy: straight-chain or branched haloalkyl groups preferably having 1 to 4 carbon atoms (as mentioned above), which are bonded to the structure via an oxygen atom (—O—);

alkylthio: straight-chain or branched alkyl groups preferably having 1 to 4 carbon atoms (as mentioned above), which are bonded to the structure via a sulfur atom (—S—);

haloalkylthio: straight-chain or branched haloalkyl groups preferably having 1 to 4 carbon atoms (as mentioned above), which are bonded to the structure via a sulfur atom (—S—);

alkenyl: unsaturated, straight-chain or branched hydrocarbon radicals preferably having 2 to 10 carbon atoms and a double bond in any desired position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-di-methyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl- 1-methyl-2-propenyl, 1-ethyl-2-methyl-1-propenyl and 1-ethyl-2-methyl-2-propenyl;

alkenyloxy: straight-chain or branched alkenyl groups preferably having 3 to 10 carbon atoms (as mentioned above), which are bonded to the structure via an oxygen atom (—O—);

alkynyl: straight-chain or branched hydrocarbon groups preferably having 2 to 10 carbon atoms and a triple bond in any desired position, eg. $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

alkynyloxy: straight-chain or branched alkynyl groups preferably having 3 to 10 carbon atoms (as mentioned above), which are bonded to the structure via an oxygen atom (—O—);

cycloalkyl: mono- or bicyclic hydrocarbon radicals preferably having 3 to 10 carbon atoms, eg. $C_3$–$C_{10}$-(bi)cycloalkyl such as cyclopropyl, cyclobutyl, cyclopentyl, cyclohexyl, cycloheptyl, bornanyl, norbornanyl, dicyclohexyl, bicyclo[3.3.0]octyl, bicyclo[3.2.1]octyl, bicyclo[2.2.2]octyl or bicyclo[3.3.1]nonyl;

a bridge bonded to two adjacent ring atoms, which contains 3 to 4 members from the group consisting of 3 or 4 carbon atoms, 2 or 3 carbon atoms and 1 or 2 nitrogen, oxygen and/or sulfur atoms, it being possible for this bridge, together with the ring to which it is bonded, to form a partially unsaturated or aromatic radical: bridges which, with the ring to which they are bonded, form, for example, one of the following systems: quinolinyl, benzofuranyl and naphthyl;

a 5 to 10-membered mono- or bicyclic, heteroaromatic ring system: 5- or 6-membered heteroaromatics which can additionally be benzo-fused or fused to a further 5- or 6-membered heteroaromatic ring system, eg.

5-membered heteroaryl, containing one to four nitrogen atoms or one to three nitrogen atoms and a sulfur or oxygen atom: 5-membered ring heteroaryl groups which, in addition to carbon atoms, can contain one to four nitrogen atoms or one to three nitrogen atoms and a sulfur or oxygen atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

benzo- or hetero-fused 5-membered heteroaryl, containing one to three nitrogen atoms or one nitrogen atom and one oxygen or sulfur atom: 5-membered ring heteroaryl groups which, in addition to carbon atoms, can contain one to four nitrogen atoms or one to three nitrogen atoms and one sulfur or oxygen atom as ring members, and in which two adjacent carbon ring members or a nitrogen and an adjacent carbon ring member can be bridged by a buta-1,3-dien-1,4-diyl group or a 3- to 4-membered unsaturated chain which, in addition to carbon ring members, can contain, for example, nitrogen atoms and/or an oxygen or sulfur atom, eg. benzimidazolyl, benzothiazolyl or benzoxazolyl;

6-membered heteroaryl, containing one to three or one to four nitrogen atoms: 6-membered ring heteroaryl groups which, in addition to carbon atoms, can contain one to three or one to four nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

benzo- or hetero-fused 6-membered heteroaryl, containing one to three or one to four nitrogen atoms and/or one oxygen or sulfur atom: 6-membered ring heteroaryl groups which, in addition to carbon atoms, can contain one to three nitrogen atoms as ring members, and in which two adjacent carbon ring members or a nitrogen and an adjacent carbon ring member can be bridged by a buta-1,3-diene-1,4-diyl group or a 3- to 4-membered unsaturated chain which, in addition to carbon ring members, can contain, for example, nitrogen atoms and/or an oxygen or sulfur atom, eg. indolyl, quinolinyl and isoquinolinyl.

The addition of unsubst. or subst. in relation to alkyl, alkenyl and alkynyl groups is intended to express that these groups can be partially or completely halogenated (ie. the hydrogen atoms of these groups can be partly or completely replaced by identical or different halogen atoms as mentioned above (preferably fluorine, chlorine or bromine) and/or can carry from one to three (preferably one) of the following radicals:

cyano, nitro, hydroxyl, amino, formyl, carboxyl, aminocarbonyl, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkylcarbonyl-N-alkylamino, it being possible for the alkyl groups in these radicals preferably to contain 1 to 6 carbon atoms, in particular 1 to 4 carbon atoms;

cycloalkyl, cycloalkoxy, cycloalkylthio, cycloalkylamino, cycloalkyl-N-alkylamino, heterocyclyl, heterocyclyloxy, heterocyclylthio, heterocyclylamino or heterocyclyl-N-alkylamino, each of which is unsubstituted or substituted by customary groups, the cyclic systems containing 3 to 12 ring members, preferably 2 to 8 ring members, in particular 3 to 6 ring members and the alkyl groups in these radicals preferably containing 1 to 6 carbon atoms, in particular 1 to 4 carbon atoms;

aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino and hetarylalkyl-N-alkylamino, each of which is unsubstituted or substituted by customary groups, the aryl radicals preferably containing 6 to 10 ring members, in particular 6 ring members (phenyl), the hetaryl radicals in particular containing 5 or 6 ring members and the alkyl groups in these radicals preferably containing 1 to 6 carbon atoms, in particular 1 to 4 carbon atoms.

The addition of unsubst. or subst. in relation to the cyclic (saturated, unsaturated or aromatic) groups is intended to express that these groups can be partially or completely halogenated (ie. the hydrogen atoms of these groups can be partly or completely replaced by identical or different halogen atoms as mentioned above (preferably fluorine, chlorine or bromine, in particular fluorine or chlorine) and/or can carry one to four (in particular one to three) of the following radicals cyano, nitro, hydroxyl, amino, carboxyl, aminocarbonyl, alkyl, haloalkyl, alkenyl, haloalkenyl, alkenyloxy, haloalkenyloxy, alkynyl, haloalkynyl, alkynyloxy, haloalkynyloxy, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkylcarbonyl-N-alkylamino, the alkyl groups in these radicals preferably containing 1 to 6 carbon atoms, in particular 1 to 4 carbon atoms and the said alkenyl or alkynyl groups in these radicals containing 2 to 8, preferably 2 to 6, in particular 2 to 4, carbon atoms;

and/or one to three (in particular one) of the following radicals cycloalkyl, cycloalkoxy, cycloalkylthio, cycloalkylamino, cycloalkyl-N-alkylamino, heterocyclyl, heterocyclyloxy, heterocyclylthio, heterocyclylamino or heterocyclyl-N-alkylamino, each of which is unsubstituted or substituted by customary groups, the cyclic systems containing 3 to 12 ring members, preferably 2 to 8 ring members, in particular 3 to 6 ring members, and the alkyl groups in these radicals preferably containing 1 to 6 carbon atoms, in particular 1 to 4 carbon atoms;

aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino and hetarylalkyl-N-alkylamino each of which is unsubstituted or substituted by customary groups, the aryl radicals preferably containing 6 to 10 ring members, in particular 6 ring members (phenyl), the hetaryl radicals in particular containing 5 or 6 ring members and the alkyl groups in these radicals preferably containing 1 to 6 carbon atoms, in particular 1 to 4 carbon atoms, and/or one or two (in particular one) of the following radicals formyl or $CR^{iii}=NOR^{iv}$, $R^{iii}$ being hydrogen or alkyl and $R^{iv}$ being alkyl, alkenyl, alkynyl or arylalkyl and said alkyl groups preferably containing 1 to 6 carbon atoms, in particular 1 to 4 car-bon atoms; said alkenyl or alkynyl groups preferably contain 2 to 6 carbon atoms, in particular 3 to 6 carbon atoms, and aryl is in particular phenyl, which is unsubstituted or can be substituted by customary groups, or in which two adjacent C atoms of the cyclic systems can carry a $C_3$–$C_5$-alkylene, $C_3$–$C_5$-alkenylene, oxy-$C_2$–$C_4$-alkylene, oxy-$C_1$–$C_3$-alkyleneoxy, oxy-$C_2$–$C_4$-alkenylene, oxy-$C_2$–$C_4$-alkenylenoxy or butadienediyl group, it being possible for these bridges in turn to be partially or completely halogenated and/or to carry one to three, in particular one or two, of the following radicals:

$C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

Customary groups which are suitable as substituents of $R^4$ are understood as meaning the radicals mentioned above as possible substituents of cyclic systems.

With respect to their biological action, preferred compounds I are those where n is 0 or 1, in particular 0.

In the case where n is 1, preferred compounds I are those where R is one of the following groups:

halogen (in particular fluorine or chlorine), methyl, trifluoromethyl, methoxy or cyano.

Preferred compounds I where n is 1 are additionally those where R is in the 3- or 6-position relative to the crotonic ester.

Particularly preferred compounds I are additionally those where $R^1$ is methyl.

Particularly preferred compounds I are equally those where $R^1$ is ethyl.

Preferred compounds I are in addition those where $R^2$ is hydrogen.

Preferred compounds I are in addition those where $R^2$ is methyl.

Particularly preferred compounds I are additionally those where $R^2$ is ethyl.

Preferred compounds I are in addition those where $R^3$ is $C_1$–$C_4$-alkyl (in particular methyl).

Particularly preferred compounds I are additionally those where $R^3$ is halogen (in particular chlorine or bromine), $C_1$–$C_4$-alkoxy or $C_1$–$C_4$-alkylthio.

Particularly preferred compounds I are equally those where $R^3$ is cyclopropyl.

Particularly preferred compounds I are in addition those where $R^3$ is trifluoromethyl.

Preferred compounds I are in addition those where $R^4$ is substituted 2-, 3- or 4-pyridinyl.

Particularly preferred compounds I are additionally those where $R^4$ is substituted 3- or 4-pyridazinyl.

Particularly preferred compounds I are equally those where $R^4$ is substituted 2-, 4- or 5-pyrimidinyl.

Particularly preferred compounds I are in addition those where $R^4$ is substituted pyrazinyl or triazinyl.

Preferred compounds I are in addition those where $R^4$ is substituted by halogen, alkyl, haloalkyl, alkoxy, haloalkoxy, alkylthio or haloalkylthio, it being possible for these radicals in turn to carry further customary substituents.

Particularly preferred compounds I are additionally those where $R^4$ is substituted by aryl, aryloxy, hetaryl and hetaryloxy, it being possible for these radicals in turn to carry further customary substituents.

In particular, with respect to their use the compounds I compiled in the following tables are particularly preferred. The groups mentioned for the substituents in these tables are additionally considered per se (independently of the combination in which they are mentioned) in each case to be a particular embodiment of the substituent concerned.

Table 1

Compounds of the formula I (n=0), where $R^1$ is methyl, $R^2$ is methyl, $R^3$ is hydrogen and $R^4$ is a substituent, in each case of one line of Table A Table 2

Compounds of the formula I (n=0), where $R^1$ is methyl, $R^2$ is ethyl, $R^3$ is hydrogen and $R^4$ for a compound in each case corresponds to one line of Table A Table 3
Compounds of the formula I (n=0), where $R^1$ is ethyl, $R^2$ is methyl, $R^3$ is hydrogen and $R^4$ for a compound in each case corresponds to one line of Table A Table 4
Compounds of the formula I (n=0), where $R^1$ is ethyl, $R^2$ is ethyl, $R^3$ is hydrogen and $R^4$ for a compound in each case corresponds to one line of Table A Table 5
Compounds of the formula I where $R_n$ is 3-chlorine, $R^1$ is methyl, $R^2$ is methyl, $R^3$ is hydrogen and $R^4$ for a compound in each case corresponds to one line of Table A Table 6
Compounds of the formula I where $R_n$ is 3-chlorine, $R^1$ is methyl, $R^2$ is ethyl, $R^3$ is hydrogen and $R^4$ for a compound in each case corresponds to one line of Table A Table 7
Compounds of the formula I where $R_n$ is 3-chlorine, $R^1$ is ethyl, $R^2$ is methyl, $R^3$ is hydrogen and $R^4$ for a compound in each case corresponds to one line of Table A Table 8
Compounds of the formula I where $R_n$ is 3-chlorine, $R^1$ is ethyl, $R^2$ is ethyl, $R^3$ is-hydrogen and $R^4$ for a compound in each case corresponds to one line of Table A Table 9
Compounds of the formula I (n=0), where $R^1$ is methyl, $R^2$ is methyl, $R^3$ is cyano and $R^4$ for a compound in each case corresponds to one line of Table A Table 10
Compounds of the formula I (n=0), where $R^1$ is methyl, $R^2$ is ethyl, $R^3$ is cyano and $R^4$ for a compound in each case corresponds to one line of Table A Table 11
Compounds of the formula I (n=0), where $R^1$ is ethyl, $R^2$ is methyl, $R^3$ is cyano and $R^4$ for a compound in each case corresponds to one line of Table A Table 12
Compounds of the formula I (n=0), where $R^1$ is ethyl, $R^2$ is ethyl, $R^3$ is cyano and $R^4$ for a compound in each case corresponds to one line of Table A Table 13
Compounds of the formula I where $R_n$ is 3-chlorine, $R^1$ is hydrogen, $R^2$ is methyl, $R^3$ is cyano and $R^4$ for a compound in each case corresponds to one line of Table A Table 14
Compounds of the formula I where $R_n$ is 3-chlorine, $R^1$ is hydrogen, $R^2$ is ethyl, $R^3$ is cyano and $R^4$ for a compound in each case corresponds to one line of Table A Table 15
Compounds of the formula I where $R_n$ is 3-chlorine, $R^1$ is methyl, $R^2$ is methyl, $R^3$ is cyano and $R^4$ for a compound in each case corresponds to one line of Table A Table 16
Compounds of the formula I where $R_n$ is 3-chlorine, $R^1$ is methyl, $R^2$ is ethyl, $R^3$ is cyano and $R^4$ for a compound in each case corresponds to one line of Table A Table 17
Compounds of the formula I where $R_n$ is 3-chlorine, $R^1$ is ethyl, $R^2$ is methyl, $R^3$ is cyano and $R^4$ for a compound in each case corresponds to one line of Table A Table 18
Compounds of the formula I where $R_n$ is 3-chlorine, $R^1$ is ethyl, $R^2$ is ethyl, $R^3$ is cyano and $R^4$ for a compound in each case corresponds to one line of Table A Table 19
Compounds of the formula I (n=0), where $R^1$ is hydrogen, $R^2$ is methyl, $R^3$ is chlorine and $R^4$ for a compound in each case corresponds to one line of Table A Table 20
Compounds of the formula I (n=0), where $R^1$ is hydrogen, $R^2$ is ethyl, $R^3$ is chlorine and $R^4$ for a compound in each case corresponds to one line of Table A Table 21
Compounds of the formula I (n=0) where $R^1$ is methyl, $R^2$ is methyl, $R^3$ is chlorine and $R^4$ for a compound in each case corresponds to one line of Table A Table 22
Compounds of the formula I (n=0), where $R^1$ is methyl, $R^2$ is ethyl, $R^3$ is chlorine and $R^4$ for a compound in each case corresponds to one line of Table A Table 23
Compounds of the formula I (n=0), where $R^1$ is ethyl, $R^2$ is methyl, $R^3$ is chlorine and $R^4$ for a compound in each case corresponds to one line of Table A Table 24
Compounds of the formula I (n=0), where $R^1$ is ethyl, $R^2$ is ethyl, $R^3$ is chlorine and $R^4$ for a compound in each case corresponds to one line of Table A Table 25
Compounds of the formula I where $R_n$ is 3-chlorine, $R^1$ is hydrogen, $R^2$ is methyl, $R^3$ is chlorine and $R^4$ for a compound in each case corresponds to one line of Table A Table 26
Compounds of the formula I where $R_n$ is 3-chlorine, $R^1$ is hydrogen, $R^2$ is ethyl, $R^3$ is chlorine and $R^4$ for a compound in each case corresponds to one line of Table A Table 27
Compounds of the formula I where $R_n$ is 3-chlorine, $R^1$ is methyl, $R^2$ is methyl, $R^3$ is chlorine and $R^4$ for a compound in each case corresponds to one line of Table A Table 28
Compounds of the formula I where $R_n$ is 3-chlorine, $R^1$ is methyl, $R^2$ is ethyl, $R^3$ is chlorine and $R^4$ for a compound in each case corresponds to one line of Table A Table 29
Compounds of the formula I where $R_n$ is 3-chlorine, $R^1$ is ethyl, $R^2$ is methyl, $R^3$ is chlorine and $R^4$ for a compound in each case corresponds to one line of Table A Table 30
Compounds of the formula I where $R_n$ is 3-chloro, $R^1$ is ethyl, $R^2$ is ethyl, $R^3$ is chlorine and $R^4$ for a compound in each case corresponds to one line of Table A Table 31
Compounds of the formula I (n=0), where $R^1$ is hydrogen, $R^2$ is methyl, $R^3$ is methyl and $R^4$ for a compound in each case corresponds to one line of Table A Table 32
Compounds of the formula I (n=0), where $R^1$ is hydrogen, $R^2$ is ethyl, $R^3$ is methyl and $R^4$ for a compound in each case corresponds to one line of Table A Table 33
Compounds of the formula I (n=0), where $R^1$ is methyl, $R^2$ is methyl, $R^3$ is methyl and $R^4$ for a compound in each case corresponds to one line of Table A Table 34
Compounds of the formula I (n=0), where $R^1$ is methyl, $R^2$ is ethyl, $R^3$ is methyl and $R^4$ for a compound in each case corresponds to one line of Table A Table 35
Compounds of the formula I (n=0), where $R^1$ is ethyl, $R^2$ is methyl, $R^3$ is methyl and $R^4$ for a compound in each case corresponds to one line of Table A Table 36
Compounds of the formula I (n=0), where $R^1$ is ethyl, $R^2$ is ethyl, $R^3$ is methyl and $R^4$ for a compound in each case corresponds to one line of Table A Table 37
Compounds of the formula I where $R_n$ is 3-chlorine, $R^1$ is hydrogen, $R^2$ is methyl, $R^3$ is methyl and $R^4$ for a compound in each case corresponds to one line of Table A Table 38
Compounds of the formula I where $R_n$ is 3-chlorine, $R^1$ is hydrogen, $R^2$ is ethyl, $R^3$ is methyl and $R^4$ for a compound in each case corresponds to one line of Table A Table 39
Compounds of the formula I where $R_n$ is 3-chlorine, $R^1$ is methyl, $R^2$ is methyl, $R^3$ is methyl and $R^4$ for a compound in each case corresponds to one line of Table A Table 40
Compounds of the formula I where $R_n$ is 3-chlorine, $R^1$ is methyl, $R^2$ is ethyl, $R^3$ is methyl and $R^4$ for a compound in each case corresponds to one line of Table A Table 41
Compounds of the formula I where $R_n$ is 3-chlorine, $R^1$ is ethyl, $R^2$ is methyl, $R^3$ is methyl and $R^4$ for a compound in each case corresponds to one line of Table A Table 42
Compounds of the formula I where $R_n$ is 3-chlorine, $R^1$ is ethyl, $R^2$ is ethyl, $R^3$ is methyl and $R^4$ for a compound in each case corresponds to one line of Table A Table 43
Compounds of the formula I (n=0), where $R^1$ is hydrogen, $R^2$ is methyl, $R^3$ is ethyl and $R^4$ for a compound in each case corresponds to one line of Table A Table 44
Compounds of the formula I (n=0), where $R^1$ is hydrogen, $R^2$ is ethyl, $R^3$ is ethyl and $R^4$ for a compound in each case corresponds to one line of Table A Table 45
Compounds of the formula I (n=0), where $R^1$ is methyl, $R^2$ is methyl, $R^3$ is ethyl and $R^4$ for a compound in each case corresponds to one line of Table A Table 46
Compounds of the formula I (n=0), where $R^1$ is methyl, $R^2$ is ethyl, $R^3$ is ethyl and $R^4$ for a compound in each case corresponds to one line of Table A Table 47
Compounds of the formula I (n=0), where $R^1$ is ethyl, $R^2$ is methyl, $R^3$ is ethyl and $R^4$ for a compound in each case corresponds to one line of Table A Table 48
Compounds of the formula I (n=0), where $R^1$ is ethyl, $R^2$ is ethyl, $R^3$ is ethyl and $R^4$ for a compound in each case corresponds to one line of Table A Table 49
Compounds of the formula I where $R_n$ is 3-chlorine, $R^1$ is hydrogen, $R^2$ is methyl, $R^3$ is ethyl and $R^4$ for a compound in each case corresponds to one line of Table A Table 50
Compounds of the formula I where $R_n$ is 3-chlorine, $R^1$ is hydrogen, $R^2$ is ethyl, $R^3$ is ethyl and $R^4$ for a compound in each case corresponds to one line of Table A Table 51
Compounds of the formula I where $R_n$ is 3-chlorine, $R^1$ is methyl, $R^2$ is methyl, $R^3$ is ethyl and $R^4$ for a compound in each case corresponds to one line of Table A Table 52
Compounds of the formula I where $R_n$ is 3-chlorine, $R^1$ is methyl, $R^2$ is ethyl, $R^3$ is ethyl and $R^4$ for a compound in each case corresponds to one line of Table A Table 53
Compounds of the formula I where $R_n$ is 3-chlorine, $R^1$ is ethyl, $R^2$ is methyl, $R^3$ is ethyl and $R^4$ for a compound in each case corresponds to one line of Table A Table 54
Compounds of the formula I where $R_n$ is 3-chlorine, $R^1$ is ethyl, $R^2$ is ethyl, $R^3$ is ethyl and $R^4$ for a compound in each case corresponds to one line of Table A Table 55
Compounds of the formula I (n=0), where $R^1$ is hydrogen, $R^2$ is methyl, $R^3$ is isopropyl and $R^4$ for a compound in each case corresponds to one line of Table A Table 56
Compounds of the formula I (n=0), where $R^1$ is hydrogen, $R^2$ is ethyl, $R^3$ is isopropyl and $R^4$ for a compound in each case corresponds to one line of Table A Table 57
Compounds of the formula I (n=0), where $R^1$ is methyl, $R^2$ is methyl, $R^3$ is isopropyl and $R^4$ for a compound in each case corresponds to one line of Table A Table 58
Compounds of the formula I (n=0), where $R^1$ is methyl, $R^2$ is ethyl, $R^3$ is isopropyl and $R^4$ for a compound in each case corresponds to one line of Table A Table 59
Compounds of the formula I (n=0), where $R^1$ is ethyl, $R^2$ is methyl, $R^3$ is isopropyl and $R^4$ for a compound in each case corresponds to one line of Table A Table 60
Compounds of the formula I (n=0), where $R^1$ is ethyl, $R^2$ is ethyl, $R^3$ is isopropyl and $R^4$ for a compound in each case corresponds to one line of Table A Table 61
Compounds of the formula I where $R_n$ is 3-chlorine, $R^1$ is hydrogen, $R^2$ is methyl, $R^3$ is isopropyl and $R^4$ for a compound in each case corresponds to one line of Table A Table 62
Compounds of the formula I where $R_n$ is 3-chloro, $R^1$ is hydrogen, $R^2$ is ethyl, $R^3$ is isopropyl and $R^4$ for a compound in each case corresponds to one line of Table A Table 63
Compounds of the formula I where $R_n$ is 3-chlorine, $R^1$ is methyl, $R^2$ is methyl, $R^3$ is isopropyl and $R^4$ for a compound in each case corresponds to one line of Table A Table 64
Compounds of the formula I where $R_n$ is 3-chlorine, $R^1$ is methyl, $R^2$ is ethyl, $R^3$ is isopropyl and $R^4$ for a compound in each case corresponds to one line of Table A Table 65
Compounds of the formula I where $R_n$ is 3-chlorine, $R^1$ is ethyl, $R^2$ is methyl, $R^3$ is isopropyl and $R^4$ for a compound in each case corresponds to one line of Table A Table 66
Compounds of the formula I where $R_n$ is 3-chlorine, where $R^1$ is ethyl, $R^2$ is ethyl, $R^3$ is isopropyl and $R^4$ for a compound in each case corresponds to one line of Table A Table 67
Compounds of the formula I (n=0), where $R^1$ is hydrogen, $R^2$ is methyl, $R^3$ is trifluoromethyl and $R^4$ for a compound in each case corresponds to one line of Table A Table 68
Compounds of the formula I (n=0), where $R^1$ is hydrogen, $R^2$ is ethyl, $R^3$ is trifluoromethyl and $R^4$ for a compound in each case corresponds to one line of Table A Table 69
Compounds of the formula I (n=0), where $R^1$ is methyl, $R^2$ is methyl, $R^3$ is trifluoromethyl and $R^4$ for a compound in each case corresponds to one line of Table A Table 70
Compounds of the formula I (n=0), where $R^1$ is methyl, $R^2$ is ethyl, $R^3$ is trifluoromethyl and $R^4$ for a compound in each case corresponds to one line of Table A Table 71
Compounds of the formula I (n=0), where $R^1$ is ethyl, $R^2$ is methyl, $R^3$ is trifluoromethyl and $R^4$ for a compound in each case corresponds to one line of Table A Table 72
Compounds of the formula I (n=0), where $R^1$ is ethyl, $R^2$ is ethyl, $R^3$ is trifluoromethyl and $R^4$ for a compound in each case corresponds to one line of Table A Table 73
Compounds of the formula I where $R_n$ is 3-chlorine, $R^1$ is hydrogen, $R^2$ is methyl, $R^3$ is trifluoromethyl and $R^4$ for a compound in each case corresponds to one line of Table A Table 74
Compounds of the formula I where $R_n$ is 3-chlorine, $R^1$ is hydrogen, $R^2$ is ethyl, $R^3$ is trifluoromethyl and $R^4$ for a compound in each case corresponds to one line of Table A Table 75
Compounds of the formula I where $R_n$ is 3-chlorine, $R^1$ is methyl, $R^2$ is methyl, $R^3$ is trifluoromethyl and $R^4$ for a compound in each case corresponds to one line of Table A Table 76
Compounds of the formula I where $R_n$ is 3-chlorine, $R^1$ is methyl, $R^2$ is ethyl, $R^3$ is trifluoromethyl and $R^4$ for a compound in each case corresponds to one line of Table A Table 77
Compounds of the formula I where $R_n$ is 3-chlorine, $R^1$ is ethyl, $R^2$ is methyl, $R^3$ is trifluoromethyl and $R^4$ for a compound in each case corresponds to one line of Table A Table 78
Compounds of the formula I where $R_n$ is 3-chlorine, $R^1$ is ethyl, $R^2$ is ethyl, $R^3$ is trifluoromethyl and $R^4$ for a compound in each case corresponds to one line of Table A Table 79
Compounds of the formula I (n=0), where $R^1$ is hydrogen, $R^2$ is methyl, $R^3$ is methoxy and $R^4$ for a compound in each case corresponds to one line of Table A Table 80
Compounds of the formula I (n=0), where $R^1$ is hydrogen, $R^2$ is ethyl, $R^3$ is methoxy and $R^4$ for a compound in each case corresponds to one line of Table A Table 81
Compounds of the formula I (n=0), where $R^1$ is methyl, $R^2$ is methyl, $R^3$ is methoxy and $R^4$ for a compound in each case corresponds to one line of Table A Table 82
Compounds of the formula I (n=0), where $R^1$ is methyl, $R^2$ is ethyl, $R^3$ is methoxy and $R^4$ for a compound in each case corresponds to one line of Table A Table 83
Compounds of the formula I (n=0), where $R^1$ is ethyl, $R^2$ is methyl, $R^3$ is methoxy and $R^4$ for a compound in each case corresponds to one line of Table A Table 84
Compounds of the formula I (n=0), where $R^1$ is ethyl, $R^2$ is ethyl, $R^3$ is methoxy and $R^4$ for a compound in each case corresponds to one line of Table A Table 85
Compounds of the formula I where $R_n$ is 3-chlorine, $R^1$ is hydrogen, $R^2$ is methyl, $R^3$ is methoxy and $R^4$ for a compound in each case corresponds to one line of Table A Table 86
Compounds of the formula I where $R_n$ is 3-chlorine, $R^1$ is hydrogen, $R^2$ is ethyl, $R^3$ is methoxy and $R^4$ for a compound in each case corresponds to one line of Table A Table 87
Compounds of the formula I where $R_n$ is 3-chlorine, $R^1$ is methyl, $R^2$ is methyl, $R^3$ is methoxy and $R^4$ for a compound in each case corresponds to one line of Table A Table 88
Compounds of the formula I where $R_n$ is 3-chlorine, $R^1$ is methyl, $R^2$ is ethyl, $R^3$ is methoxy and $R^4$ for a compound in each case corresponds to one line of Table A Table 89
Compounds of the formula I where $R_n$ is 3-chlorine, $R^1$ is ethyl, $R^2$ is methyl, $R^3$ is methoxy and $R^4$ for a compound in each case corresponds to one line of Table A Table 90
Compounds of the formula I where $R_n$ is 3-chlorine, $R^1$ is ethyl, $R^2$ is ethyl, $R^3$ is methoxy and $R^4$ for a compound in each case corresponds to one line of Table A Table 91
Compounds of the formula I (n=0), where $R^1$ is hydrogen, $R^2$ is methyl, $R^3$ is ethoxy and $R^4$ for a compound in each case corresponds to one line of Table A Table 92
Compounds of the formula I (n=0), where $R^1$ is hydrogen, $R^2$ is ethyl, $R^3$ is ethoxy and $R^4$ for a compound in each case corresponds to one line of Table A Table 93
Compounds of the formula I (n=0), where $R^1$ is methyl, $R^2$ is methyl, $R^3$ is ethoxy and $R^4$ for a compound in each case corresponds to one line of Table A Table 94
Compounds of the formula I (n=0), where $R^1$ is methyl, $R^2$ is ethyl, $R^3$ is ethoxy and $R^4$ for a compound in each case corresponds to one line of Table A Table 95
Compounds of the formula I (n=0), where $R^1$ is ethyl, $R^2$ is methyl, $R^3$ is ethoxy and $R^4$ for a compound in each case corresponds to one line of Table A Table 96
Compounds of the formula I (n=0), where $R^1$ is ethyl, $R^2$ is ethyl, $R^3$ is ethoxy and $R^4$ for a compound in each case corresponds to one line of Table A Table 97
Compounds of the formula I where $R_n$ is 3-chlorine, $R^1$ is hydrogen, $R^2$ is methyl, $R^3$ is ethoxy and $R^4$ for a compound in each case corresponds to one line of Table A Table 98
Compounds of the formula I where $R_n$ is 3-chlorine, $R^1$ is hydrogen, $R^2$ is ethyl, $R^3$ is ethoxy and $R^4$ for a compound in each case corresponds to one line of Table A Table 99
Compounds of the formula I where $R_n$ is 3-chlorine, $R^1$ is methyl, $R^2$ is methyl, $R^3$ is ethoxy and $R^4$ for a compound in each case corresponds to one line of Table A Table 100
Compounds of the formula I where $R_n$ is 3-chlorine, $R^1$ is methyl, $R^2$ is ethyl, $R^3$ is ethoxy and $R^4$ for a compound in each case corresponds to one line of Table A Table 101
Compounds of the formula I where $R_n$ is 3-chlorine, $R^1$ is ethyl, $R^2$ is methyl, $R^3$ is ethoxy and $R^4$ for a compound in each case corresponds to one line of Table A Table 102
Compounds of the formula I where $R_n$ is 3-chlorine, $R^1$ is ethyl, $R^2$ is ethyl, $R^3$ is ethoxy and $R^4$ for a compound in each case corresponds to one line of Table A Table 103
Compounds of the formula I (n=0), where $R^1$ is hydrogen, $R^2$ is methyl, $R^3$ is difluoromethoxy and $R^4$ for a compound in each case corresponds to one line of Table A Table 104
Compounds of the formula I (n=0), where $R^1$ is hydrogen, $R^2$ is ethyl, $R^3$ is difluoromethoxy and $R^4$ for a compound in each case corresponds to one line of Table A Table 105
Compounds of the formula I (n=0), where $R^1$ is methyl, $R^2$ is methyl, $R^3$ is difluoromethoxy and $R^4$ for a compound in each case corresponds to one line of Table A
Table 106
Compounds of the formula I (n=0), where $R^1$ is methyl, $R^2$ is ethyl, $R^3$ is difluoromethoxy and $R^4$ for a compound in each case corresponds to one line of Table A
Table 107
Compounds of the formula I (n=0), where $R^1$ is ethyl, $R^2$ is methyl, $R^3$ is difluoromethoxy and $R^4$ for a compound in each case corresponds to one line of Table A
Table 108
Compounds of the formula I (n=0), where $R^1$ is ethyl, $R^2$ is ethyl, $R^3$ is difluoromethoxy and $R^4$ for a compound in each case corresponds to one line of Table A
Table 109
Compounds of the formula I where $R_n$ is 3-chlorine, $R^1$ is hydrogen, $R^2$ is methyl, $R^3$ is difluoromethoxy and $R^4$ for a compound in each case corresponds to one line of Table A
Table 110
Compounds of the formula I where $R_n$ is 3-chlorine, $R^1$ is hydrogen, $R^2$ is ethyl, $R^3$ is difluoromethoxy and $R^4$ for a compound in each case corresponds to one line of Table A
Table 111
Compounds of the formula I where $R_n$ is 3-chlorine, $R^1$ is methyl, $R^2$ is methyl, $R^3$ is difluoromethoxy and $R^4$ for a compound in each case corresponds to one line of Table A
Table 112
Compounds of the formula I where $R_n$ is 3-chlorine, $R^1$ is methyl, $R^2$ is ethyl, $R^3$ is difluoromethoxy and $R^4$ for a compound in each case corresponds to one line of Table A
Table 113
Compounds of the formula I where $R_n$ is 3-chlorine, $R^1$ is ethyl, $R^2$ is methyl, $R^3$ is difluoromethoxy and $R^4$ for a compound in each case corresponds to one line of Table A
Table 114
Compounds of the formula I where $R_n$ is 3-chlorine, $R^1$ is ethyl, $R^2$ is ethyl, $R^3$ is difluoromethoxy and $R^4$ for a compound in each case corresponds to one line of Table A
Table 115
Compounds of the formula I (n=0), where $R^1$ is hydrogen, $R^2$ is methyl, $R^3$ is methylthio and $R^4$ for a compound in each case corresponds to one line of Table A
Table 116
Compounds of the formula I (n=0), where $R^1$ is hydrogen, $R^2$ is ethyl, $R^3$ is methylthio and $R^4$ for a compound in each case corresponds to one line of Table A
Table 117
Compounds of the formula I (n=0), where $R^1$ is methyl, $R^2$ is methyl, $R^3$ is methylthio and $R^4$ for a compound in each case corresponds to one line of Table A
Table 118
Compounds of the formula I (n=0), where $R^1$ is methyl, $R^2$ is ethyl, $R^3$ is methylthio and $R^4$ for a compound in each case corresponds to one line of Table A
Table 119
Compounds of the formula I (n=0), where $R^1$ is ethyl, $R^2$ is methyl, $R^3$ is methylthio and $R^4$ for a compound in each case corresponds to one line of Table A
Table 120
Compounds of the formula I (n=0), where $R^1$ is ethyl, $R^2$ is ethyl, $R^3$ is methylthio and $R^4$ for a compound in each case corresponds to one line of Table A
Table 121
Compounds of the formula I where $R_n$ is 3-chlorine, $R^1$ is hydrogen, $R^2$ is methyl, $R^3$ is methylthio and $R^4$ for a compound in each case corresponds to one line of Table A
Table 122
Compounds of the formula I where $R_n$ is 3-chlorine, $R^1$ is hydrogen, $R^2$ is ethyl, $R^3$ is methylthio and $R^4$ for a compound in each case corresponds to one line of Table A
Table 123
Compounds of the formula I where $R_n$ is 3-chlorine, $R^1$ is methyl, $R^2$ is methyl, $R^3$ is methylthio and $R^4$ for a compound in each case corresponds to one line of Table A
Table 124
Compounds of the formula I where $R_n$ is 3-chlorine, $R^1$ is methyl, $R^2$ is ethyl, $R^3$ is methylthio and $R^4$ for a compound in each case corresponds to one line of Table A
Table 125
Compounds of the formula I where $R_n$ is 3-chlorine, $R^1$ is ethyl, $R^2$ is methyl, $R^3$ is methylthio and $R^4$ for a compound in each case corresponds to one line of Table A
Table 126
Compounds of the formula I where $R_n$ is 3-chlorine, $R^1$ is ethyl, $R^2$ is ethyl, $R^3$ is methylthio and $R^4$ for a compound in each case corresponds to one line of Table A
Table 127
Compounds of the formula I (n=0), where $R^1$ is hydrogen, $R^2$ is methyl, $R^3$ is ethylthio and $R^4$ for a compound in each case corresponds to one line of Table A
Table 128
Compounds of the formula I (n=0), where $R^1$ is hydrogen, $R^2$ is ethyl, $R^3$ is ethylthio and $R^4$ for a compound in each case corresponds to one line of Table A
Table 129
Compounds of the formula I (n=0), where $R^1$ is methyl, $R^2$ is methyl, $R^3$ is ethylthio and $R^4$ for a compound in each case corresponds to one line of Table A
Table 130
Compounds of the formula I (n=0), where $R^1$ is methyl, $R^2$ is ethyl, $R^3$ is ethylthio and $R^4$ for a compound in each case corresponds to one line of Table A
Table 131
Compounds of the formula I (n=0), where $R^1$ is ethyl, $R^2$ is methyl, $R^3$ is ethylthio and $R^4$ for a compound in each case corresponds to one line of Table A
Table 132
Compounds of the formula I (n=0), where $R^1$ is ethyl, $R^2$ is ethyl, $R^3$ is ethylthio and $R^4$ for a compound in each case corresponds to one line of Table A
Table 133
Compounds of the formula I where $R_n$ is 3-chlorine, $R^1$ is hydrogen, $R^2$ is methyl, $R^3$ is ethylthio and $R^4$ for a compound in each case corresponds to one line of Table A
Table 134
Compounds of the formula I where $R_n$ is 3-chlorine, $R^1$ is hydrogen, $R^2$ is ethyl, $R^3$ is ethylthio and $R^4$ for a compound in each case corresponds to one line of Table A
Table 135
Compounds of the formula I where $R_n$ is 3-chlorine, $R^1$ is methyl, $R^2$ is methyl, $R^3$ is ethylthio and $R^4$ for a compound in each case corresponds to one line of Table A
Table 136
Compounds of the formula I where $R_n$ is 3-chlorine, $R^1$ is methyl, $R^2$ is ethyl, $R^3$ is ethylthio and $R^4$ for a compound in each case corresponds to one line of Table A
Table 137
Compounds of the formula I where $R_n$ is 3-chlorine, $R^1$ is ethyl, $R^2$ is methyl, $R^3$ is ethylthio and $R^4$ for a compound-in each case corresponds to one line of Table A
Table 138
Compounds of the formula I where $R_n$ is 3-chlorine, $R^1$ is ethyl, $R^2$ is ethyl, $R^3$ is ethylthio and $R^4$ for a compound in each case corresponds to one line of Table A Table 139
Compounds of the formula I (n=0), where $R^1$ is hydrogen, $R^2$ is methyl, $R^3$ is cyclopropyl and $R^4$ for a compound in each case corresponds to one line of Table A Table 140
Compounds of the formula I (n=0), where $R^1$ is hydrogen, $R^2$ is ethyl, $R^3$ is cyclopropyl and $R^4$ for a compound in each case corresponds to one line of Table A Table 141
Compounds of the formula I (n=0), where $R^1$ is methyl, $R^2$ is methyl, $R^3$ is cyclopropyl and $R^4$ for a compound in each case corresponds to one line of Table A Table 142
Compounds of the formula I (n=0), where $R^1$ is methyl, $R^2$ is ethyl, $R^3$ is cyclopropyl and $R^4$ for a compound in each case corresponds to one line of Table A Table 143
Compounds of the formula I (n=0), where $R^1$ is ethyl, $R^2$ is methyl, $R^3$ is cyclopropyl and $R^4$ for a compound in each case corresponds to one line of Table A Table 144
Compounds of the formula I (n=0), where $R^1$ is ethyl, $R^2$ is ethyl, $R^3$ is cyclopropyl and $R^4$ for a compound in each case corresponds to one line of Table A Table 145
Compounds of the formula I where $R_n$ is 3-chlorine, $R^1$ is hydrogen, $R^2$ is methyl, $R^3$ is cyclopropyl and $R^4$ for a compound in each case corresponds to one line of Table A Table 146
Compounds of the formula I where $R_n$ is 3-chlorine, $R^1$ is hydrogen, $R^2$ is ethyl, $R^3$ is cyclopropyl and $R^4$ for a compound in each case corresponds to one line of Table A Table 147
Compounds of the formula I where $R_n$ is 3-chlorine, $R^1$ is methyl, $R^2$ is methyl, $R^3$ is cyclopropyl and $R^4$ for a compound in each case corresponds to one line of Table A Table 148
Compounds of the formula I where $R_n$ is 3-chlorine, $R^1$ is methyl, $R^2$ is ethyl, $R^3$ is cyclopropyl and $R^4$ for a compound in each case corresponds to one line of Table A Table 149
Compounds of the formula I where $R_n$ is 3-chlorine, $R^1$ is ethyl, $R^2$ is methyl, $R^3$ is cyclopropyl and $R^4$ for a compound in each case corresponds to one line of Table A Table 150
Compounds of the formula I where $R_n$ is 3-chlorine, $R^1$ is ethyl, $R^2$ is ethyl, $R^3$ is cyclopropyl and $R^4$ for a compound in each case corresponds to one line of Table A Table 151
Compounds of the formula I (n=0), where $R^1$ is hydrogen, $R^2$ is methyl, $R^3$ is cyclopentyl and $R^4$ for a compound in each case corresponds to one line of Table A Table 152
Compounds of the formula I (n=0), where $R^1$ is hydrogen, $R^2$ is ethyl, $R^3$ is cyclopentyl and $R^4$ for a compound in each case corresponds to one line of Table A Table 153
Compounds of the formula I (n=0), where $R^1$ is methyl, $R^2$ is methyl, $R^3$ is cyclopentyl and $R^4$ for a compound in each case corresponds to one line of Table A Table 154
Compounds of the formula I (n=0), where $R^1$ is methyl, $R^2$ is ethyl, $R^3$ is cyclopentyl and $R^4$ for a compound in each case corresponds to one line of Table A Table 155
Compounds of the formula I (n=0), where $R^1$ is ethyl, $R^2$ is methyl, $R^3$ is cyclopentyl and $R^4$ for a compound in each case corresponds to one line of Table A Table 156
Compounds of the formula I (n=0), where $R^1$ is ethyl, $R^2$ is ethyl, $R^3$ is cyclopentyl and $R^4$ for a compound in each case corresponds to one line of Table A Table 157
Compounds of the formula I where $R_n$ is 3-chlorine, $R^1$ is hydrogen, $R^2$ is methyl, $R^3$ is cyclopentyl and $R^4$ for a compound in each case corresponds to one line of Table A Table 158
Compounds of the formula I where $R_n$ is 3-chlorine, $R^1$ is hydrogen, $R^2$ is ethyl, $R^3$ is cyclopentyl and $R^4$ for a compound in each case corresponds to one line of Table A Table 159
Compounds of the formula I where $R_n$ is 3-chlorine, $R^1$ is methyl, $R^2$ is methyl, $R^3$ is cyclopentyl and $R^4$ for a compound in each case corresponds to one line of Table A Table 160
Compounds of the formula I where $R_n$ is 3-chlorine, $R^1$ is methyl, $R^2$ is ethyl, $R^3$ is cyclopentyl and $R^4$ for a compound in each case corresponds to one line of Table A Table 161
Compounds of the formula I where $R_n$ is 3-chlorine, $R^1$ is ethyl, $R^2$ is methyl, $R^3$ is cyclopentyl and $R^4$ for a compound in each case corresponds to one line of Table A Table 162
Compounds of the formula I where $R_n$ is 3-chlorine, $R^1$ is ethyl, $R^2$ is ethyl, $R^3$ is cyclopentyl and $R^4$ for a compound in each case corresponds to one line of Table A Table 163
Compounds of the formula I (n=0), where $R^1$ is hydrogen, $R^2$ is methyl, $R^3$ is cyclohexyl and $R^4$ for a compound in each case corresponds to one line of Table A Table 164
Compounds of the formula I (n=0), where $R^1$ is hydrogen, $R^2$ is ethyl, $R^3$ is cyclohexyl and $R^4$ for a compound in each case corresponds to one line of Table A Table 165
Compounds of the formula I (n=0), where $R^1$ is methyl, $R^2$ is methyl, $R^3$ is cyclohexyl and $R^4$ for a compound in each case corresponds to one line of Table A Table 166
Compounds of the formula I (n=0), where $R^1$ is methyl, $R^2$ is ethyl, $R^3$ is cyclohexyl and $R^4$ for a compound in each case corresponds to one line of Table A Table 167
Compounds of the formula I (n=0), where $R^1$ is ethyl, $R^2$ is methyl, $R^3$ is cyclohexyl and $R^4$ for a compound in each case corresponds to one line of Table A Table 168
Compounds of the formula I (n=0), where $R^1$ is ethyl, $R^2$ is ethyl, $R^3$ is cyclohexyl and $R^4$ for a compound in each case corresponds to one line of Table A Table 169
Compounds of the formula I where $R_n$ is 3-chlorine, $R^1$ is hydrogen, $R^2$ is methyl, $R^3$ is cyclohexyl and $R^4$ for a compound in each case corresponds to one line of Table A Table 170
Compounds of the formula I where $R_n$ is 3-chlorine, $R^1$ is hydrogen, $R^2$ is ethyl, $R^3$ is cyclohexyl and $R^4$ for a compound in each case corresponds to one line of Table A Table 171
Compounds of the formula I where $R_n$ is 3-chlorine, $R^1$ is methyl, $R^2$ is methyl, $R^3$ is cyclohexyl and $R^4$ for a compound in each case corresponds to one line of Table A Table 172
Compounds of the formula I where $R_n$ is 3-chlorine, $R^1$ is methyl, $R^2$ is ethyl, $R^3$ is cyclohexyl and $R^4$ for a compound in each case corresponds to one line of Table A Table 173
Compounds of the formula I where $R_n$ is 3-chlorine, $R^1$ is ethyl, $R^2$ is methyl, $R^3$ is cyclohexyl and $R^4$ for a compound in each case corresponds to one line of Table A Table 174
Compounds of the formula I where $R_n$ is 3-chlorine, $R^1$ is ethyl, $R^2$ is ethyl, $R^3$ is cyclohexyl and $R^4$ for a compound in each case corresponds to one line of Table A Table 175
Compounds of the formula I where $R_n$ is 3-fluorine, $R^1$, $R^2$ and $R^3$ are methyl and $R^4$ for a compound in each case corresponds to one line of Table A Table 176
Compounds of the formula I where $R_n$ is 3-methyl, $R^1$, $R^2$ and $R^3$ are methyl and $R^4$ for a compound in each case corresponds to one line of Table A Table 177
Compounds of the formula I where $R_n$ is 3-methoxy, $R^1$, $R^2$ and $R^3$ are methyl and $R^4$ for a compound in each case corresponds to one line of Table A Table 178
Compounds of the formula I where $R_n$ is 6-fluorine, $R^1$, $R^2$ and $R^3$ are methyl and $R^4$ for a compound in each case corresponds to one line of Table A Table 179
Compounds of the formula I where $R_n$ is 6-chlorine, $R^1$, $R^2$ and $R^3$ are methyl and $R^4$ for a compound in each case corresponds to one line of Table A Table 180
Compounds of the formula I where $R_n$ is 6-methyl, $R^1$, $R^2$ and $R^3$ are methyl and $R^4$ for a compound in each case corresponds to one line of Table A Table 181
Compounds of the formula I where $R_n$ is 6-methoxy, $R^1$, $R^2$ and $R^3$ are methyl and $R^4$ for a compound in each case corresponds to one line of Table A

TABLE A

| No. | $R^4$ |
|---|---|
| 1 | 3-CH$_3$-pyridin-2-yl |
| 2 | 4-CH$_3$-pyridin-2-yl |
| 3 | 5-CH$_3$-pyridin-2-yl |
| 4 | 6-CH$_3$-pyridin-2-yl |
| 5 | 3-CH$_2$CH$_3$-pyridin-2-yl |
| 6 | 4-CH$_2$CH$_3$-pyridin-2-yl |
| 7 | 5-CH$_2$CH$_3$-pyridin-2-yl |
| 8 | 6-CH$_2$CH$_3$-pyridin-2-yl |
| 9 | 3-CF$_3$-pyridin-2-yl |
| 10 | 4-CF$_3$-pyridin-2-yl |
| 11 | 5-CF$_3$-pyridin-2-yl |
| 12 | 6-CF$_3$-pyridin-2-yl |
| 13 | 3-OCH$_3$-pyridin-2-yl |
| 14 | 4-OCH$_3$-pyridin-2-yl |
| 15 | 5-OCH$_3$-pyridin-2-yl |
| 16 | 6-OCH$_3$-pyridin-2-yl |
| 17 | 3-OCH$_2$CH$_3$-pyridin-2-yl |
| 18 | 4-OCH$_2$CH$_3$-pyridin-2-yl |
| 19 | 5-OCH$_2$CH$_3$-pyridin-2-yl |
| 20 | 6-OCH$_2$CH$_3$-pyridin-2-yl |
| 21 | 3-OCH(CH$_3$)$_2$-pyridin-2-yl |
| 22 | 4-OCH(CH$_3$)$_2$-pyridin-2-yl |
| 23 | 5-OCH(CH$_3$)$_2$-pyridin-2-yl |
| 24 | 6-OCH(CH$_3$)$_2$-pyridin-2-yl |
| 25 | 3-OCH$_2$CH$_2$OCH$_3$-pyridin-2-yl |
| 26 | 4-OCH$_2$CH$_2$OCH$_3$-pyridin-2-yl |
| 27 | 5-OCH$_2$CH$_2$OCH$_3$-pyridin-2-yl |
| 28 | 6-OCH$_2$CH$_2$OCH$_3$-pyridin-2-yl |
| 29 | 3-OCH$_2$CF$_3$-pyridin-2-yl |
| 30 | 4-OCH$_2$CF$_3$-pyridin-2-yl |
| 31 | 5-OCH$_2$CF$_3$-pyridin-2-yl |
| 32 | 6-OCH$_2$CF$_3$-pyridin-2-yl |

TABLE A-continued

| No. | $R^4$ |
|---|---|
| 33 | 3-NO$_2$-pyridin-2-yl |
| 34 | 4-NO$_2$-pyridin-2-yl |
| 35 | 5-NO$_2$-pyridin-2-yl |
| 36 | 6-NO$_2$-pyridin-2-yl |
| 37 | 3-CN-pyridin-2-yl |
| 38 | 4-CN-pyridin-2-yl |
| 39 | 5-CN-pyridin-2-yl |
| 40 | 6-CN-pyridin-2-yl |
| 41 | 4-C(O)NH$_2$-pyridin-2-yl |
| 42 | 5-C(O)NH$_2$-pyridin-2-yl |
| 43 | 6-C(O)NH$_2$-pyridin-2-yl |
| 44 | 4-C(S)NH$_2$-pyridin-2-yl |
| 45 | 5-C(S)NH$_2$-pyridin-2-yl |
| 46 | 6-C(S)NH$_2$-pyridin-2-yl |
| 47 | 3-CO$_2$CH$_3$-pyridin-2-yl |
| 48 | 4-CO$_2$CH$_3$-pyridin-2-yl |
| 49 | 5-CO$_2$CH$_3$-pyridin-2-yl |
| 50 | 6-CO$_2$CH$_3$-pyridin-2-yl |
| 51 | 4-[2-Cl-C$_6$H$_4$]pyridin-2-yl |
| 52 | 5-[2-Cl-C$_6$H$_4$]pyridin-2-yl |
| 53 | 6-[2-Cl-C$_6$H$_4$]pyridin-2-yl |
| 54 | 4-[1-CH$_3$-imidazol-2-yl]pyridin-2-yl |
| 55 | 5-[1-CH$_3$-imidazol-2-yl]pyridin-2-yl |
| 56 | 6-[1-CH$_3$-imidazol-2-yl]pyridin-2-yl |
| 57 | 4-CF$_3$, 3-OCH$_3$-pyridin-2-yl |
| 58 | 4-CF$_3$, 6-OCH$_3$-pyridin-2-yl |
| 59 | 4-CF$_3$, 3-OCH$_2$CH$_3$-pyridin-2-yl |
| 60 | 4-CF$_3$, 6-OCH$_2$CH$_3$-pyridin-2-yl |
| 61 | 4-CF$_3$, 3-OCH$_2$CF$_3$-pyridin-2-yl |
| 62 | 4-CF$_3$, 6-OCH$_2$CF$_3$-pyridin-2-yl |
| 63 | 2-CH$_3$-pyridin-3-yl |
| 64 | 4-CH$_3$-pyridin-3-yl |
| 65 | 5-CH$_3$-pyridin-3-yl |
| 66 | 6-CH$_3$-pyridin-3-yl |
| 67 | 2-CH$_2$CH$_3$-pyridin-3-yl |
| 68 | 4-CH$_2$CH$_3$-pyridin-3-yl |
| 69 | 5-CH$_2$CH$_3$-pyridin-3-yl |
| 70 | 6-CH$_2$CH$_3$-pyridin-3-yl |
| 71 | 2-CF$_3$-pyridin-3-yl |
| 72 | 4-CF$_3$-pyridin-3-yl |
| 73 | 5-CF$_3$-pyridin-3-yl |
| 74 | 6-CF$_3$-pyridin-3-yl |
| 75 | 2-OCH$_3$-pyridin-3-yl |
| 76 | 4-OCH$_3$-pyridin-3-yl |
| 77 | 5-OCH$_3$-pyridin-3-yl |
| 78 | 6-OCH$_3$-pyridin-3-yl |
| 79 | 2-OCH$_2$CH$_3$-pyridin-3-yl |
| 80 | 4-OCH$_2$CH$_3$-pyridin-3-yl |
| 81 | 5-OCH$_2$CH$_3$-pyridin-3-yl |
| 82 | 6-OCH$_2$CH$_3$-pyridin-3-yl |
| 83 | 2-CH$_3$-pyridin-4-yl |
| 84 | 3-CH$_3$-pyridin-4-yl |
| 85 | 2-CH$_2$CH$_3$-pyridin-4-yl |
| 86 | 3-CH$_2$CH$_3$-pyridin-4-yl |
| 87 | 2-CF$_3$-pyridin-4-yl |
| 88 | 3-CF$_3$-pyridin-4-yl |
| 89 | 2-OCH$_3$-pyridin-4-yl |
| 90 | 3-OCH$_3$-pyridin-4-yl |
| 91 | 2-OCH$_2$CH$_3$-pyridin-4-yl |
| 92 | 3-OCH$_2$CH$_3$-pyridin-4-yl |
| 93 | 4-CH$_3$-pyrimidin-2-yl |
| 94 | 5-CH$_3$-pyrimidin-2-yl |
| 95 | 4-CH$_2$CH$_3$-pyrimidin-2-yl |
| 96 | 5-CH$_2$CH$_3$-pyrimidin-2-yl |
| 97 | 4-CH(CH$_3$)$_2$-pyrimidin-2-yl |
| 98 | 5-CH(CH$_3$)$_2$-pyrimidin-2-yl |
| 99 | 4-CH(CH$_3$)CH$_2$CH$_3$-pyrimidin-2-yl |
| 100 | 5-CH(CH$_3$)CH$_2$CH$_3$-pyrimidin-2-yl |
| 101 | 4-CF$_3$-pyrimidin-2-yl |
| 102 | 5-CF$_3$-pyrimidin-2-yl |
| 103 | 4-CH=CH$_2$-pyrimidin-2-yl |
| 104 | 5-CH=CH$_2$-pyrimidin-2-yl |
| 105 | 4-CH=CHCH$_3$-pyrimidin-2-yl |
| 106 | 5-CH=CHCH$_3$-pyrimidin-2-yl |
| 107 | 4-CH=CHCl-pyrimidin-2-yl |
| 108 | 5-CH=CHCl-pyrimidin-2-yl |
| 109 | 4-C≡CH-pyrimidin-2-yl |

TABLE A-continued

| No. | R⁴ |
|---|---|
| 110 | 5-C≡CH-pyrimidin-2-yl |
| 111 | 4-CH$_2$C≡CH-pyrimidin-2-yl |
| 112 | 5-CH$_2$C≡CH-pyrimidin-2-yl |
| 113 | 4-CH$_2$C≡CCH$_3$-pyrimidin-2-yl |
| 114 | 5-CH$_2$C≡CCH$_3$-pyrimidin-2-yl |
| 115 | 4-cyclopropyl-pyrimidin-2-yl |
| 116 | 5-cyclopropyl-pyrimidin-2-yl |
| 117 | 4-cyclopentyl-pyrimidin-2-yl |
| 118 | 5-cyclopentyl-pyrimidin-2-yl |
| 119 | 4-OCH$_3$-pyrimidin-2-yl |
| 120 | 5-OCH$_3$-pyrimidin-2-yl |
| 121 | 4-OCH$_2$CH$_3$-pyrimidin-2-yl |
| 122 | 5-OCH$_2$CH$_3$-pyrimidin-2-yl |
| 123 | 4-OCH$_2$CH$_2$CH$_3$-pyrimidin-2-yl |
| 124 | 5-OCH$_2$CH$_2$CH$_3$-pyrimidin-2-yl |
| 125 | 4-OCH(CH$_3$)$_2$-pyrimidin-2-yl |
| 126 | 5-OCH(CH$_3$)$_2$-pyrimidin-2-yl |
| 127 | 4-OCH$_2$CH$_2$CH$_2$CH$_3$-pyrimidin-2-yl |
| 128 | 5-OCH$_2$CH$_2$CH$_2$CH$_3$-pyrimidin-2-yl |
| 129 | 4-OCH(CH$_3$)CH$_2$CH$_3$-pyrimidin-2-yl |
| 130 | 5-OCH(CH$_3$)CH$_2$CH$_3$-pyrimidin-2-yl |
| 131 | 4-OCH$_2$CH(CH$_3$)$_2$-pyrimidin-2-yl |
| 132 | 5-OCH$_2$CH(CH$_3$)$_2$-pyrimidin-2-yl |
| 133 | 4-OC(CH$_3$)$_3$-pyrimidin-2-yl |
| 134 | 5-OC(CH$_3$)$_3$-pyrimidin-2-yl |
| 135 | 4-OCH(CH$_3$)CH$_2$CH$_2$CH$_3$-pyrimidin-2-yl |
| 136 | 5-OCH(CH$_3$)CH$_2$CH$_2$CH$_3$-pyrimidin-2-yl |
| 137 | 4-OCH$_2$OCH$_3$-pyrimidin-2-yl |
| 138 | 5-OCH$_2$OCH$_3$-pyrimidin-2-yl |
| 139 | 4-OCH$_2$OCH$_2$CH$_3$-pyrimidin-2-yl |
| 140 | 5-OCH$_2$OCH$_2$CH$_3$-pyrimidin-2-yl |
| 141 | 4-OCH(CH$_3$)OCH$_3$-pyrimidin-2-yl |
| 142 | 5-OCH(CH$_3$)OCH$_3$-pyrimidin-2-yl |
| 143 | 4-OCH(CH$_3$)OCH$_2$CH$_3$-pyrimidin-2-yl |
| 144 | 5-OCH(CH$_3$)OCH$_2$CH$_3$-pyrimidin-2-yl |
| 145 | 4-OCH$_2$CH$_2$OCH$_3$-pyrimidin-2-yl |
| 146 | 5-OCH$_2$CH$_2$OCH$_3$-pyrimidin-2-yl |
| 147 | 4-OCH$_2$CH$_2$OCH$_2$CH$_3$-pyrimidin-2-yl |
| 148 | 5-OCH$_2$CH$_2$OCH$_2$CH$_3$-pyrimidin-2-yl |
| 149 | 4-OCH$_2$CH$_2$OCH(CH$_3$)$_2$-pyrimidin-2-yl |
| 150 | 5-OCH$_2$CH$_2$OCH(CH$_3$)$_2$-pyrimidin-2-yl |
| 151 | 4-OCH$_2$CH$_2$SCH$_3$-pyrimidin-2-yl |
| 152 | 5-OCH$_2$CH$_2$SCH$_3$-pyrimidin-2-yl |
| 153 | 4-OCH$_2$CH$_2$SO$_2$CH$_3$-pyrimidin-2-yl |
| 154 | 5-OCH$_2$CH$_2$SO$_2$CH$_3$-pyrimidin-2-yl |
| 155 | 4-OCH$_2$CH$_2$SCH(CH$_3$)$_2$-pyrimidin-2-yl |
| 156 | 5-OCH$_2$CH$_2$SCH(CH$_3$)$_2$-pyrimidin-2-yl |
| 157 | 4-OCH$_2$CH$_2$CN-pyrimidin-2-yl |
| 158 | 5-OCH$_2$CH$_2$CN-pyrimidin-2-yl |
| 159 | 4-OCH$_2$CH$_2$SCH$_2$CH$_2$CN-pyrimidin-2-yl |
| 160 | 5-OCH$_2$CH$_2$SCH$_2$CH$_2$CN-pyrimidin-2-yl |
| 161 | 4-OCH$_2$CH$_2$OC$_6$H$_5$-pyrimidin-2-yl |
| 162 | 5-OCH$_2$CH$_2$OC$_6$H$_5$-pyrimidin-2-yl |
| 163 | 4-OCH$_2$CH$_2$OCH$_2$C$_6$H$_5$-pyrimidin-2-yl |
| 164 | 5-OCH$_2$CH$_2$OCH$_2$C$_6$H$_5$-pyrimidin-2-yl |
| 165 | 4-OCH$_2$CH$_2$N(CH$_3$)$_2$-pyrimidin-2-yl |
| 166 | 5-OCH$_2$CH$_2$N(CH$_3$)$_2$-pyrimidin-2-yl |
| 167 | 4-OCH$_2$CH$_2$CONH$_2$-pyrimidin-2-yl |
| 168 | 5-OCH$_2$CH$_2$CONH$_2$-pyrimidin-2-yl |
| 169 | 4-OCH$_2$CH$_2$CO$_2$CH$_2$CH$_2$CH$_3$-pyrimidin-2-yl |
| 170 | 5-OCH$_2$CH$_2$CO$_2$CH$_2$CH$_2$CH$_3$-pyrimidin-2-yl |
| 171 | 4-OCH(CH$_3$)CH$_2$OCH$_3$-pyrimidin-2-yl |
| 172 | 5-OCH(CH$_3$)CH$_2$OCH$_3$-pyrimidin-2-yl |
| 173 | 4-OCH(CH$_3$)CH$_2$CO$_2$CH$_3$-pyrimidin-2-yl |
| 174 | 5-OCH(CH$_3$)CH$_2$CO$_2$CH$_3$-pyrimidin-2-yl |
| 175 | 4-OCH(CH$_3$)CH$_2$CO$_2$CH$_2$CH$_3$-pyrimidin-2-yl |
| 176 | 5-OCH(CH$_3$)CH$_2$CO$_2$CH$_2$CH$_3$-pyrimidin-2-yl |
| 177 | 4-OCH$_2$CH(CH$_3$)CO$_2$CH$_2$CH$_3$-pyrimidin-2-yl |
| 178 | 5-OCH$_2$CH(CH$_3$)CO$_2$CH$_2$CH$_3$-pyrimidin-2-yl |
| 179 | 4-OCH$_2$C(=O)CH$_3$-pyrimidin-2-yl |
| 180 | 5-OCH$_2$C(=O)CH$_3$-pyrimidin-2-yl |
| 181 | 4-OCH$_2$C(=O)CH$_2$CH$_3$-pyrimidin-2-yl |
| 182 | 5-OCH$_2$C(=O)CH$_2$CH$_3$-pyrimidin-2-yl |
| 183 | 4-OCH$_2$CO$_2$CH$_3$-pyrimidin-2-yl |
| 184 | 5-OCH$_2$CO$_2$CH$_3$-pyrimidin-2-yl |
| 185 | 4-OCH$_2$CO$_2$CH$_2$CH$_3$-pyrimidin-2-yl |
| 186 | 5-OCH$_2$CO$_2$CH$_2$CH$_3$-pyrimidin-2-yl |
| 187 | 4-OCH$_2$C(=O)NH$_2$-pyrimidin-2-yl |
| 188 | 5-OCH$_2$C(=O)NH$_2$-pyrimidin-2-yl |
| 189 | 4-OCH$_2$C(=O)NHCH$_3$-pyrimidin-2-yl |
| 190 | 5-OCH$_2$C(=O)NHCH$_3$-pyrimidin-2-yl |
| 191 | 4-OCH$_2$C(=O)SCH$_3$-pyrimidin-2-yl |
| 192 | 5-OCH$_2$C(=O)SCH$_3$-pyrimidin-2-yl |
| 193 | 4-OCH(CH$_3$)C(=O)NH$_2$-pyrimidin-2-yl |
| 194 | 5-OCH(CH$_3$)C(=O)NH$_2$-pyrimidin-2-yl |
| 195 | 4-OCH(CH$_3$)C(=O)NHCH$_3$-pyrimidin-2-yl |
| 196 | 5-OCH(CH$_3$)C(=O)NHCH$_3$-pyrimidin-2-yl |
| 197 | 4-OCH(CH$_3$)C(=O)NHNH$_2$-pyrimidin-2-yl |
| 198 | 5-OCH(CH$_3$)C(=O)NHNH$_2$-pyrimidin-2-yl |
| 199 | 4-OCH(CH$_3$)CO$_2$CH$_3$-pyrimidin-2-yl |
| 200 | 5-OCH(CH$_3$)CO$_2$CH$_3$-pyrimidin-2-yl |
| 201 | 4-OCH(CH$_3$)CO$_2$CH$_2$CH$_3$-pyrimidin-2-yl |
| 202 | 5-OCH(CH$_3$)CO$_2$CH$_2$CH$_3$-pyrimidin-2-yl |
| 203 | 4-OCH(CH$_3$)C(=O)CH$_3$-pyrimidin-2-yl |
| 204 | 5-OCH(CH$_3$)C(=O)CH$_3$-pyrimidin-2-yl |
| 205 | 4-OCH(CH$_3$)C(=O)CH$_2$CH$_3$-pyrimidin-2-yl |
| 206 | 5-OCH(CH$_3$)C(=O)CH$_2$CH$_3$-pyrimidin-2-yl |
| 207 | 4-OCH(CH$_3$)CH$_2$C(=O)CH$_3$-pyrimidin-2-yl |
| 208 | 5-OCH(CH$_3$)CH$_2$C(=O)CH$_3$-pyrimidin-2-yl |
| 209 | 4-OCH(CH$_3$)CH$_2$OC(CH$_3$)$_3$-pyrimidin-2-yl |
| 210 | 5-OCH(CH$_3$)CH$_2$OC(CH$_3$)$_3$-pyrimidin-2-yl |
| 211 | 4-OCH(CH$_3$)CH$_2$OCH$_2$CH$_3$-pyrimidin-2-yl |
| 212 | 5-OCH(CH$_3$)CH$_2$OCH$_2$CH$_3$-pyrimidin-2-yl |
| 213 | 4-OCH(CH$_3$)CH$_2$O(CH$_3$)$_2$CH$_3$-pyrimidin-2-yl |
| 214 | 5-OCH(CH$_3$)CH$_2$O(CH$_3$)$_2$CH$_3$-pyrimidin-2-yl |
| 215 | 4-OCH(CH$_3$)CH$_2$OCH$_2$CH=CH$_2$-pyrimidin-2-yl |
| 216 | 5-OCH(CH$_3$)CH$_2$OCH$_2$CH=CH$_2$-pyrimidin-2-yl |
| 217 | 4-O(CH$_2$)$_3$OCH$_3$-pyrimidin-2-yl |
| 218 | 5-O(CH$_2$)$_3$OCH$_3$-pyrimidin-2-yl |
| 219 | 4-O(CH$_2$)$_3$OCH$_2$CH$_3$-pyrimidin-2-yl |
| 220 | 5-O(CH$_2$)$_3$OCH$_2$CH$_3$-pyrimidin-2-yl |
| 221 | 4-O(CH$_2$)$_3$OCH(CH$_3$)$_2$-pyrimidin-2-yl |
| 222 | 5-O(CH$_2$)$_3$OCH(CH$_3$)$_2$-pyrimidin-2-yl |
| 223 | 4-O(CH$_2$)$_3$OC$_6$H$_5$-pyrimidin-2-yl |
| 224 | 5-O(CH$_2$)$_3$OC$_6$H$_5$-pyrimidin-2-yl |
| 225 | 4-O(CH$_2$)$_3$OCH$_2$C$_6$H$_5$-pyrimidin-2-yl |
| 226 | 5-O(CH$_2$)$_3$OCH$_2$C$_6$H$_5$-pyrimidin-2-yl |
| 227 | 4-OCH(CH$_2$CH$_3$)CH$_2$OCH$_3$-pyrimidin-2-yl |
| 228 | 5-OCH(CH$_2$CH$_3$)CH$_2$OCH$_3$-pyrimidin-2-yl |
| 229 | 4-OCH(CH$_2$CH$_3$)CH$_2$CH$_2$OCH$_3$-pyrimidin-2-yl |
| 230 | 5-OCH(CH$_2$CH$_3$)CH$_2$CH$_2$OCH$_3$-pyrimidin-2-yl |
| 231 | 4-OCH(CH$_2$CH$_3$)CH$_2$CH$_2$OCH$_2$CH$_3$-pyrimidin-2-yl |
| 232 | 5-OCH(CH$_2$CH$_3$)CH$_2$CH$_2$OCH$_2$CH$_3$-pyrimidin-2-yl |
| 233 | 4-O[(CH$_2$)$_3$O]$_2$CH$_3$-pyrimidin-2-yl |
| 234 | 5-O[(CH$_2$)$_3$O]$_2$CH$_3$-pyrimidin-2-yl |
| 235 | 4-OCH$_2$CH(CH$_3$)CH$_2$OCH$_3$-pyrimidin-2-yl |
| 236 | 5-OCH$_2$CH(CH$_3$)CH$_2$OCH$_3$-pyrimidin-2-yl |
| 237 | 4-OCH$_2$CH(CH$_3$)CH$_2$OCH$_2$CH$_3$-pyrimidin-2-yl |
| 238 | 5-OCH$_2$CH(CH$_3$)CH$_2$OCH$_2$CH$_3$-pyrimidin-2-yl |
| 239 | 4-OCH(CH$_2$Cl)CH$_2$OCH$_3$-pyrimidin-2-yl |
| 240 | 5-OCH(CH$_2$Cl)CH$_2$OCH$_3$-pyrimidin-2-yl |
| 241 | 4-OCH(CH$_2$Cl)CH$_2$OCH$_2$CH$_3$-pyrimidin-2-yl |
| 242 | 5-OCH(CH$_2$Cl)CH$_2$OCH$_2$CH$_3$-pyrimidin-2-yl |
| 243 | 4-OCH(CH$_2$Cl)CH$_2$OCH(CH$_3$)$_2$-pyrimidin-2-yl |
| 244 | 5-OCH(CH$_2$Cl)CH$_2$OCH(CH$_3$)$_2$-pyrimidin-2-yl |
| 245 | 4-OCH(CH$_2$Cl)CH$_2$OCH$_2$CH=CH$_2$-pyrimidin-2-yl |
| 246 | 5-OCH(CH$_2$Cl)CH$_2$OCH$_2$CH=CH$_2$-pyrimidin-2-yl |
| 247 | 4-OCH[CH$_2$OCH$_3$]$_2$-pyrimidin-2-yl |
| 248 | 5-OCH[CH$_2$OCH$_3$]$_2$-pyrimidin-2-yl |
| 249 | 4-OCH[CH$_2$OCH$_2$CH$_3$]$_2$-pyrimidin-2-yl |
| 250 | 5-OCH[CH$_2$OCH$_2$CH$_3$]$_2$-pyrimidin-2-yl |
| 251 | 4-OCCl$_3$-pyrimidin-2-yl |
| 252 | 5-OCCl$_3$-pyrimidin-2-yl |
| 253 | 4-OCHF$_2$-pyrimidin-2-yl |
| 254 | 5-OCHF$_2$-pyrimidin-2-yl |
| 255 | 4-OCF$_3$-pyrimidin-2-yl |
| 256 | 5-OCF$_3$-pyrimidin-2-yl |
| 257 | 4-OCF$_2$CHF$_2$-pyrimidin-2-yl |
| 258 | 5-OCF$_2$CHF$_2$-pyrimidin-2-yl |
| 259 | 4-OCH$_2$CF$_3$-pyrimidin-2-yl |
| 260 | 5-OCH$_2$CF$_3$-pyrimidin-2-yl |
| 261 | 4-OCH$_2$CHF$_2$-pyrimidin-2-yl |
| 262 | 5-OCH$_2$CHF$_2$-pyrimidin-2-yl |
| 263 | 4-O(CH$_2$)$_3$F-pyrimidin-2-yl |

TABLE A-continued

| No. | R⁴ |
|---|---|
| 264 | 5-O(CH₂)₃F-pyrimidin-2-yl |
| 265 | 4-OCH(CH₃)CF₃-pyrimidin-2-yl |
| 266 | 5-OCH(CH₃)CF₃-pyrimidin-2-yl |
| 267 | 4-O(CH₂)₄F-pyrimidin-2-yl |
| 268 | 5-O(CH₂)₄F-pyrimidin-2-yl |
| 269 | 4-O(CH₂)₃CF₃-pyrimidin-2-yl |
| 270 | 5-O(CH₂)₃CF₃-pyrimidin-2-yl |
| 271 | 4-OCH(CH₃)CF₂CF₃-pyrimidin-2-yl |
| 272 | 5-OCH(CH₃)CF₂CF₃-pyrimidin-2-yl |
| 273 | 4-OCH(CH₃)CF₂CHF₂-pyrimidin-2-yl |
| 274 | 5-OCH(CH₃)CF₂CHF₂-pyrimidin-2-yl |
| 275 | 4-OCH₂CF₂CHFCH₃-pyrimidin-2-yl |
| 276 | 5-OCH₂CF₂CHFCH₃-pyrimidin-2-yl |
| 277 | 4-OCH₂(CF₂)₂CF₃-pyrimidin-2-yl |
| 278 | 5-OCH₂(CF₂)₂CF₃-pyrimidin-2-yl |
| 279 | 4-O(CF₂)₃CF₃-pyrimidin-2-yl |
| 280 | 5-O(CF₂)₃CF₃-pyrimidin-2-yl |
| 281 | 4-OCH₂CF₂CHF₂-pyrimidin-2-yl |
| 282 | 5-OCH₂CF₂CHF₂-pyrimidin-2-yl |
| 283 | 4-CH₂CH=CH₂-pyrimidin-2-yl |
| 284 | 5-CH₂CH=CH₂-pyrimidin-2-yl |
| 285 | 4-CH₂C(CH₃)=CH₂-pyrimidin-2-yl |
| 286 | 5-CH₂C(CH₃)=CH₂-pyrimidin-2-yl |
| 287 | 4-OCH₂CH=CHCH₃-pyrimidin-2-yl |
| 288 | 5-OCH₂CH=CHCH₃-pyrimidin-2-yl |
| 289 | 4-O(CH₂)₂CH=CH₂-pyrimidin-2-yl |
| 290 | 5-O(CH₂)₂CH=CH₂-pyrimidin-2-yl |
| 291 | 4-OCH₂C(CH₃)=CH₂-pyrimidin-2-yl |
| 292 | 5-OCH₂C(CH₃)=CH₂-pyrimidin-2-yl |
| 293 | 4-OCH(CH₃)CH=CH₂-pyrimidin-2-yl |
| 294 | 5-OCH(CH₃)CH=CH₂-pyrimidin-2-yl |
| 295 | 4-OCH₂C≡CH-pyrimidin-2-yl |
| 296 | 5-OCH₂C≡CH-pyrimidin-2-yl |
| 297 | 4-OCH₂C≡CCH₃-pyrimidin-2-yl |
| 298 | 5-OCH₂C≡CCH₃-pyrimidin-2-yl |
| 299 | 4-O(CH₂)₂C≡CH-pyrimidin-2-yl |
| 300 | 5-O(CH₂)₂C≡CH-pyrimidin-2-yl |
| 301 | 4-SCH₃-pyrimidin-2-yl |
| 302 | 5-SCH₃-pyrimidin-2-yl |
| 303 | 4-SCH₂CH₃-pyrimidin-2-yl |
| 304 | 5-SCH₂CH₃-pyrimidin-2-yl |
| 305 | 4-OC₆H₅-pyrimidin-2-yl |
| 306 | 5-OC₆H₅-pyrimidin-2-yl |
| 307 | 4-OCH₂C₆H₅-pyrimidin-2-yl |
| 308 | 5-OCH₂C₆H₅-pyrimidin-2-yl |
| 309 | 4-NO₂-pyrimidin-2-yl |
| 310 | 5-NO₂-pyrimidin-2-yl |
| 311 | 4-NHCH₃-pyrimidin-2-yl |
| 312 | 5-NHCH₃-pyrimidin-2-yl |
| 313 | 4-N(CH₃)₂-pyrimidin-2-yl |
| 314 | 5-N(CH₃)₂-pyrimidin-2-yl |
| 315 | 4-N(CH₃)C₂H₅-pyrimidin-2-yl |
| 316 | 5-N(CH₃)C₂H₅-pyrimidin-2-yl |
| 317 | 4-NHCH₂CF₃-pyrimidin-2-yl |
| 318 | 5-NHCH₂CF₃-pyrimidin-2-yl |
| 319 | 4-F-pyrimidin-2-yl |
| 320 | 5-F-pyrimidin-2-yl |
| 321 | 4-Cl-pyrimidin-2-yl |
| 322 | 5-Cl-pyrimidin-2-yl |
| 323 | 4-OH-pyrimidin-2-yl |
| 324 | 5-OH-pyrimidin-2-yl |
| 325 | 4-CN-pyrimidin-2-yl |
| 326 | 5-CN-pyrimidin-2-yl |
| 327 | 4-C(O)NH₂-pyrimidin-2-yl |
| 328 | 5-C(O)NH₂-pyrimidin-2-yl |
| 329 | 4-C(S)NH₂-pyrimidin-2-yl |
| 330 | 5-C(S)NH₂-pyrimidin-2-yl |
| 331 | 4-CO₂CH₃-pyrimidin-2-yl |
| 332 | 5-CO₂CH₃-pyrimidin-2-yl |
| 333 | 4-ON=C(CH₃)₂-pyrimidin-2-yl |
| 334 | 5-ON=C(CH₃)₂-pyrimidin-2-yl |
| 335 | 4-[O-cyclopropyl]pyrimidin-2-yl |
| 336 | 5-[O-cyclopropyl]pyrimidin-2-yl |
| 337 | 4-[O-cyclobutyl]pyrimidin-2-yl |
| 338 | 5-[O-cyclobutyl]pyrimidin-2-yl |
| 339 | 4-[O-cyclopentyl]pyrimidin-2-yl |
| 340 | 5-[O-cyclopentyl]pyrimidin-2-yl |
| 341 | 4-[O-cyclohexyl]pyrimidin-2-yl |
| 342 | 5-[O-cyclohexyl]pyrimidin-2-yl |
| 343 | 4-[OCH₂-cyclopropyl]pyrimidin-2-yl |
| 344 | 5-[OCH₂-cyclopropyl]pyrimidin-2-yl |
| 345 | 5-F, 4-[OCH₂-cyclopropyl]pyrimidin-2-yl |
| 346 | 4-F, 5-[OCH₂-cyclopropyl]pyrimidin-2-yl |
| 347 | 5-CH₃, 4-[OCH₂-cyclopropyl]pyrimidin-2-yl |
| 348 | 4-CH₃, 5-[OCH₂-cyclopropyl]pyrimidin-2-yl |
| 349 | 5-CF₃, 4-[OCH₂-cyclopropyl]pyrimidin-2-yl |
| 350 | 4-CF₃, 5-[OCH₂-cyclopropyl]pyrimidin-2-yl |
| 351 | 4-[OCH(CH₃)-cyclopropyl]pyrimidin-2-yl |
| 352 | 5-[OCH(CH₃)-cyclopropyl]pyrimidin-2-yl |
| 353 | 5-F, 4-[OCH(CH₃)-cyclopropyl]pyrimidin-2-yl |
| 354 | 4-F, 5-[OCH(CH₃)-cyclopropyl]pyrimidin-2-yl |
| 355 | 5-CH₃, 4-[OCH(CH₃)-cyclopropyl]pyrimidin-2-yl |
| 356 | 4-CH₃, 5-[OCH(CH₃)-cyclopropyl]pyrimidin-2-yl |
| 357 | 5-CF₃, 4-[OCH(CH₃)-cyclopropyl]pyrimidin-2-yl |
| 358 | 4-CF₃, 5-[OCH(CH₃)-cyclopropyl]pyrimidin-2-yl |
| 359 | 4-[O-(1-CH₃-cyclopropyl)]pyrimidin-2-yl |
| 360 | 5-[O-(1-CH₃-cyclopropyl)]pyrimidin-2-yl |
| 361 | 5-F, 4-[O-(1-CH₃-cyclopropyl)]pyrimidin-2-yl |
| 362 | 4-F, 5-[O-(1-CH₃-cyclopropyl)]pyrimidin-2-yl |
| 363 | 5-CH₃, 4-[O-(1-CH₃-cyclopropyl)]pyrimidin-2-yl |
| 364 | 4-CH₃, 5-[O-(1-CH₃-cyclopropyl)]pyrimidin-2-yl |
| 365 | 5-CF₃, 4-[O-(1-CH₃-cyclopropyl)]pyrimidin-2-yl |
| 366 | 4-CF₃, 5-[O-(1-CH₃-cyclopropyl)]pyrimidin-2-yl |
| 367 | 4-[OCH₂-(1-CH₃-cyclopropyl)]pyrimidin-2-yl |
| 368 | 5-[OCH₂-(1-CH₃-cyclopropyl)]pyrimidin-2-yl |
| 369 | 5-F, 4-[OCH₂-(1-CH₃-cyclopropyl)]pyrimidin-2-yl |
| 370 | 4-F, 5-[OCH₂-(1-CH₃-cyclopropyl)]pyrimidin-2-yl |
| 371 | 5-CH₃, 4-[OCH₂-(1-CH₃-cyclopropyl)]pyrimidin-2-yl |
| 372 | 4-CH₃, 5-[OCH₂-(1-CH₃-cyclopropyl)]pyrimidin-2-yl |
| 373 | 5-CF₃, 4-[OCH₂-(1-CH₃-cyclopropyl)]pyrimidin-2-yl |
| 374 | 4-CF₃, 5-[OCH₂-(1-CH₃-cyclopropyl)]pyrimidin-2-yl |
| 375 | 4-[OCH₂-(2-CH₃-cyclopropyl)]pyrimidin-2-yl |
| 376 | 5-[OCH₂-(2-CH₃-cyclopropyl)]pyrimidin-2-yl |
| 377 | 5-F, 4-[OCH₂-(2-CH₃-cyclopropyl)]pyrimidin-2-yl |
| 378 | 4-F, 5-[OCH₂-(2-CH₃-cyclopropyl)]pyrimidin-2-yl |
| 379 | 5-CH₃, 4-[OCH₂-(2-CH₃-cyclopropyl)]pyrimidin-2-yl |
| 380 | 4-CH₃, 5-[OCH₂-(2-CH₃-cyclopropyl)]pyrimidin-2-yl |
| 381 | 5-CF₃, 4-[OCH₂-(2-CH₃-cyclopropyl)]pyrimidin-2-yl |
| 382 | 4-CF₃, 5-[OCH₂-(2-CH₃-cyclopropyl)]pyrimidin-2-yl |
| 383 | 4-[OCH₂-(tetrahydropyran-2-yl)]pyrimidin-2-yl |
| 384 | 5-[OCH₂-(tetrahydropyran-2-yl)]pyrimidin-2-yl |
| 385 | 5-F, 4-[OCH₂-(tetrahydropyran-2-yl)]pyrimidin-2-yl |
| 386 | 4-F, 5-[OCH₂-(tetrahydropyran-2-yl)]pyrimidin-2-yl |
| 387 | 5-CH₃, 4-[OCH₂-(tetrahydropyran-2-yl)]pyrimidin-2-yl |
| 388 | 4-CH₃, 5-[OCH₂-(tetrahydropyran-2-yl)]pyrimidin-2-yl |
| 389 | 5-CF₃, 4-[OCH₂-(tetrahydropyran-2-yl)]pyrimidin-2-yl |
| 390 | 4-CF₃, 5-[OCH₂-(tetrahydropyran-2-yl)]pyrimidin-2-yl |
| 391 | 4-[OCH₂-(furan-2-yl)]pyrimidin-2-yl |
| 392 | 5-[OCH₂-(furan-2-yl)]pyrimidin-2-yl |
| 393 | 5-F, 4-[OCH₂-(furan-2-yl)]pyrimidin-2-yl |
| 394 | 4-F, 5-[OCH₂-(furan-2-yl)]pyrimidin-2-yl |
| 395 | 5-CH₃, 4-[OCH₂-(furan-2-yl)]pyrimidin-2-yl |
| 396 | 4-CH₃, 5-[OCH₂-(furan-2-yl)]pyrimidin-2-yl |
| 397 | 5-CF₃, 4-[OCH₂-(furan-2-yl)]pyrimidin-2-yl |
| 399 | 4-CF₃, 5-[OCH₂-(furan-2-yl)]pyrimidin-2-yl |
| 399 | 4-[OCH₂-(furan-3-yl)]pyrimidin-2-yl |
| 400 | 5-[OCH₂-(furan-3-yl)]pyrimidin-2-yl |
| 401 | 5-F, 4-[OCH₂-(furan-3-yl)]pyrimidin-2-yl |
| 402 | 4-F, 5-[OCH₂-(furan-3-yl)]pyrimidin-2-yl |
| 403 | 5-CH₃, 4-[OCH₂-(furan-3-yl)]pyrimidin-2-yl |
| 404 | 4-CH₃, 5-[OCH₂-(furan-3-yl)]pyrimidin-2-yl |
| 405 | 5-CF₃, 4-[OCH₂-(furan-3-yl)]pyrimidin-2-yl |
| 406 | 4-CF₃, 5-[OCH₂-(furan-3-yl)]pyrimidin-2-yl |
| 407 | 4-[OCH₂-(tetrahydrofuran-3-yl)]pyrimidin-2-yl |
| 408 | 5-[OCH₂-(tetrahydrofuran-3-yl)]pyrimidin-2-yl |
| 409 | 5-F, 4-[OCH₂-(tetrahydrofuran-3-yl)]pyrimidin-2-yl |
| 410 | 4-F, 5-[OCH₂-(tetrahydrofuran-3-yl)]pyrimidin-2-yl |
| 411 | 5-CH₃, 4-[OCH₂-(tetrahydrofuran-3-yl)]pyrimidin-2-yl |
| 412 | 4-CH₃, 5-[OCH₂-(tetrahydrofuran-3-yl)]pyrimidin-2-yl |
| 413 | 5-CF₃, 4-[OCH₂-(tetrahydrofuran-3-yl)]pyrimidin-2-yl |
| 414 | 4-CF₃, 5-[OCH₂-(tetrahydrofuran-3-yl)]pyrimidin-2-yl |
| 415 | 4-[OCH₂-(tetrahydrofuran-2-yl)]pyrimidin-2-yl |
| 416 | 5-[OCH₂-(tetrahydrofuran-2-yl)]pyrimidin-2-yl |
| 417 | 5-F, 4-[OCH₂-(tetrahydrofuran-2-yl)]pyrimidin-2-yl |

TABLE A-continued

| No. | R⁴ |
|---|---|
| 418 | 4-F, 5-[OCH₂-(tetrahydrofuran-2-yl)]pyrimidin-2-yl |
| 419 | 5-CH₃, 4-[OCH₂-(tetrahydrofuran-2-yl)]pyrimidin-2-yl |
| 420 | 4-CH₃, 5-[OCH₂-(tetrahydrofuran-2-yl)]pyrimidin-2-yl |
| 421 | 5-CF₃, 4-[OCH₂-(tetrahydrofuran-2-yl)]pyrimidin-2-yl |
| 422 | 4-CF₃, 5-[OCH₂-(tetrahydrofuran-2-yl)]pyrimidin-2-yl |
| 423 | 4-[O-(tetrahydropyran-4-yl)]pyrimidin-2-yl |
| 424 | 5-[O-(tetrahydropyran-4-yl)]pyrimidin-2-yl |
| 425 | 5-F, 4-[O-(tetrahydropyran-4-yl)]pyrimidin-2-yl |
| 426 | 4-F, 5-[O-(tetrahydropyran-4-yl)]pyrimidin-2-yl |
| 427 | 5-CH₃, 4-[O-(tetrahydropyran-4-yl)]pyrimidin-2-yl |
| 428 | 4-CH₃, 5-[O-(tetrahydropyran-4-yl)]pyrimidin-2-yl |
| 429 | 5-CF₃, 4-[O-(tetrahydropyran-4-yl)]pyrimidin-2-yl |
| 430 | 4-CF₃, 5-[O-(tetrahydropyran-4-yl)]pyrimidin-2-yl |
| 431 | 4-[2-Cl—C₆H₄]pyrimidin-2-yl |
| 432 | 5-[2-Cl—C₆H₄]pyrimidin-2-yl |
| 433 | 5-F, 4-[2-Cl—C₆H₄]pyrimidin-2-yl |
| 434 | 4-F, 5-[2-Cl—C₆H₄]pyrimidin-2-yl |
| 435 | 5-CH₃, 4-[2-Cl—C₆H₄]pyrimidin-2-yl |
| 436 | 4-CH₃, 5-[2-Cl—C₆H₄]pyrimidin-2-yl |
| 437 | 5-CF₃, 4-[2-Cl—C₆H₄]pyrimidin-2-yl |
| 438 | 4-CF₃, 5-[2-Cl—C₆H₄]pyrimidin-2-yl |
| 439 | 4-[OCH₂-(pyridin-2-yl)]pyrimidin-2-yl |
| 440 | 5-[OCH₂-(pyridin-2-yl)]pyrimidin-2-yl |
| 441 | 5-F, 4-[OCH₂-(pyridin-2-yl)]pyrimidin-2-yl |
| 442 | 4-F, 5-[OCH₂-(pyridin-2-yl)]pyrimidin-2-yl |
| 443 | 5-CH₃, 4-[OCH₂-(pyridin-2-yl)]pyrimidin-2-yl |
| 444 | 4-CH₃, 5-[OCH₂-(pyridin-2-yl)]pyrimidin-2-yl |
| 445 | 5-CF₃, 4-[OCH₂-(pyridin-2-yl)]pyrimidin-2-yl |
| 446 | 4-CF₃, 5-[OCH₂-(pyridin-2-yl)]pyrimidin-2-yl |
| 447 | 4-[OCH₂-(pyridin-3-yl)]pyrimidin-2-yl |
| 448 | 5-[OCH₂-(pyridin-3-yl)]pyrimidin-2-yl |
| 449 | 5-F, 4-[OCH₂-(pyridin-3-yl)]pyrimidin-2-yl |
| 450 | 4-F, 5-[OCH₂-(pyridin-3-yl)]pyrimidin-2-yl |
| 451 | 5-CH₃, 4-[OCH₂-(pyridin-3-yl)]pyrimidin-2-yl |
| 452 | 4-CH₃, 5-[OCH₂-(pyridin-3-yl)]pyrimidin-2-yl |
| 453 | 5-CF₃, 4-[OCH₂-(pyridin-3-yl)]pyrimidin-2-yl |
| 454 | 4-CF₃, 5-[OCH₂-(pyridin-3-yl)]pyrimidin-2-yl |
| 455 | 4-[morpholin-4-yl]pyrimidin-2-yl |
| 456 | 5-[morpholin-4-yl]pyrimidin-2-yl |
| 457 | 4-[1-CH₃-imidazol-2-yl]pyrimidin-2-yl |
| 458 | 5-[1-CH₃-imidazol-2-yl]pyrimidin-2-yl |
| 459 | 5-F, 4-[1-CH₃-imidazol-2-yl]pyrimidin-2-yl |
| 460 | 4-F, 5-[1-CH₃-imidazol-2-yl]pyrimidin-2-yl |
| 461 | 5-CH₃, 4-[1-CH₃-imidazol-2-yl]pyrimidin-2-yl |
| 462 | 4-CH₃, 5-[1-CH₃-imidazol-2-yl]pyrimidin-2-yl |
| 463 | 5-CF₃, 4-[1-CH₃-imidazol-2-yl]pyrimidin-2-yl |
| 464 | 4-CF₃, 5-[1-CH₃-imidazol-2-yl]pyrimidin-2-yl |
| 465 | 4-[1,2,4-triazol-1-yl]pyrimidin-2-yl |
| 466 | 5-[1,2,4-triazol-1-yl]pyrimidin-2-yl |
| 467 | 5-F, 4-[1,2,4-triazol-1-yl]pyrimidin-2-yl |
| 468 | 4-F, 5-[1,2,4-triazol-1-yl]pyrimidin-2-yl |
| 469 | 5-CH₃, 4-[1,2,4-triazol-1-yl]pyrimidin-2-yl |
| 470 | 4-CH₃, 5-[1,2,4-triazol-1-yl]pyrimidin-2-yl |
| 471 | 5-CF₃, 4-[1,2,4-triazol-1-yl]pyrimidin-2-yl |
| 472 | 4-CF₃, 5-[1,2,4-triazol-1-yl]pyrimidin-2-yl |
| 473 | 4,5-Cl₂-pyrimidin-2-yl |
| 474 | 4,6-Cl₂-pyrimidin-2-yl |
| 475 | 4,5-(CH₃)₂-pyrimidin-2-yl |
| 476 | 4,6-(CH₃)₂-pyrimidin-2-yl |
| 477 | 4,5-(OCH₃)₂-pyrimidin-2-yl |
| 478 | 4,6-(OCH₃)₂-pyrimidin-2-yl |
| 479 | 4,5-(OCH₂CH₃)₂-pyrimidin-2-yl |
| 480 | 4,6-(OCH₂CH₃)₂-pyrimidin-2-yl |
| 481 | 4-F, 5-CH₃-pyrimidin-2-yl |
| 482 | 4-F, 6-CH₃-pyrimidin-2-yl |
| 483 | 5-F, 4-CH₃-pyrimidin-2-yl |
| 484 | 6-F, 4-CH₃-pyrimidin-2-yl |
| 485 | 4-F, 5-OCH₃-pyrimidin-2-yl |
| 486 | 4-F, 6-OCH₃-pyrimidin-2-yl |
| 487 | 5-F, 4-OCH₃-pyrimidin-2-yl |
| 488 | 6-F, 4-OCH₃-pyrimidin-2-yl |
| 489 | 4-F, 5-OCH₂CH₃-pyrimidin-2-yl |
| 490 | 4-F, 6-OCH₂CH₃-pyrimidin-2-yl |
| 491 | 5-F, 4-OCH₂CH₃-pyrimidin-2-yl |
| 492 | 6-F, 4-OCH₂CH₃-pyrimidin-2-yl |
| 493 | 4-F, 5-OCH₂CF₃-pyrimidin-2-yl |
| 494 | 4-F, 6-OCH₂CF₃-pyrimidin-2-yl |
| 495 | 5-F, 4-OCH₂CF₃-pyrimidin-2-yl |
| 496 | 6-F, 4-OCH₂CF₃-pyrimidin-2-yl |
| 497 | 4-F, 5-OCH(CH₃)₂-pyrimidin-2-yl |
| 498 | 4-F, 6-OCH(CH₃)₂-pyrimidin-2-yl |
| 499 | 5-F, 4-OCH(CH₃)₂-pyrimidin-2-yl |
| 500 | 6-F, 4-OCH(CH₃)₂-pyrimidin-2-yl |
| 501 | 4-Cl, 5-CH₃-pyrimidin-2-yl |
| 502 | 4-Cl, 6-CH₃-pyrimidin-2-yl |
| 503 | 5-Cl, 4-CH₃-pyrimidin-2-yl |
| 504 | 6-Cl, 4-CH₃-pyrimidin-2-yl |
| 505 | 4-Cl, 5-OCH₃-pyrimidin-2-yl |
| 506 | 4-Cl, 6-OCH₃-pyrimidin-2-yl |
| 507 | 5-Cl, 4-OCH₃-pyrimidin-2-yl |
| 508 | 6-Cl, 4-OCH₃-pyrimidin-2-yl |
| 509 | 4-Cl, 5-OCH₂CH₃-pyrimidin-2-yl |
| 510 | 4-Cl, 6-OCH₂CH₃-pyrimidin-2-yl |
| 511 | 5-Cl, 4-OCH₂CH₃-pyrimidin-2-yl |
| 512 | 6-Cl, 4-OCH₂CH₃-pyrimidin-2-yl |
| 513 | 4-Cl, 5-OCH₂CF₃-pyrimidin-2-yl |
| 514 | 4-Cl, 6-OCH₂CF₃-pyrimidin-2-yl |
| 515 | 5-Cl, 4-OCH₂CF₃-pyrimidin-2-yl |
| 516 | 6-Cl, 4-OCH₂CF₃-pyrimidin-2-yl |
| 517 | 4-Cl, 5-OCH(CH₃)₂-pyrimidin-2-yl |
| 518 | 4-Cl, 6-OCH(CH₃)₂-pyrimidin-2-yl |
| 519 | 5-Cl, 4-OCH(CH₃)₂-pyrimidin-2-yl |
| 520 | 6-Cl, 4-OCH(CH₃)₂-pyrimidin-2-yl |
| 521 | 4-CH₃, 5-OCH₃-pyrimidin-2-yl |
| 522 | 4-CH₃, 6-OCH₃-pyrimidin-2-yl |
| 523 | 5-CH₃, 4-OCH₃-pyrimidin-2-yl |
| 524 | 6-CH₃, 4-OCH₃-pyrimidin-2-yl |
| 525 | 4-CH₃, 5-OCH₂CH₃-pyrimidin-2-yl |
| 526 | 4-CH₃, 6-OCH₂CH₃-pyrimidin-2-yl |
| 527 | 5-CH₃, 4-OCH₂CH₃-pyrimidin-2-yl |
| 528 | 6-CH₃, 4-OCH₂CH₃-pyrimidin-2-yl |
| 529 | 4-CH₃, 5-OCH₂CF₃-pyrimidin-2-yl |
| 530 | 4-CH₃, 6-OCH₂CF₃-pyrimidin-2-yl |
| 531 | 5-CH₃, 4-OCH₂CF₃-pyrimidin-2-yl |
| 532 | 6-CH₃, 4-OCH₂CF₃-pyrimidin-2-yl |
| 533 | 4-CH₃, 5-OCH(CH₃)₂-pyrimidin-2-yl |
| 534 | 4-CH₃, 6-OCH(CH₃)₂-pyrimidin-2-yl |
| 535 | 5-CH₃, 4-OCH(CH₃)₂-pyrimidin-2-yl |
| 536 | 6-CH₃, 4-OCH(CH₃)₂-pyrimidin-2-yl |
| 537 | 4-CH₃, 5-OCH₂CH═CH₂-pyrimidin-2-yl |
| 538 | 4-CH₃, 6-OCH₂CH═CH₂-pyrimidin-2-yl |
| 539 | 5-CH₃, 4-OCH₂CH═CH₂-pyrimidin-2-yl |
| 540 | 6-CH₃, 4-OCH₂CH═CH₂-pyrimidin-2-yl |
| 541 | 4-CH₃, 5-CO₂CH₃-pyrimidin-2-yl |
| 542 | 4-CH₃, 6-CO₂CH₃-pyrimidin-2-yl |
| 543 | 4-CH₃, 5-CF₃-pyrimidin-2-yl |
| 544 | 4-CH₃, 6-CF₃-pyrimidin-2-yl |
| 545 | 5-CH₃, 4-CF₃-pyrimidin-2-yl |
| 546 | 6-CH₃, 4-CF₃-pyrimidin-2-yl |
| 547 | 4-CF₃, 5-CH₂CH₃-pyrimidin-2-yl |
| 548 | 4-CF₃, 6-CH₂CH₃-pyrimidin-2-yl |
| 549 | 5-CF₃, 4-CH₂CH₃-pyrimidin-2-yl |
| 550 | 6-CF₃, 4-CH₂CH₃-pyrimidin-2-yl |
| 551 | 4-CF₃, 5-OCH₃-pyrimidin-2-yl |
| 552 | 4-CF₃, 6-OCH₃-pyrimidin-2-yl |
| 553 | 5-CF₃, 4-OCH₃-pyrimidin-2-yl |
| 554 | 6-CF₃, 4-OCH₃-pyrimidin-2-yl |
| 555 | 4-CF₃, 5-OCH₂CH₃-pyrimidin-2-yl |
| 556 | 4-CF₃, 6-OCH₂CH₃-pyrimidin-2-yl |
| 557 | 5-CF₃, 4-OCH₂CH₃-pyrimidin-2-yl |
| 558 | 6-CF₃, 4-OCH₂CH₃-pyrimidin-2-yl |
| 559 | 4-CF₃, 5-OCH₂CF₃-pyrimidin-2-yl |
| 560 | 4-CF₃, 6-OCH₂CF₃-pyrimidin-2-yl |
| 561 | 5-CF₃, 4-OCH₂CF₃-pyrimidin-2-yl |
| 562 | 6-CF₃, 4-OCH₂CF₃-pyrimidin-2-yl |
| 563 | 4-OCH₃, 5-OCH₂CH₃-pyrimidin-2-yl |
| 564 | 4-OCH₃, 6-OCH₂CH₃-pyrimidin-2-yl |
| 565 | 5-OCH₃, 4-OCH₂CH₃-pyrimidin-2-yl |
| 566 | 6-OCH₃, 4-OCH₂CH₃-pyrimidin-2-yl |
| 567 | 4-OCH₃, 5-OCH₂CF₃-pyrimidin-2-yl |
| 568 | 4-OCH₃, 6-OCH₂CF₃-pyrimidin-2-yl |
| 569 | 5-OCH₃, 4-OCH₂CF₃-pyrimidin-2-yl |
| 570 | 6-OCH₃, 4-OCH₂CF₃-pyrimidin-2-yl |
| 571 | 4-OCH₃, 5-OCH(CH₃)-pyrimidin-2-yl |

TABLE A-continued

| No. | R⁴ |
|---|---|
| 572 | 4-OCH₃, 6-OCH(CH₃)-pyrimidin-2-yl |
| 573 | 5-OCH₃, 4-OCH(CH₃)-pyrimidin-2-yl |
| 574 | 6-OCH₃, 4-OCH(CH₃)-pyrimidin-2-yl |
| 575 | 4-OCH₂CH₃, 5-CH₂OCH₂CH₃-pyrimidin-2-yl |
| 576 | 4-OCH₂CH₃, 6-OCH₂OCH₂CH₃-pyrimidin-2-yl |
| 577 | 5-OCH₂CH₃, 4-CH₂OCH₂CH₃-pyrimidin-2-yl |
| 578 | 6-OCH₂CH₃, 4-CH₂OCH₂CH₃-pyrimidin-2-yl |
| 579 | 4-NO₂, 5-CH₃-pyrimidin-2-yl |
| 580 | 4-NO₂, 6-CH₃-pyrimidin-2-yl |
| 581 | 5-NO₂, 4-CH₃-pyrimidin-2-yl |
| 582 | 6-NO₂, 4-CH₃-pyrimidin-2-yl |
| 583 | 4-NO₂, 5-OCH₃-pyrimidin-2-yl |
| 584 | 4-NO₂, 6-OCH₃-pyrimidin-2-yl |
| 585 | 5-NO₂, 4-OCH₃-pyrimidin-2-yl |
| 586 | 6-NO₂, 4-OCH₃-pyrimidin-2-yl |
| 587 | 4-NO₂, 5-OCH₂CH₃-pyrimidin-2-yl |
| 588 | 4-NO₂, 6-OCH₂CH₃-pyrimidin-2-yl |
| 589 | 5-NO₂, 4-OCH₂CH₃-pyrimidin-2-yl |
| 590 | 6-NO₂, 4-OCH₂CH₃-pyrimidin-2-yl |
| 591 | 4-NO₂, 5-OCH(CH₃)₂-pyrimidin-2-yl |
| 592 | 4-NO₂, 6-OCH(CH₃)₂-pyrimidin-2-yl |
| 593 | 5-NO₂, 4-OCH(CH₃)₂-pyrimidin-2-yl |
| 594 | 6-NO₂, 4-OCH(CH₃)₂-pyrimidin-2-yl |
| 595 | 4-NO₂, 5-OCH₂CF₃-pyrimidin-2-yl |
| 596 | 4-NO₂, 6-OCH₂CF₃-pyrimidin-2-yl |
| 597 | 5-NO₂, 4-OCH₂CF₃-pyrimidin-2-yl |
| 598 | 6-NO₂, 4-OCH₂CF₃-pyrimidin-2-yl |
| 599 | 4-CN, 5-CH₃-pyrimidin-2-yl |
| 600 | 4-CN, 6-CH₃-pyrimidin-2-yl |
| 601 | 5-CN, 4-CH₃-pyrimidin-2-yl |
| 602 | 6-CN, 4-CH₃-pyrimidin-2-yl |
| 603 | 4-CN, 5-OCH₃-pyrimidin-2-yl |
| 604 | 4-CN, 6-OCH₃-pyrimidin-2-yl |
| 605 | 5-CN, 4-OCH₃-pyrimidin-2-yl |
| 606 | 6-CN, 4-OCH₃-pyrimidin-2-yl |
| 607 | 4-CN, 5-OCH₂CH₃-pyrimidin-2-yl |
| 608 | 4-CN, 6-OCH₂CH₃-pyrimidin-2-yl |
| 609 | 5-CN, 4-OCH₂CH₃-pyrimidin-2-yl |
| 610 | 6-CN, 4-OCH₂CH₃-pyrimidin-2-yl |
| 611 | 4-CN, 5-OCH(CH₃)₂-pyrimidin-2-yl |
| 612 | 4-CN, 6-OCH(CH₃)₂-pyrimidin-2-yl |
| 613 | 5-CN, 4-OCH(CH₃)₂-pyrimidin-2-yl |
| 614 | 6-CN, 4-OCH(CH₃)₂-pyrimidin-2-yl |
| 615 | 4-CN, 5-OCH₂CF₃-pyrimidin-2-yl |
| 616 | 4-CN, 6-OCH₂CF₃-pyrimidin-2-yl |
| 617 | 5-CN, 4-OCH₂CF₃-pyrimidin-2-yl |
| 618 | 6-CN, 4-OCH₂CF₃-pyrimidin-2-yl |
| 619 | 5,6-(CH₃)₂, 4-OCH₃-pyrimidin-2-yl |
| 620 | 2-CH₃-pyrimidin-4-yl |
| 621 | 5-CH₃-pyrimidin-4-yl |
| 622 | 6-CH₃-pyrimidin-4-yl |
| 623 | 2-CH₂CH₃-pyrimidin-4-yl |
| 624 | 5-CH₂CH₃-pyrimidin-4-yl |
| 625 | 6-CH₂CH₃-pyrimidin-4-yl |
| 626 | 2-CH(CH₃)₂-pyrimidin-4-yl |
| 627 | 5-CH(CH₃)₂-pyrimidin-4-yl |
| 628 | 6-CH(CH₃)₂-pyrimidin-4-yl |
| 629 | 2-CH(CH₃)CH₂CH₃-pyrimidin-4-yl |
| 630 | 5-CH(CH₃)CH₂CH₃-pyrimidin-4-yl |
| 631 | 6-CH(CH₃)CH₂CH₃-pyrimidin-4-yl |
| 632 | 2-CF₃-pyrimidin-4-yl |
| 633 | 5-CF₃-pyrimidin-4-yl |
| 634 | 6-CF₃-pyrimidin-4-yl |
| 635 | 2-CH=CH₂-pyrimidin-4-yl |
| 636 | 5-CH=CH₂-pyrimidin-4-yl |
| 637 | 6-CH=CH₂-pyrimidin-4-yl |
| 638 | 2-CH=CHCH₃-pyrimidin-4-yl |
| 639 | 5-CH=CHCH₃-pyrimidin-4-yl |
| 640 | 6-CH=CHCH₃-pyrimidin-4-yl |
| 641 | 2-CH=CHCl-pyrimidin-4-yl |
| 642 | 5-CH=CHCl-pyrimidin-4-yl |
| 643 | 6-CH=CHCl-pyrimidin-4-yl |
| 644 | 2-C≡CH-pyrimidin-4-yl |
| 645 | 5-C≡CH-pyrimidin-4-yl |
| 646 | 6-C≡CH-pyrimidin-4-yl |
| 647 | 2-CH₂C≡CH-pyrimidin-4-yl |
| 648 | 5-CH₂C≡CH-pyrimidin-4-yl |
| 649 | 6-CH₂C≡CH-pyrimidin-4-yl |
| 650 | 2-CH₂C≡CCH₃-pyrimidin-4-yl |
| 651 | 5-CH₂C≡CCH₃-pyrimidin-4-yl |
| 652 | 6-CH₂C≡CCH₃-pyrimidin-4-yl |
| 653 | 2-cyclopropylpyrimidin-4-yl |
| 654 | 5-cyclopropylpyrimidin-4-yl |
| 655 | 6-cyclopropylpyrimidin-4-yl |
| 656 | 2-cyclopentylpyrimidin-4-yl |
| 657 | 5-cyclopentylpyrimidin-4-yl |
| 658 | 6-cyclopentylpyrimidin-4-yl |
| 659 | 2-OCH₃-pyrimidin-4-yl |
| 660 | 5-OCH₃-pyrimidin-4-yl |
| 661 | 6-OCH₃-pyrimidin-4-yl |
| 662 | 2-OCH₂CH₃-pyrimidin-4-yl |
| 663 | 5-OCH₂CH₃-pyrimidin-4-yl |
| 664 | 6-OCH₂CH₃-pyrimidin-4-yl |
| 665 | 2-OCH₂CH₂CH₃-pyrimidin-4-yl |
| 666 | 5-OCH₂CH₂CH₃-pyrimidin-4-yl |
| 667 | 6-OCH₂CH₂CH₃-pyrimidin-4-yl |
| 668 | 2-OCH(CH₃)₂-pyrimidin-4-yl |
| 669 | 5-OCH(CH₃)₂-pyrimidin-4-yl |
| 670 | 6-OCH(CH₃)₂-pyrimidin-4-yl |
| 671 | 2-OCH₂CH₂CH₂CH₃-pyrimidin-4-yl |
| 672 | 5-OCH₂CH₂CH₂CH₃-pyrimidin-4-yl |
| 673 | 6-OCH₂CH₂CH₂CH₃-pyrimidin-4-yl |
| 674 | 2-OCH(CH₃)CH₂CH₃-pyrimidin-4-yl |
| 675 | 5-OCH(CH₃)CH₂CH₃-pyrimidin-4-yl |
| 676 | 6-OCH(CH₃)CH₂CH₃-pyrimidin-4-yl |
| 677 | 2-OCH₂CH(CH₃)₂-pyrimidin-4-yl |
| 678 | 5-OCH₂CH(CH₃)₂-pyrimidin-4-yl |
| 679 | 6-OCH₂CH(CH₃)₂-pyrimidin-4-yl |
| 680 | 2-OC(CH₃)₃-pyrimidin-4-yl |
| 681 | 5-OC(CH₃)₃-pyrimidin-4-yl |
| 682 | 6-OC(CH₃)₃-pyrimidin-4-yl |
| 683 | 2-OCH(CH₃)CH₂CH₂CH₃-pyrimidin-4-yl |
| 684 | 5-OCH(CH₃)CH₂CH₂CH₃-pyrimidin-4-yl |
| 685 | 6-OCH(CH₃)CH₂CH₂CH₃-pyrimidin-4-yl |
| 686 | 2-OCH₂OCH₃-pyrimidin-4-yl |
| 687 | 5-OCH₂OCH₃-pyrimidin-4-yl |
| 688 | 6-OCH₂OCH₃-pyrimidin-4-yl |
| 689 | 2-OCH₂OCH₂CH₃-pyrimidin-4-yl |
| 690 | 5-OCH₂OCH₂CH₃-pyrimidin-4-yl |
| 691 | 6-OCH₂OCH₂CH₃-pyrimidin-4-yl |
| 692 | 2-OCH(CH₃)OCH₃-pyrimidin-4-yl |
| 693 | 5-OCH(CH₃)OCH₃-pyrimidin-4-yl |
| 694 | 6-OCH(CH₃)OCH₃-pyrimidin-4-yl |
| 695 | 2-OCH(CH₃)OCH₂CH₃-pyrimidin-4-yl |
| 696 | 5-OCH(CH₃)OCH₂CH₃-pyrimidin-4-yl |
| 697 | 6-OCH(CH₃)OCH₂CH₃-pyrimidin-4-yl |
| 698 | 2-OCH₂CH₂OCH₃-pyrimidin-4-yl |
| 699 | 5-OCH₂CH₂OCH₃-pyrimidin-4-yl |
| 700 | 6-OCH₂CH₂OCH₃-pyrimidin-4-yl |
| 701 | 2-OCH₂CH₂OCH₂CH₃-pyrimidin-4-yl |
| 702 | 5-OCH₂CH₂OCH₂CH₃-pyrimidin-4-yl |
| 703 | 6-OCH₂CH₂OCH₂CH₃-pyrimidin-4-yl |
| 704 | 2-OCH₂CH₂OCH(CH₃)₂-pyrimidin-4-yl |
| 705 | 5-OCH₂CH₂OCH(CH₃)₂-pyrimidin-4-yl |
| 706 | 6-OCH₂CH₂OCH(CH₃)₂-pyrimidin-4-yl |
| 707 | 2-OCH₂CH₂SCH₃-pyrimidin-4-yl |
| 708 | 5-OCH₂CH₂SCH₃-pyrimidin-4-yl |
| 709 | 6-OCH₂CH₂SCH₃-pyrimidin-4-yl |
| 710 | 2-OCH₂CH₂SO₂CH₃-pyrimidin-4-yl |
| 711 | 5-OCH₂CH₂SO₂CH₃-pyrimidin-4-yl |
| 712 | 6-OCH₂CH₂SO₂CH₃-pyrimidin-4-yl |
| 713 | 2-OCH₂CH₂SCH(CH₃)₂-pyrimidin-4-yl |
| 714 | 5-OCH₂CH₂SCH(CH₃)₂-pyrimidin-4-yl |
| 715 | 6-OCH₂CH₂SCH(CH₃)₂-pyrimidin-4-yl |
| 716 | 2-OCH₂CH₂CN-pyrimidin-4-yl |
| 717 | 5-OCH₂CH₂CN-pyrimidin-4-yl |
| 718 | 6-OCH₂CH₂CN-pyrimidin-4-yl |
| 719 | 2-OCH₂CH₂SCH₂CH₂CN-pyrimidin-4-yl |
| 720 | 5-OCH₂CH₂SCH₂CH₂CN-pyrimidin-4-yl |
| 721 | 6-OCH₂CH₂SCH₂CH₂CN-pyrimidin-4-yl |
| 722 | 2-OCH₂CH₂OC₆H₅-pyrimidin-4-yl |
| 723 | 5-OCH₂CH₂OC₆H₅-pyrimidin-4-yl |
| 724 | 6-OCH₂CH₂OC₆H₅-pyrimidin-4-yl |
| 725 | 2-OCH₂CH₂OCH₂C₆H₅-pyrimidin-4-yl |

TABLE A-continued

| No. | R⁴ |
|---|---|
| 726 | 5-OCH$_2$CH$_2$OCH$_2$C$_6$H$_5$-pyrimidin-4-yl |
| 727 | 6-OCH$_2$CH$_2$OCH$_2$C$_6$H$_5$-pyrimidin-4-yl |
| 728 | 2-OCH$_2$CH$_2$N(CH$_3$)$_2$-pyrimidin-4-yl |
| 729 | 5-OCH$_2$CH$_2$N(CH$_3$)$_2$-pyrimidin-4-yl |
| 730 | 6-OCH$_2$CH$_2$N(CH$_3$)$_2$-pyrimidin-4-yl |
| 731 | 2-OCH$_2$CH$_2$CONH$_2$-pyrimidin-4-yl |
| 732 | 5-OCH$_2$CH$_2$CONH$_2$-pyrimidin-4-yl |
| 733 | 6-OCH$_2$CH$_2$CONH$_2$-pyrimidin-4-yl |
| 734 | 2-OCH$_2$CH$_2$CO$_2$CH$_2$CH$_2$CH$_3$-pyrimidin-4-yl |
| 735 | 5-OCH$_2$CH$_2$CO$_2$CH$_2$CH$_2$CH$_3$-pyrimidin-4-yl |
| 736 | 6-OCH$_2$CH$_2$CO$_2$CH$_2$CH$_2$CH$_3$-pyrimidin-4-yl |
| 737 | 2-OCH(CH$_3$)CH$_2$OCH$_3$-pyrimidin-4-yl |
| 738 | 5-OCH(CH$_3$)CH$_2$OCH$_3$-pyrimidin-4-yl |
| 739 | 6-OCH(CH$_3$)CH$_2$OCH$_3$-pyrimidin-4-yl |
| 740 | 2-OCH(CH$_3$)CH$_2$CO$_2$CH$_3$-pyrimidin-4-yl |
| 741 | 5-OCH(CH$_3$)CH$_2$CO$_2$CH$_3$-pyrimidin-4-yl |
| 742 | 6-OCH(CH$_3$)CH$_2$CO$_2$CH$_3$-pyrimidin-4-yl |
| 743 | 2-OCH(CH$_3$)CH$_2$CO$_2$CH$_2$CH$_3$-pyrimidin-4-yl |
| 744 | 5-OCH(CH$_3$)CH$_2$CO$_2$CH$_2$CH$_3$-pyrimidin-4-yl |
| 745 | 6-OCH(CH$_3$)CH$_2$CO$_2$CH$_2$CH$_3$-pyrimidin-4-yl |
| 746 | 2-OCH$_2$CH(CH$_3$)CO$_2$CH$_3$-pyrimidin-4-yl |
| 747 | 5-OCH$_2$CH(CH$_3$)CO$_2$CH$_3$-pyrimidin-4-yl |
| 748 | 6-OCH$_2$CH(CH$_3$)CO$_2$CH$_3$-pyrimidin-4-yl |
| 749 | 2-OCH$_2$C(=O)CH$_3$-pyrimidin-4-yl |
| 750 | 5-OCH$_2$C(=O)CH$_3$-pyrimidin-4-yl |
| 751 | 6-OCH$_2$C(=O)CH$_3$-pyrimidin-4-yl |
| 752 | 2-OCH$_2$C(=O)CH$_2$CH$_3$-pyrimidin-4-yl |
| 753 | 5-OCH$_2$C(=O)CH$_2$CH$_3$-pyrimidin-4-yl |
| 754 | 6-OCH$_2$C(=O)CH$_2$CH$_3$-pyrimidin-4-yl |
| 755 | 2-OCH$_2$CO$_2$CH$_3$-pyrimidin-4-yl |
| 756 | 5-OCH$_2$CO$_2$CH$_3$-pyrimidin-4-yl |
| 757 | 6-OCH$_2$CO$_2$CH$_3$-pyrimidin-4-yl |
| 758 | 2-OCH$_2$CO$_2$CH$_2$CH$_3$-pyrimidin-4-yl |
| 759 | 5-OCH$_2$CO$_2$CH$_2$CH$_3$-pyrimidin-4-yl |
| 760 | 6-OCH$_2$CO$_2$CH$_2$CH$_3$-pyrimidin-4-yl |
| 761 | 2-OCH$_2$C(=O)NH$_2$-pyrimidin-4-yl |
| 762 | 5-OCH$_2$C(=O)NH$_2$-pyrimidin-4-yl |
| 763 | 6-OCH$_2$C(=O)NH$_2$-pyrimidin-4-yl |
| 764 | 2-OCH$_2$C(=O)NHCH$_3$-pyrimidin-4-yl |
| 765 | 5-OCH$_2$C(=O)NHCH$_3$-pyrimidin-4-yl |
| 766 | 6-OCH$_2$C(=O)NHCH$_3$-pyrimidin-4-yl |
| 767 | 2-OCH$_2$C(=O)SCH$_3$-pyrimidin-4-yl |
| 768 | 5-OCH$_2$C(=O)SCH$_3$-pyrimidin-4-yl |
| 769 | 6-OCH$_2$C(=O)SCH$_3$-pyrimidin-4-yl |
| 770 | 2-OCH(CH$_3$)C(=O)NH$_2$-pyrimidin-4-yl |
| 771 | 5-OCH(CH$_3$)C(=O)NH$_2$-pyrimidin-4-yl |
| 772 | 6-OCH(CH$_3$)C(=O)NH$_2$-pyrimidin-4-yl |
| 773 | 2-OCH(CH$_3$)C(=O)NHCH$_3$-pyrimidin-4-yl |
| 774 | 5-OCH(CH$_3$)C(=O)NHCH$_3$-pyrimidin-4-yl |
| 775 | 6-OCH(CH$_3$)C(=O)NHCH$_3$-pyrimidin-4-yl |
| 776 | 2-OCH(CH$_3$)C(=O)NHNH$_2$-pyrimidin-4-yl |
| 777 | 5-OCH(CH$_3$)C(=O)NHNH$_2$-pyrimidin-4-yl |
| 778 | 6-OCH(CH$_3$)C(=O)NHNH$_2$-pyrimidin-4-yl |
| 779 | 2-OCH(CH$_3$)CO$_2$CH$_3$-pyrimidin-4-yl |
| 780 | 5-OCH(CH$_3$)CO$_2$CH$_3$-pyrimidin-4-yl |
| 781 | 6-OCH(CH$_3$)CO$_2$CH$_3$-pyrimidin-4-yl |
| 782 | 2-OCH(CH$_3$)CO$_2$CH$_2$CH$_3$-pyrimidin-4-yl |
| 783 | 5-OCH(CH$_3$)CO$_2$CH$_2$CH$_3$-pyrimidin-4-yl |
| 784 | 6-OCH(CH$_3$)CO$_2$CH$_2$CH$_3$-pyrimidin-4-yl |
| 785 | 2-OCH(CH$_3$)C(=O)CH$_3$-pyrimidin-4-yl |
| 786 | 5-OCH(CH$_3$)C(=O)CH$_3$-pyrimidin-4-yl |
| 787 | 6-OCH(CH$_3$)C(=O)CH$_3$-pyrimidin-4-yl |
| 788 | 2-OCH(CH$_3$)C(=O)CH$_2$CH$_3$-pyrimidin-4-yl |
| 789 | 5-OCH(CH$_3$)C(=O)CH$_2$CH$_3$-pyrimidin-4-yl |
| 790 | 6-OCH(CH$_3$)C(=O)CH$_2$CH$_3$-pyrimidin-4-yl |
| 791 | 2-OCH(CH$_3$)CH$_2$C(=O)CH$_3$-pyrimidin-4-yl |
| 792 | 5-OCH(CH$_3$)CH$_2$C(=O)CH$_3$-pyrimidin-4-yl |
| 793 | 6-OCH(CH$_3$)CH$_2$C(=O)CH$_3$-pyrimidin-4-yl |
| 794 | 2-OCH(CH$_3$)CH$_2$OC(CH$_3$)$_3$-pyrimidin-4-yl |
| 795 | 5-OCH(CH$_3$)CH$_2$OC(CH$_3$)$_3$-pyrimidin-4-yl |
| 796 | 6-OCH(CH$_3$)CH$_2$OC(CH$_3$)$_3$-pyrimidin-4-yl |
| 797 | 2-OCH(CH$_3$)CH$_2$OCH$_2$CH$_3$-pyrimidin-4-yl |
| 798 | 5-OCH(CH$_3$)CH$_2$OCH$_2$CH$_3$-pyrimidin-4-yl |
| 799 | 6-OCH(CH$_3$)CH$_2$OCH$_2$CH$_3$-pyrimidin-4-yl |
| 800 | 2-OCH(CH$_3$)CH$_2$O(CH$_3$)$_2$CH$_3$-pyrimidin-4-yl |
| 801 | 5-OCH(CH$_3$)CH$_2$O(CH$_3$)$_2$CH$_3$-pyrimidin-4-yl |
| 802 | 6-OCH(CH$_3$)CH$_2$O(CH$_3$)$_2$CH$_3$-pyrimidin-4-yl |
| 803 | 2-OCH(CH$_3$)CH$_2$OCH$_2$CH=CH$_2$-pyrimidin-4-yl |
| 804 | 5-OCH(CH$_3$)CH$_2$OCH$_2$CH=CH$_2$-pyrimidin-4-yl |
| 805 | 6-OCH(CH$_3$)CH$_2$OCH$_2$CH=CH$_2$-pyrimidin-4-yl |
| 806 | 2-O(CH$_2$)$_3$OCH$_3$-pyrimidin-4-yl |
| 807 | 5-O(CH$_2$)$_3$OCH$_3$-pyrimidin-4-yl |
| 808 | 6-O(CH$_2$)$_3$OCH$_3$-pyrimidin-4-yl |
| 809 | 2-O(CH$_2$)$_3$OCH$_2$CH$_3$-pyrimidin-4-yl |
| 810 | 5-O(CH$_2$)$_3$OCH$_2$CH$_3$-pyrimidin-4-yl |
| 811 | 6-O(CH$_2$)$_3$OCH$_2$CH$_3$-pyrimidin-4-yl |
| 812 | 2-O(CH$_2$)$_3$OCH(CH$_3$)$_2$-pyrimidin-4-yl |
| 813 | 5-O(CH$_2$)$_3$OCH(CH$_3$)$_2$-pyrimidin-4-yl |
| 814 | 6-O(CH$_2$)$_3$OCH(CH$_3$)$_2$-pyrimidin-4-yl |
| 815 | 2-O(CH$_2$)$_3$OC$_6$H$_5$-pyrimidin-4-yl |
| 816 | 5-O(CH$_2$)$_3$OC$_6$H$_5$-pyrimidin-4-yl |
| 817 | 6-O(CH$_2$)$_3$OC$_6$H$_5$-pyrimidin-4-yl |
| 818 | 2-O(CH$_2$)$_3$OCH$_2$C$_6$H$_5$-pyrimidin-4-yl |
| 819 | 5-O(CH$_2$)$_3$OCH$_2$C$_6$H$_5$-pyrimidin-4-yl |
| 820 | 6-O(CH$_2$)$_3$OCH$_2$C$_6$H$_5$-pyrimidin-4-yl |
| 821 | 2-OCH(CH$_2$CH$_3$)CH$_2$OCH$_3$-pyrimidin-4-yl |
| 822 | 5-OCH(CH$_2$CH$_3$)CH$_2$OCH$_3$-pyrimidin-4-yl |
| 823 | 6-OCH(CH$_2$CH$_3$)CH$_2$OCH$_3$-pyrimidin-4-yl |
| 824 | 2-OCH(CH$_2$CH$_3$)CH$_2$CH$_2$OCH$_3$-pyrimidin-4-yl |
| 825 | 5-OCH(CH$_2$CH$_3$)CH$_2$CH$_2$OCH$_3$-pyrimidin-4-yl |
| 826 | 6-OCH(CH$_2$CH$_3$)CH$_2$CH$_2$OCH$_3$-pyrimidin-4-yl |
| 827 | 2-OCH(CH$_2$CH$_3$)CH$_2$CH$_2$OCH$_2$CH$_3$-pyrimidin-4-yl |
| 828 | 5-OCH(CH$_2$CH$_3$)CH$_2$CH$_2$OCH$_2$CH$_3$-pyrimidin-4-yl |
| 829 | 6-OCH(CH$_2$CH$_3$)CH$_2$CH$_2$OCH$_2$CH$_3$-pyrimidin-4-yl |
| 830 | 2-O[(CH$_2$)$_3$O]$_2$CH$_3$-pyrimidin-4-yl |
| 831 | 5-O[(CH$_2$)$_3$O]$_2$CH$_3$-pyrimidin-4-yl |
| 832 | 6-O[(CH$_2$)$_3$O]$_2$CH$_3$-pyrimidin-4-yl |
| 833 | 2-OCH$_2$CH(CH$_3$)CH$_2$OCH$_3$-pyrimidin-4-yl |
| 834 | 5-OCH$_2$CH(CH$_3$)CH$_2$OCH$_3$-pyrimidin-4-yl |
| 835 | 6-OCH$_2$CH(CH$_3$)CH$_2$OCH$_3$-pyrimidin-4-yl |
| 836 | 2-OCH$_2$CH(CH$_3$)CH$_2$OCH$_2$CH$_3$-pyrimidin-4-yl |
| 837 | 5-OCH$_2$CH(CH$_3$)CH$_2$OCH$_2$CH$_3$-pyrimidin-4-yl |
| 838 | 6-OCH$_2$CH(CH$_3$)CH$_2$OCH$_2$CH$_3$-pyrimidin-4-yl |
| 839 | 2-OCH(CH$_2$Cl)CH$_2$OCH$_3$-pyrimidin-4-yl |
| 840 | 5-OCH(CH$_2$Cl)CH$_2$OCH$_3$-pyrimidin-4-yl |
| 841 | 6-OCH(CH$_2$Cl)CH$_2$OCH$_3$-pyrimidin-4-yl |
| 842 | 2-OCH(CH$_2$Cl)CH$_2$OCH$_2$CH$_3$-pyrimidin-4-yl |
| 843 | 5-OCH(CH$_2$Cl)CH$_2$OCH$_2$CH$_3$-pyrimidin-4-yl |
| 844 | 6-OCH(CH$_2$Cl)CH$_2$OCH$_2$CH$_3$-pyrimidin-4-yl |
| 845 | 2-OCH(CH$_2$Cl)CH$_2$OCH(CH$_3$)$_2$-pyrimidin-4-yl |
| 846 | 5-OCH(CH$_2$Cl)CH$_2$OCH(CH$_3$)$_2$-pyrimidin-4-yl |
| 847 | 6-OCH(CH$_2$Cl)CH$_2$OCH(CH$_3$)$_2$-pyrimidin-4-yl |
| 848 | 2-OCH(CH$_2$Cl)CH$_2$OCH$_2$CH=CH$_2$-pyrimidin-4-yl |
| 849 | 5-OCH(CH$_2$Cl)CH$_2$OCH$_2$CH=CH$_2$-pyrimidin-4-yl |
| 850 | 6-OCH(CH$_2$Cl)CH$_2$OCH$_2$CH=CH$_2$-pyrimidin-4-yl |
| 851 | 2-OCH[CH$_2$OCH$_3$]$_2$-pyrimidin-4-yl |
| 852 | 5-OCH[CH$_2$OCH$_3$]$_2$-pyrimidin-4-yl |
| 853 | 6-OCH[CH$_2$OCH$_3$]$_2$-pyrimidin-4-yl |
| 854 | 2-OCH[CH$_2$OCH$_2$CH$_3$]$_2$-pyrimidin-4-yl |
| 855 | 5-OCH[CH$_2$OCH$_2$CH$_3$]$_2$-pyrimidin-4-yl |
| 856 | 6-OCH[CH$_2$OCH$_2$CH$_3$]$_2$-pyrimidin-4-yl |
| 857 | 2-OCCl$_3$-pyrimidin-4-yl |
| 858 | 5-OCCl$_3$-pyrimidin-4-yl |
| 859 | 6-OCCl$_3$-pyrimidin-4-yl |
| 860 | 2-OCHF$_2$-pyrimidin-4-yl |
| 861 | 5-OCHF$_2$-pyrimidin-4-yl |
| 862 | 6-OCHF$_2$-pyrimidin-4-yl |
| 863 | 2-OCF$_3$-pyrimidin-4-yl |
| 864 | 5-OCF$_3$-pyrimidin-4-yl |
| 865 | 6-OCF$_3$-pyrimidin-4-yl |
| 866 | 2-OCF$_2$CHF$_2$-pyrimidin-4-yl |
| 867 | 5-OCF$_2$CHF$_2$-pyrimidin-4-yl |
| 868 | 6-OCF$_2$CHF$_2$-pyrimidin-4-yl |
| 869 | 2-OCH$_2$CF$_3$-pyrimidin-4-yl |
| 870 | 5-OCH$_2$CF$_3$-pyrimidin-4-yl |
| 871 | 6-OCH$_2$CF$_3$-pyrimidin-4-yl |
| 872 | 2-OCH$_2$CHF$_2$-pyrimidin-4-yl |
| 873 | 5-OCH$_2$CHF$_2$-pyrimidin-4-yl |
| 874 | 6-OCH$_2$CHF$_2$-pyrimidin-4-yl |
| 875 | 2-O(CH$_2$)$_3$F-pyrimidin-4-yl |
| 876 | 5-O(CH$_2$)$_3$F-pyrimidin-4-yl |
| 877 | 6-O(CH$_2$)$_3$F-pyrimidin-4-yl |
| 878 | 2-OCH(CH$_3$)CF$_3$-pyrimidin-4-yl |
| 879 | 5-OCH(CH$_3$)CF$_3$-pyrimidin-4-yl |

TABLE A-continued

| No. | R⁴ |
|---|---|
| 880 | 6-OCH(CH₃)CF₃-pyrimidin-4-yl |
| 881 | 2-O(CH₂)₄F-pyrimidin-4-yl |
| 882 | 5-O(CH₂)₄F-pyrimidin-4-yl |
| 883 | 6-O(CH₂)₄F-pyrimidin-4-yl |
| 884 | 2-O(CH₂)₃CF₃-pyrimidin-4-yl |
| 885 | 5-O(CH₂)₃CF₃-pyrimidin-4-yl |
| 886 | 6-O(CH₂)₃CF₃-pyrimidin-4-yl |
| 887 | 2-OCH(CH₃)CF₂CF₃-pyrimidin-4-yl |
| 888 | 5-OCH(CH₃)CF₂CF₃-pyrimidin-4-yl |
| 889 | 6-OCH(CH₃)CF₂CF₃-pyrimidin-4-yl |
| 890 | 2-OCH(CH₃)CF₂CHF₂-pyrimidin-4-yl |
| 891 | 5-OCH(CH₃)CF₂CHF₂-pyrimidin-4-yl |
| 892 | 6-OCH(CH₃)CF₂CHF₂-pyrimidin-4-yl |
| 893 | 2-OCH₂CF₂CHFCH₃-pyrimidin-4-yl |
| 894 | 5-OCH₂CF₂CHFCH₃-pyrimidin-4-yl |
| 895 | 6-OCH₂CF₂CHFCH₃-pyrimidin-4-yl |
| 896 | 2-OCH₂(CF₂)₂CF₃-pyrimidin-4-yl |
| 897 | 5-OCH₂(CF₂)₂CF₃-pyrimidin-4-yl |
| 898 | 6-OCH₂(CF₂)₂CF₃-pyrimidin-4-yl |
| 899 | 2-O(CF₂)₃CF₃-pyrimidin-4-yl |
| 900 | 5-O(CF₂)₃CF₃-pyrimidin-4-yl |
| 901 | 6-O(CF₂)₃CF₃-pyrimidin-4-yl |
| 902 | 2-OCH₂CF₂CHF₂-pyrimidin-4-yl |
| 903 | 5-OCH₂CF₂CHF₂-pyrimidin-4-yl |
| 904 | 6-OCH₂CF₂CHF₂-pyrimidin-4-yl |
| 905 | 2-CH₂CH=CH₂-pyrimidin-4-yl |
| 906 | 5-CH₂CH=CH₂-pyrimidin-4-yl |
| 907 | 6-CH₂CH=CH₂-pyrimidin-4-yl |
| 908 | 2-CH₂C(CH₃)=CH₂-pyrimidin-4-yl |
| 909 | 5-CH₂C(CH₃)=CH₂-pyrimidin-4-yl |
| 910 | 6-CH₂C(CH₃)=CH₂-pyrimidin-4-yl |
| 911 | 2-OCH₂CH=CHCH₃-pyrimidin-4-yl |
| 912 | 5-OCH₂CH=CHCH₃-pyrimidin-4-yl |
| 913 | 6-OCH₂CH=CHCH₃-pyrimidin-4-yl |
| 914 | 2-O(CH₂)₂CH=CH₂-pyrimidin-4-yl |
| 915 | 5-O(CH₂)₂CH=CH₂-pyrimidin-4-yl |
| 916 | 6-O(CH₂)₂CH=CH₂-pyrimidin-4-yl |
| 917 | 2-OCH₂C(CH₃)=CH₂-pyrimidin-4-yl |
| 918 | 5-OCH₂C(CH₃)=CH₂-pyrimidin-4-yl |
| 919 | 6-OCH₂C(CH₃)=CH₂-pyrimidin-4-yl |
| 920 | 2-OCH(CH₃)CH=CH₂-pyrimidin-4-yl |
| 921 | 5-OCH(CH₃)CH=CH₂-pyrimidin-4-yl |
| 922 | 6-OCH(CH₃)CH=CH₂-pyrimidin-4-yl |
| 923 | 2-OCH₂C≡CH-pyrimidin-4-yl |
| 924 | 5-OCH₂C≡CH-pyrimidin-4-yl |
| 925 | 6-OCH₂C≡CH-pyrimidin-4-yl |
| 926 | 2-OCH₂C≡CCH₃-pyrimidin-4-yl |
| 927 | 5-OCH₂C≡CCH₃-pyrimidin-4-yl |
| 928 | 6-OCH₂C≡CCH₃-pyrimidin-4-yl |
| 929 | 2-O(CH₂)₂C≡CH-pyrimidin-4-yl |
| 930 | 5-O(CH₂)₂C≡CH-pyrimidin-4-yl |
| 931 | 6-O(CH₂)₂C≡CH-pyrimidin-4-yl |
| 932 | 2-SCH₃-pyrimidin-4-yl |
| 933 | 5-SCH₃-pyrimidin-4-yl |
| 934 | 6-SCH₃-pyrimidin-4-yl |
| 935 | 2-SCH₂CH₃-pyrimidin-4-yl |
| 936 | 5-SCH₂CH₃-pyrimidin-4-yl |
| 937 | 6-SCH₂CH₃-pyrimidin-4-yl |
| 938 | 2-OC₆H₅-pyrimidin-4-yl |
| 939 | 5-OC₆H₅-pyrimidin-4-yl |
| 940 | 6-OC₆H₅-pyrimidin-4-yl |
| 941 | 2-OCH₂C₆H₅-pyrimidin-4-yl |
| 942 | 5-OCH₂C₆H₅-pyrimidin-4-yl |
| 943 | 6-OCH₂C₆H₅-pyrimidin-4-yl |
| 944 | 2-NO₂-pyrimidin-4-yl |
| 945 | 5-NO₂-pyrimidin-4-yl |
| 946 | 6-NO₂-pyrimidin-4-yl |
| 947 | 2-NHCH₃-pyrimidin-4-yl |
| 948 | 5-NHCH₃-pyrimidin-4-yl |
| 949 | 6-NHCH₃-pyrimidin-4-yl |
| 950 | 2-N(CH₃)₂-pyrimidin-4-yl |
| 951 | 5-N(CH₃)₂-pyrimidin-4-yl |
| 952 | 6-N(CH₃)₂-pyrimidin-4-yl |
| 953 | 2-N(CH₃)C₂H₅-pyrimidin-4-yl |
| 954 | 5-N(CH₃)C₂H₅-pyrimidin-4-yl |
| 955 | 6-N(CH₃)C₂H₅-pyrimidin-4-yl |
| 956 | 2-NHCH₂CF₃-pyrimidin-4-yl |
| 957 | 5-NHCH₂CF₃-pyrimidin-4-yl |
| 958 | 6-NHCH₂CF₃-pyrimidin-4-yl |
| 959 | 2-F-pyrimidin-4-yl |
| 960 | 5-F-pyrimidin-4-yl |
| 961 | 6-F-pyrimidin-4-yl |
| 962 | 2-Cl-pyrimidin-4-yl |
| 963 | 5-Cl-pyrimidin-4-yl |
| 964 | 6-Cl-pyrimidin-4-yl |
| 965 | 2-OH-pyrimidin-4-yl |
| 966 | 5-OH-pyrimidin-4-yl |
| 967 | 6-OH-pyrimidin-4-yl |
| 968 | 2-CN-pyrimidin-4-yl |
| 969 | 5-CN-pyrimidin-4-yl |
| 970 | 6-CN-pyrimidin-4-yl |
| 971 | 2-C(O)NH₂-pyrimidin-4-yl |
| 972 | 5-C(O)NH₂-pyrimidin-4-yl |
| 973 | 6-C(O)NH₂-pyrimidin-4-yl |
| 974 | 2-C(S)NH₂-pyrimidin-4-yl |
| 975 | 5-C(S)NH₂-pyrimidin-4-yl |
| 976 | 6-C(S)NH₂-pyrimidin-4-yl |
| 977 | 2-CO₂CH₃-pyrimidin-4-yl |
| 978 | 5-CO₂CH₃-pyrimidin-4-yl |
| 979 | 6-CO₂CH₃-pyrimidin-4-yl |
| 980 | 2-ON=C(CH₃)₂-pyrimidin-4-yl |
| 981 | 5-ON=C(CH₃)₂-pyrimidin-4-yl |
| 982 | 6-ON=C(CH₃)₂-pyrimidin-4-yl |
| 983 | 2-[O-cyclopropyl]pyrimidin-4-yl |
| 984 | 5-[O-cyclopropyl]pyrimidin-4-yl |
| 985 | 6-[O-cyclopropyl]pyrimidin-4-yl |
| 986 | 2-[O-cyclobutyl]pyrimidin-4-yl |
| 987 | 5-[O-cyclobutyl]pyrimidin-4-yl |
| 988 | 6-[O-cyclobutyl]pyrimidin-4-yl |
| 989 | 2-[O-cyclopentyl]pyrimidin-4-yl |
| 990 | 5-[O-cyclopentyl]pyrimidin-4-yl |
| 991 | 6-[O-cyclopentyl]pyrimidin-4-yl |
| 992 | 2-[O-cyclohexyl]pyrimidin-4-yl |
| 993 | 5-[O-cyclohexyl]pyrimidin-4-yl |
| 994 | 6-[O-cyclohexyl]pyrimidin-4-yl |
| 995 | 2-[OCH₂-cyclopropyl]pyrimidin-4-yl |
| 996 | 5-[OCH₂-cyclopropyl]pyrimidin-4-yl |
| 997 | 6-[OCH₂-cyclopropyl]pyrimidin-4-yl |
| 998 | 6-F, 2-[OCH₂-cyclopropyl]pyrimidin-4-yl |
| 999 | 2-F, 6-[OCH₂-cyclopropyl]pyrimidin-4-yl |
| 1000 | 5-F, 2-[OCH₂-cyclopropyl]pyrimidin-4-yl |
| 1001 | 6-CH₃, 2-[OCH₂-cyclopropyl]pyrimidin-4-yl |
| 1002 | 2-CH₃, 6-[OCH₂-cyclopropyl]pyrimidin-4-yl |
| 1003 | 5-CH₃, 2-[OCH₂-cyclopropyl]pyrimidin-4-yl |
| 1004 | 6-CF₃, 2-[OCH₂-cyclopropyl]pyrimidin-4-yl |
| 1005 | 2-CF₃, 6-[OCH₂-cyclopropyl]pyrimidin-4-yl |
| 1006 | 5-CF₃, 2-[OCH₂-cyclopropyl]pyrimidin-4-yl |
| 1007 | 2-[OCH(CH₃)-cyclopropyl]pyrimidin-4-yl |
| 1008 | 5-[OCH(CH₃)-cyclopropyl]pyrimidin-4-yl |
| 1009 | 6-[OCH(CH₃)-cyclopropyl]pyrimidin-4-yl |
| 1010 | 6-F, 2-[OCH(CH₃)-cyclopropyl]pyrimidin-4-yl |
| 1011 | 2-F, 6-[OCH(CH₃)-cyclopropyl]pyrimidin-4-yl |
| 1012 | 5-F, 2-[OCH(CH₃)-cyclopropyl]pyrimidin-4-yl |
| 1013 | 6-CH₃, 2-[OCH(CH₃)-cyclopropyl]pyrimidin-4-yl |
| 1014 | 2-CH₃, 6-[OCH(CH₃)-cyclopropyl]pyrimidin-4-yl |
| 1015 | 5-CH₃, 2-[OCH(CH₃)-cyclopropyl]pyrimidin-4-yl |
| 1016 | 6-CF₃, 2-[OCH(CH₃)-cyclopropyl]pyrimidin-4-yl |
| 1017 | 2-CF₃, 6-[OCH(CH₃)-cyclopropyl]pyrimidin-4-yl |
| 1018 | 5-CF₃, 2-[OCH(CH₃)-cyclopropyl]pyrimidin-4-yl |
| 1019 | 2-[O-(1-CH₃-cyclopropyl)]pyrimidin-4-yl |
| 1020 | 5-[O-(1-CH₃-cyclopropyl)]pyrimidin-4-yl |
| 1021 | 6-[O-(1-CH₃-cyclopropyl)]pyrimidin-4-yl |
| 1022 | 6-F, 2-[O-(1-CH₃-cyclopropyl)]pyrimidin-4-yl |
| 1023 | 2-F, 6-[O-(1-CH₃-cyclopropyl)]pyrimidin-4-yl |
| 1024 | 5-F, 2-[O-(1-CH₃-cyclopropyl)]pyrimidin-4-yl |
| 1025 | 6-CH₃, 2-[O-(1-CH₃-cyclopropyl)]pyrimidin-4-yl |
| 1026 | 2-CH₃, 6-[O-(1-CH₃-cyclopropyl)]pyrimidin-4-yl |
| 1027 | 5-CH₃, 2-[O-(1-CH₃-cyclopropyl)]pyrimidin-4-yl |
| 1028 | 6-CF₃, 2-[O-(1-CH₃-cyclopropyl)]pyrimidin-4-yl |
| 1029 | 2-CF₃, 6-[O-(1-CH₃-cyclopropyl)]pyrimidin-4-yl |
| 1030 | 5-CF₃, 2-[O-(1-CH₃-cyclopropyl)]pyrimidin-4-yl |
| 1031 | 2-[OCH₂-(1-CH₃-cyclopropyl)]pyrimidin-4-yl |
| 1032 | 5-[OCH₂-(1-CH₃-cyclopropyl)]pyrimidin-4-yl |
| 1033 | 6-[OCH₂-(1-CH₃-cyclopropyl)]pyrimidin-4-yl |

TABLE A-continued

| No. | R⁴ |
|---|---|
| 1034 | 6-F, 2-[OCH₂-(1-CH₃-cyclopropyl)]pyrimidin-4-yl |
| 1035 | 2-F, 6-[OCH₂-(1-CH₃-cyclopropyl)]pyrimidin-4-yl |
| 1036 | 5-F, 2-[OCH₂-(1-CH₃-cyclopropyl)]pyrimidin-4-yl |
| 1037 | 6-CH₃, 2-[OCH₂-(1-CH₃-cyclopropyl)]pyrimidin-4-yl |
| 1038 | 2-CH₃, 6-[OCH₂-(1-CH₃-cyclopropyl)]pyrimidin-4-yl |
| 1039 | 5-CH₃, 2-[OCH₂-(1-CH₃-cyclopropyl)]pyrimidin-4-yl |
| 1040 | 6-CF₃, 2-[OCH₂-(1-CH₃-cyclopropyl)]pyrimidin-4-yl |
| 1041 | 2-CF₃, 6-[OCH₂-(1-CH₃-cyclopropyl)]pyrimidin-4-yl |
| 1042 | 5-CF₃, 2-[OCH₂-(1-CH₃-cyclopropyl)]pyrimidin-4-yl |
| 1043 | 2-[OCH₂-(2-CH₃-cyclopropyl)]pyrimidin-4-yl |
| 1044 | 5-[OCH₂-(2-CH₃-cyclopropyl)]pyrimidin-4-yl |
| 1045 | 6-[OCH₂-(2-CH₃-cyclopropyl)]pyrimidin-4-yl |
| 1046 | 6-F, 2-[OCH₂-(2-CH₃-cyclopropyl)]pyrimidin-4-yl |
| 1047 | 2-F, 6-[OCH₂-(2-CH₃-cyclopropyl)]pyrimidin-4-yl |
| 1048 | 5-F, 2-[OCH₂-(2-CH₃-cyclopropyl)]pyrimidin-4-yl |
| 1049 | 6-CH₃, 2-[OCH₂-(2-CH₃-cyclopropyl)]pyrimidin-4-yl |
| 1050 | 2-CH₃, 6-[OCH₂-(2-CH₃-cyclopropyl)]pyrimidin-4-yl |
| 1051 | 5-CH₃, 2-[OCH₂-(2-CH₃-cyclopropyl)]pyrimidin-4-yl |
| 1052 | 6-CF₃, 2-[OCH₂-(2-CH₃-cyclopropyl)]pyrimidin-4-yl |
| 1053 | 2-CF₃, 6-[OCH₂-(2-CH₃-cyclopropyl)]pyrimidin-4-yl |
| 1054 | 5-CF₃, 2-[OCH₂-(2-CH₃-cyclopropyl)]pyrimidin-4-yl |
| 1055 | 2-[OCH₂-(tetrahydropyran-2-yl)]pyrimidin-4-yl |
| 1056 | 5-[OCH₂-(tetrahydropyran-2-yl)]pyrimidin-4-yl |
| 1057 | 6-[OCH₂-(tetrahydropyran-2-yl)]pyrimidin-4-yl |
| 1058 | 6-F, 2-[OCH₂-(tetrahydropyran-2-yl)]pyrimidin-4-yl |
| 1059 | 2-F, 6-[OCH₂-(tetrahydropyran-2-yl)]pyrimidin-4-yl |
| 1060 | 5-F, 2-[OCH₂-(tetrahydropyran-2-yl)]pyrimidin-4-yl |
| 1061 | 6-CH₃, 2-[OCH₂-(tetrahydropyran-2-yl)]pyrimidin-4-yl |
| 1062 | 2-CH₃, 6-[OCH₂-(tetrahydropyran-2-yl)]pyrimidin-4-yl |
| 1063 | 5-CH₃, 2-[OCH₂-(tetrahydropyran-2-yl)]pyrimidin-4-yl |
| 1064 | 6-CF₃, 2-[OCH₂-(tetrahydropyran-2-yl)]pyrimidin-4-yl |
| 1065 | 2-CF₃, 6-[OCH₂-(tetrahydropyran-2-yl)]pyrimidin-4-yl |
| 1066 | 5-CF₃, 2-[OCH₂-(tetrahydropyran-2-yl)]pyrimidin-4-yl |
| 1067 | 2-[OCH₂-(furan-2-yl)]pyrimidin-4-yl |
| 1068 | 5-[OCH₂-(furan-2-yl)]pyrimidin-4-yl |
| 1069 | 6-[OCH₂-(furan-2-yl)]pyrimidin-4-yl |
| 1070 | 6-F, 2-[OCH₂-(furan-2-yl)]pyrimidin-4-yl |
| 1071 | 2-F, 6-[OCH₂-(furan-2-yl)]pyrimidin-4-yl |
| 1072 | 5-F, 2-[OCH₂-(furan-2-yl)]pyrimidin-4-yl |
| 1073 | 6-CH₃, 2-[OCH₂-(furan-2-yl)]pyrimidin-4-yl |
| 1074 | 2-CH₃, 6-[OCH₂-(furan-2-yl)]pyrimidin-4-yl |
| 1075 | 5-CH₃, 2-[OCH₂-(furan-2-yl)]pyrimidin-4-yl |
| 1076 | 6-CF₃, 2-[OCH₂-(furan-2-yl)]pyrimidin-4-yl |
| 1077 | 2-CF₃, 6-[OCH₂-(furan-2-yl)]pyrimidin-4-yl |
| 1078 | 5-CF₃, 2-[OCH₂-(furan-2-yl)]pyrimidin-4-yl |
| 1079 | 2-[OCH₂-(furan-3-yl)]pyrimidin-4-yl |
| 1080 | 5-[OCH₂-(furan-3-yl)]pyrimidin-4-yl |
| 1081 | 6-[OCH₂-(furan-3-yl)]pyrimidin-4-yl |
| 1082 | 6-F, 2-[OCH₂-(furan-3-yl)]pyrimidin-4-yl |
| 1083 | 2-F, 6-[OCH₂-(furan-3-yl)]pyrimidin-4-yl |
| 1084 | 5-F, 2-[OCH₂-(furan-3-yl)]pyrimidin-4-yl |
| 1085 | 6-CH₃, 2-[OCH₂-(furan-3-yl)]pyrimidin-4-yl |
| 1086 | 2-CH₃, 6-[OCH₂-(furan-3-yl)]pyrimidin-4-yl |
| 1087 | 5-CH₃, 2-[OCH₂-(furan-3-yl)]pyrimidin-4-yl |
| 1088 | 6-CF₃, 2-[OCH₂-(furan-3-yl)]pyrimidin-4-yl |
| 1089 | 2-CF₃, 6-[OCH₂-(furan-3-yl)]pyrimidin-4-yl |
| 1090 | 5-CF₃, 2-[OCH₂-(furan-3-yl)]pyrimidin-4-yl |
| 1091 | 2-[OCH₂-(tetrahydrofuran-3-yl)]pyrimidin-4-yl |
| 1092 | 5-[OCH₂-(tetrahydrofuran-3-yl)]pyrimidin-4-yl |
| 1093 | 6-[OCH₂-(tetrahydrofuran-3-yl)]pyrimidin-4-yl |
| 1094 | 6-F, 2-[OCH₂-(tetrahydrofuran-3-yl)]pyrimidin-4-yl |
| 1095 | 2-F, 6-[OCH₂-(tetrahydrofuran-3-yl)]pyrimidin-4-yl |
| 1096 | 5-F, 2-[OCH₂-(tetrahydrofuran-3-yl)]pyrimidin-4-yl |
| 1097 | 6-CH₃, 2-[OCH₂-(tetrahydrofuran-3-yl)]pyrimidin-4-yl |
| 1098 | 2-CH₃, 6-[OCH₂-(tetrahydrofuran-3-yl)]pyrimidin-4-yl |
| 1099 | 5-CH₃, 2-[OCH₂-(tetrahydrofuran-3-yl)]pyrimidin-4-yl |
| 1100 | 6-CF₃, 2-[OCH₂-(tetrahydrofuran-3-yl)]pyrimidin-4-yl |
| 1101 | 2-CF₃, 6-[OCH₂-(tetrahydrofuran-3-yl)]pyrimidin-4-yl |
| 1102 | 5-CF₃, 2-[OCH₂-(tetrahydrofuran-3-yl)]pyrimidin-4-yl |
| 1103 | 2-[OCH₂-(tetrahydrofuran-2-yl)]pyrimidin-4-yl |
| 1104 | 5-[OCH₂-(tetrahydrofuran-2-yl)]pyrimidin-4-yl |
| 1105 | 6-[OCH₂-(tetrahydrofuran-2-yl)]pyrimidin-4-yl |
| 1106 | 6-F, 2-[OCH₂-(tetrahydrofuran-2-yl)]pyrimidin-4-yl |
| 1107 | 2-F, 6-[OCH₂-(tetrahydrofuran-2-yl)]pyrimidin-4-yl |
| 1108 | 5-F, 2-[OCH₂-(tetrahydrofuran-2-yl)]pyrimidin-4-yl |
| 1109 | 6-CH₃, 2-[OCH₂-(tetrahydrofuran-2-yl)]pyrimidin-4-yl |
| 1110 | 2-CH₃, 6-[OCH₂-(tetrahydrofuran-2-yl)]pyrimidin-4-yl |
| 1111 | 5-CH₃, 2-[OCH₂-(tetrahydrofuran-2-yl)]pyrimidin-4-yl |
| 1112 | 6-CF₃, 2-[OCH₂-(tetrahydrofuran-2-yl)]pyrimidin-4-yl |
| 1113 | 2-CF₃, 6-[OCH₂-(tetrahydrofuran-2-yl)]pyrimidin-4-yl |
| 1114 | 5-CF₃, 2-[OCH₂-(tetrahydrofuran-2-yl)]pyrimidin-4-yl |
| 1115 | 2-[O-(tetrahydropyran-2-yl)]pyrimidin-4-yl |
| 1116 | 5-[O-(tetrahydropyran-2-yl)]pyrimidin-4-yl |
| 1117 | 6-[O-(tetrahydropyran-2-yl)]pyrimidin-4-yl |
| 1118 | 6-F, 2-[O-(tetrahydropyran-2-yl)]pyrimidin-4-yl |
| 1119 | 2-F, 6-[O-(tetrahydropyran-2-yl)]pyrimidin-4-yl |
| 1120 | 5-F, 2-[O-(tetrahydropyran-2-yl)]pyrimidin-4-yl |
| 1121 | 6-CH₃, 2-[O-(tetrahydropyran-2-yl)]pyrimidin-4-yl |
| 1122 | 2-CH₃, 6-[O-(tetrahydropyran-2-yl)]pyrimidin-4-yl |
| 1123 | 5-CH₃, 2-[O-(tetrahydropyran-2-yl)]pyrimidin-4-yl |
| 1124 | 6-CF₃, 2-[O-(tetrahydropyran-2-yl)]pyrimidin-4-yl |
| 1125 | 2-CF₃, 6-[O-(tetrahydropyran-2-yl)]pyrimidin-4-yl |
| 1126 | 5-CF₃, 2-[O-(tetrahydropyran-2-yl)]pyrimidin-4-yl |
| 1127 | 2-[2-Cl—C₆H₄]pyrimidin-4-yl |
| 1128 | 5-[2-Cl—C₆H₄]pyrimidin-4-yl |
| 1129 | 6-[2-Cl—C₆H₄]pyrimidin-4-yl |
| 1130 | 6-F, 2-[2-Cl—C₆H₄]pyrimidin-4-yl |
| 1131 | 2-F, 6-[2-Cl—C₆H₄]pyrimidin-4-yl |
| 1132 | 5-F, 2-[2-Cl—C₆H₄]pyrimidin-4-yl |
| 1133 | 6-CH₃, 2-[2-Cl—C₆H₄]pyrimidin-4-yl |
| 1134 | 2-CH₃, 6-[2-Cl—C₆H₄]pyrimidin-4-yl |
| 1135 | 5-CH₃, 2-[2-Cl—C₆H₄]pyrimidin-4-yl |
| 1136 | 6-CF₃, 2-[2-Cl—C₆H₄]pyrimidin-4-yl |
| 1137 | 2-CF₃, 6-[2-Cl—C₆H₄]pyrimidin-4-yl |
| 1138 | 5-CF₃, 2-[2-Cl—C₆H₄]pyrimidin-4-yl |
| 1139 | 2-[OCH₂-(pyridin-4-yl)]pyrimidin-4-yl |
| 1140 | 5-[OCH₂-(pyridin-4-yl)]pyrimidin-4-yl |
| 1141 | 6-[OCH₂-(pyridin-4-yl)]pyrimidin-4-yl |
| 1142 | 6-F, 2-[OCH₂-(pyridin-4-yl)]pyrimidin-4-yl |
| 1143 | 2-F, 6-[OCH₂-(pyridin-4-yl)]pyrimidin-4-yl |
| 1144 | 5-F, 2-[OCH₂-(pyridin-4-yl)]pyrimidin-4-yl |
| 1145 | 6-CH₃, 2-[OCH₂-(pyridin-4-yl)]pyrimidin-4-yl |
| 1146 | 2-CH₃, 6-[OCH₂-(pyridin-4-yl)]pyrimidin-4-yl |
| 1147 | 5-CH₃, 2-[OCH₂-(pyridin-4-yl)]pyrimidin-4-yl |
| 1148 | 6-CF₃, 2-[OCH₂-(pyridin-4-yl)]pyrimidin-4-yl |
| 1149 | 2-CF₃, 6-[OCH₂-(pyridin-4-yl)]pyrimidin-4-yl |
| 1150 | 5-CF₃, 2-[OCH₂-(pyridin-4-yl)]pyrimidin-4-yl |
| 1151 | 2-[OCH₂-(pyridin-3-yl)]pyrimidin-4-yl |
| 1152 | 5-[OCH₂-(pyridin-3-yl)]pyrimidin-4-yl |
| 1153 | 6-[OCH₂-(pyridin-3-yl)]pyrimidin-4-yl |
| 1154 | 6-F, 2-[OCH₂-(pyridin-3-yl)]pyrimidin-4-yl |
| 1155 | 2-F, 6-[OCH₂-(pyridin-3-yl)]pyrimidin-4-yl |
| 1156 | 5-F, 2-[OCH₂-(pyridin-3-yl)]pyrimidin-4-yl |
| 1157 | 6-CH₃, 2-[OCH₂-(pyridin-3-yl)]pyrimidin-4-yl |
| 1158 | 2-CH₃, 6-[OCH₂-(pyridin-3-yl)]pyrimidin-4-yl |
| 1159 | 5-CH₃, 2-[OCH₂-(pyridin-3-yl)]pyrimidin-4-yl |
| 1160 | 6-CF₃, 2-[OCH₂-(pyridin-3-yl)]pyrimidin-4-yl |
| 1161 | 2-CF₃, 6-[OCH₂-(pyridin-3-yl)]pyrimidin-4-yl |
| 1162 | 5-CF₃, 2-[OCH₂-(pyridin-3-yl)]pyrimidin-4-yl |
| 1163 | 2-[morpholin-2-yl]pyrimidin-4-yl |
| 1164 | 5-[morpholin-2-yl]pyrimidin-4-yl |
| 1165 | 6-[morpholin-2-yl]pyrimidin-4-yl |
| 1166 | 2-[1-CH₃-imidazol-2-yl]pyrimidin-4-yl |
| 1167 | 5-[1-CH₃-imidazol-2-yl]pyrimidin-4-yl |
| 1168 | 6-[1-CH₃-imidazol-2-yl]pyrimidin-4-yl |
| 1169 | 6-F, 2-[1-CH₃-imidazol-2-yl]pyrimidin-4-yl |
| 1170 | 2-F, 6-[1-CH₃-imidazol-2-yl]pyrimidin-4-yl |
| 1171 | 5-F, 2-[1-CH₃-imidazol-2-yl]pyrimidin-4-yl |
| 1172 | 6-CH₃, 2-[1-CH₃-imidazol-2-yl]pyrimidin-4-yl |
| 1173 | 2-CH₃, 6-[1-CH₃-imidazol-2-yl]pyrimidin-4-yl |
| 1174 | 5-CH₃, 2-[1-CH₃-imidazol-2-yl]pyrimidin-4-yl |
| 1175 | 6-CF₃, 2-[1-CH₃-imidazol-2-yl]pyrimidin-4-yl |
| 1176 | 2-CF₃, 6-[1-CH₃-imidazol-2-yl]pyrimidin-4-yl |
| 1177 | 5-CF₃, 2-[1-CH₃-imidazol-2-yl]pyrimidin-4-yl |
| 1178 | 2-[1,2,2-triazol-1-yl]pyrimidin-4-yl |
| 1179 | 5-[1,2,2-triazol-1-yl]pyrimidin-4-yl |
| 1180 | 6-[1,2,2-triazol-1-yl]pyrimidin-4-yl |
| 1181 | 6-F, 2-[1,2,2-triazol-1-yl]pyrimidin-4-yl |
| 1182 | 2-F, 6-[1,2,2-triazol-1-yl]pyrimidin-4-yl |
| 1183 | 5-F, 2-[1,2,2-triazol-1-yl]pyrimidin-4-yl |
| 1184 | 6-CH₃, 2-[1,2,2-triazol-1-yl]pyrimidin-4-yl |
| 1185 | 2-CH₃, 6-[1,2,2-triazol-1-yl]pyrimidin-4-yl |
| 1186 | 5-CH₃, 2-[1,2,2-triazol-1-yl]pyrimidin-4-yl |
| 1187 | 6-CF₃, 2-[1,2,2-triazol-1-yl]pyrimidin-4-yl |

TABLE A-continued

| No. | R⁴ |
|---|---|
| 1188 | 2-CF₃, 6-[1,2,2-triazol-1-yl]pyrimidin-4-yl |
| 1189 | 5-CF₃, 2-[1,2,2-triazol-1-yl]pyrimidin-4-yl |
| 1190 | 2,5-Cl₂-pyrimidin-4-yl |
| 1191 | 2,6-Cl₂-pyrimidin-4-yl |
| 1192 | 5,6-Cl₂-pyrimidin-4-yl |
| 1193 | 2,5-(CH₃)₂-pyrimidin-4-yl |
| 1194 | 2,6-(CH₃)₂-pyrimidin-4-yl |
| 1195 | 5,6-(CH₃)₂-pyrimidin-4-yl |
| 1196 | 2,5-(OCH₃)₂-pyrimidin-4-yl |
| 1197 | 2,6-(OCH₃)₂-pyrimidin-4-yl |
| 1198 | 5,6-(OCH₃)₂-pyrimidin-4-yl |
| 1199 | 2,5-(OCH₂CH₃)₂-pyrimidin-4-yl |
| 1200 | 2,6-(OCH₂CH₃)₂-pyrimidin-4-yl |
| 1201 | 5,6-(OCH₂CH₃)₂-pyrimidin-4-yl |
| 1202 | 2-F, 5-CH₃-pyrimidin-4-yl |
| 1203 | 2-F, 6-CH₃-pyrimidin-4-yl |
| 1204 | 5-F, 6-CH₃-pyrimidin-4-yl |
| 1205 | 5-F, 2-CH₃-pyrimidin-4-yl |
| 1206 | 6-F, 2-CH₃-pyrimidin-4-yl |
| 1207 | 6-F, 5-CH₃-pyrimidin-4-yl |
| 1208 | 2-F, 5-OCH₃-pyrimidin-4-yl |
| 1209 | 2-F, 6-OCH₃-pyrimidin-4-yl |
| 1210 | 5-F, 6-OCH₃-pyrimidin-4-yl |
| 1211 | 5-F, 2-OCH₃-pyrimidin-4-yl |
| 1212 | 6-F, 2-OCH₃-pyrimidin-4-yl |
| 1213 | 6-F, 5-OCH₃-pyrimidin-4-yl |
| 1214 | 2-F, 5-OCH₂CH₃-pyrimidin-4-yl |
| 1215 | 2-F, 6-OCH₂CH₃-pyrimidin-4-yl |
| 1216 | 5-F, 6-OCH₂CH₃-pyrimidin-4-yl |
| 1217 | 5-F, 2-OCH₂CH₃-pyrimidin-4-yl |
| 1218 | 6-F, 2-OCH₂CH₃-pyrimidin-4-yl |
| 1219 | 6-F, 5-OCH₂CH₃-pyrimidin-4-yl |
| 1220 | 2-F, 5-OCH₂CF₃-pyrimidin-4-yl |
| 1221 | 2-F, 6-OCH₂CF₃-pyrimidin-4-yl |
| 1222 | 5-F, 6-OCH₂CF₃-pyrimidin-4-yl |
| 1223 | 5-F, 2-OCH₂CF₃-pyrimidin-4-yl |
| 1224 | 6-F, 2-OCH₂CF₃-pyrimidin-4-yl |
| 1225 | 6-F, 5-OCH₂CF₃-pyrimidin-4-yl |
| 1226 | 2-F, 5-OCH(CH₃)₂-pyrimidin-4-yl |
| 1227 | 2-F, 6-OCH(CH₃)₂-pyrimidin-4-yl |
| 1228 | 5-F, 6-OCH(CH₃)₂-pyrimidin-4-yl |
| 1229 | 5-F, 2-OCH(CH₃)₂-pyrimidin-4-yl |
| 1230 | 6-F, 2-OCH(CH₃)₂-pyrimidin-4-yl |
| 1231 | 6-F, 5-OCH(CH₃)₂-pyrimidin-4-yl |
| 1232 | 2-Cl, 5-CH₃-pyrimidin-4-yl |
| 1233 | 2-Cl, 6-CH₃-pyrimidin-4-yl |
| 1234 | 5-Cl, 6-CH₃-pyrimidin-4-yl |
| 1235 | 5-Cl, 2-CH₃-pyrimidin-4-yl |
| 1236 | 6-Cl, 2-CH₃-pyrimidin-4-yl |
| 1237 | 6-Cl, 5-CH₃-pyrimidin-4-yl |
| 1238 | 2-Cl, 5-OCH₃-pyrimidin-4-yl |
| 1239 | 2-Cl, 6-OCH₃-pyrimidin-4-yl |
| 1240 | 5-Cl, 6-OCH₃-pyrimidin-4-yl |
| 1241 | 5-Cl, 2-OCH₃-pyrimidin-4-yl |
| 1242 | 6-Cl, 2-OCH₃-pyrimidin-4-yl |
| 1243 | 6-Cl, 5-OCH₃-pyrimidin-4-yl |
| 1244 | 2-Cl, 5-OCH₂CH₃-pyrimidin-4-yl |
| 1245 | 2-Cl, 6-OCH₂CH₃-pyrimidin-4-yl |
| 1246 | 5-Cl, 6-OCH₂CH₃-pyrimidin-4-yl |
| 1247 | 5-Cl, 2-OCH₂CH₃-pyrimidin-4-yl |
| 1248 | 6-Cl, 2-OCH₂CH₃-pyrimidin-4-yl |
| 1249 | 6-Cl, 5-OCH₂CH₃-pyrimidin-4-yl |
| 1250 | 2-Cl, 5-OCH₂CF₃-pyrimidin-4-yl |
| 1251 | 2-Cl, 6-OCH₂CF₃-pyrimidin-4-yl |
| 1252 | 5-Cl, 6-OCH₂CF₃-pyrimidin-4-yl |
| 1253 | 5-Cl, 2-OCH₂CF₃-pyrimidin-4-yl |
| 1254 | 6-Cl, 2-OCH₂CF₃-pyrimidin-4-yl |
| 1255 | 6-Cl, 5-OCH₂CF₃-pyrimidin-4-yl |
| 1256 | 2-Cl, 5-OCH(CH₃)₂-pyrimidin-4-yl |
| 1257 | 2-Cl, 6-OCH(CH₃)₂-pyrimidin-4-yl |
| 1258 | 5-Cl, 6-OCH(CH₃)₂-pyrimidin-4-yl |
| 1259 | 5-Cl, 2-OCH(CH₃)₂-pyrimidin-4-yl |
| 1260 | 6-Cl, 2-OCH(CH₃)₂-pyrimidin-4-yl |
| 1261 | 6-Cl, 5-OCH(CH₃)₂-pyrimidin-4-yl |
| 1262 | 2-CH₃, 5-OCH₃-pyrimidin-4-yl |
| 1263 | 2-CH₃, 6-OCH₃-pyrimidin-4-yl |
| 1264 | 5-CH₃, 6-OCH₃-pyrimidin-4-yl |
| 1265 | 5-CH₃, 2-OCH₃-pyrimidin-4-yl |
| 1266 | 6-CH₃, 2-OCH₃-pyrimidin-4-yl |
| 1267 | 6-CH₃, 5-OCH₃-pyrimidin-4-yl |
| 1268 | 2-CH₃, 5-OCH₂CH₃-pyrimidin-4-yl |
| 1269 | 2-CH₃, 6-OCH₂CH₃-pyrimidin-4-yl |
| 1270 | 5-CH₃, 6-OCH₂CH₃-pyrimidin-4-yl |
| 1271 | 5-CH₃, 2-OCH₂CH₃-pyrimidin-4-yl |
| 1272 | 6-CH₃, 2-OCH₂CH₃-pyrimidin-4-yl |
| 1273 | 6-CH₃, 5-OCH₂CH₃-pyrimidin-4-yl |
| 1274 | 2-CH₃, 5-OCH₂CF₃-pyrimidin-4-yl |
| 1275 | 2-CH₃, 6-OCH₂CF₃-pyrimidin-4-yl |
| 1276 | 5-CH₃, 6-OCH₂CF₃-pyrimidin-4-yl |
| 1277 | 5-CH₃, 2-OCH₂CF₃-pyrimidin-4-yl |
| 1278 | 6-CH₃, 2-OCH₂CF₃-pyrimidin-4-yl |
| 1279 | 6-CH₃, 5-OCH₂CF₃-pyrimidin-4-yl |
| 1280 | 2-CH₃, 5-OCH(CH₃)₂-pyrimidin-4-yl |
| 1281 | 2-CH₃, 5-OCH(CH₃)₂-pyrimidin-4-yl |
| 1282 | 5-CH₃, 6-OCH(CH₃)₂-pyrimidin-4-yl |
| 1283 | 5-CH₃, 2-OCH(CH₃)₂-pyrimidin-4-yl |
| 1284 | 6-CH₃, 2-OCH(CH₃)₂-pyrimidin-4-yl |
| 1285 | 6-CH₃, 5-OCH(CH₃)₂-pyrimidin-4-yl |
| 1286 | 2-CH₃, 5-OCH₂CH=CH₂-pyrimidin-4-yl |
| 1287 | 2-CH₃, 6-OCH₂CH=CH₂-pyrimidin-4-yl |
| 1288 | 5-CH₃, 6-OCH₂CH=CH₂-pyrimidin-4-yl |
| 1289 | 5-CH₃, 2-OCH₂CH=CH₂-pyrimidin-4-yl |
| 1290 | 6-CH₃, 2-OCH₂CH=CH₂-pyrimidin-4-yl |
| 1291 | 6-CH₃, 5-OCH₂CH=CH₂-pyrimidin-4-yl |
| 1292 | 2-CH₃, 5-CO₂CH₃-pyrimidin-4-yl |
| 1293 | 2-CH₃, 6-CO₂CH₃-pyrimidin-4-yl |
| 1294 | 5-CH₃, 6-CO₂CH₃-pyrimidin-4-yl |
| 1295 | 2-CH₃, 5-CF₃-pyrimidin-4-yl |
| 1296 | 2-CH₃, 6-CF₃-pyrimidin-4-yl |
| 1297 | 5-CH₃, 6-CF₃-pyrimidin-4-yl |
| 1298 | 5-CH₃, 2-CF₃-pyrimidin-4-yl |
| 1299 | 6-CH₃, 2-CF₃-pyrimidin-4-yl |
| 1300 | 6-CH₃, 5-CF₃-pyrimidin-4-yl |
| 1301 | 2-CF₃, 5-CH₂CH₃-pyrimidin-4-yl |
| 1302 | 2-CF₃, 6-CH₂CH₃-pyrimidin-4-yl |
| 1303 | 5-CF₃, 6-CH₂CH₃-pyrimidin-4-yl |
| 1304 | 5-CF₃, 2-CH₂CH₃-pyrimidin-4-yl |
| 1305 | 6-CF₃, 2-CH₂CH₃-pyrimidin-4-yl |
| 1306 | 6-CF₃, 5-CH₂CH₃-pyrimidin-4-yl |
| 1307 | 2-CF₃, 5-OCH₃-pyrimidin-4-yl |
| 1308 | 2-CF₃, 6-OCH₃-pyrimidin-4-yl |
| 1309 | 5-CF₃, 6-OCH₃-pyrimidin-4-yl |
| 1310 | 5-CF₃, 2-OCH₃-pyrimidin-4-yl |
| 1311 | 6-CF₃, 2-OCH₃-pyrimidin-4-yl |
| 1312 | 6-CF₃, 5-OCH₃-pyrimidin-4-yl |
| 1313 | 2-CF₃, 5-OCH₂CH₃-pyrimidin-4-yl |
| 1314 | 2-CF₃, 6-OCH₂CH₃-pyrimidin-4-yl |
| 1315 | 5-CF₃, 6-OCH₂CH₃-pyrimidin-4-yl |
| 1316 | 5-CF₃, 2-OCH₂CH₃-pyrimidin-4-yl |
| 1317 | 6-CF₃, 2-OCH₂CH₃-pyrimidin-4-yl |
| 1318 | 6-CF₃, 5-OCH₂CH₃-pyrimidin-4-yl |
| 1319 | 2-CF₃, 5-OCH₂CF₃-pyrimidin-4-yl |
| 1320 | 2-CF₃, 6-OCH₂CF₃-pyrimidin-4-yl |
| 1321 | 5-CF₃, 6-OCH₂CF₃-pyrimidin-4-yl |
| 1322 | 5-CF₃, 2-OCH₂CF₃-pyrimidin-4-yl |
| 1323 | 6-CF₃, 2-OCH₂CF₃-pyrimidin-4-yl |
| 1324 | 6-CF₃, 5-OCH₂CF₃-pyrimidin-4-yl |
| 1325 | 2-OCH₃, 5-OCH₂CH₃-pyrimidin-4-yl |
| 1326 | 2-OCH₃, 6-OCH₂CH₃-pyrimidin-4-yl |
| 1327 | 5-OCH₃, 6-OCH₂CH₃-pyrimidin-4-yl |
| 1328 | 5-OCH₃, 2-OCH₂CH₃-pyrimidin-4-yl |
| 1329 | 6-OCH₃, 2-OCH₂CH₃-pyrimidin-4-yl |
| 1330 | 6-OCH₃, 5-OCH₂CH₃-pyrimidin-4-yl |
| 1331 | 2-OCH₃, 5-OCH₂CF₃-pyrimidin-4-yl |
| 1332 | 2-OCH₃, 6-OCH₂CF₃-pyrimidin-4-yl |
| 1333 | 5-OCH₃, 6-OCH₂CF₃-pyrimidin-4-yl |
| 1334 | 5-OCH₃, 2-OCH₂CF₃-pyrimidin-4-yl |
| 1335 | 6-OCH₃, 2-OCH₂CF₃-pyrimidin-4-yl |
| 1336 | 6-OCH₃, 5-OCH₂CF₃-pyrimidin-4-yl |
| 1337 | 2-OCH₃, 5-OCH(CH₃)-pyrimidin-4-yl |
| 1338 | 2-OCH₃, 6-OCH(CH₃)-pyrimidin-4-yl |
| 1339 | 5-OCH₃, 6-OCH(CH₃)-pyrimidin-4-yl |
| 1340 | 5-OCH₃, 2-OCH(CH₃)-pyrimidin-4-yl |
| 1341 | 6-OCH₃, 2-OCH(CH₃)-pyrimidin-4-yl |

TABLE A-continued

| No. | R⁴ |
|---|---|
| 1342 | 6-OCH$_3$, 5-OCH(CH$_3$)-pyrimidin-4-yl |
| 1343 | 2-OCH$_2$CH$_3$, 5-CH$_2$OCH$_2$CH$_3$-pyrimidin-4-yl |
| 1344 | 2-OCH$_2$CH$_3$, 6-CH$_2$OCH$_2$CH$_3$-pyrimidin-4-yl |
| 1345 | 5-OCH$_2$CH$_3$, 6-CH$_2$OCH$_2$CH$_3$-pyrimidin-4-yl |
| 1346 | 5-OCH$_2$CH$_3$, 2-CH$_2$OCH$_2$CH$_3$-pyrimidin-4-yl |
| 1347 | 6-OCH$_2$CH$_3$, 2-CH$_2$OCH$_2$CH$_3$-pyrimidin-4-yl |
| 1348 | 6-OCH$_2$CH$_3$, 5-CH$_2$OCH$_2$CH$_3$-pyrimidin-4-yl |
| 1349 | 2-NO$_2$, 5-CH$_3$-pyrimidin-4-yl |
| 1350 | 2-NO$_2$, 6-CH$_3$-pyrimidin-4-yl |
| 1351 | 5-NO$_2$, 6-CH$_3$-pyrimidin-4-yl |
| 1352 | 5-NO$_2$, 2-CH$_3$-pyrimidin-4-yl |
| 1353 | 6-NO$_2$, 2-CH$_3$-pyrimidin-4-yl |
| 1354 | 6-NO$_2$, 5-CH$_3$-pyrimidin-4-yl |
| 1355 | 2-NO$_2$, 5-OCH$_3$-pyrimidin-4-yl |
| 1356 | 2-NO$_2$, 6-OCH$_3$-pyrimidin-4-yl |
| 1357 | 5-NO$_2$, 6-OCH$_3$-pyrimidin-4-yl |
| 1358 | 5-NO$_2$, 2-OCH$_3$-pyrimidin-4-yl |
| 1359 | 6-NO$_2$, 2-OCH$_3$-pyrimidin-4-yl |
| 1360 | 6-NO$_2$, 5-OCH$_3$-pyrimidin-4-yl |
| 1361 | 2-NO$_2$, 5-OCH$_2$CH$_3$-pyrimidin-4-yl |
| 1362 | 2-NO$_2$, 6-OCH$_2$CH$_3$-pyrimidin-4-yl |
| 1363 | 5-NO$_2$, 6-OCH$_2$CH$_3$-pyrimidin-4-yl |
| 1364 | 5-NO$_2$, 2-OCH$_2$CH$_3$-pyrimidin-4-yl |
| 1365 | 6-NO$_2$, 2-OCH$_2$CH$_3$-pyrimidin-4-yl |
| 1366 | 6-NO$_2$, 5-OCH$_2$CH$_3$-pyrimidin-4-yl |
| 1367 | 2-NO$_2$, 5-OCH(CH$_3$)$_2$-pyrimidin-4-yl |
| 1368 | 2-NO$_2$, 6-OCH(CH$_3$)$_2$-pyrimidin-4-yl |
| 1369 | 5-NO$_2$, 6-OCH(CH$_3$)$_2$-pyrimidin-4-yl |
| 1370 | 5-NO$_2$, 2-OCH(CH$_3$)$_2$-pyrimidin-4-yl |
| 1371 | 6-NO$_2$, 2-OCH(CH$_3$)$_2$-pyrimidin-4-yl |
| 1372 | 6-NO$_2$, 5-OCH(CH$_3$)$_2$-pyrimidin-4-yl |
| 1373 | 2-NO$_2$, 5-OCH$_2$CF$_3$-pyrimidin-4-yl |
| 1374 | 2-NO$_2$, 6-OCH$_2$CF$_3$-pyrimidin-4-yl |
| 1375 | 5-NO$_2$, 6-OCH$_2$CF$_3$-pyrimidin-4-yl |
| 1376 | 5-NO$_2$, 2-OCH$_2$CF$_3$-pyrimidin-4-yl |
| 1377 | 6-NO$_2$, 2-OCH$_2$CF$_3$-pyrimidin-4-yl |
| 1378 | 6-NO$_2$, 5-OCH$_2$CF$_3$-pyrimidin-4-yl |
| 1379 | 2-CN, 5-CH$_3$-pyrimidin-4-yl |
| 1380 | 2-CN, 6-CH$_3$-pyrimidin-4-yl |
| 1381 | 5-CN, 6-CH$_3$-pyrimidin-4-yl |
| 1382 | 5-CN, 2-CH$_3$-pyrimidin-4-yl |
| 1383 | 6-CN, 2-CH$_3$-pyrimidin-4-yl |
| 1384 | 6-CN, 5-CH$_3$-pyrimidin-4-yl |
| 1385 | 2-CN, 5-OCH$_3$-pyrimidin-4-yl |
| 1386 | 2-CN, 6-OCH$_3$-pyrimidin-4-yl |
| 1387 | 5-CN, 6-OCH$_3$-pyrimidin-4-yl |
| 1388 | 5-CN, 2-OCH$_3$-pyrimidin-4-yl |
| 1389 | 6-CN, 2-OCH$_3$-pyrimidin-4-yl |
| 1390 | 6-CN, 5-OCH$_3$-pyrimidin-4-yl |
| 1391 | 2-CN, 5-OCH$_2$CH$_3$-pyrimidin-4-yl |
| 1392 | 2-CN, 6-OCH$_2$CH$_3$-pyrimidin-4-yl |
| 1393 | 5-CN, 6-OCH$_2$CH$_3$-pyrimidin-4-yl |
| 1394 | 5-CN, 2-OCH$_2$CH$_3$-pyrimidin-4-yl |
| 1395 | 6-CN, 2-OCH$_2$CH$_3$-pyrimidin-4-yl |
| 1396 | 6-CN, 5-OCH$_2$CH$_3$-pyrimidin-4-yl |
| 1397 | 2-CN, 5-OCH(CH$_3$)$_2$-pyrimidin-4-yl |
| 1398 | 2-CN, 6-OCH(CH$_3$)$_2$-pyrimidin-4-yl |
| 1399 | 5-CN, 6-OCH(CH$_3$)$_2$-pyrimidin-4-yl |
| 1400 | 5-CN, 2-OCH(CH$_3$)$_2$-pyrimidin-4-yl |
| 1401 | 6-CN, 2-OCH(CH$_3$)$_2$-pyrimidin-4-yl |
| 1402 | 6-CN, 5-OCH(CH$_3$)$_2$-pyrimidin-4-yl |
| 1403 | 2-CN, 5-OCH$_2$CF$_3$-pyrimidin-4-yl |
| 1404 | 2-CN, 6-OCH$_2$CF$_3$-pyrimidin-4-yl |
| 1405 | 5-CN, 6-OCH$_2$CF$_3$-pyrimidin-4-yl |
| 1406 | 5-CN, 2-OCH$_2$CF$_3$-pyrimidin-4-yl |
| 1407 | 6-CN, 2-OCH$_2$CF$_3$-pyrimidin-4-yl |
| 1408 | 6-CN, 5-OCH$_2$CF$_3$-pyrimidin-4-yl |
| 1409 | 2,5-(CH$_3$)$_2$, 6-OCH$_3$-pyrimidin-4-yl |
| 1410 | 2,6-(CH$_3$)$_2$, 5-OCH$_3$-pyrimidin-4-yl |
| 1411 | 5,6-(CH$_3$)$_2$, 2-OCH$_3$-pyrimidin-4-yl |
| 1412 | 4-CH$_3$-pyrimidin-5-yl |
| 1413 | 2-CH$_3$-pyrimidin-5-yl |
| 1414 | 4-CH$_2$CH$_3$-pyrimidin-5-yl |
| 1415 | 2-CH$_2$CH$_3$-pyrimidin-5-yl |
| 1416 | 4-CH(CH$_3$)$_2$-pyrimidin-5-yl |
| 1417 | 2-CH(CH$_3$)$_2$-pyrimidin-5-yl |
| 1418 | 4-CH(CH$_3$)CH$_2$CH$_3$-pyrimidin-5-yl |
| 1419 | 2-CH(CH$_3$)CH$_2$CH$_3$-pyrimidin-5-yl |
| 1420 | 4-CF$_3$-pyrimidin-5-yl |
| 1421 | 2-CF$_3$-pyrimidin-5-yl |
| 1422 | 4-CH=CH$_2$-pyrimidin-5-yl |
| 1423 | 2-CH=CH$_2$-pyrimidin-5-yl |
| 1424 | 4-CH=CHCH$_3$-pyrimidin-5-yl |
| 1425 | 2-CH=CHCH$_3$-pyrimidin-5-yl |
| 1426 | 4-CH=CHCl-pyrimidin-5-yl |
| 1427 | 2-CH=CHCl-pyrimidin-5-yl |
| 1428 | 4-C≡CH-pyrimidin-5-yl |
| 1429 | 2-C≡CH-pyrimidin-5-yl |
| 1430 | 4-CH$_2$C≡CH-pyrimidin-5-yl |
| 1431 | 2-CH$_2$C≡CH-pyrimidin-5-yl |
| 1432 | 4-CH$_2$C≡CCH$_3$-pyrimidin-5-yl |
| 1433 | 2-CH$_2$C≡CCH$_3$-pyrimidin-5-yl |
| 1434 | 4-cyclopropylpyrimidin-5-yl |
| 1435 | 2-cyclopropylpyrimidin-5-yl |
| 1436 | 4-cyclopentylpyrimidin-5-yl |
| 1437 | 2-cyclopentylpyrimidin-5-yl |
| 1438 | 4-OCH$_3$-pyrimidin-5-yl |
| 1439 | 2-OCH$_3$-pyrimidin-5-yl |
| 1440 | 4-OCH$_2$CH$_3$-pyrimidin-5-yl |
| 1441 | 2-OCH$_2$CH$_3$-pyrimidin-5-yl |
| 1442 | 4-OCH$_2$CH$_2$CH$_3$-pyrimidin-5-yl |
| 1443 | 2-OCH$_2$CH$_2$CH$_3$-pyrimidin-5-yl |
| 1444 | 4-OCH(CH$_3$)$_2$-pyrimidin-5-yl |
| 1445 | 2-OCH(CH$_3$)$_2$-pyrimidin-5-yl |
| 1446 | 4-OCH$_2$CH$_2$CH$_2$CH$_3$-pyrimidin-5-yl |
| 1447 | 2-OCH$_2$CH$_2$CH$_2$CH$_3$-pyrimidin-5-yl |
| 1448 | 4-OCH(CH$_3$)CH$_2$CH$_3$-pyrimidin-5-yl |
| 1449 | 2-OCH(CH$_3$)CH$_2$CH$_3$-pyrimidin-5-yl |
| 1450 | 4-OCH$_2$CH(CH$_3$)$_2$-pyrimidin-5-yl |
| 1451 | 2-OCH$_2$CH(CH$_3$)$_2$-pyrimidin-5-yl |
| 1452 | 4-OC(CH$_3$)$_3$-pyrimidin-5-yl |
| 1453 | 2-OC(CH$_3$)$_3$-pyrimidin-5-yl |
| 1454 | 4-OCH(CH$_3$)CH$_2$CH$_2$CH$_3$-pyrimidin-5-yl |
| 1455 | 2-OCH(CH$_3$)CH$_2$CH$_2$CH$_3$-pyrimidin-5-yl |
| 1456 | 4-OCH$_2$OCH$_3$-pyrimidin-5-yl |
| 1457 | 2-OCH$_2$OCH$_3$-pyrimidin-5-yl |
| 1458 | 4-OCH$_2$OCH$_2$CH$_3$-pyrimidin-5-yl |
| 1459 | 2-OCH$_2$OCH$_2$CH$_3$-pyrimidin-5-yl |
| 1460 | 4-OCH(CH$_3$)OCH$_3$-pyrimidin-5-yl |
| 1461 | 2-OCH(CH$_3$)OCH$_3$-pyrimidin-5-yl |
| 1462 | 4-OCH(CH$_3$)OCH$_2$CH$_3$-pyrimidin-5-yl |
| 1463 | 2-OCH(CH$_3$)OCH$_2$CH$_3$-pyrimidin-5-yl |
| 1464 | 4-OCH$_2$CH$_2$OCH$_3$-pyrimidin-5-yl |
| 1465 | 2-OCH$_2$CH$_2$OCH$_3$-pyrimidin-5-yl |
| 1466 | 4-OCH$_2$CH$_2$OCH$_2$CH$_3$-pyrimidin-5-yl |
| 1467 | 2-OCH$_2$CH$_2$OCH$_2$CH$_3$-pyrimidin-5-yl |
| 1468 | 4-OCH$_2$CH$_2$OCH(CH$_3$)$_2$-pyrimidin-5-yl |
| 1469 | 2-OCH$_2$CH$_2$OCH(CH$_3$)$_2$-pyrimidin-5-yl |
| 1470 | 4-OCH$_2$CH$_2$SCH$_3$-pyrimidin-5-yl |
| 1471 | 2-OCH$_2$CH$_2$SCH$_3$-pyrimidin-5-yl |
| 1472 | 4-OCH$_2$CH$_2$SO$_2$CH$_3$-pyrimidin-5-yl |
| 1473 | 2-OCH$_2$CH$_2$SO$_2$CH$_3$-pyrimidin-5-yl |
| 1474 | 4-OCH$_2$CH$_2$SCH(CH$_3$)$_2$-pyrimidin-5-yl |
| 1475 | 2-OCH$_2$CH$_2$SCH(CH$_3$)$_2$-pyrimidin-5-yl |
| 1476 | 4-OCH$_2$CH$_2$CN-pyrimidin-5-yl |
| 1477 | 2-OCH$_2$CH$_2$CN-pyrimidin-5-yl |
| 1478 | 4-OCH$_2$CH$_2$SCH$_2$CH$_2$CN-pyrimidin-5-yl |
| 1479 | 2-OCH$_2$CH$_2$SCH$_2$CH$_2$CN-pyrimidin-5-yl |
| 1480 | 4-OCH$_2$CH$_2$OC$_6$H$_2$-pyrimidin-5-yl |
| 1481 | 2-OCH$_2$CH$_2$OC$_6$H$_2$-pyrimidin-5-yl |
| 1482 | 4-OCH$_2$CH$_2$OCH$_2$C$_6$H$_2$-pyrimidin-5-yl |
| 1483 | 2-OCH$_2$CH$_2$OCH$_2$C$_6$H$_2$-pyrimidin-5-yl |
| 1484 | 4-OCH$_2$CH$_2$N(CH$_3$)$_2$-pyrimidin-5-yl |
| 1485 | 2-OCH$_2$CH$_2$N(CH$_3$)$_2$-pyrimidin-5-yl |
| 1486 | 4-OCH$_2$CH$_2$CONH$_2$-pyrimidin-5-yl |
| 1487 | 2-OCH$_2$CH$_2$CONH$_2$-pyrimidin-5-yl |
| 1488 | 4-OCH$_2$CH$_2$CO$_2$CH$_2$CH$_3$-pyrimidin-5-yl |
| 1489 | 2-OCH$_2$CH$_2$CO$_2$CH$_2$CH$_3$-pyrimidin-5-yl |
| 1490 | 4-OCH(CH$_3$)CH$_2$OCH$_3$-pyrimidin-5-yl |
| 1491 | 2-OCH(CH$_3$)CH$_2$OCH$_3$-pyrimidin-5-yl |
| 1492 | 4-OCH(CH$_3$)CH$_2$CO$_2$CH$_3$-pyrimidin-5-yl |
| 1493 | 2-OCH(CH$_3$)CH$_2$CO$_2$CH$_3$-pyrimidin-5-yl |
| 1494 | 4-OCH(CH$_3$)CH$_2$CO$_2$CH$_2$CH$_3$-pyrimidin-5-yl |
| 1495 | 2-OCH(CH$_3$)CH$_2$CO$_2$CH$_2$CH$_3$-pyrimidin-5-yl |

TABLE A-continued

| No. | R⁴ |
|---|---|
| 1496 | 4-OCH$_2$CH(CH$_3$)CO$_2$CH$_3$-pyrimidin-5-yl |
| 1497 | 2-OCH$_2$CH(CH$_3$)CO$_2$CH$_3$-pyrimidin-5-yl |
| 1498 | 4-OCH$_2$C(=O)CH$_3$-pyrimidin-5-yl |
| 1499 | 2-OCH$_2$C(=O)CH$_3$-pyrimidin-5-yl |
| 1500 | 4-OCH$_2$C(=O)CH$_2$CH$_3$-pyrimidin-5-yl |
| 1501 | 2-OCH$_2$C(=O)CH$_2$CH$_3$-pyrimidin-5-yl |
| 1502 | 4-OCH$_2$CO$_2$CH$_3$-pyrimidin-5-yl |
| 1503 | 2-OCH$_2$CO$_2$CH$_3$-pyrimidin-5-yl |
| 1504 | 4-OCH$_2$CO$_2$CH$_2$CH$_3$-pyrimidin-5-yl |
| 1505 | 2-OCH$_2$CO$_2$CH$_2$CH$_3$-pyrimidin-5-yl |
| 1506 | 4-OCH$_2$C(=O)NH$_2$-pyrimidin-5-yl |
| 1507 | 2-OCH$_2$C(=O)NH$_2$-pyrimidin-5-yl |
| 1508 | 4-OCH$_2$C(=O)NHCH$_3$-pyrimidin-5-yl |
| 1509 | 2-OCH$_2$C(=O)NHCH$_3$-pyrimidin-5-yl |
| 1510 | 4-OCH$_2$C(=O)SCH$_3$-pyrimidin-5-yl |
| 1511 | 2-OCH$_2$C(=O)SCH$_3$-pyrimidin-5-yl |
| 1512 | 4-OCH(CH$_3$)C(=O)NH$_2$-pyrimidin-5-yl |
| 1513 | 2-OCH(CH$_3$)C(=O)NH$_2$-pyrimidin-5-yl |
| 1514 | 4-OCH(CH$_3$)C(=O)NHCH$_3$-pyrimidin-5-yl |
| 1515 | 2-OCH(CH$_3$)C(=O)NHCH$_3$-pyrimidin-5-yl |
| 1516 | 4-OCH(CH$_3$)C(=O)NHNH$_2$-pyrimidin-5-yl |
| 1517 | 2-OCH(CH$_3$)C(=O)NHNH$_2$-pyrimidin-5-yl |
| 1518 | 4-OCH(CH$_3$)CO$_2$CH$_3$-pyrimidin-5-yl |
| 1519 | 2-OCH(CH$_3$)CO$_2$CH$_3$-pyrimidin-5-yl |
| 1520 | 4-OCH(CH$_3$)CO$_2$CH$_2$CH$_3$-pyrimidin-5-yl |
| 1521 | 2-OCH(CH$_3$)CO$_2$CH$_2$CH$_3$-pyrimidin-5-yl |
| 1522 | 4-OCH(CH$_3$)C(=O)CH$_3$-pyrimidin-5-yl |
| 1523 | 2-OCH(CH$_3$)C(=O)CH$_3$-pyrimidin-5-yl |
| 1524 | 4-OCH(CH$_3$)C(=O)CH$_2$CH$_3$-pyrimidin-5-yl |
| 1525 | 2-OCH(CH$_3$)C(=O)CH$_2$CH$_3$-pyrimidin-5-yl |
| 1526 | 4-OCH(CH$_3$)CH$_2$C(=O)CH$_3$-pyrimidin-5-yl |
| 1527 | 2-OCH(CH$_3$)CH$_2$C(=O)CH$_3$-pyrimidin-5-yl |
| 1528 | 4-OCH(CH$_3$)CH$_2$OC(CH$_3$)$_3$-pyrimidin-5-yl |
| 1529 | 2-OCH(CH$_3$)CH$_2$OC(CH$_3$)$_3$-pyrimidin-5-yl |
| 1530 | 4-OCH(CH$_3$)CH$_2$OCH$_2$CH$_3$-pyrimidin-5-yl |
| 1531 | 2-OCH(CH$_3$)CH$_2$OCH$_2$CH$_3$-pyrimidin-5-yl |
| 1532 | 4-OCH(CH$_3$)CH$_2$O(CH$_3$)$_2$CH$_3$-pyrimidin-5-yl |
| 1533 | 2-OCH(CH$_3$)CH$_2$O(CH$_3$)$_2$CH$_3$-pyrimidin-5-yl |
| 1534 | 4-OCH(CH$_3$)CH$_2$OCH$_2$CH=CH$_2$-pyrimidin-5-yl |
| 1535 | 2-OCH(CH$_3$)CH$_2$OCH$_2$CH=CH$_2$-pyrimidin-5-yl |
| 1536 | 4-O(CH$_2$)$_3$OCH$_3$-pyrimidin-5-yl |
| 1537 | 2-O(CH$_2$)$_3$OCH$_3$-pyrimidin-5-yl |
| 1538 | 4-O(CH$_2$)$_3$OCH$_2$CH$_3$-pyrimidin-5-yl |
| 1539 | 2-O(CH$_2$)$_3$OCH$_2$CH$_3$-pyrimidin-5-yl |
| 1540 | 4-O(CH$_2$)$_3$OCH(CH$_3$)$_2$-pyrimidin-5-yl |
| 1541 | 2-O(CH$_2$)$_3$OCH(CH$_3$)$_2$-pyrimidin-5-yl |
| 1542 | 4-O(CH$_2$)$_3$OC$_6$H$_2$-pyrimidin-5-yl |
| 1543 | 2-O(CH$_2$)$_3$OC$_6$H$_2$-pyrimidin-5-yl |
| 1544 | 4-O(CH$_2$)$_3$OCH$_2$C$_6$H$_2$-pyrimidin-5-yl |
| 1545 | 2-O(CH$_2$)$_3$OCH$_2$C$_6$H$_2$-pyrimidin-5-yl |
| 1546 | 4-OCH(CH$_2$CH$_3$)CH$_2$OCH$_3$-pyrimidin-5-yl |
| 1547 | 2-OCH(CH$_2$CH$_3$)CH$_2$OCH$_3$-pyrimidin-5-yl |
| 1548 | 4-OCH(CH$_2$CH$_3$)CH$_2$CH$_2$OCH$_3$-pyrimidin-5-yl |
| 1549 | 2-OCH(CH$_2$CH$_3$)CH$_2$CH$_2$OCH$_3$-pyrimidin-5-yl |
| 1550 | 4-OCH(CH$_2$CH$_3$)CH$_2$CH$_2$OCH$_2$CH$_3$-pyrimidin-5-yl |
| 1551 | 2-OCH(CH$_2$CH$_3$)CH$_2$CH$_2$OCH$_2$CH$_3$-pyrimidin-5-yl |
| 1552 | 4-O[(CH$_2$)$_3$O]$_2$CH$_3$-pyrimidin-5-yl |
| 1553 | 2-O[(CH$_2$)$_3$O]$_2$CH$_3$-pyrimidin-5-yl |
| 1554 | 4-OCH$_2$CH(CH$_3$)CH$_2$OCH$_3$-pyrimidin-5-yl |
| 1555 | 2-OCH$_2$CH(CH$_3$)CH$_2$OCH$_3$-pyrimidin-5-yl |
| 1556 | 4-OCH$_2$CH(CH$_3$)CH$_2$OCH$_2$CH$_3$-pyrimidin-5-yl |
| 1557 | 2-OCH$_2$CH(CH$_3$)CH$_2$OCH$_2$CH$_3$-pyrimidin-5-yl |
| 1558 | 4-OCH(CH$_2$Cl)CH$_2$OCH$_3$-pyrimidin-5-yl |
| 1559 | 2-OCH(CH$_2$Cl)CH$_2$OCH$_3$-pyrimidin-5-yl |
| 1560 | 4-OCH(CH$_2$Cl)CH$_2$OCH$_2$CH$_3$-pyrimidin-5-yl |
| 1561 | 2-OCH(CH$_2$Cl)CH$_2$OCH$_2$CH$_3$-pyrimidin-5-yl |
| 1562 | 4-OCH(CH$_2$Cl)CH$_2$OCH(CH$_3$)$_2$-pyrimidin-5-yl |
| 1563 | 2-OCH(CH$_2$Cl)CH$_2$OCH(CH$_3$)$_2$-pyrimidin-5-yl |
| 1564 | 4-OCH(CH$_2$Cl)CH$_2$OCH$_2$CH=CH$_2$-pyrimidin-5-yl |
| 1565 | 2-OCH(CH$_2$Cl)CH$_2$OCH$_2$CH=CH$_2$-pyrimidin-5-yl |
| 1566 | 4-OCH[CH$_2$OCH$_3$]$_2$-pyrimidin-5-yl |
| 1567 | 2-OCH[CH$_2$OCH$_3$]$_2$-pyrimidin-5-yl |
| 1568 | 4-OCH[CH$_2$OCH$_2$CH$_3$]$_2$-pyrimidin-5-yl |
| 1569 | 2-OCH[CH$_2$OCH$_2$CH$_3$]$_2$-pyrimidin-5-yl |
| 1570 | 4-OCCl$_3$-pyrimidin-5-yl |
| 1571 | 2-OCCl$_3$-pyrimidin-5-yl |
| 1572 | 4-OCHF$_2$-pyrimidin-5-yl |
| 1573 | 2-OCHF$_2$-pyrimidin-5-yl |
| 1574 | 4-OCF$_3$-pyrimidin-5-yl |
| 1575 | 2-OCF$_3$-pyrimidin-5-yl |
| 1576 | 4-OCF$_2$CHF$_2$-pyrimidin-5-yl |
| 1577 | 2-OCF$_2$CHF$_2$-pyrimidin-5-yl |
| 1578 | 4-OCH$_2$CF$_3$-pyrimidin-5-yl |
| 1579 | 2-OCH$_2$CF$_3$-pyrimidin-5-yl |
| 1580 | 4-OCH$_2$CHF$_2$-pyrimidin-5-yl |
| 1581 | 2-OCH$_2$CHF$_2$-pyrimidin-5-yl |
| 1582 | 4-O(CH$_2$)$_3$F-pyrimidin-5-yl |
| 1583 | 2-O(CH$_2$)$_3$F-pyrimidin-5-yl |
| 1584 | 4-OCH(CH$_3$)CF$_3$-pyrimidin-5-yl |
| 1585 | 2-OCH(CH$_3$)CF$_3$-pyrimidin-5-yl |
| 1586 | 4-O(CH$_2$)$_4$F-pyrimidin-5-yl |
| 1587 | 2-O(CH$_2$)$_4$F-pyrimidin-5-yl |
| 1588 | 4-O(CH$_2$)$_3$CF$_3$-pyrimidin-5-yl |
| 1589 | 2-O(CH$_2$)$_3$CF$_3$-pyrimidin-5-yl |
| 1590 | 4-OCH(CH$_3$)CF$_2$CF$_3$-pyrimidin-5-yl |
| 1591 | 2-OCH(CH$_3$)CF$_2$CF$_3$-pyrimidin-5-yl |
| 1592 | 4-OCH(CH$_3$)CF$_2$CHF$_2$-pyrimidin-5-yl |
| 1593 | 2-OCH(CH$_3$)CF$_2$CHF$_2$-pyrimidin-5-yl |
| 1594 | 4-OCH$_2$CF$_2$CHFCH$_3$-pyrimidin-5-yl |
| 1595 | 2-OCH$_2$CF$_2$CHFCH$_3$-pyrimidin-5-yl |
| 1596 | 4-OCH$_2$(CF$_2$)$_2$CF$_3$-pyrimidin-5-yl |
| 1597 | 2-OCH$_2$(CF$_2$)$_2$CF$_3$-pyrimidin-5-yl |
| 1598 | 4-O(CF$_2$)$_3$CF$_3$-pyrimidin-5-yl |
| 1599 | 2-O(CF$_2$)$_3$CF$_3$-pyrimidin-5-yl |
| 1600 | 4-OCH$_2$CF$_2$CHF$_2$-pyrimidin-5-yl |
| 1601 | 2-OCH$_2$CF$_2$CHF$_2$-pyrimidin-5-yl |
| 1602 | 4-CH$_2$CH=CH$_2$-pyrimidin-5-yl |
| 1603 | 2-CH$_2$CH=CH$_2$-pyrimidin-5-yl |
| 1604 | 4-CH$_2$C(CH$_3$)=CH$_2$-pyrimidin-5-yl |
| 1605 | 2-CH$_2$C(CH$_3$)=CH$_2$-pyrimidin-5-yl |
| 1606 | 4-OCH$_2$CH=CHCH$_3$-pyrimidin-5-yl |
| 1607 | 2-OCH$_2$CH=CHCH$_3$-pyrimidin-5-yl |
| 1608 | 4-O(CH$_2$)$_2$CH=CH$_2$-pyrimidin-5-yl |
| 1609 | 2-O(CH$_2$)$_2$CH=CH$_2$-pyrimidin-5-yl |
| 1610 | 4-OCH$_2$C(CH$_3$)=CH$_2$-pyrimidin-5-yl |
| 1611 | 2-OCH$_2$C(CH$_3$)=CH$_2$-pyrimidin-5-yl |
| 1612 | 4-OCH(CH$_3$)CH=CH$_2$-pyrimidin-5-yl |
| 1613 | 2-OCH(CH$_3$)CH=CH$_2$-pyrimidin-5-yl |
| 1614 | 4-OCH$_2$C≡CH-pyrimidin-5-yl |
| 1615 | 2-OCH$_2$C≡CH-pyrimidin-5-yl |
| 1616 | 4-OCH$_2$C≡CCH$_3$-pyrimidin-5-yl |
| 1617 | 2-OCH$_2$C≡CCH$_3$-pyrimidin-5-yl |
| 1618 | 4-O(CH$_2$)$_2$C≡CH-pyrimidin-5-yl |
| 1619 | 2-O(CH$_2$)$_2$C≡CH-pyrimidin-5-yl |
| 1620 | 4-SCH$_3$-pyrimidin-5-yl |
| 1621 | 2-SCH$_3$-pyrimidin-5-yl |
| 1622 | 4-SCH$_2$CH$_3$-pyrimidin-5-yl |
| 1623 | 2-SCH$_2$CH$_3$-pyrimidin-5-yl |
| 1624 | 4-OC$_6$H$_2$-pyrimidin-5-yl |
| 1625 | 2-OC$_6$H$_2$-pyrimidin-5-yl |
| 1626 | 4-OCH$_2$C$_6$H$_2$-pyrimidin-5-yl |
| 1627 | 2-OCH$_2$C$_6$H$_2$-pyrimidin-5-yl |
| 1628 | 4-NO$_2$-pyrimidin-5-yl |
| 1629 | 2-NO$_2$-pyrimidin-5-yl |
| 1630 | 4-NHCH$_3$-pyrimidin-5-yl |
| 1631 | 2-NHCH$_3$-pyrimidin-5-yl |
| 1632 | 4-N(CH$_3$)$_2$-pyrimidin-5-yl |
| 1633 | 2-N(CH$_3$)$_2$-pyrimidin-5-yl |
| 1634 | 4-N(CH$_3$)C$_2$H$_5$-pyrimidin-5-yl |
| 1635 | 2-N(CH$_3$)C$_2$H$_5$-pyrimidin-5-yl |
| 1636 | 4-NHCH$_2$CF$_3$-pyrimidin-5-yl |
| 1637 | 2-NHCH$_2$CF$_3$-pyrimidin-5-yl |
| 1638 | 4-F-pyrimidin-5-yl |
| 1639 | 2-F-pyrimidin-5-yl |
| 1640 | 4-Cl-pyrimidin-5-yl |
| 1641 | 2-Cl-pyrimidin-5-yl |
| 1642 | 4-OH-pyrimidin-5-yl |
| 1643 | 2-OH-pyrimidin-5-yl |
| 1644 | 4-CN-pyrimidin-5-yl |
| 1645 | 2-CN-pyrimidin-5-yl |
| 1646 | 4-C(O)NH$_2$-pyrimidin-5-yl |
| 1647 | 2-C(O)NH$_2$-pyrimidin-5-yl |
| 1648 | 4-C(S)NH$_2$-pyrimidin-5-yl |
| 1649 | 2-C(S)NH$_2$-pyrimidin-5-yl |

TABLE A-continued

| No. | R⁴ |
|---|---|
| 1650 | 4-CO₂CH₃-pyrimidin-5-yl |
| 1651 | 2-CO₂CH₃-pyrimidin-5-yl |
| 1652 | 4-ON=C(CH₃)₂-pyrimidin-5-yl |
| 1653 | 2-ON=C(CH₃)₂-pyrimidin-5-yl |
| 1654 | 4-[O-cyclopropyl]pyrimidin-5-yl |
| 1655 | 2-[O-cyclopropyl]pyrimidin-5-yl |
| 1656 | 4-[O-cyclobutyl]pyrimidin-5-yl |
| 1657 | 2-[O-cyclobutyl]pyrimidin-5-yl |
| 1658 | 4-[O-cyclopentyl]pyrimidin-5-yl |
| 1659 | 2-[O-cyclopentyl]pyrimidin-5-yl |
| 1660 | 4-[O-cyclohexyl]pyrimidin-5-yl |
| 1661 | 2-[O-cyclohexyl]pyrimidin-5-yl |
| 1662 | 4-[OCH₂-cyclopropyl]pyrimidin-5-yl |
| 1663 | 2-[OCH₂-cyclopropyl]pyrimidin-5-yl |
| 1664 | 2-F, 4-[OCH₂-cyclopropyl]pyrimidin-5-yl |
| 1665 | 4-F, 2-[OCH₂-cyclopropyl]pyrimidin-5-yl |
| 1666 | 2-CH₃, 4-[OCH₂-cyclopropyl]pyrimidin-5-yl |
| 1667 | 4-CH₃, 2-[OCH₂-cyclopropyl]pyrimidin-5-yl |
| 1668 | 2-CF₃, 4-[OCH₂-cyclopropyl]pyrimidin-5-yl |
| 1669 | 4-CF₃, 2-[OCH₂-cyclopropyl]pyrimidin-5-yl |
| 1670 | 4-[OCH(CH₃)-cyclopropyl]pyrimidin-5-yl |
| 1671 | 2-[OCH(CH₃)-cyclopropyl]pyrimidin-5-yl |
| 1672 | 2-F, 4-[OCH(CH₃)-cyclopropyl]pyrimidin-5-yl |
| 1673 | 4-F, 2-[OCH(CH₃)-cyclopropyl]pyrimidin-5-yl |
| 1674 | 2-CH₃, 4-[OCH(CH₃)-cyclopropyl]pyrimidin-5-yl |
| 1675 | 4-CH₃, 2-[OCH(CH₃)-cyclopropyl]pyrimidin-5-yl |
| 1676 | 2-CF₃, 4-[OCH(CH₃)-cyclopropyl]pyrimidin-5-yl |
| 1677 | 4-CF₃, 2-[OCH(CH₃)-cyclopropyl]pyrimidin-5-yl |
| 1678 | 4-[O-(1-CH₃-cyclopropyl)]pyrimidin-5-yl |
| 1679 | 2-[O-(1-CH₃-cyclopropyl)]pyrimidin-5-yl |
| 1680 | 2-F, 4-[O-(1-CH₃-cyclopropyl)]pyrimidin-5-yl |
| 1681 | 4-F, 2-[O-(1-CH₃-cyclopropyl)]pyrimidin-5-yl |
| 1682 | 2-CH₃, 4-[O-(1-CH₃-cyclopropyl)]pyrimidin-5-yl |
| 1683 | 4-CH₃, 2-[O-(1-CH₃-cyclopropyl)]pyrimidin-5-yl |
| 1684 | 2-CF₃, 4-[O-(1-CH₃-cyclopropyl)]pyrimidin-5-yl |
| 1685 | 4-CF₃, 2-[O-(1-CH₃-cyclopropyl)]pyrimidin-5-yl |
| 1686 | 4-[OCH₂-(1-CH₃-cyclopropyl)]pyrimidin-5-yl |
| 1687 | 2-[OCH₂-(1-CH₃-cyclopropyl)]pyrimidin-5-yl |
| 1688 | 2-F, 4-[OCH₂-(1-CH₃-cyclopropyl)]pyrimidin-5-yl |
| 1689 | 4-F, 2-[OCH₂-(1-CH₃-cyclopropyl)]pyrimidin-5-yl |
| 1690 | 2-CH₃, 4-[OCH₂-(1-CH₃-cyclopropyl)]pyrimidin-5-yl |
| 1691 | 4-CH₃, 2-[OCH₂-(1-CH₃-cyclopropyl)]pyrimidin-5-yl |
| 1692 | 2-CF₃, 4-[OCH₂-(1-CH₃-cyclopropyl)]pyrimidin-5-yl |
| 1693 | 4-CF₃, 2-[OCH₂-(1-CH₃-cyclopropyl)]pyrimidin-5-yl |
| 1694 | 4-[OCH₂-(2-CH₃-cyclopropyl)]pyrimidin-5-yl |
| 1695 | 2-[OCH₂-(2-CH₃-cyclopropyl)]pyrimidin-5-yl |
| 1696 | 2-F, 4-[OCH₂-(2-CH₃-cyclopropyl)]pyrimidin-5-yl |
| 1697 | 4-F, 2-[OCH₂-(2-CH₃-cyclopropyl)]pyrimidin-5-yl |
| 1698 | 2-CH₃, 4-[OCH₂-(2-CH₃-cyclopropyl)]pyrimidin-5-yl |
| 1699 | 4-CH₃, 2-[OCH₂-(2-CH₃-cyclopropyl)]pyrimidin-5-yl |
| 1700 | 2-CF₃, 4-[OCH₂-(2-CH₃-cyclopropyl)]pyrimidin-5-yl |
| 1701 | 4-CF₃, 2-[OCH₂-(2-CH₃-cyclopropyl)]pyrimidin-5-yl |
| 1702 | 4-[OCH₂-(tetrahydropyran-2-yl)]pyrimidin-5-yl |
| 1703 | 2-[OCH₂-(tetrahydropyran-2-yl)]pyrimidin-5-yl |
| 1704 | 2-F, 4-[OCH₂-(tetrahydropyran-2-yl)]pyrimidin-5-yl |
| 1705 | 4-F, 2-[OCH₂-(tetrahydropyran-2-yl)]pyrimidin-5-yl |
| 1706 | 2-CH₃, 4-[OCH₂-(tetrahydropyran-2-yl)]pyrimidin-5-yl |
| 1707 | 4-CH₃, 2-[OCH₂-(tetrahydropyran-2-yl)]pyrimidin-5-yl |
| 1708 | 2-CF₃, 4-[OCH₂-(tetrahydropyran-2-yl)]pyrimidin-5-yl |
| 1709 | 4-CF₃, 2-[OCH₂-(tetrahydropyran-2-yl)]pyrimidin-5-yl |
| 1710 | 4-[OCH₂-(furan-2-yl)]pyrimidin-5-yl |
| 1711 | 2-[OCH₂-(furan-2-yl)]pyrimidin-5-yl |
| 1712 | 2-F, 4-[OCH₂-(furan-2-yl)]pyrimidin-5-yl |
| 1713 | 4-F, 2-[OCH₂-(furan-2-yl)]pyrimidin-5-yl |
| 1714 | 2-CH₃, 4-[OCH₂-(furan-2-yl)]pyrimidin-5-yl |
| 1715 | 4-CH₃, 2-[OCH₂-(furan-2-yl)]pyrimidin-5-yl |
| 1716 | 2-CF₃, 4-[OCH₂-(furan-2-yl)]pyrimidin-5-yl |
| 1717 | 4-CF₃, 2-[OCH₂-(furan-2-yl)]pyrimidin-5-yl |
| 1718 | 4-[OCH₂-(furan-3-yl)]pyrimidin-5-yl |
| 1719 | 2-[OCH₂-(furan-3-yl)]pyrimidin-5-yl |
| 1720 | 2-F, 4-[OCH₂-(furan-3-yl)]pyrimidin-5-yl |
| 1721 | 4-F, 2-[OCH₂-(furan-3-yl)]pyrimidin-5-yl |
| 1722 | 2-CH₃, 4-[OCH₂-(furan-3-yl)]pyrimidin-5-yl |
| 1723 | 4-CH₃, 2-[OCH₂-(furan-3-yl)]pyrimidin-5-yl |
| 1724 | 2-CF₃, 4-[OCH₂-(furan-3-yl)]pyrimidin-5-yl |
| 1725 | 4-CF₃, 2-[OCH₂-(furan-3-yl)]pyrimidin-5-yl |
| 1726 | 4-[OCH₂-(tetrahydrofuran-3-yl)]pyrimidin-5-yl |
| 1727 | 2-[OCH₂-(tetrahydrofuran-3-yl)]pyrimidin-5-yl |
| 1728 | 2-F, 4-[OCH₂-(tetrahydrofuran-3-yl)]pyrimidin-5-yl |
| 1729 | 4-F, 2-[OCH₂-(tetrahydrofuran-3-yl)]pyrimidin-5-yl |
| 1730 | 2-CH₃, 4-[OCH₂-(tetrahydrofuran-3-yl)]pyrimidin-5-yl |
| 1731 | 4-CH₃, 2-[OCH₂-(tetrahydrofuran-3-yl)]pyrimidin-5-yl |
| 1732 | 2-CF₃, 4-[OCH₂-(tetrahydrofuran-3-yl)]pyrimidin-5-yl |
| 1733 | 4-CF₃, 2-[OCH₂-(tetrahydrofuran-3-yl)]pyrimidin-5-yl |
| 1734 | 4-[OCH₂-(tetrahydrofuran-2-yl)]pyrimidin-5-yl |
| 1735 | 2-[OCH₂-(tetrahydrofuran-2-yl)]pyrimidin-5-yl |
| 1736 | 2-F, 4-[OCH₂-(tetrahydrofuran-2-yl)]pyrimidin-5-yl |
| 1737 | 4-F, 2-[OCH₂-(tetrahydrofuran-2-yl)]pyrimidin-5-yl |
| 1738 | 2-CH₃, 4-[OCH₂-(tetrahydrofuran-2-yl)]pyrimidin-5-yl |
| 1739 | 4-CH₃, 2-[OCH₂-(tetrahydrofuran-2-yl)]pyrimidin-5-yl |
| 1740 | 2-CF₃, 4-[OCH₂-(tetrahydrofuran-2-yl)]pyrimidin-5-yl |
| 1741 | 4-CF₃, 2-[OCH₂-(tetrahydrofuran-2-yl)]pyrimidin-5-yl |
| 1742 | 4-[O-(tetrahydropyran-4-yl)]pyrimidin-5-yl |
| 1743 | 2-[O-(tetrahydropyran-4-yl)]pyrimidin-5-yl |
| 1744 | 2-F, 4-[O-(tetrahydropyran-4-yl)]pyrimidin-5-yl |
| 1745 | 4-F, 2-[O-(tetrahydropyran-4-yl)]pyrimidin-5-yl |
| 1746 | 2-CH₃, 4-[O-(tetrahydropyran-4-yl)]pyrimidin-5-yl |
| 1747 | 4-CH₃, 2-[O-(tetrahydropyran-4-yl)]pyrimidin-5-yl |
| 1748 | 2-CF₃, 4-[O-(tetrahydropyran-4-yl)]pyrimidin-5-yl |
| 1749 | 4-CF₃, 2-[O-(tetrahydropyran-4-yl)]pyrimidin-5-yl |
| 1750 | 4-[2-Cl—C₆H₄]pyrimidin-5-yl |
| 1751 | 2-[2-Cl—C₆H₄]pyrimidin-5-yl |
| 1752 | 2-F, 4-[2-Cl—C₆H₄]pyrimidin-5-yl |
| 1753 | 4-F, 2-[2-Cl—C₆H₄]pyrimidin-5-yl |
| 1754 | 2-CH₃, 4-[2-Cl—C₆H₄]pyrimidin-5-yl |
| 1755 | 4-CH₃, 2-[2-Cl—C₆H₄]pyrimidin-5-yl |
| 1756 | 2-CF₃, 4-[2-Cl—C₆H₄]pyrimidin-5-yl |
| 1757 | 4-CF₃, 2-[2-Cl—C₆H₄]pyrimidin-5-yl |
| 1758 | 4-[OCH₂-(pyridin-5-yl)]pyrimidin-5-yl |
| 1759 | 2-[OCH₂-(pyridin-5-yl)]pyrimidin-5-yl |
| 1760 | 2-F, 4-[OCH₂-(pyridin-5-yl)]pyrimidin-5-yl |
| 1761 | 4-F, 2-[OCH₂-(pyridin-5-yl)]pyrimidin-5-yl |
| 1762 | 2-CH₃, 4-[OCH₂-(pyridin-5-yl)]pyrimidin-5-yl |
| 1763 | 4-CH₃, 2-[OCH₂-(pyridin-5-yl)]pyrimidin-5-yl |
| 1764 | 2-CF₃, 4-[OCH₂-(pyridin-5-yl)]pyrimidin-5-yl |
| 1765 | 4-CF₃, 2-[OCH₂-(pyridin-5-yl)]pyrimidin-5-yl |
| 1766 | 4-[OCH₂-(pyridin-3-yl)]pyrimidin-5-yl |
| 1767 | 2-[OCH₂-(pyridin-3-yl)]pyrimidin-5-yl |
| 1768 | 2-F, 4-[OCH₂-(pyridin-3-yl)]pyrimidin-5-yl |
| 1769 | 4-F, 2-[OCH₂-(pyridin-3-yl)]pyrimidin-5-yl |
| 1770 | 2-CH₃, 4-[OCH₂-(pyridin-3-yl)]pyrimidin-5-yl |
| 1771 | 4-CH₃, 2-[OCH₂-(pyridin-3-yl)]pyrimidin-5-yl |
| 1772 | 2-CF₃, 4-[OCH₂-(pyridin-3-yl)]pyrimidin-5-yl |
| 1773 | 4-CF₃, 2-[OCH₂-(pyridin-3-yl)]pyrimidin-5-yl |
| 1774 | 4-[morpholin-4-yl]pyrimidin-5-yl |
| 1775 | 2-[morpholin-4-yl]pyrimidin-5-yl |
| 1776 | 4-[1-CH₃-imidazol-2-yl]pyrimidin-5-yl |
| 1777 | 2-[1-CH₃-imidazol-2-yl]pyrimidin-5-yl |
| 1778 | 2-F, 4-[1-CH₃-imidazol-2-yl]pyrimidin-5-yl |
| 1779 | 4-F, 2-[1-CH₃-imidazol-2-yl]pyrimidin-5-yl |
| 1780 | 2-CH₃, 4-[1-CH₃-imidazol-2-yl]pyrimidin-5-yl |
| 1781 | 4-CH₃, 2-[1-CH₃-imidazol-2-yl]pyrimidin-5-yl |
| 1782 | 2-CF₃, 4-[1-CH₃-imidazol-2-yl]pyrimidin-5-yl |
| 1783 | 4-CF₃, 2-[1-CH₃-imidazol-2-yl]pyrimidin-5-yl |
| 1784 | 4-[1,2,4-triazol-1-yl]pyrimidin-5-yl |
| 1785 | 2-[1,2,4-triazol-1-yl]pyrimidin-5-yl |
| 1786 | 2-F, 4-[1,2,4-triazol-1-yl]pyrimidin-5-yl |
| 1787 | 4-F, 2-[1,2,4-triazol-1-yl]pyrimidin-5-yl |
| 1788 | 2-CH₃, 4-[1,2,4-triazol-1-yl]pyrimidin-5-yl |
| 1789 | 4-CH₃, 2-[1,2,4-triazol-1-yl]pyrimidin-5-yl |
| 1790 | 2-CF₃, 4-[1,2,4-triazol-1-yl]pyrimidin-5-yl |
| 1791 | 4-CF₃, 2-[1,2,4-triazol-1-yl]pyrimidin-5-yl |
| 1792 | 4,2-Cl₂-pyrimidin-5-yl |
| 1793 | 4,6-Cl₂-pyrimidin-5-yl |
| 1794 | 4,2-(CH₃)₂-pyrimidin-5-yl |
| 1795 | 4,6-(CH₃)₂-pyrimidin-5-yl |
| 1796 | 4,2-(OCH₃)₂-pyrimidin-5-yl |
| 1797 | 4,6-(OCH₃)₂-pyrimidin-5-yl |
| 1798 | 4,2-(OCH₂CH₃)₂-pyrimidin-5-yl |
| 1799 | 4,6-(OCH₂CH₃)₂-pyrimidin-5-yl |
| 1800 | 4-F, 2-CH₃-pyrimidin-5-yl |
| 1801 | 4-F, 6-CH₃-pyrimidin-5-yl |
| 1802 | 2-F, 4-CH₃-pyrimidin-5-yl |
| 1803 | 6-F, 4-CH₃-pyrimidin-5-yl |

TABLE A-continued

| No. | R⁴ |
|---|---|
| 1804 | 4-F, 2-OCH₃-pyrimidin-5-yl |
| 1805 | 4-F, 6-OCH₃-pyrimidin-5-yl |
| 1806 | 2-F, 4-OCH₃-pyrimidin-5-yl |
| 1807 | 6-F, 4-OCH₃-pyrimidin-5-yl |
| 1808 | 4-F, 2-OCH₂CH₃-pyrimidin-5-yl |
| 1809 | 4-F, 6-OCH₂CH₃-pyrimidin-5-yl |
| 1810 | 2-F, 4-OCH₂CH₃-pyrimidin-5-yl |
| 1811 | 6-F, 4-OCH₂CH₃-pyrimidin-5-yl |
| 1812 | 4-F, 2-OCH₂CF₃-pyrimidin-5-yl |
| 1813 | 4-F, 6-OCH₂CF₃-pyrimidin-5-yl |
| 1814 | 2-F, 4-OCH₂CF₃-pyrimidin-5-yl |
| 1815 | 6-F, 4-OCH₂CF₃-pyrimidin-5-yl |
| 1816 | 4-F, 2-OCH(CH₃)₂-pyrimidin-5-yl |
| 1817 | 4-F, 6-OCH(CH₃)₂-pyrimidin-5-yl |
| 1818 | 2-F, 4-OCH(CH₃)₂-pyrimidin-5-yl |
| 1819 | 6-F, 4-OCH(CH₃)₂-pyrimidin-5-yl |
| 1820 | 4-Cl, 2-CH₃-pyrimidin-5-yl |
| 1821 | 4-Cl, 6-CH₃-pyrimidin-5-yl |
| 1822 | 2-Cl, 4-CH₃-pyrimidin-5-yl |
| 1823 | 6-Cl, 4-CH₃-pyrimidin-5-yl |
| 1824 | 4-Cl, 2-OCH₃-pyrimidin-5-yl |
| 1825 | 4-Cl, 6-OCH₃-pyrimidin-5-yl |
| 1826 | 2-Cl, 4-OCH₃-pyrimidin-5-yl |
| 1827 | 6-Cl, 4-OCH₃-pyrimidin-5-yl |
| 1828 | 4-Cl, 2-OCH₂CH₃-pyrimidin-5-yl |
| 1829 | 4-Cl, 6-OCH₂CH₃-pyrimidin-5-yl |
| 1830 | 2-Cl, 4-OCH₂CH₃-pyrimidin-5-yl |
| 1831 | 6-Cl, 4-OCH₂CH₃-pyrimidin-5-yl |
| 1832 | 4-Cl, 2-OCH₂CF₃-pyrimidin-5-yl |
| 1833 | 4-Cl, 6-OCH₂CF₃-pyrimidin-5-yl |
| 1834 | 2-Cl, 4-OCH₂CF₃-pyrimidin-5-yl |
| 1835 | 6-Cl, 4-OCH₂CF₃-pyrimidin-5-yl |
| 1836 | 4-Cl, 2-OCH(CH₃)₂-pyrimidin-5-yl |
| 1837 | 4-Cl, 6-OCH(CH₃)₂-pyrimidin-5-yl |
| 1838 | 2-Cl, 4-OCH(CH₃)₂-pyrimidin-5-yl |
| 1839 | 6-Cl, 4-OCH(CH₃)₂-pyrimidin-5-yl |
| 1840 | 4-CH₃, 2-OCH₃-pyrimidin-5-yl |
| 1841 | 4-CH₃, 6-OCH₃-pyrimidin-5-yl |
| 1842 | 2-CH₃, 4-OCH₃-pyrimidin-5-yl |
| 1843 | 6-CH₃, 4-OCH₃-pyrimidin-5-yl |
| 1844 | 6-CH₃, 4-OCH₂CH₃-pyrimidin-5-yl |
| 1845 | 2-CH₃, 4-OCH₂CH₃-pyrimidin-5-yl |
| 1846 | 4-CH₃, 2-OCH₂CH₃-pyrimidin-5-yl |
| 1847 | 4-CH₃, 6-OCH₂CH₃-pyrimidin-5-yl |
| 1848 | 4-CH₃, 2-OCH₂CF₃-pyrimidin-5-yl |
| 1849 | 4-CH₃, 6-OCH₂CF₃-pyrimidin-5-yl |
| 1850 | 2-CH₃, 4-OCH₂CF₃-pyrimidin-5-yl |
| 1851 | 6-CH₃, 4-OCH₂CF₃-pyrimidin-5-yl |
| 1852 | 4-CH₃, 2-OCH(CH₃)₂-pyrimidin-5-yl |
| 1853 | 4-CH₃, 2-OCH(CH₃)₂-pyrimidin-5-yl |
| 1854 | 2-CH₃, 4-OCH(CH₃)₂-pyrimidin-5-yl |
| 1855 | 6-CH₃, 4-OCH(CH₃)₂-pyrimidin-5-yl |
| 1856 | 4-CH₃, 2-OCH₂CH═CH₂-pyrimidin-5-yl |
| 1857 | 4-CH₃, 6-OCH₂CH═CH₂-pyrimidin-5-yl |
| 1858 | 2-CH₃, 4-OCH₂CH═CH₂-pyrimidin-5-yl |
| 1859 | 6-CH₃, 4-OCH₂CH═CH₂-pyrimidin-5-yl |
| 1860 | 4-CH₃, 2-CO₂CH₃-pyrimidin-5-yl |
| 1861 | 4-CH₃, 6-CO₂CH₃-pyrimidin-5-yl |
| 1862 | 4-CH₃, 2-CF₃-pyrimidin-5-yl |
| 1863 | 4-CH₃, 6-CF₃-pyrimidin-5-yl |
| 1864 | 2-CH₃, 4-CF₃-pyrimidin-5-yl |
| 1865 | 6-CH₃, 4-CF₃-pyrimidin-5-yl |
| 1866 | 4-CF₃, 2-CH₂CH₃-pyrimidin-5-yl |
| 1867 | 4-CF₃, 6-CH₂CH₃-pyrimidin-5-yl |
| 1868 | 2-CF₃, 4-CH₂CH₃-pyrimidin-5-yl |
| 1869 | 6-CF₃, 4-CH₂CH₃-pyrimidin-5-yl |
| 1870 | 4-CF₃, 2-OCH₃-pyrimidin-5-yl |
| 1871 | 4-CF₃, 6-OCH₃-pyrimidin-5-yl |
| 1872 | 2-CF₃, 4-OCH₃-pyrimidin-5-yl |
| 1873 | 6-CF₃, 4-OCH₃-pyrimidin-5-yl |
| 1874 | 4-CF₃, 2-OCH₂CH₃-pyrimidin-5-yl |
| 1875 | 4-CF₃, 6-OCH₂CH₃-pyrimidin-5-yl |
| 1876 | 2-CF₃, 4-OCH₂CH₃-pyrimidin-5-yl |
| 1877 | 6-CF₃, 4-OCH₂CH₃-pyrimidin-5-yl |
| 1878 | 4-CF₃, 2-OCH₂CF₃-pyrimidin-5-yl |
| 1879 | 4-CF₃, 6-OCH₂CF₃-pyrimidin-5-yl |
| 1880 | 2-CF₃, 4-OCH₂CF₃-pyrimidin-5-yl |
| 1881 | 6-CF₃, 4-OCH₂CF₃-pyrimidin-5-yl |
| 1882 | 4-OCH₃, 2-OCH₂CH₃-pyrimidin-5-yl |
| 1883 | 4-OCH₃, 6-OCH₂CH₃-pyrimidin-5-yl |
| 1884 | 2-OCH₃, 4-OCH₂CH₃-pyrimidin-5-yl |
| 1885 | 6-OCH₃, 4-OCH₂CH₃-pyrimidin-5-yl |
| 1886 | 4-OCH₃, 2-OCH₂CF₃-pyrimidin-5-yl |
| 1887 | 4-OCH₃, 6-OCH₂CF₃-pyrimidin-5-yl |
| 1888 | 2-OCH₃, 4-OCH₂CF₃-pyrimidin-5-yl |
| 1889 | 6-OCH₃, 4-OCH₂CF₃-pyrimidin-5-yl |
| 1890 | 4-OCH₃, 2-OCH(CH₃)-pyrimidin-5-yl |
| 1891 | 4-OCH₃, 6-OCH(CH₃)-pyrimidin-5-yl |
| 1892 | 2-OCH₃, 4-OCH(CH₃)-pyrimidin-5-yl |
| 1893 | 6-OCH₃, 4-OCH(CH₃)-pyrimidin-5-yl |
| 1894 | 4-OCH₂CH₃, 2-CH₂OCH₂CH₃-pyrimidin-5-yl |
| 1895 | 4-OCH₂CH₃, 6-CH₂OCH₂CH₃-pyrimidin-5-yl |
| 1896 | 2-OCH₂CH₃, 4-CH₂OCH₂CH₃-pyrimidin-5-yl |
| 1897 | 6-OCH₂CH₃, 4-CH₂OCH₂CH₃-pyrimidin-5-yl |
| 1898 | 4-NO₂, 2-CH₃-pyrimidin-5-yl |
| 1899 | 4-NO₂, 6-CH₃-pyrimidin-5-yl |
| 1900 | 2-NO₂, 4-CH₃-pyrimidin-5-yl |
| 1901 | 6-NO₂, 4-CH₃-pyrimidin-5-yl |
| 1902 | 4-NO₂, 2-OCH₃-pyrimidin-5-yl |
| 1903 | 4-NO₂, 6-OCH₃-pyrimidin-5-yl |
| 1904 | 2-NO₂, 4-OCH₃-pyrimidin-5-yl |
| 1905 | 6-NO₂, 4-OCH₃-pyrimidin-5-yl |
| 1906 | 4-NO₂, 2-OCH₂CH₃-pyrimidin-5-yl |
| 1907 | 4-NO₂, 6-OCH₂CH₃-pyrimidin-5-yl |
| 1908 | 2-NO₂, 4-OCH₂CH₃-pyrimidin-5-yl |
| 1909 | 6-NO₂, 4-OCH₂CH₃-pyrimidin-5-yl |
| 1910 | 4-NO₂, 2-OCH(CH₃)₂-pyrimidin-5-yl |
| 1911 | 4-NO₂, 6-OCH(CH₃)₂-pyrimidin-5-yl |
| 1912 | 2-NO₂, 4-OCH(CH₃)₂-pyrimidin-5-yl |
| 1913 | 6-NO₂, 4-OCH(CH₃)₂-pyrimidin-5-yl |
| 1914 | 4-NO₂, 2-OCH₂CF₃-pyrimidin-5-yl |
| 1915 | 4-NO₂, 6-OCH₂CF₃-pyrimidin-5-yl |
| 1916 | 2-NO₂, 4-OCH₂CF₃-pyrimidin-5-yl |
| 1917 | 6-NO₂, 4-OCH₂CF₃-pyrimidin-5-yl |
| 1918 | 4-CN, 2-CH₃-pyrimidin-5-yl |
| 1919 | 4-CN, 6-CH₃-pyrimidin-5-yl |
| 1920 | 2-CN, 4-CH₃-pyrimidin-5-yl |
| 1921 | 6-CN, 4-CH₃-pyrimidin-5-yl |
| 1922 | 4-CN, 2-OCH₃-pyrimidin-5-yl |
| 1923 | 4-CN, 6-OCH₃-pyrimidin-5-yl |
| 1924 | 2-CN, 4-OCH₃-pyrimidin-5-yl |
| 1925 | 6-CN, 4-OCH₃-pyrimidin-5-yl |
| 1926 | 4-CN, 2-OCH₂CH₃-pyrimidin-5-yl |
| 1927 | 4-CN, 6-OCH₂CH₃-pyrimidin-5-yl |
| 1928 | 2-CN, 4-OCH₂CH₃-pyrimidin-5-yl |
| 1929 | 6-CN, 4-OCH₂CH₃-pyrimidin-5-yl |
| 1930 | 4-CN, 2-OCH(CH₃)₂-pyrimidin-5-yl |
| 1931 | 4-CN, 6-OCH(CH₃)₂-pyrimidin-5-yl |
| 1932 | 2-CN, 4-OCH(CH₃)₂-pyrimidin-5-yl |
| 1933 | 6-CN, 4-OCH(CH₃)₂-pyrimidin-5-yl |
| 1934 | 4-CN, 2-OCH₂CF₃-pyrimidin-5-yl |
| 1935 | 4-CN, 6-OCH₂CF₃-pyrimidin-5-yl |
| 1936 | 2-CN, 4-OCH₂CF₃-pyrimidin-5-yl |
| 1937 | 6-CN, 4-OCH₂CF₃-pyrimidin-5-yl |
| 1938 | 2,6-(CH₃)₂, 4-OCH₃-pyrimidin-5-yl |
| 1939 | 4-CH₃-pyridazin-3-yl |
| 1940 | 6-CH₃-pyridazin-3-yl |
| 1941 | 4-CH₂CH₃-pyridazin-3-yl |
| 1942 | 6-CH₂CH₃-pyridazin-3-yl |
| 1943 | 4-CH(CH₃)₂-pyridazin-3-yl |
| 1944 | 6-CH(CH₃)₂-pyridazin-3-yl |
| 1945 | 4-CH(CH₃)CH₂CH₃-pyridazin-3-yl |
| 1946 | 6-CH(CH₃)CH₂CH₃-pyridazin-3-yl |
| 1947 | 4-CF₃-pyridazin-3-yl |
| 1948 | 6-CF₃-pyridazin-3-yl |
| 1949 | 4-CH═CH₂-pyridazin-3-yl |
| 1950 | 6-CH═CH₂-pyridazin-3-yl |
| 1951 | 4-CH═CHCH₃-pyridazin-3-yl |
| 1952 | 6-CH═CHCH₃-pyridazin-3-yl |
| 1953 | 4-CH═CHCl-pyridazin-3-yl |
| 1954 | 6-CH═CHCl-pyridazin-3-yl |
| 1955 | 4-C≡CH-pyridazin-3-yl |
| 1956 | 6-C≡CH-pyridazin-3-yl |
| 1957 | 4-CH₂C≡CH-pyridazin-3-yl |

TABLE A-continued

| No. | R⁴ |
|---|---|
| 1958 | 6-CH$_2$C≡CH-pyridazin-3-yl |
| 1959 | 4-CH$_2$C≡CCH$_3$-pyridazin-3-yl |
| 1960 | 6-CH$_2$C≡CCH$_3$-pyridazin-3-yl |
| 1961 | 4-cyclopropylpyridazin-3-yl |
| 1962 | 6-cyclopropylpyridazin-3-yl |
| 1963 | 4-cyclopentylpyridazin-3-yl |
| 1964 | 6-cyclopentylpyridazin-3-yl |
| 1965 | 4-OCH$_3$-pyridazin-3-yl |
| 1966 | 6-OCH$_3$-pyridazin-3-yl |
| 1967 | 4-OCH$_2$CH$_3$-pyridazin-3-yl |
| 1968 | 6-OCH$_2$CH$_3$-pyridazin-3-yl |
| 1969 | 4-OCH$_2$CH$_2$CH$_3$-pyridazin-3-yl |
| 1970 | 6-OCH$_2$CH$_2$CH$_3$-pyridazin-3-yl |
| 1971 | 4-OCH(CH$_3$)$_2$-pyridazin-3-yl |
| 1972 | 6-OCH(CH$_3$)$_2$-pyridazin-3-yl |
| 1973 | 4-OCH$_2$CH$_2$CH$_2$CH$_3$-pyridazin-3-yl |
| 1974 | 6-OCH$_2$CH$_2$CH$_2$CH$_3$-pyridazin-3-yl |
| 1975 | 4-OCH(CH$_3$)CH$_2$CH$_3$-pyridazin-3-yl |
| 1976 | 6-OCH(CH$_3$)CH$_2$CH$_3$-pyridazin-3-yl |
| 1977 | 4-OCH$_2$CH(CH$_3$)$_2$-pyridazin-3-yl |
| 1978 | 6-OCH$_2$CH(CH$_3$)$_2$-pyridazin-3-yl |
| 1979 | 4-OC(CH$_3$)$_3$-pyridazin-3-yl |
| 1980 | 6-OC(CH$_3$)$_3$-pyridazin-3-yl |
| 1981 | 4-OCH(CH$_3$)CH$_2$CH$_2$CH$_3$-pyridazin-3-yl |
| 1982 | 6-OCH(CH$_3$)CH$_2$CH$_2$CH$_3$-pyridazin-3-yl |
| 1983 | 4-OCH$_2$OCH$_3$-pyridazin-3-yl |
| 1984 | 6-OCH$_2$OCH$_3$-pyridazin-3-yl |
| 1985 | 4-OCH$_2$OCH$_2$CH$_3$-pyridazin-3-yl |
| 1986 | 6-OCH$_2$OCH$_2$CH$_3$-pyridazin-3-yl |
| 1987 | 4-OCH(CH$_3$)OCH$_3$-pyridazin-3-yl |
| 1988 | 6-OCH(CH$_3$)OCH$_3$-pyridazin-3-yl |
| 1989 | 4-OCH(CH$_3$)OCH$_2$CH$_3$-pyridazin-3-yl |
| 1990 | 6-OCH(CH$_3$)OCH$_2$CH$_3$-pyridazin-3-yl |
| 1991 | 4-OCH$_2$CH$_2$OCH$_3$-pyridazin-3-yl |
| 1992 | 6-OCH$_2$CH$_2$OCH$_3$-pyridazin-3-yl |
| 1993 | 4-OCH$_2$CH$_2$OCH$_2$CH$_3$-pyridazin-3-yl |
| 1994 | 6-OCH$_2$CH$_2$OCH$_2$CH$_3$-pyridazin-3-yl |
| 1995 | 4-OCH$_2$CH$_2$OCH(CH$_3$)$_2$-pyridazin-3-yl |
| 1996 | 6-OCH$_2$CH$_2$OCH(CH$_3$)$_2$-pyridazin-3-yl |
| 1997 | 4-OCH$_2$CH$_2$SCH$_3$-pyridazin-3-yl |
| 1998 | 6-OCH$_2$CH$_2$SCH$_3$-pyridazin-3-yl |
| 1999 | 4-OCH$_2$CH$_2$SO$_2$CH$_3$-pyridazin-3-yl |
| 2000 | 6-OCH$_2$CH$_2$SO$_2$CH$_3$-pyridazin-3-yl |
| 2001 | 4-OCH$_2$CH$_2$SCH(CH$_3$)$_2$-pyridazin-3-yl |
| 2002 | 6-OCH$_2$CH$_2$SCH(CH$_3$)$_2$-pyridazin-3-yl |
| 2003 | 4-OCH$_2$CH$_2$CN-pyridazin-3-yl |
| 2004 | 6-OCH$_2$CH$_2$CN-pyridazin-3-yl |
| 2005 | 4-OCH$_2$CH$_2$SCH$_2$CH$_2$CN-pyridazin-3-yl |
| 2006 | 6-OCH$_2$CH$_2$SCH$_2$CH$_2$CN-pyridazin-3-yl |
| 2007 | 4-OCH$_2$CH$_2$OC$_5$H$_6$-pyridazin-3-yl |
| 2008 | 6-OCH$_2$CH$_2$OC$_5$H$_6$-pyridazin-3-yl |
| 2009 | 4-OCH$_2$CH$_2$OCH$_2$C$_5$H$_6$-pyridazin-3-yl |
| 2010 | 6-OCH$_2$CH$_2$OCH$_2$C$_5$H$_6$-pyridazin-3-yl |
| 2011 | 4-OCH$_2$CH$_2$N(CH$_3$)$_2$-pyridazin-3-yl |
| 2012 | 6-OCH$_2$CH$_2$N(CH$_3$)$_2$-pyridazin-3-yl |
| 2013 | 4-OCH$_2$CH$_2$CONH$_2$-pyridazin-3-yl |
| 2014 | 6-OCH$_2$CH$_2$CONH$_2$-pyridazin-3-yl |
| 2015 | 4-OCH$_2$CH$_2$CO$_2$CH$_2$CH$_2$CH$_3$-pyridazin-3-yl |
| 2016 | 6-OCH$_2$CH$_2$CO$_2$CH$_2$CH$_2$CH$_3$-pyridazin-3-yl |
| 2017 | 4-OCH(CH$_3$)CH$_2$OCH$_3$-pyridazin-3-yl |
| 2018 | 6-OCH(CH$_3$)CH$_2$OCH$_3$-pyridazin-3-yl |
| 2019 | 4-OCH(CH$_3$)CH$_2$CO$_2$CH$_3$-pyridazin-3-yl |
| 2020 | 6-OCH(CH$_3$)CH$_2$CO$_2$CH$_3$-pyridazin-3-yl |
| 2021 | 4-OCH(CH$_3$)CH$_2$CO$_2$CH$_2$CH$_3$-pyridazin-3-yl |
| 2022 | 6-OCH(CH$_3$)CH$_2$CO$_2$CH$_2$CH$_3$-pyridazin-3-yl |
| 2023 | 4-OCH$_2$CH(CH$_3$)CO$_2$CH$_3$-pyridazin-3-yl |
| 2024 | 6-OCH$_2$CH(CH$_3$)CO$_2$CH$_3$-pyridazin-3-yl |
| 2025 | 4-OCH$_2$C(=O)CH$_3$-pyridazin-3-yl |
| 2026 | 6-OCH$_2$C(=O)CH$_3$-pyridazin-3-yl |
| 2027 | 4-OCH$_2$C(=O)CH$_2$CH$_3$-pyridazin-3-yl |
| 2028 | 6-OCH$_2$C(=O)CH$_2$CH$_3$-pyridazin-3-yl |
| 2029 | 4-OCH$_2$CO$_2$CH$_3$-pyridazin-3-yl |
| 2030 | 6-OCH$_2$CO$_2$CH$_3$-pyridazin-3-yl |
| 2031 | 4-OCH$_2$CO$_2$CH$_2$CH$_3$-pyridazin-3-yl |
| 2032 | 6-OCH$_2$CO$_2$CH$_2$CH$_3$-pyridazin-3-yl |
| 2033 | 4-OCH$_2$C(=O)NH$_2$-pyridazin-3-yl |
| 2034 | 6-OCH$_2$C(=O)NH$_2$-pyridazin-3-yl |
| 2035 | 4-OCH$_2$C(=O)NHCH$_3$-pyridazin-3-yl |
| 2036 | 6-OCH$_2$C(=O)NHCH$_3$-pyridazin-3-yl |
| 2037 | 4-OCH$_2$C(=O)SCH$_3$-pyridazin-3-yl |
| 2038 | 6-OCH$_2$C(=O)SCH$_3$-pyridazin-3-yl |
| 2039 | 4-OCH(CH$_3$)C(=O)NH$_2$-pyridazin-3-yl |
| 2040 | 6-OCH(CH$_3$)C(=O)NH$_2$-pyridazin-3-yl |
| 2041 | 4-OCH(CH$_3$)C(=O)NHCH$_3$-pyridazin-3-yl |
| 2042 | 6-OCH(CH$_3$)C(=O)NHCH$_3$-pyridazin-3-yl |
| 2043 | 4-OCH(CH$_3$)C(=O)NHNH$_2$-pyridazin-3-yl |
| 2044 | 6-OCH(CH$_3$)C(=O)NHNH$_2$-pyridazin-3-yl |
| 2045 | 4-OCH(CH$_3$)CO$_2$CH$_3$-pyridazin-3-yl |
| 2046 | 6-OCH(CH$_3$)CO$_2$CH$_3$-pyridazin-3-yl |
| 2047 | 4-OCH(CH$_3$)CO$_2$CH$_2$CH$_3$-pyridazin-3-yl |
| 2048 | 6-OCH(CH$_3$)CO$_2$CH$_2$CH$_3$-pyridazin-3-yl |
| 2049 | 4-OCH(CH$_3$)C(=O)CH$_3$-pyridazin-3-yl |
| 2050 | 6-OCH(CH$_3$)C(=O)CH$_3$-pyridazin-3-yl |
| 2051 | 4-OCH(CH$_3$)C(=O)CH$_2$CH$_3$-pyridazin-3-yl |
| 2052 | 6-OCH(CH$_3$)C(=O)CH$_2$CH$_3$-pyridazin-3-yl |
| 2053 | 4-OCH(CH$_3$)CH$_2$C(=O)CH$_3$-pyridazin-3-yl |
| 2054 | 6-OCH(CH$_3$)CH$_2$C(=O)CH$_3$-pyridazin-3-yl |
| 2055 | 4-OCH(CH$_3$)CH$_2$OC(CH$_3$)$_3$-pyridazin-3-yl |
| 2056 | 6-OCH(CH$_3$)CH$_2$OC(CH$_3$)$_3$-pyridazin-3-yl |
| 2057 | 4-OCH(CH$_3$)CH$_2$OCH$_2$CH$_3$-pyridazin-3-yl |
| 2058 | 6-OCH(CH$_3$)CH$_2$OCH$_2$CH$_3$-pyridazin-3-yl |
| 2059 | 4-OCH(CH$_3$)CH$_2$O(CH$_3$)$_2$CH$_3$-pyridazin-3-yl |
| 2060 | 6-OCH(CH$_3$)CH$_2$O(CH$_3$)$_2$CH$_3$-pyridazin-3-yl |
| 2061 | 4-OCH(CH$_3$)CH$_2$OCH$_2$CH=CH$_2$-pyridazin-3-yl |
| 2062 | 6-OCH(CH$_3$)CH$_2$OCH$_2$CH=CH$_2$-pyridazin-3-yl |
| 2063 | 4-O(CH$_2$)$_3$OCH$_3$-pyridazin-3-yl |
| 2064 | 6-O(CH$_2$)$_3$OCH$_3$-pyridazin-3-yl |
| 2065 | 4-O(CH$_2$)$_3$OCH$_2$CH$_3$-pyridazin-3-yl |
| 2066 | 6-O(CH$_2$)$_3$OCH$_2$CH$_3$-pyridazin-3-yl |
| 2067 | 4-O(CH$_2$)$_3$OCH(CH$_3$)$_2$-pyridazin-3-yl |
| 2068 | 6-O(CH$_2$)$_3$OCH(CH$_3$)$_2$-pyridazin-3-yl |
| 2069 | 4-O(CH$_2$)$_3$OC$_5$H$_6$-pyridazin-3-yl |
| 2070 | 6-O(CH$_2$)$_3$OC$_5$H$_6$-pyridazin-3-yl |
| 2071 | 4-O(CH$_2$)$_3$OCH$_2$C$_5$H$_6$-pyridazin-3-yl |
| 2072 | 6-O(CH$_2$)$_3$OCH$_2$C$_5$H$_6$-pyridazin-3-yl |
| 2073 | 4-OCH(CH$_2$CH$_3$)CH$_2$OCH$_3$-pyridazin-3-yl |
| 2074 | 6-OCH(CH$_2$CH$_3$)CH$_2$OCH$_3$-pyridazin-3-yl |
| 2075 | 4-OCH(CH$_2$CH$_3$)CH$_2$OCH$_3$-pyridazin-3-yl |
| 2076 | 6-OCH(CH$_2$CH$_3$)CH$_2$OCH$_3$-pyridazin-3-yl |
| 2077 | 4-OCH(CH$_2$CH$_3$)CH$_2$CH$_2$OCH$_2$CH$_3$-pyridazin-3-yl |
| 2078 | 6-OCH(CH$_2$CH$_3$)CH$_2$CH$_2$OCH$_2$CH$_3$-pyridazin-3-yl |
| 2079 | 4-O[(CH$_2$)$_3$O]$_2$CH$_3$-pyridazin-3-yl |
| 2080 | 6-O[(CH$_2$)$_3$O]$_2$CH$_3$-pyridazin-3-yl |
| 2081 | 4-OCH$_2$CH(CH$_3$)CH$_2$OCH$_3$-pyridazin-3-yl |
| 2082 | 6-OCH$_2$CH(CH$_3$)CH$_2$OCH$_3$-pyridazin-3-yl |
| 2083 | 4-OCH$_2$CH(CH$_3$)CH$_2$OCH$_2$CH$_3$-pyridazin-3-yl |
| 2084 | 6-OCH$_2$CH(CH$_3$)CH$_2$OCH$_2$CH$_3$-pyridazin-3-yl |
| 2085 | 4-OCH(CH$_2$Cl)CH$_2$OCH$_3$-pyridazin-3-yl |
| 2086 | 6-OCH(CH$_2$Cl)CH$_2$OCH$_3$-pyridazin-3-yl |
| 2087 | 4-OCH(CH$_2$Cl)CH$_2$OCH$_2$CH$_3$-pyridazin-3-yl |
| 2088 | 6-OCH(CH$_2$Cl)CH$_2$OCH$_2$CH$_3$-pyridazin-3-yl |
| 2089 | 4-OCH(CH$_2$Cl)CH$_2$OCH(CH$_3$)$_2$-pyridazin-3-yl |
| 2090 | 6-OCH(CH$_2$Cl)CH$_2$OCH(CH$_3$)$_2$-pyridazin-3-yl |
| 2091 | 4-OCH(CH$_2$Cl)CH$_2$OCH$_2$CH=CH$_2$-pyridazin-3-yl |
| 2092 | 6-OCH(CH$_2$Cl)CH$_2$OCH$_2$CH=CH$_2$-pyridazin-3-yl |
| 2093 | 4-OCH[CH$_2$OCH$_3$]$_2$-pyridazin-3-yl |
| 2094 | 6-OCH[CH$_2$OCH$_3$]$_2$-pyridazin-3-yl |
| 2095 | 4-OCH[CH$_2$OCH$_2$CH$_3$]$_2$-pyridazin-3-yl |
| 2096 | 6-OCH[CH$_2$OCH$_2$CH$_3$]$_2$-pyridazin-3-yl |
| 2097 | 4-OCCl$_3$-pyridazin-3-yl |
| 2098 | 6-OCCl$_3$-pyridazin-3-yl |
| 2099 | 4-OCHF$_2$-pyridazin-3-yl |
| 2100 | 6-OCHF$_2$-pyridazin-3-yl |
| 2101 | 4-OCF$_3$-pyridazin-3-yl |
| 2102 | 6-OCF$_3$-pyridazin-3-yl |
| 2103 | 4-OCF$_2$CHF$_2$-pyridazin-3-yl |
| 2104 | 6-OCF$_2$CHF$_2$-pyridazin-3-yl |
| 2105 | 4-OCH$_2$CF$_3$-pyridazin-3-yl |
| 2106 | 6-OCH$_2$CF$_3$-pyridazin-3-yl |
| 2107 | 4-OCH$_2$CHF$_2$-pyridazin-3-yl |
| 2108 | 6-OCH$_2$CHF$_2$-pyridazin-3-yl |
| 2109 | 4-O(CH$_2$)$_3$F-pyridazin-3-yl |
| 2110 | 6-O(CH$_2$)$_3$F-pyridazin-3-yl |
| 2111 | 4-OCH(CH$_3$)CF$_3$-pyridazin-3-yl |

TABLE A-continued

| No. | R⁴ |
|---|---|
| 2112 | 6-OCH(CH₃)CF₃-pyridazin-3-yl |
| 2113 | 4-O(CH₂)₄F-pyridazin-3-yl |
| 2114 | 6-O(CH₂)₄F-pyridazin-3-yl |
| 2115 | 4-O(CH₂)₃CF₃-pyridazin-3-yl |
| 2116 | 6-O(CH₂)₃CF₃-pyridazin-3-yl |
| 2117 | 4-OCH(CH₃)CF₂CF₃-pyridazin-3-yl |
| 2118 | 6-OCH(CH₃)CF₂CF₃-pyridazin-3-yl |
| 2119 | 4-OCH(CH₃)CF₂CHF₂-pyridazin-3-yl |
| 2120 | 6-OCH(CH₃)CF₂CHF₂-pyridazin-3-yl |
| 2121 | 4-OCH₂CF₂CHFCH₃-pyridazin-3-yl |
| 2122 | 6-OCH₂CF₂CHFCH₃-pyridazin-3-yl |
| 2123 | 4-OCH₂(CF₂)₂CF₃-pyridazin-3-yl |
| 2124 | 6-OCH₂(CF₂)₂CF₃-pyridazin-3-yl |
| 2125 | 4-O(CF₂)₃CF₃-pyridazin-3-yl |
| 2126 | 6-O(CF₂)₃CF₃-pyridazin-3-yl |
| 2127 | 4-OCH₂CF₂CHF₂-pyridazin-3-yl |
| 2128 | 6-OCH₂CF₂CHF₂-pyridazin-3-yl |
| 2129 | 4-CH₂CH=CH₂-pyridazin-3-yl |
| 2130 | 6-CH₂CH=CH₂-pyridazin-3-yl |
| 2131 | 4-CH₂C(CH₃)=CH₂-pyridazin-3-yl |
| 2132 | 6-CH₂C(CH₃)=CH₂-pyridazin-3-yl |
| 2133 | 4-OCH₂CH=CHCH₃-pyridazin-3-yl |
| 2134 | 6-OCH₂CH=CHCH₃-pyridazin-3-yl |
| 2135 | 4-O(CH₂)₂CH=CH₂-pyridazin-3-yl |
| 2136 | 6-O(CH₂)₂CH=CH₂-pyridazin-3-yl |
| 2137 | 4-OCH₂C(CH₃)=CH₂-pyridazin-3-yl |
| 2138 | 6-OCH₂C(CH₃)=CH₂-pyridazin-3-yl |
| 2139 | 4-OCH(CH₃)CH=CH₂-pyridazin-3-yl |
| 2140 | 6-OCH(CH₃)CH=CH₂-pyridazin-3-yl |
| 2141 | 4-OCH₂C≡CH-pyridazin-3-yl |
| 2142 | 6-OCH₂C≡CH-pyridazin-3-yl |
| 2143 | 4-OCH₂C≡CCH₃-pyridazin-3-yl |
| 2144 | 6-OCH₂C≡CCH₃-pyridazin-3-yl |
| 2145 | 4-O(CH₂)₂C≡CH-pyridazin-3-yl |
| 2146 | 6-O(CH₂)₂C≡CH-pyridazin-3-yl |
| 2147 | 4-SCH₃-pyridazin-3-yl |
| 2148 | 6-SCH₃-pyridazin-3-yl |
| 2149 | 4-SCH₂CH₃-pyridazin-3-yl |
| 2150 | 6-SCH₂CH₃-pyridazin-3-yl |
| 2151 | 4-OC₆H₆-pyridazin-3-yl |
| 2152 | 6-OC₆H₆-pyridazin-3-yl |
| 2153 | 4-OCH₂C₆H₆-pyridazin-3-yl |
| 2154 | 6-OCH₂C₆H₆-pyridazin-3-yl |
| 2155 | 4-NO₂-pyridazin-3-yl |
| 2156 | 6-NO₂-pyridazin-3-yl |
| 2157 | 4-NHCH₃-pyridazin-3-yl |
| 2158 | 6-NHCH₃-pyridazin-3-yl |
| 2159 | 4-N(CH₃)₂-pyridazin-3-yl |
| 2160 | 6-N(CH₃)₂-pyridazin-3-yl |
| 2161 | 4-N(CH₃)C₂H₆-pyridazin-3-yl |
| 2162 | 6-N(CH₃)C₂H₆-pyridazin-3-yl |
| 2163 | 4-NHCH₂CF₃-pyridazin-3-yl |
| 2164 | 6-NHCH₂CF₃-pyridazin-3-yl |
| 2165 | 4-F-pyridazin-3-yl |
| 2166 | 6-F-pyridazin-3-yl |
| 2167 | 4-Cl-pyridazin-3-yl |
| 2168 | 6-Cl-pyridazin-3-yl |
| 2169 | 4-OH-pyridazin-3-yl |
| 2170 | 6-OH-pyridazin-3-yl |
| 2171 | 4-CN-pyridazin-3-yl |
| 2172 | 6-CN-pyridazin-3-yl |
| 2173 | 4-C(O)NH₂-pyridazin-3-yl |
| 2174 | 6-C(O)NH₂-pyridazin-3-yl |
| 2175 | 4-C(S)NH₂-pyridazin-3-yl |
| 2176 | 6-C(S)NH₂-pyridazin-3-yl |
| 2177 | 4-CO₂CH₃-pyridazin-3-yl |
| 2178 | 6-CO₂CH₃-pyridazin-3-yl |
| 2179 | 4-ON=C(CH₃)₂-pyridazin-3-yl |
| 2180 | 6-ON=C(CH₃)₂-pyridazin-3-yl |
| 2181 | 4-[O-cyclopropyl]pyridazin-3-yl |
| 2182 | 6-[O-cyclopropyl]pyridazin-3-yl |
| 2183 | 4-[O-cyclobutyl]pyridazin-3-yl |
| 2184 | 6-[O-cyclobutyl]pyridazin-3-yl |
| 2185 | 4-[O-cyclopentyl]pyridazin-3-yl |
| 2186 | 6-[O-cyclopentyl]pyridazin-3-yl |
| 2187 | 4-[O-cyclohexyl]pyridazin-3-yl |
| 2188 | 6-[O-cyclohexyl]pyridazin-3-yl |
| 2189 | 4-[OCH₂-cyclopropyl]pyridazin-3-yl |
| 2190 | 6-[OCH₂-cyclopropyl]pyridazin-3-yl |
| 2191 | 6-F, 4-[OCH₂-cyclopropyl]pyridazin-3-yl |
| 2192 | 4-F, 6-[OCH₂-cyclopropyl]pyridazin-3-yl |
| 2193 | 6-CH₃, 4-[OCH₂-cyclopropyl]pyridazin-3-yl |
| 2194 | 4-CH₃, 6-[OCH₂-cyclopropyl]pyridazin-3-yl |
| 2195 | 6-CF₃, 4-[OCH₂-cyclopropyl]pyridazin-3-yl |
| 2196 | 4-CF₃, 6-[OCH₂-cyclopropyl]pyridazin-3-yl |
| 2197 | 4-[OCH(CH₃)-cyclopropyl]pyridazin-3-yl |
| 2198 | 6-[OCH(CH₃)-cyclopropyl]pyridazin-3-yl |
| 2199 | 6-F, 4-[OCH(CH₃)-cyclopropyl]pyridazin-3-yl |
| 2200 | 4-F, 6-[OCH(CH₃)-cyclopropyl]pyridazin-3-yl |
| 2201 | 6-CH₃, 4-[OCH(CH₃)-cyclopropyl]pyridazin-3-yl |
| 2202 | 4-CH₃, 6-[OCH(CH₃)-cyclopropyl]pyridazin-3-yl |
| 2203 | 6-CF₃, 4-[OCH(CH₃)-cyclopropyl]pyridazin-3-yl |
| 2204 | 4-CF₃, 6-[OCH(CH₃)-cyclopropyl]pyridazin-3-yl |
| 2205 | 4-[O-(1-CH₃-cyclopropyl)]pyridazin-3-yl |
| 2206 | 6-[O-(1-CH₃-cyclopropyl)]pyridazin-3-yl |
| 2207 | 6-F, 4-[O-(1-CH₃-cyclopropyl)]pyridazin-3-yl |
| 2208 | 4-F, 6-[O-(1-CH₃-cyclopropyl)]pyridazin-3-yl |
| 2209 | 6-CH₃, 4-[O-(1-CH₃-cyclopropyl)]pyridazin-3-yl |
| 2210 | 4-CH₃, 6-[O-(1-CH₃-cyclopropyl)]pyridazin-3-yl |
| 2211 | 6-CF₃, 4-[O-(1-CH₃-cyclopropyl)]pyridazin-3-yl |
| 2212 | 4-CF₃, 6-[O-(1-CH₃-cyclopropyl)]pyridazin-3-yl |
| 2213 | 4-[OCH₂-(1-CH₃-cyclopropyl)]pyridazin-3-yl |
| 2214 | 6-[OCH₂-(1-CH₃-cyclopropyl)]pyridazin-3-yl |
| 2215 | 6-F, 4-[OCH₂-(1-CH₃-cyclopropyl)]pyridazin-3-yl |
| 2216 | 4-F, 6-[OCH₂-(1-CH₃-cyclopropyl)]pyridazin-3-yl |
| 2217 | 6-CH₃, 4-[OCH₂-(1-CH₃-cyclopropyl)]pyridazin-3-yl |
| 2218 | 4-CH₃, 6-[OCH₂-(1-CH₃-cyclopropyl)]pyridazin-3-yl |
| 2219 | 6-CF₃, 4-[OCH₂-(1-CH₃-cyclopropyl)]pyridazin-3-yl |
| 2220 | 4-CF₃, 6-[OCH₂-(1-CH₃-cyclopropyl)]pyridazin-3-yl |
| 2221 | 4-[OCH₂-(2-CH₃-cyclopropyl)]pyridazin-3-yl |
| 2222 | 6-[OCH₂-(2-CH₃-cyclopropyl)]pyridazin-3-yl |
| 2223 | 6-F, 4-[OCH₂-(2-CH₃-cyclopropyl)]pyridazin-3-yl |
| 2224 | 4-F, 6-[OCH₂-(2-CH₃-cyclopropyl)]pyridazin-3-yl |
| 2225 | 6-CH₃, 4-[OCH₂-(2-CH₃-cyclopropyl)]pyridazin-3-yl |
| 2226 | 4-CH₃, 6-[OCH₂-(2-CH₃-cyclopropyl)]pyridazin-3-yl |
| 2227 | 6-CF₃, 4-[OCH₂-(2-CH₃-cyclopropyl)]pyridazin-3-yl |
| 2228 | 4-CF₃, 6-[OCH₂-(2-CH₃-cyclopropyl)]pyridazin-3-yl |
| 2229 | 4-[OCH₂-(tetrahydropyran-2-yl)]pyridazin-3-yl |
| 2230 | 6-[OCH₂-(tetrahydropyran-2-yl)]pyridazin-3-yl |
| 2231 | 6-F, 4-[OCH₂-(tetrahydropyran-2-yl)]pyridazin-3-yl |
| 2232 | 4-F, 6-[OCH₂-(tetrahydropyran-2-yl)]pyridazin-3-yl |
| 2233 | 6-CH₃, 4-[OCH₂-(tetrahydropyran-2-yl)]pyridazin-3-yl |
| 2234 | 4-CH₃, 6-[OCH₂-(tetrahydropyran-2-yl)]pyridazin-3-yl |
| 2235 | 6-CF₃, 4-[OCH₂-(tetrahydropyran-2-yl)]pyridazin-3-yl |
| 2236 | 4-CF₃, 6-[OCH₂-(tetrahydropyran-2-yl)]pyridazin-3-yl |
| 2237 | 4-[OCH₂-(furan-2-yl)]pyridazin-3-yl |
| 2238 | 6-[OCH₂-(furan-2-yl)]pyridazin-3-yl |
| 2239 | 6-F, 4-[OCH₂-(furan-2-yl)]pyridazin-3-yl |
| 2240 | 4-F, 6-[OCH₂-(furan-2-yl)]pyridazin-3-yl |
| 2241 | 6-CH₃, 4-[OCH₂-(furan-2-yl)]pyridazin-3-yl |
| 2242 | 4-CH₃, 6-[OCH₂-(furan-2-yl)]pyridazin-3-yl |
| 2243 | 6-CF₃, 4-[OCH₂-(furan-2-yl)]pyridazin-3-yl |
| 2244 | 4-CF₃, 6-[OCH₂-(furan-2-yl)]pyridazin-3-yl |
| 2245 | 4-[OCH₂-(furan-3-yl)]pyridazin-3-yl |
| 2246 | 6-[OCH₂-(furan-3-yl)]pyridazin-3-yl |
| 2247 | 6-F, 4-[OCH₂-(furan-3-yl)]pyridazin-3-yl |
| 2248 | 4-F, 6-[OCH₂-(furan-3-yl)]pyridazin-3-yl |
| 2249 | 6-CH₃, 4-[OCH₂-(furan-3-yl)]pyridazin-3-yl |
| 2250 | 4-CH₃, 6-[OCH₂-(furan-3-yl)]pyridazin-3-yl |
| 2251 | 6-CF₃, 4-[OCH₂-(furan-3-yl)]pyridazin-3-yl |
| 2252 | 4-CF₃, 6-[OCH₂-(furan-3-yl)]pyridazin-3-yl |
| 2253 | 4-[OCH₂-(tetrahydrofuran-3-yl)]pyridazin-3-yl |
| 2254 | 6-[OCH₂-(tetrahydrofuran-3-yl)]pyridazin-3-yl |
| 2255 | 6-F, 4-[OCH₂-(tetrahydrofuran-3-yl)]pyridazin-3-yl |
| 2256 | 4-F, 6-[OCH₂-(tetrahydrofuran-3-yl)]pyridazin-3-yl |
| 2257 | 6-CH₃, 4-[OCH₂-(tetrahydrofuran-3-yl)]pyridazin-3-yl |
| 2258 | 4-CH₃, 6-[OCH₂-(tetrahydrofuran-3-yl)]pyridazin-3-yl |
| 2259 | 6-CF₃, 4-[OCH₂-(tetrahydrofuran-3-yl)]pyridazin-3-yl |
| 2260 | 4-CF₃, 6-[OCH₂-(tetrahydrofuran-3-yl)]pyridazin-3-yl |
| 2261 | 4-[OCH₂-(tetrahydrofuran-2-yl)]pyridazin-3-yl |
| 2262 | 6-[OCH₂-(tetrahydrofuran-2-yl)]pyridazin-3-yl |
| 2263 | 6-F, 4-[OCH₂-(tetrahydrofuran-2-yl)]pyridazin-3-yl |
| 2264 | 4-F, 6-[OCH₂-(tetrahydrofuran-2-yl)]pyridazin-3-yl |
| 2265 | 6-CH₃, 4-[OCH₂-(tetrahydrofuran-2-yl)]pyridazin-3-yl |

TABLE A-continued

| No. | R⁴ |
|---|---|
| 2266 | 4-CH₃, 6-[OCH₂-(tetrahydrofuran-2-yl)]pyridazin-3-yl |
| 2267 | 6-CF₃, 4-[OCH₂-(tetrahydrofuran-2-yl)]pyridazin-3-yl |
| 2268 | 4-CF₃, 6-[OCH₂-(tetrahydrofuran-2-yl)]pyridazin-3-yl |
| 2269 | 4-[O-(tetrahydropyran-4-yl)]pyridazin-3-yl |
| 2270 | 6-[O-(tetrahydropyran-4-yl)]pyridazin-3-yl |
| 2271 | 6-F, 4-[O-(tetrahydropyran-4-yl)]pyridazin-3-yl |
| 2272 | 4-F, 6-[O-(tetrahydropyran-4-yl)]pyridazin-3-yl |
| 2273 | 6-CH₃, 4-[O-(tetrahydropyran-4-yl)]pyridazin-3-yl |
| 2274 | 4-CH₃, 6-[O-(tetrahydropyran-4-yl)]pyridazin-3-yl |
| 2275 | 6-CF₃, 4-[O-(tetrahydropyran-4-yl)]pyridazin-3-yl |
| 2276 | 4-CF₃, 6-[O-(tetrahydropyran-4-yl)]pyridazin-3-yl |
| 2277 | 4-[2-Cl—C₅H₄]pyridazin-3-yl |
| 2278 | 6-[2-Cl—C₅H₄]pyridazin-3-yl |
| 2279 | 6-F, 4-[2-Cl—C₅H₄]pyridazin-3-yl |
| 2280 | 4-F, 6-[2-Cl—C₅H₄]pyridazin-3-yl |
| 2281 | 6-CH₃, 4-[2-Cl—C₅H₄]pyridazin-3-yl |
| 2282 | 4-CH₃, 6-[2-Cl—C₅H₄]pyridazin-3-yl |
| 2283 | 6-CF₃, 4-[2-Cl—C₅H₄]pyridazin-3-yl |
| 2284 | 4-CF₃, 6-[2-Cl—C₅H₄]pyridazin-3-yl |
| 2285 | 4-[OCH₂-(pyridin-2-yl)]pyridazin-3-yl |
| 2286 | 6-[OCH₂-(pyridin-2-yl)]pyridazin-3-yl |
| 2287 | 6-F, 4-[OCH₂-(pyridin-2-yl)]pyridazin-3-yl |
| 2288 | 4-F, 6-[OCH₂-(pyridin-2-yl)]pyridazin-3-yl |
| 2289 | 6-CH₃, 4-[OCH₂-(pyridin-2-yl)]pyridazin-3-yl |
| 2290 | 4-CH₃, 6-[OCH₂-(pyridin-2-yl)]pyridazin-3-yl |
| 2291 | 6-CF₃, 4-[OCH₂-(pyridin-2-yl)]pyridazin-3-yl |
| 2292 | 4-CF₃, 6-[OCH₂-(pyridin-2-yl)]pyridazin-3-yl |
| 2293 | 4-[OCH₂-(pyridin-3-yl)]pyridazin-3-yl |
| 2294 | 6-[OCH₂-(pyridin-3-yl)]pyridazin-3-yl |
| 2295 | 6-F, 4-[OCH₂-(pyridin-3-yl)]pyridazin-3-yl |
| 2296 | 4-F, 6-[OCH₂-(pyridin-3-yl)]pyridazin-3-yl |
| 2297 | 6-CH₃, 4-[OCH₂-(pyridin-3-yl)]pyridazin-3-yl |
| 2298 | 4-CH₃, 6-[OCH₂-(pyridin-3-yl)]pyridazin-3-yl |
| 2299 | 6-CF₃, 4-[OCH₂-(pyridin-3-yl)]pyridazin-3-yl |
| 2300 | 4-CF₃, 6-[OCH₂-(pyridin-3-yl)]pyridazin-3-yl |
| 2301 | 4-[morpholin-4-yl]pyridazin-3-yl |
| 2302 | 6-[morpholin-4-yl]pyridazin-3-yl |
| 2303 | 4-[1-CH₃-imidazol-2-yl]pyridazin-3-yl |
| 2304 | 6-[1-CH₃-imidazol-2-yl]pyridazin-3-yl |
| 2305 | 6-F, 4-[1-CH₃-imidazol-2-yl]pyridazin-3-yl |
| 2306 | 4-F, 6-[1-CH₃-imidazol-2-yl]pyridazin-3-yl |
| 2307 | 6-CH₃, 4-[1-CH₃-imidazol-2-yl]pyridazin-3-yl |
| 2308 | 4-CH₃, 6-[1-CH₃-imidazol-2-yl]pyridazin-3-yl |
| 2309 | 6-CF₃, 4-[1-CH₃-imidazol-2-yl]pyridazin-3-yl |
| 2310 | 4-CF₃, 6-[1-CH₃-imidazol-2-yl]pyridazin-3-yl |
| 2311 | 4-[1,2,4-triazol-1-yl]pyridazin-3-yl |
| 2312 | 6-[1,2,4-triazol-1-yl]pyridazin-3-yl |
| 2313 | 6-F, 4-[1,2,4-triazol-1-yl)pyridazin-3-yl |
| 2314 | 4-F, 6-[1,2,4-triazol-1-yl)pyridazin-3-yl |
| 2315 | 6-CH₃, 4-[1,2,4-triazol-1-yl]pyridazin-3-yl |
| 2316 | 4-CH₃, 6-[1,2,4-triazol-1-yl]pyridazin-3-yl |
| 2317 | 6-CF₃, 4-[1,2,4-triazol-1-yl]pyridazin-3-yl |
| 2318 | 4-CF₃, 6-[1,2,4-triazol-1-yl]pyridazin-3-yl |
| 2319 | 4,6-Cl₂-pyridazin-3-yl |
| 2320 | 4,5-Cl₂-pyridazin-3-yl |
| 2321 | 4,6-(CH₃)₂-pyridazin-3-yl |
| 2322 | 4,5-(CH₃)₂-pyridazin-3-yl |
| 2323 | 4,6-(OCH₃)₂-pyridazin-3-yl |
| 2324 | 4,5-(OCH₃)₂-pyridazin-3-yl |
| 2325 | 4,6-(OCH₂CH₃)₂-pyridazin-3-yl |
| 2326 | 4,5-(OCH₂CH₃)₂-pyridazin-3-yl |
| 2327 | 4-F, 6-CH₃-pyridazin-3-yl |
| 2328 | 4-F, 5-CH₃-pyridazin-3-yl |
| 2329 | 6-F, 4-CH₃-pyridazin-3-yl |
| 2330 | 5-F, 4-CH₃-pyridazin-3-yl |
| 2331 | 4-F, 6-OCH₃-pyridazin-3-yl |
| 2332 | 4-F, 5-OCH₃-pyridazin-3-yl |
| 2333 | 6-F, 4-OCH₃-pyridazin-3-yl |
| 2334 | 5-F, 4-OCH₃-pyridazin-3-yl |
| 2335 | 4-F, 6-OCH₂CH₃-pyridazin-3-yl |
| 2336 | 4-F, 5-OCH₂CH₃-pyridazin-3-yl |
| 2337 | 6-F, 4-OCH₂CH₃-pyridazin-3-yl |
| 2338 | 5-F, 4-OCH₂CH₃-pyridazin-3-yl |
| 2339 | 4-F, 6-OCH₂CF₃-pyridazin-3-yl |
| 2340 | 4-F, 5-OCH₂CF₃-pyridazin-3-yl |
| 2341 | 6-F, 4-OCH₂CF₃-pyridazin-3-yl |
| 2342 | 5-F, 4-OCH₂CF₃-pyridazin-3-yl |
| 2343 | 4-F, 6-OCH(CH₃)₂-pyridazin-3-yl |
| 2344 | 4-F, 5-OCH(CH₃)₂-pyridazin-3-yl |
| 2345 | 6-F, 4-OCH(CH₃)₂-pyridazin-3-yl |
| 2346 | 5-F, 4-OCH(CH₃)₂-pyridazin-3-yl |
| 2347 | 4-Cl, 6-CH₃-pyridazin-3-yl |
| 2348 | 4-Cl, 5-CH₃-pyridazin-3-yl |
| 2349 | 6-Cl, 4-CH₃-pyridazin-3-yl |
| 2350 | 5-Cl, 4-CH₃-pyridazin-3-yl |
| 2351 | 4-Cl, 6-OCH₃-pyridazin-3-yl |
| 2352 | 4-Cl, 5-OCH₃-pyridazin-3-yl |
| 2353 | 6-Cl, 4-OCH₃-pyridazin-3-yl |
| 2354 | 5-Cl, 4-OCH₃-pyridazin-3-yl |
| 2355 | 4-Cl, 6-OCH₂CH₃-pyridazin-3-yl |
| 2356 | 4-Cl, 5-OCH₂CH₃-pyridazin-3-yl |
| 2357 | 6-Cl, 4-OCH₂CH₃-pyridazin-3-yl |
| 2358 | 5-Cl, 4-OCH₂CH₃-pyridazin-3-yl |
| 2359 | 4-Cl, 6-OCH₂CF₃-pyridazin-3-yl |
| 2360 | 4-Cl, 5-OCH₂CF₃-pyridazin-3-yl |
| 2361 | 6-Cl, 4-OCH₂CF₃-pyridazin-3-yl |
| 2362 | 5-Cl, 4-OCH₂CF₃-pyridazin-3-yl |
| 2363 | 4-Cl, 6-OCH(CH₃)₂-pyridazin-3-yl |
| 2364 | 4-Cl, 5-OCH(CH₃)₂-pyridazin-3-yl |
| 2365 | 6-Cl, 4-OCH(CH₃)₂-pyridazin-3-yl |
| 2366 | 5-Cl, 4-OCH(CH₃)₂-pyridazin-3-yl |
| 2367 | 4-CH₃, 6-OCH₃-pyridazin-3-yl |
| 2368 | 4-CH₃, 5-OCH₃-pyridazin-3-yl |
| 2369 | 6-CH₃, 4-OCH₃-pyridazin-3-yl |
| 2370 | 5-CH₃, 4-OCH₃-pyridazin-3-yl |
| 2371 | 5-CH₃, 4-OCH₂CH₃-pyridazin-3-yl |
| 2372 | 6-CH₃, 4-OCH₂CH₃-pyridazin-3-yl |
| 2373 | 4-CH₃, 6-OCH₃-pyridazin-3-yl |
| 2374 | 4-CH₃, 5-OCH₂CH₃-pyridazin-3-yl |
| 2375 | 4-CH₃, 6-OCH₂CF₃-pyridazin-3-yl |
| 2376 | 4-CH₃, 5-OCH₂CF₃-pyridazin-3-yl |
| 2377 | 6-CH₃, 4-OCH₂CF₃-pyridazin-3-yl |
| 2378 | 5-CH₃, 4-OCH₂CF₃-pyridazin-3-yl |
| 2379 | 4-CH₃, 6-OCH(CH₃)₂-pyridazin-3-yl |
| 2380 | 4-CH₃, 5-OCH(CH₃)₂-pyridazin-3-yl |
| 2381 | 6-CH₃, 4-OCH(CH₃)₂-pyridazin-3-yl |
| 2382 | 5-CH₃, 4-OCH(CH₃)₂-pyridazin-3-yl |
| 2383 | 4-CH₃, 6-OCH₂CH=CH₂-pyridazin-3-yl |
| 2384 | 4-CH₃, 5-OCH₂CH=CH₂-pyridazin-3-yl |
| 2385 | 6-CH₃, 4-OCH₂CH=CH₂-pyridazin-3-yl |
| 2386 | 5-CH₃, 4-OCH₂CH=CH₂-pyridazin-3-yl |
| 2387 | 4-CH₃, 6-CO₂CH₃-pyridazin-3-yl |
| 2388 | 4-CH₃, 5-CO₂CH₃-pyridazin-3-yl |
| 2389 | 4-CH₃, 6-CF₃-pyridazin-3-yl |
| 2390 | 4-CH₃, 5-CF₃-pyridazin-3-yl |
| 2391 | 6-CH₃, 4-CF₃-pyridazin-3-yl |
| 2392 | 5-CH₃, 4-CF₃-pyridazin-3-yl |
| 2393 | 4-CF₃, 6-CH₂CH₃-pyridazin-3-yl |
| 2394 | 4-CF₃, 5-CH₂CH₃-pyridazin-3-yl |
| 2395 | 6-CF₃, 4-CH₂CH₃-pyridazin-3-yl |
| 2396 | 5-CF₃, 4-CH₂CH₃-pyridazin-3-yl |
| 2397 | 4-CF₃, 6-OCH₃-pyridazin-3-yl |
| 2398 | 4-CF₃, 5-OCH₃-pyridazin-3-yl |
| 2399 | 6-CF₃, 4-OCH₃-pyridazin-3-yl |
| 2400 | 5-CF₃, 4-OCH₃-pyridazin-3-yl |
| 2401 | 4-CF₃, 6-OCH₂CH₃-pyridazin-3-yl |
| 2402 | 4-CF₃, 5-OCH₂CH₃-pyridazin-3-yl |
| 2403 | 6-CF₃, 4-OCH₂CH₃-pyridazin-3-yl |
| 2404 | 5-CF₃, 4-OCH₂CH₃-pyridazin-3-yl |
| 2405 | 4-CF₃, 6-OCH₂CF₃-pyridazin-3-yl |
| 2406 | 4-CF₃, 5-OCH₂CF₃-pyridazin-3-yl |
| 2407 | 6-CF₃, 4-OCH₂CF₃-pyridazin-3-yl |
| 2408 | 5-CF₃, 4-OCH₂CF₃-pyridazin-3-yl |
| 2409 | 4-OCH₃, 6-OCH₂CH₃-pyridazin-3-yl |
| 2410 | 4-OCH₃, 5-OCH₂CH₃-pyridazin-3-yl |
| 2411 | 6-OCH₃, 4-OCH₂CH₃-pyridazin-3-yl |
| 2412 | 5-OCH₃, 4-OCH₂CH₃-pyridazin-3-yl |
| 2413 | 4-OCH₃, 6-OCH₂CF₃-pyridazin-3-yl |
| 2414 | 4-OCH₃, 5-OCH₂CF₃-pyridazin-3-yl |
| 2415 | 6-OCH₃, 4-OCH₂CF₃-pyridazin-3-yl |
| 2416 | 5-OCH₃, 4-OCH₂CF₃-pyridazin-3-yl |
| 2417 | 4-OCH₃, 6-OCH(CH₃)-pyridazin-3-yl |
| 2418 | 4-OCH₃, 5-OCH(CH₃)-pyridazin-3-yl |
| 2419 | 6-OCH₃, 4-OCH(CH₃)-pyridazin-3-yl |

TABLE A-continued

| No. | R⁴ |
|---|---|
| 2420 | 5-OCH₃, 4-OCH(CH₃)-pyridazin-3-yl |
| 2421 | 4-OCH₂CH₃, 6-CH₂OCH₂CH₃-pyridazin-3-yl |
| 2422 | 4-OCH₂CH₃, 5-CH₂OCH₂CH₃-pyridazin-3-yl |
| 2423 | 6-OCH₂CH₃, 4-CH₂OCH₂CH₃-pyridazin-3-yl |
| 2424 | 5-OCH₂CH₃, 4-CH₂OCH₂CH₃-pyridazin-3-yl |
| 2425 | 4-NO₂, 6-CH₃-pyridazin-3-yl |
| 2426 | 4-NO₂, 5-CH₃-pyridazin-3-yl |
| 2427 | 6-NO₂, 4-CH₃-pyridazin-3-yl |
| 2428 | 5-NO₂, 4-CH₃-pyridazin-3-yl |
| 2429 | 4-NO₂, 6-OCH₃-pyridazin-3-yl |
| 2430 | 4-NO₂, 5-OCH₃-pyridazin-3-yl |
| 2431 | 6-NO₂, 4-OCH₃-pyridazin-3-yl |
| 2432 | 5-NO₂, 4-OCH₃-pyridazin-3-yl |
| 2433 | 4-NO₂, 6-OCH₂CH₃-pyridazin-3-yl |
| 2434 | 4-NO₂, 5-OCH₂CH₃-pyridazin-3-yl |
| 2435 | 6-NO₂, 4-OCH₂CH₃-pyridazin-3-yl |
| 2436 | 5-NO₂, 4-OCH₂CH₃-pyridazin-3-yl |
| 2437 | 4-NO₂, 6-OCH(CH₃)₂-pyridazin-3-yl |
| 2438 | 4-NO₂, 5-OCH(CH₃)₂-pyridazin-3-yl |
| 2439 | 6-NO₂, 4-OCH(CH₃)₂-pyridazin-3-yl |
| 2440 | 5-NO₂, 4-OCH(CH₃)₂-pyridazin-3-yl |
| 2441 | 4-NO₂, 6-OCH₂CF₃-pyridazin-3-yl |
| 2442 | 4-NO₂, 5-OCH₂CF₃-pyridazin-3-yl |
| 2443 | 6-NO₂, 4-OCH₂CF₃-pyridazin-3-yl |
| 2444 | 5-NO₂, 4-OCH₂CF₃-pyridazin-3-yl |
| 2445 | 4-CN, 6-CH₃-pyridazin-3-yl |
| 2446 | 4-CN, 5-CH₃-pyridazin-3-yl |
| 2447 | 6-CN, 4-CH₃-pyridazin-3-yl |
| 2448 | 5-CN, 4-CH₃-pyridazin-3-yl |
| 2449 | 4-CN, 6-OCH₃-pyridazin-3-yl |
| 2450 | 4-CN, 5-OCH₃-pyridazin-3-yl |
| 2451 | 6-CN, 4-OCH₃-pyridazin-3-yl |
| 2452 | 5-CN, 4-OCH₃-pyridazin-3-yl |
| 2453 | 4-CN, 6-OCH₂CH₃-pyridazin-3-yl |
| 2454 | 4-CN, 5-OCH₂CH₃-pyridazin-3-yl |
| 2455 | 6-CN, 4-OCH₂CH₃-pyridazin-3-yl |
| 2456 | 5-CN, 4-OCH₂CH₃-pyridazin-3-yl |
| 2457 | 4-CN, 6-OCH(CH₃)₂-pyridazin-3-yl |
| 2458 | 4-CN, 5-OCH(CH₃)₂-pyridazin-3-yl |
| 2459 | 6-CN, 4-OCH(CH₃)₂-pyridazin-3-yl |
| 2460 | 5-CN, 4-OCH(CH₃)₂-pyridazin-3-yl |
| 2461 | 4-CN, 6-OCH₂CF₃-pyridazin-3-yl |
| 2462 | 4-CN, 5-OCH₂CF₃-pyridazin-3-yl |
| 2463 | 6-CN, 4-OCH₂CF₃-pyridazin-3-yl |
| 2464 | 5-CN, 4-OCH₂CF₃-pyridazin-3-yl |
| 2465 | 5,6-(CH₃)₂, 4-OCH₃-pyridazin-3-yl |
| 2466 | 3-CH₃-pyridazin-4-yl |
| 2467 | 6-CH₃-pyridazin-4-yl |
| 2468 | 3-CH₂CH₃-pyridazin-4-yl |
| 2469 | 6-CH₂CH₃-pyridazin-4-yl |
| 2470 | 3-CH(CH₃)₂-pyridazin-4-yl |
| 2471 | 6-CH(CH₃)₂-pyridazin-4-yl |
| 2472 | 3-CH(CH₃)CH₂CH₃-pyridazin-4-yl |
| 2473 | 6-CH(CH₃)CH₂CH₃-pyridazin-4-yl |
| 2474 | 3-CF₃-pyridazin-4-yl |
| 2475 | 6-CF₃-pyridazin-4-yl |
| 2476 | 3-CH=CH₂-pyridazin-4-yl |
| 2477 | 6-CH=CH₂-pyridazin-4-yl |
| 2478 | 3-CH=CHCH₃-pyridazin-4-yl |
| 2479 | 6-CH=CHCH₃-pyridazin-4-yl |
| 2480 | 3-CH=CHCl-pyridazin-4-yl |
| 2481 | 6-CH=CHCl-pyridazin-4-yl |
| 2482 | 3-C≡CH-pyridazin-4-yl |
| 2483 | 6-C≡CH-pyridazin-4-yl |
| 2484 | 3-CH₂C≡CH-pyridazin-4-yl |
| 2485 | 6-CH₂C≡CH-pyridazin-4-yl |
| 2486 | 3-CH₂C≡CCH₃-pyridazin-4-yl |
| 2487 | 6-CH₂C≡CCH₃-pyridazin-4-yl |
| 2488 | 3-cyclopropylpyridazin-4-yl |
| 2489 | 6-cyclopropylpyridazin-4-yl |
| 2490 | 3-cyclopentylpyridazin-4-yl |
| 2491 | 6-cyclopentylpyridazin-4-yl |
| 2492 | 3-OCH₃-pyridazin-4-yl |
| 2493 | 6-OCH₃-pyridazin-4-yl |
| 2494 | 3-OCH₂CH₃-pyridazin-4-yl |
| 2495 | 6-OCH₂CH₃-pyridazin-4-yl |
| 2496 | 3-OCH₂CH₂CH₃-pyridazin-4-yl |
| 2497 | 6-OCH₂CH₂CH₃-pyridazin-4-yl |
| 2498 | 3-OCH(CH₃)₂-pyridazin-4-yl |
| 2499 | 6-OCH(CH₃)₂-pyridazin-4-yl |
| 2500 | 3-OCH₂CH₂CH₂CH₃-pyridazin-4-yl |
| 2501 | 6-OCH₂CH₂CH₂CH₃-pyridazin-4-yl |
| 2502 | 3-OCH(CH₃)CH₂CH₃-pyridazin-4-yl |
| 2503 | 6-OCH(CH₃)CH₂CH₃-pyridazin-4-yl |
| 2504 | 3-OCH₂CH(CH₃)₂-pyridazin-4-yl |
| 2505 | 6-OCH₂CH(CH₃)₂-pyridazin-4-yl |
| 2506 | 3-OC(CH₃)₃-pyridazin-4-yl |
| 2507 | 6-OC(CH₃)₃-pyridazin-4-yl |
| 2508 | 3-OCH(CH₃)CH₂CH₂CH₃-pyridazin-4-yl |
| 2509 | 6-OCH(CH₃)CH₂CH₂CH₃-pyridazin-4-yl |
| 2510 | 3-OCH₂OCH₃-pyridazin-4-yl |
| 2511 | 6-OCH₂OCH₃-pyridazin-4-yl |
| 2512 | 3-OCH₂OCH₂CH₃-pyridazin-4-yl |
| 2513 | 6-OCH₂OCH₂CH₃-pyridazin-4-yl |
| 2514 | 3-OCH(CH₃)OCH₃-pyridazin-4-yl |
| 2515 | 6-OCH(CH₃)OCH₃-pyridazin-4-yl |
| 2516 | 3-OCH(CH₃)OCH₂CH₃-pyridazin-4-yl |
| 2517 | 6-OCH(CH₃)OCH₂CH₃-pyridazin-4-yl |
| 2518 | 3-OCH₂CH₂OCH₃-pyridazin-4-yl |
| 2519 | 6-OCH₂CH₂OCH₃-pyridazin-4-yl |
| 2520 | 3-OCH₂CH₂OCH₂CH₃-pyridazin-4-yl |
| 2521 | 6-OCH₂CH₂OCH₂CH₃-pyridazin-4-yl |
| 2522 | 3-OCH₂CH₂OCH(CH₃)₂-pyridazin-4-yl |
| 2523 | 6-OCH₂CH₂OCH(CH₃)₂-pyridazin-4-yl |
| 2524 | 3-OCH₂CH₂SCH₃-pyridazin-4-yl |
| 2525 | 6-OCH₂CH₂SCH₃-pyridazin-4-yl |
| 2526 | 3-OCH₂CH₂SO₂CH₃-pyridazin-4-yl |
| 2527 | 6-OCH₂CH₂SO₂CH₃-pyridazin-4-yl |
| 2528 | 3-OCH₂CH₂SCH(CH₃)₂-pyridazin-4-yl |
| 2529 | 6-OCH₂CH₂SCH(CH₃)₂-pyridazin-4-yl |
| 2530 | 3-OCH₂CH₂CN-pyridazin-4-yl |
| 2531 | 6-OCH₂CH₂CN-pyridazin-4-yl |
| 2532 | 3-OCH₂CH₂SCH₂CH₂CN-pyridazin-4-yl |
| 2533 | 6-OCH₂CH₂SCH₂CH₂CN-pyridazin-4-yl |
| 2534 | 3-OCH₂CH₂OC₅H₆-pyridazin-4-yl |
| 2535 | 6-OCH₂CH₂OC₅H₆-pyridazin-4-yl |
| 2536 | 3-OCH₂CH₂OCH₂C₅H₆-pyridazin-4-yl |
| 2537 | 6-OCH₂CH₂OCH₂C₅H₆-pyridazin-4-yl |
| 2538 | 3-OCH₂CH₂N(CH₃)₂-pyridazin-4-yl |
| 2539 | 6-OCH₂CH₂N(CH₃)₂-pyridazin-4-yl |
| 2540 | 3-OCH₂CH₂CONH₂-pyridazin-4-yl |
| 2541 | 6-OCH₂CH₂CONH₂-pyridazin-4-yl |
| 2542 | 3-OCH₂CH₂CO₂CH₂CH₂CH₃-pyridazin-4-yl |
| 2543 | 6-OCH₂CH₂CO₂CH₂CH₂CH₃-pyridazin-4-yl |
| 2544 | 3-OCH(CH₃)CH₂OCH₃-pyridazin-4-yl |
| 2545 | 6-OCH(CH₃)CH₂OCH₃-pyridazin-4-yl |
| 2546 | 3-OCH(CH₃)CH₂CO₂CH₃-pyridazin-4-yl |
| 2547 | 6-OCH(CH₃)CH₂CO₂CH₃-pyridazin-4-yl |
| 2548 | 3-OCH(CH₃)CH₂CO₂CH₂CH₃-pyridazin-4-yl |
| 2549 | 6-OCH(CH₃)CH₂CO₂CH₂CH₃-pyridazin-4-yl |
| 2550 | 3-OCH₂CH(CH₃)CO₂CH₃-pyridazin-4-yl |
| 2551 | 6-OCH₂CH(CH₃)CO₂CH₃-pyridazin-4-yl |
| 2552 | 3-OCH₂C(=O)CH₃-pyridazin-4-yl |
| 2553 | 6-OCH₂C(=O)CH₃-pyridazin-4-yl |
| 2554 | 3-OCH₂C(=O)CH₂CH₃-pyridazin-4-yl |
| 2555 | 6-OCH₂C(=O)CH₂CH₃-pyridazin-4-yl |
| 2556 | 3-OCH₂CO₂CH₃-pyridazin-4-yl |
| 2557 | 6-OCH₂CO₂CH₃-pyridazin-4-yl |
| 2558 | 3-OCH₂CO₂CH₂CH₃-pyridazin-4-yl |
| 2559 | 6-OCH₂CO₂CH₂CH₃-pyridazin-4-yl |
| 2560 | 3-OCH₂C(=O)NH₂-pyridazin-4-yl |
| 2561 | 6-OCH₂C(=O)NH₂-pyridazin-4-yl |
| 2562 | 3-OCH₂C(=O)NHCH₃-pyridazin-4-yl |
| 2563 | 6-OCH₂C(=O)NHCH₃-pyridazin-4-yl |
| 2564 | 3-OCH₂C(=O)SCH₃-pyridazin-4-yl |
| 2565 | 6-OCH₂C(=O)SCH₃-pyridazin-4-yl |
| 2566 | 3-OCH(CH₃)C(=O)NH₂-pyridazin-4-yl |
| 2567 | 6-OCH(CH₃)C(=O)NH₂-pyridazin-4-yl |
| 2568 | 3-OCH(CH₃)C(=O)NHCH₃-pyridazin-4-yl |
| 2569 | 6-OCH(CH₃)C(=O)NHCH₃-pyridazin-4-yl |
| 2570 | 3-OCH(CH₃)C(=O)NHNH₂-pyridazin-4-yl |
| 2571 | 6-OCH(CH₃)C(=O)NHNH₂-pyridazin-4-yl |
| 2572 | 3-OCH(CH₃)CO₂CH₃-pyridazin-4-yl |
| 2573 | 6-OCH(CH₃)CO₂CH₃-pyridazin-4-yl |

TABLE A-continued

| No. | R⁴ |
|---|---|
| 2574 | 3-OCH(CH₃)CO₂CH₂CH₃-pyridazin-4-yl |
| 2575 | 6-OCH(CH₃)CO₂CH₂CH₃-pyridazin-4-yl |
| 2576 | 3-OCH(CH₃)C(=O)CH₃-pyridazin-4-yl |
| 2577 | 6-OCH(CH₃)C(=O)CH₃-pyridazin-4-yl |
| 2578 | 3-OCH(CH₃)C(=O)CH₂CH₃-pyridazin-4-yl |
| 2579 | 6-OCH(CH₃)C(=O)CH₂CH₃-pyridazin-4-yl |
| 2580 | 3-OCH(CH₃)CH₂C(=O)CH₃-pyridazin-4-yl |
| 2581 | 6-OCH(CH₃)CH₂C(=O)CH₃-pyridazin-4-yl |
| 2582 | 3-OCH(CH₃)CH₂OC(CH₃)₃-pyridazin-4-yl |
| 2583 | 6-OCH(CH₃)CH₂OC(CH₃)₃-pyridazin-4-yl |
| 2584 | 3-OCH(CH₃)CH₂OCH₂CH₃-pyridazin-4-yl |
| 2585 | 6-OCH(CH₃)CH₂OCH₂CH₃-pyridazin-4-yl |
| 2586 | 3-OCH(CH₃)CH₂O(CH₃)₂CH₃-pyridazin-4-yl |
| 2587 | 6-OCH(CH₃)CH₂O(CH₃)₂CH₃-pyridazin-4-yl |
| 2588 | 3-OCH(CH₃)CH₂OCH₂CH=CH₂-pyridazin-4-yl |
| 2589 | 6-OCH(CH₃)CH₂OCH₂CH=CH₂-pyridazin-4-yl |
| 2590 | 3-O(CH₂)₃OCH₃-pyridazin-4-yl |
| 2591 | 6-O(CH₂)₃OCH₃-pyridazin-4-yl |
| 2592 | 3-O(CH₂)₃OCH₂CH₃-pyridazin-4-yl |
| 2593 | 6-O(CH₂)₃OCH₂CH₃-pyridazin-4-yl |
| 2594 | 3-O(CH₂)₃OCH(CH₃)₂-pyridazin-4-yl |
| 2595 | 6-O(CH₂)₃OCH(CH₃)₂-pyridazin-4-yl |
| 2596 | 3-O(CH₂)₃OC₅H₆-pyridazin-4-yl |
| 2597 | 6-O(CH₂)₃OC₅H₆-pyridazin-4-yl |
| 2598 | 3-O(CH₂)₃OCH₂C₅H₆-pyridazin-4-yl |
| 2599 | 6-O(CH₂)₃OCH₂C₅H₆-pyridazin-4-yl |
| 2600 | 3-OCH(CH₂CH₃)CH₂OCH₃-pyridazin-4-yl |
| 2601 | 6-OCH(CH₂CH₃)CH₂OCH₃-pyridazin-4-yl |
| 2602 | 3-OCH(CH₂CH₃)CH₂CH₂OCH₃-pyridazin-4-yl |
| 2603 | 6-OCH(CH₂CH₃)CH₂CH₂OCH₃-pyridazin-4-yl |
| 2604 | 3-OCH(CH₂CH₃)CH₂CH₂OCH₂CH₃-pyridazin-4-yl |
| 2605 | 6-OCH(CH₂CH₃)CH₂CH₂OCH₂CH₃-pyridazin-4-yl |
| 2606 | 3-O[(CH₂)₃O]₂CH₃-pyridazin-4-yl |
| 2607 | 6-O[(CH₂)₃O]₂CH₃-pyridazin-4-yl |
| 2608 | 3-OCH₂CH(CH₃)CH₂OCH₃-pyridazin-4-yl |
| 2609 | 6-OCH₂CH(CH₃)CH₂OCH₃-pyridazin-4-yl |
| 2610 | 3-OCH₂CH(CH₃)CH₂OCH₂CH₃-pyridazin-4-yl |
| 2611 | 6-OCH₂CH(CH₃)CH₂OCH₂CH₃-pyridazin-4-yl |
| 2612 | 3-OCH(CH₂Cl)CH₂OCH₃-pyridazin-4-yl |
| 2613 | 6-OCH(CH₂Cl)CH₂OCH₃-pyridazin-4-yl |
| 2614 | 3-OCH(CH₂Cl)CH₂OCH₂CH₃-pyridazin-4-yl |
| 2615 | 6-OCH(CH₂Cl)CH₂OCH₂CH₃-pyridazin-4-yl |
| 2616 | 3-OCH(CH₂Cl)CH₂OCH(CH₃)₂-pyridazin-4-yl |
| 2617 | 6-OCH(CH₂Cl)CH₂OCH(CH₃)₂-pyridazin-4-yl |
| 2618 | 3-OCH(CH₂Cl)CH₂OCH₂CH=CH₂-pyridazin-4-yl |
| 2619 | 6-OCH(CH₂Cl)CH₂OCH₂CH=CH₂-pyridazin-4-yl |
| 2620 | 3-OCH[CH₂OCH₃]₂-pyridazin-4-yl |
| 2621 | 6-OCH[CH₂OCH₃]₂-pyridazin-4-yl |
| 2622 | 3-OCH[CH₂OCH₂CH₃]₂-pyridazin-4-yl |
| 2623 | 6-OCH[CH₂OCH₂CH₃]₂-pyridazin-4-yl |
| 2624 | 3-OCCl₃-pyridazin-4-yl |
| 2625 | 6-OCCl₃-pyridazin-4-yl |
| 2626 | 3-OCHF₂-pyridazin-4-yl |
| 2627 | 6-OCHF₂-pyridazin-4-yl |
| 2628 | 3-OCF₃-pyridazin-4-yl |
| 2629 | 6-OCF₃-pyridazin-4-yl |
| 2630 | 3-OCF₂CHF₂-pyridazin-4-yl |
| 2631 | 6-OCF₂CHF₂-pyridazin-4-yl |
| 2632 | 3-OCH₂CF₃-pyridazin-4-yl |
| 2633 | 6-OCH₂CF₃-pyridazin-4-yl |
| 2634 | 3-OCH₂CHF₂-pyridazin-4-yl |
| 2635 | 6-OCH₂CHF₂-pyridazin-4-yl |
| 2636 | 3-O(CH₂)₃F-pyridazin-4-yl |
| 2637 | 6-O(CH₂)₃F-pyridazin-4-yl |
| 2638 | 3-OCH(CH₃)CF₃-pyridazin-4-yl |
| 2639 | 6-OCH(CH₃)CF₃-pyridazin-4-yl |
| 2640 | 3-O(CH₂)₄F-pyridazin-4-yl |
| 2641 | 6-O(CH₂)₄F-pyridazin-4-yl |
| 2642 | 3-O(CH₂)₃CF₃-pyridazin-4-yl |
| 2643 | 6-O(CH₂)₃CF₃-pyridazin-4-yl |
| 2644 | 3-OCH(CH₃)CF₂CF₃-pyridazin-4-yl |
| 2645 | 6-OCH(CH₃)CF₂CF₃-pyridazin-4-yl |
| 2646 | 3-OCH(CH₃)CF₂CHF₂-pyridazin-4-yl |
| 2647 | 6-OCH(CH₃)CF₂CHF₂-pyridazin-4-yl |
| 2648 | 3-OCH₂CF₂CHFCH₃-pyridazin-4-yl |
| 2649 | 6-OCH₂CF₂CHFCH₃-pyridazin-4-yl |
| 2650 | 3-OCH₂(CF₂)₂CF₃-pyridazin-4-yl |
| 2651 | 6-OCH₂(CF₂)₂CF₃-pyridazin-4-yl |
| 2652 | 3-O(CF₂)₃CF₃-pyridazin-4-yl |
| 2653 | 6-O(CF₂)₃CF₃-pyridazin-4-yl |
| 2654 | 3-OCH₂CF₂CHF₂-pyridazin-4-yl |
| 2655 | 6-OCH₂CF₂CHF₂-pyridazin-4-yl |
| 2656 | 3-CH₂CH=CH₂-pyridazin-4-yl |
| 2657 | 6-CH₂CH=CH₂-pyridazin-4-yl |
| 2658 | 3-CH₂C(CH₃)=CH₂-pyridazin-4-yl |
| 2659 | 6-CH₂C(CH₃)=CH₂-pyridazin-4-yl |
| 2660 | 3-OCH₂CH=CHCH₃-pyridazin-4-yl |
| 2661 | 6-OCH₂CH=CHCH₃-pyridazin-4-yl |
| 2662 | 3-O(CH₂)₂CH=CH₂-pyridazin-4-yl |
| 2663 | 6-O(CH₂)₂CH=CH₂-pyridazin-4-yl |
| 2664 | 3-OCH₂C(CH₃)=CH₂-pyridazin-4-yl |
| 2665 | 6-OCH₂C(CH₃)=CH₂-pyridazin-4-yl |
| 2666 | 3-OCH(CH₃)CH=CH₂-pyridazin-4-yl |
| 2667 | 6-OCH(CH₃)CH=CH₂-pyridazin-4-yl |
| 2668 | 3-OCH₂C≡CH-pyridazin-4-yl |
| 2669 | 6-OCH₂C≡CH-pyridazin-4-yl |
| 2670 | 3-OCH₂C≡CCH₃-pyridazin-4-yl |
| 2671 | 6-OCH₂C≡CCH₃-pyridazin-4-yl |
| 2672 | 3-O(CH₂)₂C≡CH-pyridazin-4-yl |
| 2673 | 6-O(CH₂)₂C≡CH-pyridazin-4-yl |
| 2674 | 3-SCH₃-pyridazin-4-yl |
| 2675 | 6-SCH₃-pyridazin-4-yl |
| 2676 | 3-SCH₂CH₃-pyridazin-4-yl |
| 2677 | 6-SCH₂CH₃-pyridazin-4-yl |
| 2678 | 3-OC₅H₆-pyridazin-4-yl |
| 2679 | 6-OC₅H₆-pyridazin-4-yl |
| 2680 | 3-OCH₂C₅H₆-pyridazin-4-yl |
| 2681 | 6-OCH₂C₅H₆-pyridazin-4-yl |
| 2682 | 3-NO₂-pyridazin-4-yl |
| 2683 | 6-NO₂-pyridazin-4-yl |
| 2684 | 3-NHCH₃-pyridazin-4-yl |
| 2685 | 6-NHCH₃-pyridazin-4-yl |
| 2686 | 3-N(CH₃)₂-pyridazin-4-yl |
| 2687 | 6-N(CH₃)₂-pyridazin-4-yl |
| 2688 | 3-N(CH₃)C₂H₆-pyridazin-4-yl |
| 2689 | 6-N(CH₃)C₂H₆-pyridazin-4-yl |
| 2690 | 3-NHCH₂CF₃-pyridazin-4-yl |
| 2691 | 6-NHCH₂CF₃-pyridazin-4-yl |
| 2692 | 3-F-pyridazin-4-yl |
| 2693 | 6-F-pyridazin-4-yl |
| 2694 | 3-Cl-pyridazin-4-yl |
| 2695 | 6-Cl-pyridazin-4-yl |
| 2696 | 3-OH-pyridazin-4-yl |
| 2697 | 6-OH-pyridazin-4-yl |
| 2698 | 3-CN-pyridazin-4-yl |
| 2699 | 6-CN-pyridazin-4-yl |
| 2700 | 3-C(O)NH₂-pyridazin-4-yl |
| 2701 | 6-C(O)NH₂-pyridazin-4-yl |
| 2702 | 3-C(S)NH₂-pyridazin-4-yl |
| 2703 | 6-C(S)NH₂-pyridazin-4-yl |
| 2704 | 3-CO₂CH₃-pyridazin-4-yl |
| 2705 | 6-CO₂CH₃-pyridazin-4-yl |
| 2706 | 3-ON=C(CH₃)₂-pyridazin-4-yl |
| 2707 | 6-ON=C(CH₃)₂-pyridazin-4-yl |
| 2708 | 3-[O-cyclopropyl]pyridazin-4-yl |
| 2709 | 6-[O-cyclopropyl]pyridazin-4-yl |
| 2710 | 3-[O-cyclobutyl]pyridazin-4-yl |
| 2711 | 6-[O-cyclobutyl]pyridazin-4-yl |
| 2712 | 3-[O-cyclopentyl]pyridazin-4-yl |
| 2713 | 6-[O-cyclopentyl]pyridazin-4-yl |
| 2714 | 3-[O-cyclohexyl]pyridazin-4-yl |
| 2715 | 6-[O-cyclohexyl]pyridazin-4-yl |
| 2716 | 3-[OCH₂-cyclopropyl]pyridazin-4-yl |
| 2717 | 6-[OCH₂-cyclopropyl]pyridazin-4-yl |
| 2718 | 6-F, 3-[OCH₂-cyclopropyl]pyridazin-4-yl |
| 2719 | 3-F, 6-[OCH₂-cyclopropyl]pyridazin-4-yl |
| 2720 | 6-CH₃, 3-[OCH₂-cyclopropyl]pyridazin-4-yl |
| 2721 | 3-CH₃, 6-[OCH₂-cyclopropyl]pyridazin-4-yl |
| 2722 | 6-CF₃, 3-[OCH₂-cyclopropyl]pyridazin-4-yl |
| 2723 | 3-CF₃, 6-[OCH₂-cyclopropyl]pyridazin-4-yl |
| 2724 | 3-[OCH(CH₃)-cyclopropyl]pyridazin-4-yl |
| 2725 | 6-[OCH(CH₃)-cyclopropyl]pyridazin-4-yl |
| 2726 | 6-F, 3-[OCH(CH₃)-cyclopropyl]pyridazin-4-yl |
| 2727 | 3-F, 6-[OCH(CH₃)-cyclopropyl]pyridazin-4-yl |

TABLE A-continued

| No. | R$^4$ |
|---|---|
| 2728 | 6-CH$_3$, 3-[OCH(CH$_3$)-cyclopropyl]pyridazin-4-yl |
| 2729 | 3-CH$_3$, 6-[OCH(CH$_3$)-cyclopropyl]pyridazin-4-yl |
| 2730 | 6-CF$_3$, 3-[OCH(CH$_3$)-cyclopropyl]pyridazin-4-yl |
| 2731 | 3-CF$_3$, 6-[OCH(CH$_3$)-cyclopropyl]pyridazin-4-yl |
| 2732 | 3-[O-(1-CH$_3$-cyclopropyl)]pyridazin-4-yl |
| 2733 | 6-[O-(1-CH$_3$-cyclopropyl)]pyridazin-4-yl |
| 2734 | 6-F, 3-[O-(1-CH$_3$-cyclopropyl)]pyridazin-4-yl |
| 2735 | 3-F, 6-[O-(1-CH$_3$-cyclopropyl)]pyridazin-4-yl |
| 2736 | 6-CH$_3$, 3-[O-(1-CH$_3$-cyclopropyl)]pyridazin-4-yl |
| 2737 | 3-CH$_3$, 6-[O-(1-CH$_3$-cyclopropyl)]pyridazin-4-yl |
| 2738 | 6-CF$_3$, 3-[O-(1-CH$_3$-cyclopropyl)]pyridazin-4-yl |
| 2739 | 3-CF$_3$, 6-[O-(1-CH$_3$-cyclopropyl)]pyridazin-4-yl |
| 2740 | 3-[OCH$_2$-(1-CH$_3$-cyclopropyl)]pyridazin-4-yl |
| 2741 | 6-[OCH$_2$-(1-CH$_3$-cyclopropyl)]pyridazin-4-yl |
| 2742 | 6-F, 3-[OCH$_2$-(1-CH$_3$-cyclopropyl)]pyridazin-4-yl |
| 2743 | 3-F, 6-[OCH$_2$-(1-CH$_3$-cyclopropyl)]pyridazin-4-yl |
| 2744 | 6-CH$_3$, 3-[OCH$_2$-(1-CH$_3$-cyclopropyl)]pyridazin-4-yl |
| 2745 | 3-CH$_3$, 6-[OCH$_2$-(1-CH$_3$-cyclopropyl)]pyridazin-4-yl |
| 2746 | 6-CF$_3$, 3-[OCH$_2$-(1-CH$_3$-cyclopropyl)]pyridazin-4-yl |
| 2747 | 3-CF$_3$, 6-[OCH$_2$-(1-CH$_3$-cyclopropyl)]pyridazin-4-yl |
| 2748 | 3-[OCH$_2$-(2-CH$_3$-cyclopropyl)]pyridazin-4-yl |
| 2749 | 6-[OCH$_2$-(2-CH$_3$-cyclopropyl)]pyridazin-4-yl |
| 2750 | 6-F, 3-[OCH$_2$-(2-CH$_3$-cyclopropyl)]pyridazin-4-yl |
| 2751 | 3-F, 6-[OCH$_2$-(2-CH$_3$-cyclopropyl)]pyridazin-4-yl |
| 2752 | 6-CH$_3$, 3-[OCH$_2$-(2-CH$_3$-cyclopropyl)]pyridazin-4-yl |
| 2753 | 3-CH$_3$, 6-[OCH$_2$-(2-CH$_3$-cyclopropyl)]pyridazin-4-yl |
| 2754 | 6-CF$_3$, 3-[OCH$_2$-(2-CH$_3$-cyclopropyl)]pyridazin-4-yl |
| 2755 | 3-CF$_3$, 6-[OCH$_2$-(2-CH$_3$-cyclopropyl)]pyridazin-4-yl |
| 2756 | 3-[OCH$_2$-(tetrahydropyran-2-yl)]pyridazin-4-yl |
| 2757 | 6-[OCH$_2$-(tetrahydropyran-2-yl)]pyridazin-4-yl |
| 2758 | 6-F, 3-[OCH$_2$-(tetrahydropyran-2-yl)]pyridazin-4-yl |
| 2759 | 3-F, 6-[OCH$_2$-(tetrahydropyran-2-yl)]pyridazin-4-yl |
| 2760 | 6-CH$_3$, 3-[OCH$_2$-(tetrahydropyran-2-yl)]pyridazin-4-yl |
| 2761 | 3-CH$_3$, 6-[OCH$_2$-(tetrahydropyran-2-yl)]pyridazin-4-yl |
| 2762 | 6-CF$_3$, 3-[OCH$_2$-(tetrahydropyran-2-yl)]pyridazin-4-yl |
| 2763 | 3-CF$_3$, 6-[OCH$_2$-(tetrahydropyran-2-yl)]pyridazin-4-yl |
| 2764 | 3-[OCH$_2$-(furan-2-yl)]pyridazin-4-yl |
| 2765 | 6-[OCH$_2$-(furan-2-yl)]pyridazin-4-yl |
| 2766 | 6-F, 3-[OCH$_2$-(furan-2-yl)]pyridazin-4-yl |
| 2767 | 3-F, 6-[OCH$_2$-(furan-2-yl)]pyridazin-4-yl |
| 2768 | 6-CH$_3$, 3-[OCH$_2$-(furan-2-yl)]pyridazin-4-yl |
| 2769 | 3-CH$_3$, 6-[OCH$_2$-(furan-2-yl)]pyridazin-4-yl |
| 2770 | 6-CF$_3$, 3-[OCH$_2$-(furan-2-yl)]pyridazin-4-yl |
| 2771 | 3-CF$_3$, 6-[OCH$_2$-(furan-2-yl)]pyridazin-4-yl |
| 2772 | 3-[OCH$_2$-(furan-3-yl)]pyridazin-4-yl |
| 2773 | 6-[OCH$_2$-(furan-3-yl)]pyridazin-4-yl |
| 2774 | 6-F, 3-[OCH$_2$-(furan-3-yl)]pyridazin-4-yl |
| 2775 | 3-F, 6-[OCH$_2$-(furan-3-yl)]pyridazin-4-yl |
| 2776 | 6-CH$_3$, 3-[OCH$_2$-(furan-3-yl)]pyridazin-4-yl |
| 2777 | 3-CH$_3$, 6-[OCH$_2$-(furan-3-yl)]pyridazin-4-yl |
| 2778 | 6-CF$_3$, 3-[OCH$_2$-(furan-3-yl)]pyridazin-4-yl |
| 2779 | 3-CF$_3$, 6-[OCH$_2$-(furan-3-yl)]pyridazin-4-yl |
| 2780 | 3-[OCH$_2$-(tetrahydrofuran-3-yl)]pyridazin-4-yl |
| 2781 | 6-[OCH$_2$-(tetrahydrofuran-3-yl)]pyridazin-4-yl |
| 2782 | 6-F, 3-[OCH$_2$-(tetrahydrofuran-3-yl)]pyridazin-4-yl |
| 2783 | 3-F, 6-[OCH$_2$-(tetrahydrofuran-3-yl)]pyridazin-4-yl |
| 2784 | 6-CH$_3$, 3-[OCH$_2$-(tetrahydrofuran-3-yl)]pyridazin-4-yl |
| 2785 | 3-CH$_3$, 6-[OCH$_2$-(tetrahydrofuran-3-yl)]pyridazin-4-yl |
| 2786 | 6-CF$_3$, 3-[OCH$_2$-(tetrahydrofuran-3-yl)]pyridazin-4-yl |
| 2787 | 3-CF$_3$, 6-[OCH$_2$-(tetrahydrofuran-3-yl)]pyridazin-4-yl |
| 2788 | 3-[OCH$_2$-(tetrahydrofuran-2-yl)]pyridazin-4-yl |
| 2789 | 6-[OCH$_2$-(tetrahydrofuran-2-yl)]pyridazin-4-yl |
| 2790 | 6-F, 3-[OCH$_2$-(tetrahydrofuran-2-yl)]pyridazin-4-yl |
| 2791 | 3-F, 6-[OCH$_2$-(tetrahydrofuran-2-yl)]pyridazin-4-yl |
| 2792 | 6-CH$_3$, 3-[OCH$_2$-(tetrahydrofuran-2-yl)]pyridazin-4-yl |
| 2793 | 3-CH$_3$, 6-[OCH$_2$-(tetrahydrofuran-2-yl)]pyridazin-4-yl |
| 2794 | 6-CF$_3$, 3-[OCH$_2$-(tetrahydrofuran-2-yl)]pyridazin-4-yl |
| 2795 | 3-CF$_3$, 6-[OCH$_2$-(tetrahydrofuran-2-yl)]pyridazin-4-yl |
| 2796 | 3-[O-(tetrahydropyran-3-yl)]pyridazin-4-yl |
| 2797 | 6-[O-(tetrahydropyran-3-yl)]pyridazin-4-yl |
| 2798 | 6-F, 3-[O-(tetrahydropyran-3-yl)]pyridazin-4-yl |
| 2799 | 3-F, 6-[O-(tetrahydropyran-3-yl)]pyridazin-4-yl |
| 2800 | 6-CH$_3$, 3-[O-(tetrahydropyran-3-yl)]pyridazin-4-yl |
| 2801 | 3-CH$_3$, 6-[O-(tetrahydropyran-3-yl)]pyridazin-4-yl |
| 2802 | 6-CF$_3$, 3-[O-(tetrahydropyran-3-yl)]pyridazin-4-yl |
| 2803 | 3-CF$_3$, 6-[O-(tetrahydropyran-3-yl)]pyridazin-4-yl |
| 2804 | 3-[2-Cl-C$_5$H$_4$]pyridazin-4-yl |
| 2805 | 6-[2-Cl-C$_5$H$_4$]pyridazin-4-yl |
| 2806 | 6-F, 3-[2-Cl-C$_5$H$_4$]pyridazin-4-yl |
| 2807 | 3-F, 6-[2-Cl-C$_5$H$_4$]pyridazin-4-yl |
| 2808 | 6-CH$_3$, 3-[2-Cl-C$_5$H$_4$]pyridazin-4-yl |
| 2809 | 3-CH$_3$, 6-[2-Cl-C$_5$H$_4$]pyridazin-4-yl |
| 2810 | 6-CF$_3$, 3-[2-Cl-C$_5$H$_4$]pyridazin-4-yl |
| 2811 | 3-CF$_3$, 6-[2-Cl-C$_5$H$_4$]pyridazin-4-yl |
| 2812 | 3-[OCH$_2$-(pyridin-2-yl)]pyridazin-4-yl |
| 2813 | 6-[OCH$_2$-(pyridin-2-yl)]pyridazin-4-yl |
| 2814 | 6-F, 3-[OCH$_2$-(pyridin-2-yl)]pyridazin-4-yl |
| 2815 | 3-F, 6-[OCH$_2$-(pyridin-2-yl)]pyridazin-4-yl |
| 2816 | 6-CH$_3$, 3-[OCH$_2$-(pyridin-2-yl)]pyridazin-4-yl |
| 2817 | 3-CH$_3$, 6-[OCH$_2$-(pyridin-2-yl)]pyridazin-4-yl |
| 2818 | 6-CF$_3$, 3-[OCH$_2$-(pyridin-2-yl)]pyridazin-4-yl |
| 2819 | 3-CF$_3$, 6-[OCH$_2$-(pyridin-2-yl)]pyridazin-4-yl |
| 2820 | 3-[OCH$_2$-(pyridin-4-yl)]pyridazin-4-yl |
| 2821 | 6-[OCH$_2$-(pyridin-4-yl)]pyridazin-4-yl |
| 2822 | 6-F, 3-[OCH$_2$-(pyridin-4-yl)]pyridazin-4-yl |
| 2823 | 3-F, 6-[OCH$_2$-(pyridin-4-yl)]pyridazin-4-yl |
| 2824 | 6-CH$_3$, 3-[OCH$_2$-(pyridin-4-yl)]pyridazin-4-yl |
| 2825 | 3-CH$_3$, 6-[OCH$_2$-(pyridin-4-yl)]pyridazin-4-yl |
| 2826 | 6-CF$_3$, 3-[OCH$_2$-(pyridin-4-yl)]pyridazin-4-yl |
| 2827 | 3-CF$_3$, 6-[OCH$_2$-(pyridin-4-yl)]pyridazin-4-yl |
| 2828 | 3-[morpholin-4-yl]pyridazin-4-yl |
| 2829 | 6-[morpholin-4-yl]pyridazin-4-yl |
| 2830 | 3-[1-CH$_3$-imidazol-2-yl]pyridazin-4-yl |
| 2831 | 6-[1-CH$_3$-imidazol-2-yl]pyridazin-4-yl |
| 2832 | 6-F, 3-[1-CH$_3$-imidazol-2-yl]pyridazin-4-yl |
| 2833 | 3-F, 6-[1-CH$_3$-imidazol-2-yl]pyridazin-4-yl |
| 2834 | 6-CH$_3$, 3-[1-CH$_3$-imidazol-2-yl]pyridazin-4-yl |
| 2835 | 3-CH$_3$, 6-[1-CH$_3$-imidazol-2-yl]pyridazin-4-yl |
| 2836 | 6-CF$_3$, 3-[1-CH$_3$-imidazol-2-yl]pyridazin-4-yl |
| 2837 | 3-CF$_3$, 6-[1-CH$_3$-imidazol-2-yl]pyridazin-4-yl |
| 2838 | 3-[1,2,3-triazol-1-yl]pyridazin-4-yl |
| 2839 | 6-[1,2,3-triazol-1-yl]pyridazin-4-yl |
| 2840 | 6-F, 3-[1,2,3-triazol-1-yl]pyridazin-4-yl |
| 2841 | 3-F, 6-[1,2,3-triazol-1-yl]pyridazin-4-yl |
| 2842 | 6-CH$_3$, 3-[1,2,3-triazol-1-yl]pyridazin-4-yl |
| 2843 | 3-CH$_3$, 6-[1,2,3-triazol-1-yl]pyridazin-4-yl |
| 2844 | 6-CF$_3$, 3-[1,2,3-triazol-1-yl]pyridazin-4-yl |
| 2845 | 3-CF$_3$, 6-[1,2,3-triazol-1-yl]pyridazin-4-yl |
| 2846 | 3,6-Cl$_2$-pyridazin-4-yl |
| 2847 | 3,5-Cl$_2$-pyridazin-4-yl |
| 2848 | 3,6-(CH$_3$)$_2$-pyridazin-4-yl |
| 2849 | 3,5-(CH$_3$)$_2$-pyridazin-4-yl |
| 2850 | 3,6-(OCH$_3$)$_2$-pyridazin-4-yl |
| 2851 | 3,5-(OCH$_3$)$_2$-pyridazin-4-yl |
| 2852 | 3,6-(OCH$_2$CH$_3$)$_2$-pyridazin-4-yl |
| 2853 | 3,5-(OCH$_2$CH$_3$)$_2$-pyridazin-4-yl |
| 2854 | 3-F, 6-CH$_3$-pyridazin-4-yl |
| 2855 | 3-F, 5-CH$_3$-pyridazin-4-yl |
| 2856 | 6-F, 3-CH$_3$-pyridazin-4-yl |
| 2857 | 5-F, 3-CH$_3$-pyridazin-4-yl |
| 2858 | 3-F, 6-OCH$_3$-pyridazin-4-yl |
| 2859 | 3-F, 5-OCH$_3$-pyridazin-4-yl |
| 2860 | 6-F, 3-OCH$_3$-pyridazin-4-yl |
| 2861 | 5-F, 3-OCH$_3$-pyridazin-4-yl |
| 2862 | 3-F, 6-OCH$_2$CH$_3$-pyridazin-4-yl |
| 2863 | 3-F, 5-OCH$_2$CH$_3$-pyridazin-4-yl |
| 2864 | 6-F, 3-OCH$_2$CH$_3$-pyridazin-4-yl |
| 2865 | 5-F, 3-OCH$_2$CH$_3$-pyridazin-4-yl |
| 2866 | 3-F, 6-OCH$_2$CF$_3$-pyridazin-4-yl |
| 2867 | 3-F, 5-OCH$_2$CF$_3$-pyridazin-4-yl |
| 2868 | 6-F, 3-OCH$_2$CF$_3$-pyridazin-4-yl |
| 2869 | 5-F, 3-OCH$_2$CF$_3$-pyridazin-4-yl |
| 2870 | 3-F, 6-OCH(CH$_3$)$_2$-pyridazin-4-yl |
| 2871 | 3-F, 5-OCH(CH$_3$)$_2$-pyridazin-4-yl |
| 2872 | 6-F, 3-OCH(CH$_3$)$_2$-pyridazin-4-yl |
| 2873 | 5-F, 3-OCH(CH$_3$)$_2$-pyridazin-4-yl |
| 2874 | 3-Cl, 6-CH$_3$-pyridazin-4-yl |
| 2875 | 3-Cl, 5-CH$_3$-pyridazin-4-yl |
| 2876 | 6-Cl, 3-CH$_3$-pyridazin-4-yl |
| 2877 | 5-Cl, 3-CH$_3$-pyridazin-4-yl |
| 2878 | 3-Cl, 6-OCH$_3$-pyridazin-4-yl |
| 2879 | 3-Cl, 5-OCH$_3$-pyridazin-4-yl |
| 2880 | 6-Cl, 3-OCH$_3$-pyridazin-4-yl |
| 2881 | 5-Cl, 3-OCH$_3$-pyridazin-4-yl |

TABLE A-continued

| No. | R⁴ |
|---|---|
| 2882 | 3-Cl, 6-OCH$_2$CH$_3$-pyridazin-4-yl |
| 2883 | 3-Cl, 5-OCH$_2$CH$_3$-pyridazin-4-yl |
| 2884 | 6-Cl, 3-OCH$_2$CH$_3$-pyridazin-4-yl |
| 2885 | 5-Cl, 3-OCH$_2$CH$_3$-pyridazin-4-yl |
| 2886 | 3-Cl, 6-OCH$_2$CF$_3$-pyridazin-4-yl |
| 2887 | 3-Cl, 5-OCH$_2$CF$_3$-pyridazin-4-yl |
| 2888 | 6-Cl, 3-OCH$_2$CF$_3$-pyridazin-4-yl |
| 2889 | 5-Cl, 3-OCH$_2$CF$_3$-pyridazin-4-yl |
| 2890 | 3-Cl, 6-OCH(CH$_3$)$_2$-pyridazin-4-yl |
| 2891 | 3-Cl, 5-OCH(CH$_3$)$_2$-pyridazin-4-yl |
| 2892 | 6-Cl, 3-OCH(CH$_3$)$_2$-pyridazin-4-yl |
| 2893 | 5-Cl, 3-OCH(CH$_3$)$_2$-pyridazin-4-yl |
| 2894 | 3-CH$_3$, 6-OCH$_3$-pyridazin-4-yl |
| 2895 | 3-CH$_3$, 5-OCH$_3$-pyridazin-4-yl |
| 2896 | 6-CH$_3$, 3-OCH$_3$-pyridazin-4-yl |
| 2897 | 5-CH$_3$, 3-OCH$_3$-pyridazin-4-yl |
| 2898 | 5-CH$_3$, 3-OCH$_2$CH$_3$-pyridazin-4-yl |
| 2899 | 6-CH$_3$, 3-OCH$_2$CH$_3$-pyridazin-4-yl |
| 2900 | 3-CH$_3$, 6-OCH$_2$CH$_3$-pyridazin-4-yl |
| 2901 | 3-CH$_3$, 5-OCH$_2$CH$_3$-pyridazin-4-yl |
| 2902 | 3-CH$_3$, 6-OCH$_2$CF$_3$-pyridazin-4-yl |
| 2903 | 3-CH$_3$, 5-OCH$_2$CF$_3$-pyridazin-4-yl |
| 2904 | 6-CH$_3$, 3-OCH$_2$CF$_3$-pyridazin-4-yl |
| 2905 | 5-CH$_3$, 3-OCH$_2$CF$_3$-pyridazin-4-yl |
| 2906 | 3-CH$_3$, 6-OCH(CH$_3$)$_2$-pyridazin-4-yl |
| 2907 | 3-CH$_3$, 6-OCH(CH$_3$)$_2$-pyridazin-4-yl |
| 2908 | 6-CH$_3$, 3-OCH(CH$_3$)$_2$-pyridazin-4-yl |
| 2909 | 5-CH$_3$, 3-OCH(CH$_3$)$_2$-pyridazin-4-yl |
| 2910 | 3-CH$_3$, 6-OCH$_2$CH=CH$_2$-pyridazin-4-yl |
| 2911 | 3-CH$_3$, 5-OCH$_2$CH=CH$_2$-pyridazin-4-yl |
| 2912 | 6-CH$_3$, 3-OCH$_2$CH=CH$_2$-pyridazin-4-yl |
| 2913 | 5-CH$_3$, 3-OCH$_2$CH=CH$_2$-pyridazin-4-yl |
| 2914 | 3-CH$_3$, 6-CO$_2$CH$_3$-pyridazin-4-yl |
| 2915 | 3-CH$_3$, 5-CO$_2$CH$_3$-pyridazin-4-yl |
| 2916 | 3-CH$_3$, 6-CF$_3$-pyridazin-4-yl |
| 2917 | 3-CH$_3$, 5-CF$_3$-pyridazin-4-yl |
| 2918 | 6-CH$_3$, 3-CF$_3$-pyridazin-4-yl |
| 2919 | 5-CH$_3$, 3-CF$_3$-pyridazin-4-yl |
| 2920 | 3-CF$_3$, 6-CH$_2$CH$_3$-pyridazin-4-yl |
| 2921 | 3-CF$_3$, 5-CH$_2$CH$_3$-pyridazin-4-yl |
| 2922 | 6-CF$_3$, 3-CH$_2$CH$_3$-pyridazin-4-yl |
| 2923 | 5-CF$_3$, 3-CH$_2$CH$_3$-pyridazin-4-yl |
| 2924 | 3-CF$_3$, 6-OCH$_3$-pyridazin-4-yl |
| 2925 | 3-CF$_3$, 5-OCH$_3$-pyridazin-4-yl |
| 2926 | 6-CF$_3$, 3-OCH$_3$-pyridazin-4-yl |
| 2927 | 5-CF$_3$, 3-OCH$_3$-pyridazin-4-yl |
| 2928 | 3-CF$_3$, 6-OCH$_2$CH$_3$-pyridazin-4-yl |
| 2929 | 3-CF$_3$, 5-OCH$_2$CH$_3$-pyridazin-4-yl |
| 2930 | 6-CF$_3$, 3-OCH$_2$CH$_3$-pyridazin-4-yl |
| 2931 | 5-CF$_3$, 3-OCH$_2$CH$_3$-pyridazin-4-yl |
| 2932 | 3-CF$_3$, 6-OCH$_2$CF$_3$-pyridazin-4-yl |
| 2933 | 3-CF$_3$, 5-OCH$_2$CF$_3$-pyridazin-4-yl |
| 2934 | 6-CF$_3$, 3-OCH$_2$CF$_3$-pyridazin-4-yl |
| 2935 | 5-CF$_3$, 3-OCH$_2$CF$_3$-pyridazin-4-yl |
| 2936 | 3-OCH$_3$, 6-OCH$_2$CH$_3$-pyridazin-4-yl |
| 2937 | 3-OCH$_3$, 5-OCH$_2$CH$_3$-pyridazin-4-yl |
| 2938 | 6-OCH$_3$, 3-OCH$_2$CH$_3$-pyridazin-4-yl |
| 2939 | 5-OCH$_3$, 3-OCH$_2$CH$_3$-pyridazin-4-yl |
| 2940 | 3-OCH$_3$, 6-OCH$_2$CF$_3$-pyridazin-4-yl |
| 2941 | 3-OCH$_3$, 5-OCH$_2$CF$_3$-pyridazin-4-yl |
| 2942 | 6-OCH$_3$, 3-OCH$_2$CF$_3$-pyridazin-4-yl |
| 2943 | 5-OCH$_3$, 3-OCH$_2$CF$_3$-pyridazin-4-yl |
| 2944 | 3-OCH$_3$, 6-OCH(CH$_3$)-pyridazin-4-yl |
| 2945 | 3-OCH$_3$, 5-OCH(CH$_3$)-pyridazin-4-yl |
| 2946 | 6-OCH$_3$, 3-OCH(CH$_3$)-pyridazin-4-yl |
| 2947 | 5-OCH$_3$, 3-OCH(CH$_3$)-pyridazin-4-yl |
| 2948 | 3-OCH$_2$CH$_3$, 6-CH$_2$OCH$_2$CH$_3$-pyridazin-4-yl |
| 2949 | 3-OCH$_2$CH$_3$, 5-CH$_2$OCH$_2$CH$_3$-pyridazin-4-yl |
| 2950 | 6-OCH$_2$CH$_3$, 3-CH$_2$OCH$_2$CH$_3$-pyridazin-4-yl |
| 2951 | 5-OCH$_2$CH$_3$, 3-CH$_2$OCH$_2$CH$_3$-pyridazin-4-yl |
| 2952 | 3-NO$_2$, 6-CH$_3$-pyridazin-4-yl |
| 2953 | 3-NO$_2$, 5-CH$_3$-pyridazin-4-yl |
| 2954 | 6-NO$_2$, 3-CH$_3$-pyridazin-4-yl |
| 2955 | 5-NO$_2$, 3-CH$_3$-pyridazin-4-yl |
| 2956 | 3-NO$_2$, 6-OCH$_3$-pyridazin-4-yl |
| 2957 | 3-NO$_2$, 5-OCH$_3$-pyridazin-4-yl |
| 2958 | 6-NO$_2$, 3-OCH$_3$-pyridazin-4-yl |
| 2959 | 5-NO$_2$, 3-OCH$_3$-pyridazin-4-yl |
| 2960 | 3-NO$_2$, 6-OCH$_2$CH$_3$-pyridazin-4-yl |
| 2961 | 3-NO$_2$, 5-OCH$_2$CH$_3$-pyridazin-4-yl |
| 2962 | 6-NO$_2$, 3-OCH$_2$CH$_3$-pyridazin-4-yl |
| 2963 | 5-NO$_2$, 3-OCH$_2$CH$_3$-pyridazin-4-yl |
| 2964 | 3-NO$_2$, 6-OCH(CH$_3$)$_2$-pyridazin-4-yl |
| 2965 | 3-NO$_2$, 5-OCH(CH$_3$)$_2$-pyridazin-4-yl |
| 2966 | 6-NO$_2$, 3-OCH(CH$_3$)$_2$-pyridazin-4-yl |
| 2967 | 5-NO$_2$, 3-OCH(CH$_3$)$_2$-pyridazin-4-yl |
| 2968 | 3-NO$_2$, 6-OCH$_2$CF$_3$-pyridazin-4-yl |
| 2969 | 3-NO$_2$, 5-OCH$_2$CF$_3$-pyridazin-4-yl |
| 2970 | 6-NO$_2$, 3-OCH$_2$CF$_3$-pyridazin-4-yl |
| 2971 | 5-NO$_2$, 3-OCH$_2$CF$_3$-pyridazin-4-yl |
| 2972 | 3-CN, 6-CH$_3$-pyridazin-4-yl |
| 2973 | 3-CN, 5-CH$_3$-pyridazin-4-yl |
| 2974 | 6-CN, 3-CH$_3$-pyridazin-4-yl |
| 2975 | 5-CN, 3-CH$_3$-pyridazin-4-yl |
| 2976 | 3-CN, 6-OCH$_3$-pyridazin-4-yl |
| 2977 | 3-CN, 5-OCH$_3$-pyridazin-4-yl |
| 2978 | 6-CN, 3-OCH$_3$-pyridazin-4-yl |
| 2979 | 5-CN, 3-OCH$_3$-pyridazin-4-yl |
| 2980 | 3-CN, 6-OCH$_2$CH$_3$-pyridazin-4-yl |
| 2981 | 3-CN, 5-OCH$_2$CH$_3$-pyridazin-4-yl |
| 2982 | 6-CN, 3-OCH$_2$CH$_3$-pyridazin-4-yl |
| 2983 | 5-CN, 3-OCH$_2$CH$_3$-pyridazin-4-yl |
| 2984 | 3-CN, 6-OCH(CH$_3$)$_2$-pyridazin-4-yl |
| 2985 | 3-CN, 5-OCH(CH$_3$)$_2$-pyridazin-4-yl |
| 2986 | 6-CN, 3-OCH(CH$_3$)$_2$-pyridazin-4-yl |
| 2987 | 5-CN, 3-OCH(CH$_3$)$_2$-pyridazin-4-yl |
| 2988 | 3-CN, 6-OCH$_2$CF$_3$-pyridazin-4-yl |
| 2989 | 3-CN, 5-OCH$_2$CF$_3$-pyridazin-4-yl |
| 2990 | 6-CN, 3-OCH$_2$CF$_3$-pyridazin-4-yl |
| 2991 | 5-CN, 3-OCH$_2$CF$_3$-pyridazin-4-yl |
| 2992 | 5,6-(CH$_3$)$_2$, 3-OCH$_3$-pyridazin-4-yl |
| 2993 | 3-CH$_3$-pyrazin-2-yl |
| 2994 | 6-CH$_3$-pyrazin-2-yl |
| 2995 | 3-CH$_2$CH$_3$-pyrazin-2-yl |
| 2996 | 6-CH$_2$CH$_3$-pyrazin-2-yl |
| 2997 | 3-CH(CH$_3$)$_2$-pyrazin-2-yl |
| 2998 | 6-CH(CH$_3$)$_2$-pyrazin-2-yl |
| 2999 | 3-CH(CH$_3$)CH$_2$CH$_3$-pyrazin-2-yl |
| 3000 | 6-CH(CH$_3$)CH$_2$CH$_3$-pyrazin-2-yl |
| 3001 | 3-CF$_3$-pyrazin-2-yl |
| 3002 | 6-CF$_3$-pyrazin-2-yl |
| 3003 | 3-CH=CH$_2$-pyrazin-2-yl |
| 3004 | 6-CH=CH$_2$-pyrazin-2-yl |
| 3005 | 3-CH=CHCH$_3$-pyrazin-2-yl |
| 3006 | 6-CH=CHCH$_3$-pyrazin-2-yl |
| 3007 | 3-CH=CHCl-pyrazin-2-yl |
| 3008 | 6-CH=CHCl-pyrazin-2-yl |
| 3009 | 3-C≡CH-pyrazin-2-yl |
| 3010 | 6-C≡CH-pyrazin-2-yl |
| 3011 | 3-CH$_2$C≡CH-pyrazin-2-yl |
| 3012 | 6-CH$_2$C≡CH-pyrazin-2-yl |
| 3013 | 3-CH$_2$C≡CCH$_3$-pyrazin-2-yl |
| 3014 | 6-CH$_2$C≡CCH$_3$-pyrazin-2-yl |
| 3015 | 3-cyclopropylpyrazin-2-yl |
| 3016 | 6-cyclopropylpyrazin-2-yl |
| 3017 | 3-cyclopentylpyrazin-2-yl |
| 3018 | 6-cyclopentylpyrazin-2-yl |
| 3019 | 3-OCH$_3$-pyrazin-2-yl |
| 3020 | 6-OCH$_3$-pyrazin-2-yl |
| 3021 | 3-OCH$_2$CH$_3$-pyrazin-2-yl |
| 3022 | 6-OCH$_2$CH$_3$-pyrazin-2-yl |
| 3023 | 3-OCH$_2$CH$_2$CH$_3$-pyrazin-2-yl |
| 3024 | 6-OCH$_2$CH$_2$CH$_3$-pyrazin-2-yl |
| 3025 | 3-OCH(CH$_3$)$_2$-pyrazin-2-yl |
| 3026 | 6-OCH(CH$_3$)$_2$-pyrazin-2-yl |
| 3027 | 3-OCH$_2$CH$_2$CH$_2$CH$_3$-pyrazin-2-yl |
| 3028 | 6-OCH$_2$CH$_2$CH$_2$CH$_3$-pyrazin-2-yl |
| 3029 | 3-OCH(CH$_3$)CH$_2$CH$_3$-pyrazin-2-yl |
| 3030 | 6-OCH(CH$_3$)CH$_2$CH$_3$-pyrazin-2-yl |
| 3031 | 3-OCH$_2$CH(CH$_3$)$_2$-pyrazin-2-yl |
| 3032 | 6-OCH$_2$CH(CH$_3$)$_2$-pyrazin-2-yl |
| 3033 | 3-OC(CH$_3$)$_3$-pyrazin-2-yl |
| 3034 | 6-OC(CH$_3$)$_3$-pyrazin-2-yl |
| 3035 | 3-OCH(CH$_3$)CH$_2$CH$_2$CH$_3$-pyrazin-2-yl |

TABLE A-continued

| No. | R⁴ |
|---|---|
| 3036 | 6-OCH(CH₃)CH₂CH₂CH₃-pyrazin-2-yl |
| 3037 | 3-OCH₂OCH₃-pyrazin-2-yl |
| 3038 | 6-OCH₂OCH₃-pyrazin-2-yl |
| 3039 | 3-OCH₂OCH₂CH₃-pyrazin-2-yl |
| 3040 | 6-OCH₂OCH₂CH₃-pyrazin-2-yl |
| 3041 | 3-OCH(CH₃)OCH₃-pyrazin-2-yl |
| 3042 | 6-OCH(CH₃)OCH₃-pyrazin-2-yl |
| 3043 | 3-OCH(CH₃)OCH₂CH₃-pyrazin-2-yl |
| 3044 | 6-OCH(CH₃)OCH₂CH₃-pyrazin-2-yl |
| 3045 | 3-OCH₂CH₂OCH₃-pyrazin-2-yl |
| 3046 | 6-OCH₂CH₂OCH₃-pyrazin-2-yl |
| 3047 | 3-OCH₂CH₂OCH₂CH₃-pyrazin-2-yl |
| 3048 | 6-OCH₂CH₂OCH₂CH₃-pyrazin-2-yl |
| 3049 | 3-OCH₂CH₂OCH(CH₃)₂-pyrazin-2-yl |
| 3050 | 6-OCH₂CH₂OCH(CH₃)₂-pyrazin-2-yl |
| 3051 | 3-OCH₂CH₂SCH₃-pyrazin-2-yl |
| 3052 | 6-OCH₂CH₂SCH₃-pyrazin-2-yl |
| 3053 | 3-OCH₂CH₂SO₂CH₃-pyrazin-2-yl |
| 3054 | 6-OCH₂CH₂SO₂CH₃-pyrazin-2-yl |
| 3055 | 3-OCH₂CH₂SCH(CH₃)₂-pyrazin-2-yl |
| 3056 | 6-OCH₂CH₂SCH(CH₃)₂-pyrazin-2-yl |
| 3057 | 3-OCH₂CH₂CN-pyrazin-2-yl |
| 3058 | 6-OCH₂CH₂CN-pyrazin-2-yl |
| 3059 | 3-OCH₂CH₂SCH₂CN-pyrazin-2-yl |
| 3060 | 6-OCH₂CH₂SCH₂CN-pyrazin-2-yl |
| 3061 | 3-OCH₂CH₂OC₅H₆-pyrazin-2-yl |
| 3062 | 6-OCH₂CH₂OC₅H₆-pyrazin-2-yl |
| 3063 | 3-OCH₂CH₂OCH₂C₅H₆-pyrazin-2-yl |
| 3064 | 6-OCH₂CH₂OCH₂C₅H₆-pyrazin-2-yl |
| 3065 | 3-OCH₂CH₂N(CH₃)₂-pyrazin-2-yl |
| 3066 | 6-OCH₂CH₂N(CH₃)₂-pyrazin-2-yl |
| 3067 | 3-OCH₂CH₂CONH₂-pyrazin-2-yl |
| 3068 | 6-OCH₂CH₂CONH₂-pyrazin-2-yl |
| 3069 | 3-OCH₂CH₂CO₂CH₂CH₃-pyrazin-2-yl |
| 3070 | 6-OCH₂CH₂CO₂CH₂CH₃-pyrazin-2-yl |
| 3071 | 3-OCH(CH₃)CH₂OCH₃-pyrazin-2-yl |
| 3072 | 6-OCH(CH₃)CH₂OCH₃-pyrazin-2-yl |
| 3073 | 3-OCH(CH₃)CH₂CO₂CH₃-pyrazin-2-yl |
| 3074 | 6-OCH(CH₃)CH₂CO₂CH₃-pyrazin-2-yl |
| 3075 | 3-OCH(CH₃)CH₂CO₂CH₂CH₃-pyrazin-2-yl |
| 3076 | 6-OCH(CH₃)CH₂CO₂CH₂CH₃-pyrazin-2-yl |
| 3077 | 3-OCH₂CH(CH₃)CO₂CH₃-pyrazin-2-yl |
| 3078 | 6-OCH₂CH(CH₃)CO₂CH₃-pyrazin-2-yl |
| 3079 | 3-OCH₂C(=O)CH₃-pyrazin-2-yl |
| 3080 | 6-OCH₂C(=O)CH₃-pyrazin-2-yl |
| 3081 | 3-OCH₂C(=O)CH₂CH₃-pyrazin-2-yl |
| 3082 | 6-OCH₂C(=O)CH₂CH₃-pyrazin-2-yl |
| 3083 | 3-OCH₂CO₂CH₃-pyrazin-2-yl |
| 3084 | 6-OCH₂CO₂CH₃-pyrazin-2-yl |
| 3085 | 3-OCH₂CO₂CH₂CH₃-pyrazin-2-yl |
| 3086 | 6-OCH₂CO₂CH₂CH₃-pyrazin-2-yl |
| 3087 | 3-OCH₂C(=O)NH₂-pyrazin-2-yl |
| 3088 | 6-OCH₂C(=O)NH₂-pyrazin-2-yl |
| 3089 | 3-OCH₂C(=O)NHCH₃-pyrazin-2-yl |
| 3090 | 6-OCH₂C(=O)NHCH₃-pyrazin-2-yl |
| 3091 | 3-OCH₂C(=O)SCH₃-pyrazin-2-yl |
| 3092 | 6-OCH₂C(=O)SCH₃-pyrazin-2-yl |
| 3093 | 3-OCH(CH₃)C(=O)NH₂-pyrazin-2-yl |
| 3094 | 6-OCH(CH₃)C(=O)NH₂-pyrazin-2-yl |
| 3095 | 3-OCH(CH₃)C(=O)NHCH₃-pyrazin-2-yl |
| 3096 | 6-OCH(CH₃)C(=O)NHCH₃-pyrazin-2-yl |
| 3097 | 3-OCH(CH₃)C(=O)NHNH₂-pyrazin-2-yl |
| 3098 | 6-OCH(CH₃)C(=O)NHNH₂-pyrazin-2-yl |
| 3099 | 3-OCH(CH₃)CO₂CH₃-pyrazin-2-yl |
| 3100 | 6-OCH(CH₃)CO₂CH₃-pyrazin-2-yl |
| 3101 | 3-OCH(CH₃)CO₂CH₂CH₃-pyrazin-2-yl |
| 3102 | 6-OCH(CH₃)CO₂CH₂CH₃-pyrazin-2-yl |
| 3103 | 3-OCH(CH₃)C(=O)CH₃-pyrazin-2-yl |
| 3104 | 6-OCH(CH₃)C(=O)CH₃-pyrazin-2-yl |
| 3105 | 3-OCH(CH₃)C(=O)CH₂CH₃-pyrazin-2-yl |
| 3106 | 6-OCH(CH₃)C(=O)CH₂CH₃-pyrazin-2-yl |
| 3107 | 3-OCH(CH₃)CH₂C(=O)CH₃-pyrazin-2-yl |
| 3108 | 6-OCH(CH₃)CH₂C(=O)CH₃-pyrazin-2-yl |
| 3109 | 3-OCH(CH₃)CH₂OC(CH₃)₃-pyrazin-2-yl |
| 3110 | 6-OCH(CH₃)CH₂OC(CH₃)₃-pyrazin-2-yl |
| 3111 | 3-OCH(CH₃)CH₂OCH₂CH₃-pyrazin-2-yl |
| 3112 | 6-OCH(CH₃)CH₂OCH₂CH₃-pyrazin-2-yl |
| 3113 | 3-OCH(CH₃)CH₂O(CH₃)₂CH₃-pyrazin-2-yl |
| 3114 | 6-OCH(CH₃)CH₂O(CH₃)₂CH₃-pyrazin-2-yl |
| 3115 | 3-OCH(CH₃)CH₂OCH₂CH=CH₂-pyrazin-2-yl |
| 3116 | 6-OCH(CH₃)CH₂OCH₂CH=CH₂-pyrazin-2-yl |
| 3117 | 3-O(CH₂)₃OCH₃-pyrazin-2-yl |
| 3118 | 6-O(CH₂)₃OCH₃-pyrazin-2-yl |
| 3119 | 3-O(CH₂)₃OCH₂CH₃-pyrazin-2-yl |
| 3120 | 6-O(CH₂)₃OCH₂CH₃-pyrazin-2-yl |
| 3121 | 3-O(CH₂)₃OCH(CH₃)₂-pyrazin-2-yl |
| 3122 | 6-O(CH₂)₃OCH(CH₃)₂-pyrazin-2-yl |
| 3123 | 3-O(CH₂)₃OC₅H₆-pyrazin-2-yl |
| 3124 | 6-O(CH₂)₃OC₅H₆-pyrazin-2-yl |
| 3125 | 3-O(CH₂)₃OCH₂C₅H₆-pyrazin-2-yl |
| 3126 | 6-O(CH₂)₃OCH₂C₅H₆-pyrazin-2-yl |
| 3127 | 3-OCH(CH₂CH₃)CH₂OCH₃-pyrazin-2-yl |
| 3128 | 6-OCH(CH₂CH₃)CH₂OCH₃-pyrazin-2-yl |
| 3129 | 3-OCH(CH₂CH₃)CH₂CH₂OCH₃-pyrazin-2-yl |
| 3130 | 6-OCH(CH₂CH₃)CH₂CH₂OCH₃-pyrazin-2-yl |
| 3131 | 3-OCH(CH₂CH₃)CH₂CH₂OCH₂CH₃-pyrazin-2-yl |
| 3132 | 6-OCH(CH₂CH₃)CH₂CH₂OCH₂CH₃-pyrazin-2-yl |
| 3133 | 3-O[(CH₂)₃O]₂CH₃-pyrazin-2-yl |
| 3134 | 6-O[(CH₂)₃O]₂CH₃-pyrazin-2-yl |
| 3135 | 3-OCH₂CH(CH₃)CH₂OCH₃-pyrazin-2-yl |
| 3136 | 6-OCH₂CH(CH₃)CH₂OCH₃-pyrazin-2-yl |
| 3137 | 3-OCH₂CH(CH₃)CH₂OCH₂CH₃-pyrazin-2-yl |
| 3138 | 6-OCH₂CH(CH₃)CH₂OCH₂CH₃-pyrazin-2-yl |
| 3139 | 3-OCH(CH₂Cl)CH₂OCH₃-pyrazin-2-yl |
| 3140 | 6-OCH(CH₂Cl)CH₂OCH₃-pyrazin-2-yl |
| 3141 | 3-OCH(CH₂Cl)CH₂OCH₂CH₃-pyrazin-2-yl |
| 3142 | 6-OCH(CH₂Cl)CH₂OCH₂CH₃-pyrazin-2-yl |
| 3143 | 3-OCH(CH₂Cl)CH₂OCH(CH₃)₂-pyrazin-2-yl |
| 3144 | 6-OCH(CH₂Cl)CH₂OCH(CH₃)₂-pyrazin-2-yl |
| 3145 | 3-OCH(CH₂Cl)CH₂OCH₂CH=CH₂-pyrazin-2-yl |
| 3146 | 6-OCH(CH₂Cl)CH₂OCH₂CH=CH₂-pyrazin-2-yl |
| 3147 | 3-OCH[CH₂OCH₃]₂-pyrazin-2-yl |
| 3148 | 6-OCH[CH₂OCH₃]₂-pyrazin-2-yl |
| 3149 | 3-OCH[CH₂OCH₂CH₃]₂-pyrazin-2-yl |
| 3150 | 6-OCH[CH₂OCH₂CH₃]₂-pyrazin-2-yl |
| 3151 | 3-OCCl₃-pyrazin-2-yl |
| 3152 | 6-OCCl₃-pyrazin-2-yl |
| 3153 | 3-OCHF₂-pyrazin-2-yl |
| 3154 | 6-OCHF₂-pyrazin-2-yl |
| 3155 | 3-OCF₃-pyrazin-2-yl |
| 3156 | 6-OCF₃-pyrazin-2-yl |
| 3157 | 3-OCF₂CHF₂-pyrazin-2-yl |
| 3158 | 6-OCF₂CHF₂-pyrazin-2-yl |
| 3159 | 3-OCH₂CF₃-pyrazin-2-yl |
| 3160 | 6-OCH₂CF₃-pyrazin-2-yl |
| 3161 | 3-OCH₂CHF₂-pyrazin-2-yl |
| 3162 | 6-OCH₂CHF₂-pyrazin-2-yl |
| 3163 | 3-O(CH₂)₃F-pyrazin-2-yl |
| 3164 | 6-O(CH₂)₃F-pyrazin-2-yl |
| 3165 | 3-OCH(CH₃)CF₃-pyrazin-2-yl |
| 3166 | 6-OCH(CH₃)CF₃-pyrazin-2-yl |
| 3167 | 3-O(CH₂)₄F-pyrazin-2-yl |
| 3168 | 6-O(CH₂)₄F-pyrazin-2-yl |
| 3169 | 3-O(CH₂)₃CF₃-pyrazin-2-yl |
| 3170 | 6-O(CH₂)₃CF₃-pyrazin-2-yl |
| 3171 | 3-OCH(CH₃)CF₂CF₃-pyrazin-2-yl |
| 3172 | 6-OCH(CH₃)CF₂CF₃-pyrazin-2-yl |
| 3173 | 3-OCH(CH₃)CF₂CHF₂-pyrazin-2-yl |
| 3174 | 6-OCH(CH₃)CF₂CHF₂-pyrazin-2-yl |
| 3175 | 3-OCH₂CF₂CHFCH₃-pyrazin-2-yl |
| 3176 | 6-OCH₂CF₂CHFCH₃-pyrazin-2-yl |
| 3177 | 3-OCH₂(CF₂)₂CF₃-pyrazin-2-yl |
| 3178 | 6-OCH₂(CF₂)₂CF₃-pyrazin-2-yl |
| 3179 | 3-O(CF₂)₃CF₃-pyrazin-2-yl |
| 3180 | 6-O(CF₂)₃CF₃-pyrazin-2-yl |
| 3181 | 3-OCH₂CF₂CHF₂-pyrazin-2-yl |
| 3182 | 6-OCH₂CF₂CHF₂-pyrazin-2-yl |
| 3183 | 3-CH₂CH=CH₂-pyrazin-2-yl |
| 3184 | 6-CH₂CH=CH₂-pyrazin-2-yl |
| 3185 | 3-CH₂C(CH₃)=CH₂-pyrazin-2-yl |
| 3186 | 6-CH₂C(CH₃)=CH₂-pyrazin-2-yl |
| 3187 | 3-OCH₂CH=CHCH₃-pyrazin-2-yl |
| 3188 | 6-OCH₂CH=CHCH₃-pyrazin-2-yl |
| 3189 | 3-O(CH₂)₂CH=CH₂-pyrazin-2-yl |

TABLE A-continued

| No. | R⁴ |
|---|---|
| 3190 | 6-O(CH₂)₂CH=CH₂-pyrazin-2-yl |
| 3191 | 3-OCH₂C(CH₃)=CH₂-pyrazin-2-yl |
| 3192 | 6-OCH₂C(CH₃)=CH₂-pyrazin-2-yl |
| 3193 | 3-OCH(CH₃)CH=CH₂-pyrazin-2-yl |
| 3194 | 6-OCH(CH₃)CH=CH₂-pyrazin-2-yl |
| 3195 | 3-OCH₂C≡CH-pyrazin-2-yl |
| 3196 | 6-OCH₂C≡CH-pyrazin-2-yl |
| 3197 | 3-OCH₂C≡CCH₃-pyrazin-2-yl |
| 3198 | 6-OCH₂C≡CCH₃-pyrazin-2-yl |
| 3199 | 3-O(CH₂)₂C≡CH-pyrazin-2-yl |
| 3200 | 6-O(CH₂)₂C≡CH-pyrazin-2-yl |
| 3201 | 3-SCH₃-pyrazin-2-yl |
| 3202 | 6-SCH₃-pyrazin-2-yl |
| 3203 | 3-SCH₂CH₃-pyrazin-2-yl |
| 3204 | 6-SCH₂CH₃-pyrazin-2-yl |
| 3205 | 3-OC₅H₆-pyrazin-2-yl |
| 3206 | 6-OC₅H₆-pyrazin-2-yl |
| 3207 | 3-OCH₂C₅H₆-pyrazin-2-yl |
| 3208 | 6-OCH₂C₅H₆-pyrazin-2-yl |
| 3209 | 3-NO₂-pyrazin-2-yl |
| 3210 | 6-NO₂-pyrazin-2-yl |
| 3211 | 3-NHCH₃-pyrazin-2-yl |
| 3212 | 6-NHCH₃-pyrazin-2-yl |
| 3213 | 3-N(CH₃)₂-pyrazin-2-yl |
| 3214 | 6-N(CH₃)₂-pyrazin-2-yl |
| 3215 | 3-N(CH₃)C₂H₆-pyrazin-2-yl |
| 3216 | 6-N(CH₃)C₂H₆-pyrazin-2-yl |
| 3217 | 3-NHCH₂CF₃-pyrazin-2-yl |
| 3218 | 6-NHCH₂CF₃-pyrazin-2-yl |
| 3219 | 3-F-pyrazin-2-yl |
| 3220 | 6-F-pyrazin-2-yl |
| 3221 | 3-Cl-pyrazin-2-yl |
| 3222 | 6-Cl-pyrazin-2-yl |
| 3223 | 3-OH-pyrazin-2-yl |
| 3224 | 6-OH-pyrazin-2-yl |
| 3225 | 3-CN-pyrazin-2-yl |
| 3226 | 6-CN-pyrazin-2-yl |
| 3227 | 3-C(O)NH₂-pyrazin-2-yl |
| 3228 | 6-C(O)NH₂-pyrazin-2-yl |
| 3229 | 3-C(S)NH₂-pyrazin-2-yl |
| 3230 | 6-C(S)NH₂-pyrazin-2-yl |
| 3231 | 3-CO₂CH₃-pyrazin-2-yl |
| 3232 | 6-CO₂CH₃-pyrazin-2-yl |
| 3233 | 3-ON=C(CH₃)₂-pyrazin-2-yl |
| 3234 | 6-ON=C(CH₃)₂-pyrazin-2-yl |
| 3235 | 3-[O-cyclopropyl]pyrazin-2-yl |
| 3236 | 6-[O-cyclopropyl]pyrazin-2-yl |
| 3237 | 3-[O-cyclobutyl]pyrazin-2-yl |
| 3238 | 6-[O-cyclobutyl]pyrazin-2-yl |
| 3239 | 3-[O-cyclopentyl]pyrazin-2-yl |
| 3240 | 6-[O-cyclopentyl]pyrazin-2-yl |
| 3241 | 3-[O-cyclohexyl]pyrazin-2-yl |
| 3242 | 6-[O-cyclohexyl]pyrazin-2-yl |
| 3243 | 3-[OCH₂-cyclopropyl]pyrazin-2-yl |
| 3244 | 6-[OCH₂-cyclopropyl]pyrazin-2-yl |
| 3245 | 6-F, 3-[OCH₂-cyclopropyl]pyrazin-2-yl |
| 3246 | 3-F, 6-[OCH₂-cyclopropyl]pyrazin-2-yl |
| 3247 | 6-CH₃, 3-[OCH₂-cyclopropyl]pyrazin-2-yl |
| 3248 | 3-CH₃, 6-[OCH₂-cyclopropyl]pyrazin-2-yl |
| 3249 | 6-CF₃, 3-[OCH₂-cyclopropyl]pyrazin-2-yl |
| 3250 | 3-CF₃, 6-[OCH₂-cyclopropyl]pyrazin-2-yl |
| 3251 | 3-[OCH(CH₃)-cyclopropyl]pyrazin-2-yl |
| 3252 | 6-[OCH(CH₃)-cyclopropyl]pyrazin-2-yl |
| 3253 | 6-F, 3-[OCH(CH₃)-cyclopropyl]pyrazin-2-yl |
| 3254 | 3-F, 6-[OCH(CH₃)-cyclopropyl]pyrazin-2-yl |
| 3255 | 6-CH₃, 3-[OCH(CH₃)-cyclopropyl]pyrazin-2-yl |
| 3256 | 3-CH₃, 6-[OCH(CH₃)-cyclopropyl]pyrazin-2-yl |
| 3257 | 6-CF₃, 3-[OCH(CH₃)-cyclopropyl]pyrazin-2-yl |
| 3258 | 3-CF₃, 6-[OCH(CH₃)-cyclopropyl]pyrazin-2-yl |
| 3259 | 3-[O-(1-CH₃-cyclopropyl)]pyrazin-2-yl |
| 3260 | 6-[O-(1-CH₃-cyclopropyl)]pyrazin-2-yl |
| 3261 | 6-F, 3-[O-(1-CH₃-cyclopropyl)]pyrazin-2-yl |
| 3262 | 3-F, 6-[O-(1-CH₃-cyclopropyl)]pyrazin-2-yl |
| 3263 | 6-CH₃, 3-[O-(1-CH₃-cyclopropyl)]pyrazin-2-yl |
| 3264 | 3-CH₃, 6-[O-(1-CH₃-cyclopropyl)]pyrazin-2-yl |
| 3265 | 6-CF₃, 3-[O-(1-CH₃-cyclopropyl)]pyrazin-2-yl |
| 3266 | 3-CF₃, 6-[O-(1-CH₃-cyclopropyl)]pyrazin-2-yl |
| 3267 | 3-[OCH₂-(1-CH₃-cyclopropyl)]pyrazin-2-yl |
| 3268 | 6-[OCH₂-(1-CH₃-cyclopropyl)]pyrazin-2-yl |
| 3269 | 6-F, 3-[OCH₂-(1-CH₃-cyclopropyl)]pyrazin-2-yl |
| 3270 | 3-F, 6-[OCH₂-(1-CH₃-cyclopropyl)]pyrazin-2-yl |
| 3271 | 6-CH₃, 3-[OCH₂-(1-CH₃-cyclopropyl)]pyrazin-2-yl |
| 3272 | 3-CH₃, 6-[OCH₂-(1-CH₃-cyclopropyl)]pyrazin-2-yl |
| 3273 | 6-CF₃, 3-[OCH₂-(1-CH₃-cyclopropyl)]pyrazin-2-yl |
| 3274 | 3-CF₃, 6-[OCH₂-(1-CH₃-cyclopropyl)]pyrazin-2-yl |
| 3275 | 3-[OCH₂-(2-CH₃-cyclopropyl)]pyrazin-2-yl |
| 3276 | 6-[OCH₂-(2-CH₃-cyclopropyl)]pyrazin-2-yl |
| 3277 | 6-F, 3-[OCH₂-(2-CH₃-cyclopropyl)]pyrazin-2-yl |
| 3278 | 3-F, 6-[OCH₂-(2-CH₃-cyclopropyl)]pyrazin-2-yl |
| 3279 | 6-CH₃, 3-[OCH₂-(2-CH₃-cyclopropyl)]pyrazin-2-yl |
| 3280 | 3-CH₃, 6-[OCH₂-(2-CH₃-cyclopropyl)]pyrazin-2-yl |
| 3281 | 6-CF₃, 3-[OCH₂-(2-CH₃-cyclopropyl)]pyrazin-2-yl |
| 3282 | 3-CF₃, 6-[OCH₂-(2-CH₃-cyclopropyl)]pyrazin-2-yl |
| 3283 | 3-[OCH₂-(tetrahydropyran-2-yl)]pyrazin-2-yl |
| 3284 | 6-[OCH₂-(tetrahydropyran-2-yl)]pyrazin-2-yl |
| 3285 | 6-F, 3-[OCH₂-(tetrahydropyran-2-yl)]pyrazin-2-yl |
| 3286 | 3-F, 6-[OCH₂-(tetrahydropyran-2-yl)]pyrazin-2-yl |
| 3287 | 6-CH₃, 3-[OCH₂-(tetrahydropyran-2-yl)]pyrazin-2-yl |
| 3288 | 3-CH₃, 6-[OCH₂-(tetrahydropyran-2-yl)]pyrazin-2-yl |
| 3289 | 6-CF₃, 3-[OCH₂-(tetrahydropyran-2-yl)]pyrazin-2-yl |
| 3290 | 3-CF₃, 6-[OCH₂-(tetrahydropyran-2-yl)]pyrazin-2-yl |
| 3291 | 3-[OCH₂-(furan-2-yl)]pyrazin-2-yl |
| 3292 | 6-[OCH₂-(furan-2-yl)]pyrazin-2-yl |
| 3293 | 6-F, 3-[OCH₂-(furan-2-yl)]pyrazin-2-yl |
| 3294 | 3-F, 6-[OCH₂-(furan-2-yl)]pyrazin-2-yl |
| 3295 | 6-CH₃, 3-[OCH₂-(furan-2-yl)]pyrazin-2-yl |
| 3296 | 3-CH₃, 6-[OCH₂-(furan-2-yl)]pyrazin-2-yl |
| 3297 | 6-CF₃, 3-[OCH₂-(furan-2-yl)]pyrazin-2-yl |
| 3298 | 3-CF₃, 6-[OCH₂-(furan-2-yl)]pyrazin-2-yl |
| 3299 | 3-[OCH₂-(furan-3-yl)]pyrazin-2-yl |
| 3300 | 6-[OCH₂-(furan-3-yl)]pyrazin-2-yl |
| 3301 | 6-F, 3-[OCH₂-(furan-3-yl)]pyrazin-2-yl |
| 3302 | 3-F, 6-[OCH₂-(furan-3-yl)]pyrazin-2-yl |
| 3303 | 6-CH₃, 3-[OCH₂-(furan-3-yl)]pyrazin-2-yl |
| 3304 | 3-CH₃, 6-[OCH₂-(furan-3-yl)]pyrazin-2-yl |
| 3305 | 6-CF₃, 3-[OCH₂-(furan-3-yl)]pyrazin-2-yl |
| 3306 | 3-CF₃, 6-[OCH₂-(furan-3-yl)]pyrazin-2-yl |
| 3307 | 3-[OCH₂-(tetrahydrofuran-3-yl)]pyrazin-2-yl |
| 3308 | 6-[OCH₂-(tetrahydrofuran-3-yl)]pyrazin-2-yl |
| 3309 | 6-F, 3-[OCH₂-(tetrahydrofuran-3-yl)]pyrazin-2-yl |
| 3310 | 3-F, 6-[OCH₂-(tetrahydrofuran-3-yl)]pyrazin-2-yl |
| 3311 | 6-CH₃, 3-[OCH₂-(tetrahydrofuran-3-yl)]pyrazin-2-yl |
| 3312 | 3-CH₃, 6-[OCH₂-(tetrahydrofuran-3-yl)]pyrazin-2-yl |
| 3313 | 6-CF₃, 3-[OCH₂-(tetrahydrofuran-3-yl)]pyrazin-2-yl |
| 3314 | 3-CF₃, 6-[OCH₂-(tetrahydrofuran-3-yl)]pyrazin-2-yl |
| 3315 | 3-[OCH₂-(tetrahydrofuran-2-yl)]pyrazin-2-yl |
| 3316 | 6-[OCH₂-(tetrahydrofuran-2-yl)]pyrazin-2-yl |
| 3317 | 6-F, 3-[OCH₂-(tetrahydrofuran-2-yl)]pyrazin-2-yl |
| 3318 | 3-F, 6-[OCH₂-(tetrahydrofuran-2-yl)]pyrazin-2-yl |
| 3319 | 6-CH₃, 3-[OCH₂-(tetrahydrofuran-2-yl)]pyrazin-2-yl |
| 3320 | 3-CH₃, 6-[OCH₂-(tetrahydrofuran-2-yl)]pyrazin-2-yl |
| 3321 | 6-CF₃, 3-[OCH₂-(tetrahydrofuran-2-yl)]pyrazin-2-yl |
| 3322 | 3-CF₃, 6-[OCH₂-(tetrahydrofuran-2-yl)]pyrazin-2-yl |
| 3323 | 3-[O-(tetrahydropyran-3-yl)]pyrazin-2-yl |
| 3324 | 6-[O-(tetrahydropyran-3-yl)]pyrazin-2-yl |
| 3325 | 6-F, 3-[O-(tetrahydropyran-3-yl)]pyrazin-2-yl |
| 3326 | 3-F, 6-[O-(tetrahydropyran-3-yl)]pyrazin-2-yl |
| 3327 | 6-CH₃, 3-[O-(tetrahydropyran-3-yl)]pyrazin-2-yl |
| 3328 | 3-CH₃, 6-[O-(tetrahydropyran-3-yl)]pyrazin-2-yl |
| 3329 | 6-CF₃, 3-[O-(tetrahydropyran-3-yl)]pyrazin-2-yl |
| 3330 | 3-CF₃, 6-[O-(tetrahydropyran-3-yl)]pyrazin-2-yl |
| 3331 | 3-[2-Cl—C₅H₄]pyrazin-2-yl |
| 3332 | 6-[2-Cl—C₅H₄]pyrazin-2-yl |
| 3333 | 6-F, 3-[2-Cl—C₅H₄]pyrazin-2-yl |
| 3334 | 3-F, 6-[2-Cl—C₅H₄]pyrazin-2-yl |
| 3335 | 6-CH₃, 3-[2-Cl—C₅H₄]pyrazin-2-yl |
| 3336 | 3-CH₃, 6-[2-Cl—C₅H₄]pyrazin-2-yl |
| 3337 | 6-CF₃, 3-[2-Cl—C₅H₄]pyrazin-2-yl |
| 3338 | 3-CF₃, 6-[2-Cl—C₅H₄]pyrazin-2-yl |
| 3339 | 3-[OCH₂-(pyridin-2-yl)]pyrazin-2-yl |
| 3340 | 6-[OCH₂-(pyridin-2-yl)]pyrazin-2-yl |
| 3341 | 6-F, 3-[OCH₂-(pyridin-2-yl)]pyrazin-2-yl |
| 3342 | 3-F, 6-[OCH₂-(pyridin-2-yl)]pyrazin-2-yl |
| 3343 | 6-CH₃, 3-[OCH₂-(pyridin-2-yl)]pyrazin-2-yl |

TABLE A-continued

| No. | R⁴ |
|---|---|
| 3344 | 3-CH₃, 6-[OCH₂-(pyridin-2-yl)]pyrazin-2-yl |
| 3345 | 6-CF₃, 3-[OCH₂-(pyridin-2-yl)]pyrazin-2-yl |
| 3346 | 3-CF₃, 6-[OCH₂-(pyridin-2-yl)]pyrazin-2-yl |
| 3347 | 3-[OCH₂-(pyridin-4-yl)]pyrazin-2-yl |
| 3348 | 6-[OCH₂-(pyridin-4-yl)]pyrazin-2-yl |
| 3349 | 6-F, 3-[OCH₂-(pyridin-4-yl)]pyrazin-2-yl |
| 3350 | 3-F, 6-[OCH₂-(pyridin-4-yl)]pyrazin-2-yl |
| 3351 | 6-CH₃, 3-[OCH₂-(pyridin-4-yl)]pyrazin-2-yl |
| 3352 | 3-CH₃, 6-[OCH₂-(pyridin-4-yl)]pyrazin-2-yl |
| 3353 | 6-CF₃, 3-[OCH₂-(pyridin-4-yl)]pyrazin-2-yl |
| 3354 | 3-CF₃, 6-[OCH₂-(pyridin-4-yl)]pyrazin-2-yl |
| 3355 | 3-[morpholin-4-yl]pyrazin-2-yl |
| 3356 | 6-[morpholin-4-yl]pyrazin-2-yl |
| 3357 | 3-[1-CH₃-imidazol-2-yl]pyrazin-2-yl |
| 3358 | 6-[1-CH₃-imidazol-2-yl]pyrazin-2-yl |
| 3359 | 6-F, 3-[1-CH₃-imidazol-2-yl]pyrazin-2-yl |
| 3360 | 3-F, 6-[1-CH₃-imidazol-2-yl]pyrazin-2-yl |
| 3361 | 6-CH₃, 3-[1-CH₃-imidazol-2-yl]pyrazin-2-yl |
| 3362 | 3-CH₃, 6-[1-CH₃-imidazol-2-yl]pyrazin-2-yl |
| 3363 | 6-CF₃, 3-[1-CH₃-imidazol-2-yl]pyrazin-2-yl |
| 3364 | 3-CF₃, 6-[1-CH₃-imidazol-2-yl]pyrazin-2-yl |
| 3365 | 3-[1,2,3-triazol-1-yl]pyrazin-2-yl |
| 3366 | 6-[1,2,3-triazol-1-yl]pyrazin-2-yl |
| 3367 | 6-F, 3-[1,2,3-triazol-1-yl]pyrazin-2-yl |
| 3368 | 3-F, 6-[1,2,3-triazol-1-yl]pyrazin-2-yl |
| 3369 | 6-CH₃, 3-[1,2,3-triazol-1-yl]pyrazin-2-yl |
| 3370 | 3-CH₃, 6-[1,2,3-triazol-1-yl]pyrazin-2-yl |
| 3371 | 6-CF₃, 3-[1,2,3-triazol-1-yl]pyrazin-2-yl |
| 3372 | 3-CF₃, 6-[1,2,3-triazol-1-yl]pyrazin-2-yl |
| 3373 | 3,6-Cl₂-pyrazin-2-yl |
| 3374 | 3,5-Cl₂-pyrazin-2-yl |
| 3375 | 3,6-(CH₃)₂-pyrazin-2-yl |
| 3376 | 3,5-(CH₃)₂-pyrazin-2-yl |
| 3377 | 3,6-(OCH₃)₂-pyrazin-2-yl |
| 3378 | 3,5-(OCH₃)₂-pyrazin-2-yl |
| 3379 | 3,6-(OCH₂CH₃)₂-pyrazin-2-yl |
| 3380 | 3,5-(OCH₂CH₃)₂-pyrazin-2-yl |
| 3381 | 3-F, 6-CH₃-pyrazin-2-yl |
| 3382 | 3-F, 5-CH₃-pyrazin-2-yl |
| 3383 | 6-F, 3-CH₃-pyrazin-2-yl |
| 3384 | 5-F, 3-CH₃-pyrazin-2-yl |
| 3385 | 3-F, 6-OCH₃-pyrazin-2-yl |
| 3386 | 3-F, 5-OCH₃-pyrazin-2-yl |
| 3387 | 6-F, 3-OCH₃-pyrazin-2-yl |
| 3388 | 5-F, 3-OCH₃-pyrazin-2-yl |
| 3389 | 3-F, 6-OCH₂CH₃-pyrazin-2-yl |
| 3390 | 3-F, 5-OCH₂CH₃-pyrazin-2-yl |
| 3391 | 6-F, 3-OCH₂CH₃-pyrazin-2-yl |
| 3392 | 5-F, 3-OCH₂CH₃-pyrazin-2-yl |
| 3393 | 3-F, 6-OCH₂CF₃-pyrazin-2-yl |
| 3394 | 3-F, 5-OCH₂CF₃-pyrazin-2-yl |
| 3395 | 6-F, 3-OCH₂CF₃-pyrazin-2-yl |
| 3396 | 5-F, 3-OCH₂CF₃-pyrazin-2-yl |
| 3397 | 3-F, 6-OCH(CH₃)₂-pyrazin-2-yl |
| 3398 | 3-F, 5-OCH(CH₃)₂-pyrazin-2-yl |
| 3399 | 6-F, 3-OCH(CH₃)₂-pyrazin-2-yl |
| 3400 | 5-F, 3-OCH(CH₃)₂-pyrazin-2-yl |
| 3401 | 3-Cl, 6-CH₃-pyrazin-2-yl |
| 3402 | 3-Cl, 5-CH₃-pyrazin-2-yl |
| 3403 | 6-Cl, 3-CH₃-pyrazin-2-yl |
| 3404 | 5-Cl, 3-CH₃-pyrazin-2-yl |
| 3405 | 3-Cl, 6-OCH₃-pyrazin-2-yl |
| 3406 | 3-Cl, 5-OCH₃-pyrazin-2-yl |
| 3407 | 6-Cl, 3-OCH₃-pyrazin-2-yl |
| 3408 | 5-Cl, 3-OCH₃-pyrazin-2-yl |
| 3409 | 3-Cl, 6-OCH₂CH₃-pyrazin-2-yl |
| 3410 | 3-Cl, 5-OCH₂CH₃-pyrazin-2-yl |
| 3411 | 6-Cl, 3-OCH₂CH₃-pyrazin-2-yl |
| 3412 | 5-Cl, 3-OCH₂CH₃-pyrazin-2-yl |
| 3413 | 3-Cl, 6-OCH₂CF₃-pyrazin-2-yl |
| 3414 | 3-Cl, 5-OCH₂CF₃-pyrazin-2-yl |
| 3415 | 6-Cl, 3-OCH₂CF₃-pyrazin-2-yl |
| 3416 | 5-Cl, 3-OCH₂CF₃-pyrazin-2-yl |
| 3417 | 3-Cl, 6-OCH(CH₃)₂-pyrazin-2-yl |
| 3418 | 3-Cl, 5-OCH(CH₃)₂-pyrazin-2-yl |
| 3419 | 6-Cl, 3-OCH(CH₃)₂-pyrazin-2-yl |
| 3420 | 5-Cl, 3-OCH(CH₃)₂-pyrazin-2-yl |
| 3421 | 3-CH₃, 6-OCH₃-pyrazin-2-yl |
| 3422 | 3-CH₃, 5-OCH₃-pyrazin-2-yl |
| 3423 | 6-CH₃, 3-OCH₃-pyrazin-2-yl |
| 3424 | 5-CH₃, 3-OCH₃-pyrazin-2-yl |
| 3425 | 5-CH₃, 3-OCH₃-pyrazin-2-yl |
| 3426 | 6-CH₃, 3-OCH₂CH₃-pyrazin-2-yl |
| 3427 | 3-CH₃, 6-OCH₂CH₃-pyrazin-2-yl |
| 3428 | 3-CH₃, 5-OCH₂CH₃-pyrazin-2-yl |
| 3429 | 3-CH₃, 6-OCH₂CF₃-pyrazin-2-yl |
| 3430 | 3-CH₃, 5-OCH₂CF₃-pyrazin-2-yl |
| 3431 | 6-CH₃, 3-OCH₂CF₃-pyrazin-2-yl |
| 3432 | 5-CH₃, 3-OCH₂CF₃-pyrazin-2-yl |
| 3433 | 3-CH₃, 6-OCH(CH₃)₂-pyrazin-2-yl |
| 3434 | 3-CH₃, 6-OCH(CH₃)₂-pyrazin-2-yl |
| 3435 | 6-CH₃, 3-OCH(CH₃)₂-pyrazin-2-yl |
| 3436 | 5-CH₃, 3-OCH(CH₃)₂-pyrazin-2-yl |
| 3437 | 3-CH₃, 6-OCH₂CH=CH₂-pyrazin-2-yl |
| 3438 | 3-CH₃, 5-OCH₂CH=CH₂-pyrazin-2-yl |
| 3439 | 6-CH₃, 3-OCH₂CH=CH₂-pyrazin-2-yl |
| 3440 | 5-CH₃, 3-OCH₂CH=CH₂-pyrazin-2-yl |
| 3441 | 3-CH₃, 6-CO₂CH₃-pyrazin-2-yl |
| 3442 | 3-CH₃, 5-CO₂CH₃-pyrazin-2-yl |
| 3443 | 3-CH₃, 6-CF₃-pyrazin-2-yl |
| 3444 | 3-CH₃, 5-CF₃-pyrazin-2-yl |
| 3445 | 6-CH₃, 3-CF₃-pyrazin-2-yl |
| 3446 | 5-CH₃, 3-CF₃-pyrazin-2-yl |
| 3447 | 3-CF₃, 6-CH₂CH₃-pyrazin-2-yl |
| 3448 | 3-CF₃, 5-CH₂CH₃-pyrazin-2-yl |
| 3449 | 6-CF₃, 3-CH₂CH₃-pyrazin-2-yl |
| 3450 | 5-CF₃, 3-CH₂CH₃-pyrazin-2-yl |
| 3451 | 3-CF₃, 6-OCH₃-pyrazin-2-yl |
| 3452 | 3-CF₃, 5-OCH₃-pyrazin-2-yl |
| 3453 | 6-CF₃, 3-OCH₃-pyrazin-2-yl |
| 3454 | 5-CF₃, 3-OCH₃-pyrazin-2-yl |
| 3455 | 3-CF₃, 6-OCH₂CH₃-pyrazin-2-yl |
| 3456 | 3-CF₃, 5-OCH₂CH₃-pyrazin-2-yl |
| 3457 | 6-CF₃, 3-OCH₂CH₃-pyrazin-2-yl |
| 3458 | 5-CF₃, 3-OCH₂CH₃-pyrazin-2-yl |
| 3459 | 3-CF₃, 6-OCH₂CF₃-pyrazin-2-yl |
| 3460 | 3-CF₃, 5-OCH₂CF₃-pyrazin-2-yl |
| 3461 | 6-CF₃, 3-OCH₂CF₃-pyrazin-2-yl |
| 3462 | 5-CF₃, 3-OCH₂CF₃-pyrazin-2-yl |
| 3463 | 3-OCH₃, 6-OCH₂CH₃-pyrazin-2-yl |
| 3464 | 3-OCH₃, 5-OCH₂CH₃-pyrazin-2-yl |
| 3465 | 6-OCH₃, 3-OCH₂CH₃-pyrazin-2-yl |
| 3466 | 5-OCH₃, 3-OCH₂CH₃-pyrazin-2-yl |
| 3467 | 3-OCH₃, 6-OCH₂CF₃-pyrazin-2-yl |
| 3468 | 3-OCH₃, 5-OCH₂CF₃-pyrazin-2-yl |
| 3469 | 6-OCH₃, 3-OCH₂CF₃-pyrazin-2-yl |
| 3470 | 5-OCH₃, 3-OCH₂CF₃-pyrazin-2-yl |
| 3471 | 3-OCH₃, 6-OCH(CH₃)-pyrazin-2-yl |
| 3472 | 3-OCH₃, 5-OCH(CH₃)-pyrazin-2-yl |
| 3473 | 6-OCH₃, 3-OCH(CH₃)-pyrazin-2-yl |
| 3474 | 5-OCH₃, 3-OCH(CH₃)-pyrazin-2-yl |
| 3475 | 3-OCH₂CH₃, 6-CH₂OCH₂CH₃-pyrazin-2-yl |
| 3476 | 3-OCH₂CH₃, 5-CH₂OCH₂CH₃-pyrazin-2-yl |
| 3477 | 6-OCH₂CH₃, 3-CH₂OCH₂CH₃-pyrazin-2-yl |
| 3478 | 5-OCH₂CH₃, 3-CH₂OCH₂CH₃-pyrazin-2-yl |
| 3479 | 3-NO₂, 6-CH₃-pyrazin-2-yl |
| 3480 | 3-NO₂, 5-CH₃-pyrazin-2-yl |
| 3481 | 6-NO₂, 3-CH₃-pyrazin-2-yl |
| 3482 | 5-NO₂, 3-CH₃-pyrazin-2-yl |
| 3483 | 3-NO₂, 6-OCH₃-pyrazin-2-yl |
| 3484 | 3-NO₂, 5-OCH₃-pyrazin-2-yl |
| 3485 | 6-NO₂, 3-OCH₃-pyrazin-2-yl |
| 3486 | 5-NO₂, 3-OCH₃-pyrazin-2-yl |
| 3487 | 3-NO₂, 6-OCH₂CH₃-pyrazin-2-yl |
| 3488 | 3-NO₂, 5-OCH₂CH₃-pyrazin-2-yl |
| 3489 | 6-NO₂, 3-OCH₂CH₃-pyrazin-2-yl |
| 3490 | 5-NO₂, 3-OCH₂CH₃-pyrazin-2-yl |
| 3491 | 3-NO₂, 6-OCH(CH₃)₂-pyrazin-2-yl |
| 3492 | 3-NO₂, 5-OCH(CH₃)₂-pyrazin-2-yl |
| 3493 | 6-NO₂, 3-OCH(CH₃)₂-pyrazin-2-yl |
| 3494 | 5-NO₂, 3-OCH(CH₃)₂-pyrazin-2-yl |
| 3495 | 3-NO₂, 6-OCH₂CF₃-pyrazin-2-yl |
| 3496 | 3-NO₂, 5-OCH₂CF₃-pyrazin-2-yl |
| 3497 | 6-NO₂, 3-OCH₂CF₃-pyrazin-2-yl |

TABLE A-continued

| No. | R⁴ |
|---|---|
| 3498 | 5-NO₂, 3-OCH₂CF₃-pyrazin-2-yl |
| 3499 | 3-CN, 6-CH₃-pyrazin-2-yl |
| 3500 | 3-CN, 5-CH₃-pyrazin-2-yl |
| 3501 | 6-CN, 3-CH₃-pyrazin-2-yl |
| 3502 | 5-CN, 3-CH₃-pyrazin-2-yl |
| 3503 | 3-CN, 6-OCH₃-pyrazin-2-yl |
| 3504 | 3-CN, 5-OCH₃-pyrazin-2-yl |
| 3505 | 6-CN, 3-OCH₃-pyrazin-2-yl |
| 3506 | 5-CN, 3-OCH₃-pyrazin-2-yl |
| 3507 | 3-CN, 6-OCH₂CH₃-pyrazin-2-yl |
| 3508 | 3-CN, 5-OCH₂CH₃-pyrazin-2-yl |
| 3509 | 6-CN, 3-OCH₂CH₃-pyrazin-2-yl |
| 3510 | 5-CN, 3-OCH₂CH₃-pyrazin-2-yl |
| 3511 | 3-CN, 6-OCH(CH₃)₂-pyrazin-2-yl |
| 3512 | 3-CN, 5-OCH(CH₃)₂-pyrazin-2-yl |
| 3513 | 6-CN, 3-OCH(CH₃)₂-pyrazin-2-yl |
| 3514 | 5-CN, 3-OCH(CH₃)₂-pyrazin-2-yl |
| 3515 | 3-CN, 6-OCH₂CF₃-pyrazin-2-yl |
| 3516 | 3-CN, 5-OCH₂CF₃-pyrazin-2-yl |
| 3517 | 6-CN, 3-OCH₂CF₃-pyrazin-2-yl |
| 3518 | 5-CN, 3-OCH₂CF₃-pyrazin-2-yl |
| 3519 | 5,6-(CH₃)₂, 3-OCH₃-pyrazin-2-yl |
| 3520 | 4-CH₃-1,3,5-triazin-2-yl |
| 3521 | 4-CH₂CH₃-1,3,5-triazin-2-yl |
| 3522 | 4-CH(CH₃)₂-1,3,5-triazin-2-yl |
| 3523 | 4-CH(CH₃)CH₂CH₃-1,3,5-triazin-2-yl |
| 3524 | 4-CF₃-1,3,5-triazin-2-yl |
| 3525 | 4-CH=CH₂-1,3,5-triazin-2-yl |
| 3526 | 4-CH=CHCH₃-1,3,5-triazin-2-yl |
| 3527 | 4-CH=CHCl-1,3,5-triazin-2-yl |
| 3528 | 4-C≡CH-1,3,5-triazin-2-yl |
| 3529 | 4-CH₂C≡CH-1,3,5-triazin-2-yl |
| 3530 | 4-CH₂C≡CCH₃-1,3,5-triazin-2-yl |
| 3531 | 4-cyclopropyl-1,3,5-triazin-2-yl |
| 3532 | 4-cyclopentyl-1,3,5-triazin-2-yl |
| 3533 | 4-OCH₃-1,3,5-triazin-2-yl |
| 3534 | 4-OCH₂CH₃-1,3,5-triazin-2-yl |
| 3535 | 4-OCH₂CH₂CH₃-1,3,5-triazin-2-yl |
| 3536 | 4-OCH(CH₃)₂-1,3,5-triazin-2-yl |
| 3537 | 4-OCH₂CH₂CH₂CH₃-1,3,5-triazin-2-yl |
| 3538 | 4-OCH(CH₃)CH₂CH₃-1,3,5-triazin-2-yl |
| 3539 | 4-OCH₂CH(CH₃)₂-1,3,5-triazin-2-yl |
| 3540 | 4-OC(CH₃)₄-1,3,5-triazin-2-yl |
| 3541 | 4-OCH(CH₃)CH₂CH₂CH₃-1,3,5-triazin-2-yl |
| 3542 | 4-OCH₂OCH₃-1,3,5-triazin-2-yl |
| 3543 | 4-OCH₂OCH₂CH₃-1,3,5-triazin-2-yl |
| 3544 | 4-OCH(CH₃)OCH₃-1,3,5-triazin-2-yl |
| 3545 | 4-OCH(CH₃)OCH₂CH₃-1,3,5-triazin-2-yl |
| 3546 | 4-OCH₂CH₂OCH₃-1,3,5-triazin-2-yl |
| 3547 | 4-OCH₂CH₂OCH₂CH₃-1,3,5-triazin-2-yl |
| 3548 | 4-OCH₂CH₂OCH(CH₃)₂-1,3,5-triazin-2-yl |
| 3549 | 4-OCH₂CH₂SCH₃-1,3,5-triazin-2-yl |
| 3550 | 4-OCH₂CH₂SO₂CH₃-1,3,5-triazin-2-yl |
| 3551 | 4-OCH₂CH₂SCH(CH₃)₂-1,3,5-triazin-2-yl |
| 3552 | 4-OCH₂CH₂CN-1,3,5-triazin-2-yl |
| 3553 | 4-OCH₂CH₂SCH₂CH₂CN-1,3,5-triazin-2-yl |
| 3554 | 4-OCH₂CH₂OC₆H₅-1,3,5-triazin-2-yl |
| 3555 | 4-OCH₂CH₂OCH₂C₆H₅-1,3,5-triazin-2-yl |
| 3556 | 4-OCH₂CH₂N(CH₃)₂-1,3,5-triazin-2-yl |
| 3557 | 4-OCH₂CH₂CONH₂-1,3,5-triazin-2-yl |
| 3558 | 4-OCH₂CH₂CO₂CH₂CH₂CH₃-1,3,5-triazin-2-yl |
| 3559 | 4-OCH(CH₃)CH₂OCH₃-1,3,5-triazin-2-yl |
| 3560 | 4-OCH(CH₃)CH₂CO₂CH₃-1,3,5-triazin-2-yl |
| 3561 | 4-OCH(CH₃)CH₂CO₂CH₂CH₃-1,3,5-triazin-2-yl |
| 3562 | 4-OCH₂CH(CH₃)CO₂CH₃-1,3,5-triazin-2-yl |
| 3563 | 4-OCH₂C(=O)CH₃-1,3,5-triazin-2-yl |
| 3564 | 4-OCH₂C(=O)CH₂CH₃-1,3,5-triazin-2-yl |
| 3565 | 4-OCH₂CO₂CH₃-1,3,5-triazin-2-yl |
| 3566 | 4-OCH₂CO₂CH₂CH₃-1,3,5-triazin-2-yl |
| 3567 | 4-OCH₂C(=O)NH₂-1,3,5-triazin-2-yl |
| 3568 | 4-OCH₂C(=O)NHCH₃-1,3,5-triazin-2-yl |
| 3569 | 4-OCH₂C(=O)SCH₃-1,3,5-triazin-2-yl |
| 3570 | 4-OCH(CH₃)C(=O)NH₂-1,3,5-triazin-2-yl |
| 3571 | 4-OCH(CH₃)C(=O)NHCH₃-1,3,5-triazin-2-yl |
| 3572 | 4-OCH(CH₃)C(=O)NHNH₂-1,3,5-triazin-2-yl |
| 3573 | 4-OCH(CH₃)CO₂CH₃-1,3,5-triazin-2-yl |
| 3574 | 4-OCH(CH₃)CO₂CH₂CH₃-1,3,5-triazin-2-yl |
| 3575 | 4-OCH(CH₃)C(=O)CH₃-1,3,5-triazin-2-yl |
| 3576 | 4-OCH(CH₃)C(=O)CH₂CH₃-1,3,5-triazin-2-yl |
| 3577 | 4-OCH(CH₃)CH₂C(=O)CH₃-1,3,5-triazin-2-yl |
| 3578 | 4-OCH(CH₃)CH₂OC(CH₃)₄-1,3,5-triazin-2-yl |
| 3579 | 4-OCH(CH₃)CH₂OCH₂CH₃-1,3,5-triazin-2-yl |
| 3580 | 4-OCH(CH₃)CH₂O(CH₃)₂CH₃-1,3,5-triazin-2-yl |
| 3581 | 4-OCH(CH₃)CH₂OCH₂CH=CH₂-1,3,5-triazin-2-yl |
| 3582 | 4-O(CH₂)₃OCH₃-1,3,5-triazin-2-yl |
| 3583 | 4-O(CH₂)₃OCH₂CH₃-1,3,5-triazin-2-yl |
| 3584 | 4-O(CH₂)₃OCH(CH₃)₂-1,3,5-triazin-2-yl |
| 3585 | 4-O(CH₂)₃OC₆H₅-1,3,5-triazin-2-yl |
| 3586 | 4-O(CH₂)₃OCH₂C₆H₅-1,3,5-triazin-2-yl |
| 3587 | 4-OCH(CH₂CH₃)CH₂OCH₃-1,3,5-triazin-2-yl |
| 3588 | 4-OCH(CH₂CH₃)CH₂CH₂OCH₃-1,3,5-triazin-2-yl |
| 3589 | 4-OCH(CH₂CH₃)CH₂CH₂OCH₂CH₃-1,3,5-triazin-2-yl |
| 3590 | 4-O[(CH₂)₃O]₂CH₃-1,3,5-triazin-2-yl |
| 3591 | 4-OCH₂CH(CH₃)CH₂OCH₃-1,3,5-triazin-2-yl |
| 3592 | 4-OCH₂CH(CH₃)CH₂OCH₂CH₃-1,3,5-triazin-2-yl |
| 3593 | 4-OCH(CH₂Cl)CH₂OCH₃-1,3,5-triazin-2-yl |
| 3594 | 4-OCH(CH₂Cl)CH₂OCH₂CH₃-1,3,5-triazin-2-yl |
| 3595 | 4-OCH(CH₂Cl)CH₂OCH(CH₃)₂-1,3,5-triazin-2-yl |
| 3596 | 4-OCH(CH₂Cl)CH₂OCH₂CH=CH₂-1,3,5-triazin-2-yl |
| 3597 | 4-OCH[CH₂OCH₃]₂-1,3,5-triazin-2-yl |
| 3598 | 4-OCH[CH₂OCH₂CH₃]₂-1,3,5-triazin-2-yl |
| 3599 | 4-OCCl₄-1,3,5-triazin-2-yl |
| 3600 | 4-OCHF₂-1,3,5-triazin-2-yl |
| 3601 | 4-OCF₃-1,3,5-triazin-2-yl |
| 3602 | 4-OCF₂CHF₂-1,3,5-triazin-2-yl |
| 3603 | 4-OCH₂CF₃-1,3,5-triazin-2-yl |
| 3604 | 4-OCH₂CHF₂-1,3,5-triazin-2-yl |
| 3605 | 4-O(CH₂)₃F-1,3,5-triazin-2-yl |
| 3606 | 4-OCH(CH₃)CF₃-1,3,5-triazin-2-yl |
| 3607 | 4-O(CH₂)₄F-1,3,5-triazin-2-yl |
| 3608 | 4-O(CH₂)₃CF₃-1,3,5-triazin-2-yl |
| 3609 | 4-OCH(CH₃)CF₂CF₃-1,3,5-triazin-2-yl |
| 3610 | 4-OCH(CH₃)CF₂CHF₂-1,3,5-triazin-2-yl |
| 3611 | 4-OCH₂CF₂CHFCH₃-1,3,5-triazin-2-yl |
| 3612 | 4-OCH₂(CF₂)₂CF₃-1,3,5-triazin-2-yl |
| 3613 | 4-O(CF₂)₃CF₃-1,3,5-triazin-2-yl |
| 3614 | 4-OCH₂CF₂CHF₂-1,3,5-triazin-2-yl |
| 3615 | 4-CH₂CH=CH₂-1,3,5-triazin-2-yl |
| 3616 | 4-CH₂C(CH₃)=CH₂-1,3,5-triazin-2-yl |
| 3617 | 4-OCH₂CH=CHCH₃-1,3,5-triazin-2-yl |
| 3618 | 4-O(CH₂)₂CH=CH₂-1,3,5-triazin-2-yl |
| 3619 | 4-OCH₂C(CH₃)=CH₂-1,3,5-triazin-2-yl |
| 3620 | 4-OCH(CH₃)CH=CH₂-1,3,5-triazin-2-yl |
| 3621 | 4-OCH₂C≡CH-1,3,5-triazin-2-yl |
| 3622 | 4-OCH₂C≡CCH₃-1,3,5-triazin-2-yl |
| 3623 | 4-O(CH₂)₂C≡CH-1,3,5-triazin-2-yl |
| 3624 | 4-SCH₃-1,3,5-triazin-2-yl |
| 3625 | 4-SCH₂CH₃-1,3,5-triazin-2-yl |
| 3626 | 4-OC₆H₅-1,3,5-triazin-2-yl |
| 3627 | 4-OCH₂C₆H₅-1,3,5-triazin-2-yl |
| 3628 | 4-NO₂-1,3,5-triazin-2-yl |
| 3629 | 4-NHCH₃-1,3,5-triazin-2-yl |
| 3630 | 4-N(CH₃)₂-1,3,5-triazin-2-yl |
| 3631 | 4-N(CH₃)C₂H₆-1,3,5-triazin-2-yl |
| 3632 | 4-NHCH₂CF₃-1,3,5-triazin-2-yl |
| 3633 | 4-F-1,3,5-triazin-2-yl |
| 3634 | 4-Cl-1,3,5-triazin-2-yl |
| 3635 | 4-OH-1,3,5-triazin-2-yl |
| 3636 | 4-CN-1,3,5-triazin-2-yl |
| 3637 | 4-C(O)NH₂-1,3,5-triazin-2-yl |
| 3638 | 4-C(S)NH₂-1,3,5-triazin-2-yl |
| 3639 | 4-CO₂CH₃-1,3,5-triazin-2-yl |
| 3640 | 4-ON=C(CH₃)₂-1,3,5-triazin-2-yl |
| 3641 | 4-[O-cyclopropyl]-1,3,5-triazin-2-yl |
| 3642 | 4-[O-cyclobutyl]-1,3,5-triazin-2-yl |
| 3643 | 4-[O-cyclopentyl]-1,3,5-triazin-2-yl |
| 3644 | 4-[O-cyclohexyl]-1,3,5-triazin-2-yl |
| 3645 | 4-[OCH₂-cyclopropyl]-1,3,5-triazin-2-yl |
| 3646 | 6-F, 4-[OCH₂-cyclopropyl]-1,3,5-triazin-2-yl |
| 3647 | 6-CH₃, 4-[OCH₂-cyclopropyl]-1,3,5-triazin-2-yl |
| 3648 | 6-CF₃, 4-[OCH₂-cyclopropyl]-1,3,5-triazin-2-yl |
| 3649 | 4-[OCH(CH₃)-cyclopropyl]-1,3,5-triazin-2-yl |
| 3650 | 6-F, 4-[OCH(CH₃)-cyclopropyl]-1,3,5-triazin-2-yl |
| 3651 | 6-CH₃, 4-[OCH(CH₃)-cyclopropyl]-1,3,5-triazin-2-yl |

TABLE A-continued

| No. | R⁴ |
|---|---|
| 3652 | 6-CF₃, 4-[OCH(CH₃)-cyclopropyl]-1,3,5-triazin-2-yl |
| 3653 | 4-[O-(1-CH₃-cyclopropyl)]-1,3,5-triazin-2-yl |
| 3654 | 6-F, 4-[O-(1-CH₃-cyclopropyl)]-1,3,5-triazin-2-yl |
| 3655 | 6-CH₃, 4-[O-(1-CH₃-cyclopropyl)]-1,3,5-triazin-2-yl |
| 3656 | 6-CF₃, 4-[O-(1-CH₃-cyclopropyl)]-1,3,5-triazin-2-yl |
| 3657 | 4-[OCH₂-(1-CH₃-cyclopropyl)]-1,3,5-triazin-2-yl |
| 3658 | 6-F, 4-[OCH₂-(1-CH₃-cyclopropyl)]-1,3,5-triazin-2-yl |
| 3659 | 6-CH₃, 4-[OCH₂-(1-CH₃-cyclopropyl)]-1,3,5-triazin-2-yl |
| 3660 | 6-CF₃, 4-[OCH₂-(1-CH₃-cyclopropyl)]-1,3,5-triazin-2-yl |
| 3661 | 4-[OCH₂-(2-CH₃-cyclopropyl)]-1,3,5-triazin-2-yl |
| 3662 | 6-F, 4-[OCH₂-(2-CH₃-cyclopropyl)]-1,3,5-triazin-2-yl |
| 3663 | 6-CH₃, 4-[OCH₂-(2-CH₃-cyclopropyl)]-1,3,5-triazin-2-yl |
| 3664 | 6-CF₃, 4-[OCH₂-(2-CH₃-cyclopropyl)]-1,3,5-triazin-2-yl |
| 3665 | 4-[OCH₂-(tetrahydropyran-2-yl)]-1,3,5-triazin-2-yl |
| 3666 | 6-F, 4-[OCH₂-(tetrahydropyran-2-yl)]-1,3,5-triazin-2-yl |
| 3667 | 6-CH₃, 4-[OCH₂-(tetrahydropyran-2-yl)]-1,3,5-triazin-2-yl |
| 3668 | 6-CF₃, 4-[OCH₂-(tetrahydropyran-2-yl)]-1,3,5-triazin-2-yl |
| 3669 | 4-[OCH₂-(furan-2-yl)]-1,3,5-triazin-2-yl |
| 3670 | 6-F, 4-[OCH₂-(furan-2-yl)]-1,3,5-triazin-2-yl |
| 3671 | 6-CH₃, 4-[OCH₂-(furan-2-yl)]-1,3,5-triazin-2-yl |
| 3672 | 6-CF₃, 4-[OCH₂-(furan-2-yl)]-1,3,5-triazin-2-yl |
| 3673 | 4-[OCH₂-(furan-4-yl)]-1,3,5-triazin-2-yl |
| 3674 | 6-F, 4-[OCH₂-(furan-4-yl)]-1,3,5-triazin-2-yl |
| 3675 | 6-CH₃, 4-[OCH₂-(furan-4-yl)]-1,3,5-triazin-2-yl |
| 3676 | 6-CF₃, 4-[OCH₂-(furan-4-yl)]-1,3,5-triazin-2-yl |
| 3677 | 4-[OCH₂-(tetrahydrofuran-4-yl)]-1,3,5-triazin-2-yl |
| 3678 | 6-F, 4-[OCH₂-(tetrahydrofuran-4-yl)]-1,3,5-triazin-2-yl |
| 3679 | 6-CH₃, 4-[OCH₂-(tetrahydrofuran-4-yl)]-1,3,5-triazin-2-yl |
| 3680 | 6-CF₃, 4-[OCH₂-(tetrahydrofuran-4-yl)]-1,3,5-triazin-2-yl |
| 3681 | 4-[OCH₂-(tetrahydrofuran-2-yl)]-1,3,5-triazin-2-yl |
| 3682 | 6-F, 4-[OCH₂-(tetrahydrofuran-2-yl)]-1,3,5-triazin-2-yl |
| 3683 | 6-CH₃, 4-[OCH₂-(tetrahydrofuran-2-yl)]-1,3,5-triazin-2-yl |
| 3684 | 6-CF₃, 4-[OCH₂-(tetrahydrofuran-2-yl)]-1,3,5-triazin-2-yl |
| 3685 | 4-[O-(tetrahydropyran-4-yl)]-1,3,5-triazin-2-yl |
| 3686 | 6-F, 4-[O-(tetrahydropyran-4-yl)]-1,3,5-triazin-2-yl |
| 3687 | 6-CH₃, 4-[O-(tetrahydropyran-4-yl)]-1,3,5-triazin-2-yl |
| 3688 | 6-CF₃, 4-[O-(tetrahydropyran-4-yl)]-1,3,5-triazin-2-yl |
| 3689 | 4-[2-Cl—C₅H₄]-1,3,5-triazin-2-yl |
| 3690 | 6-F, 4-[2-Cl—C₅H₄]-1,3,5-triazin-2-yl |
| 3691 | 6-CH₃, 4-[2-Cl—C₅H₄]-1,3,5-triazin-2-yl |
| 3692 | 6-CF₃, 4-[2-Cl—C₅H₄]-1,3,5-triazin-2-yl |
| 3693 | 4-[OCH₂-(pyridin-2-yl)]-1,3,5-triazin-2-yl |
| 3694 | 6-F, 4-[OCH₂-(pyridin-2-yl)]-1,3,5-triazin-2-yl |
| 3695 | 6-CH₃, 4-[OCH₂-(pyridin-2-yl)]-1,3,5-triazin-2-yl |
| 3696 | 6-CF₃, 4-[OCH₂-(pyridin-2-yl)]-1,3,5-triazin-2-yl |
| 3697 | 4-[OCH₂-(pyridin-4-yl)]-1,3,5-triazin-2-yl |
| 3698 | 6-F, 4-[OCH₂-(pyridin-4-yl)]-1,3,5-triazin-2-yl |
| 3699 | 6-CH₃, 4-[OCH₂-(pyridin-4-yl)]-1,3,5-triazin-2-yl |
| 3700 | 6-CF₃, 4-[OCH₂-(pyridin-4-yl)]-1,3,5-triazin-2-yl |
| 3701 | 4-[morpholin-4-yl]-1,3,5-triazin-2-yl |
| 3702 | 4-[1-CH₃-imidazol-2-yl]-1,3,5-triazin-2-yl |
| 3703 | 6-F, 4-[1-CH₃-imidazol-2-yl]-1,3,5-triazin-2-yl |
| 3704 | 6-CH₃, 4-[1-CH₃-imidazol-2-yl]-1,3,5-triazin-2-yl |
| 3705 | 6-CF₃, 4-[1-CH₃-imidazol-2-yl]-1,3,5-triazin-2-yl |
| 3706 | 4-[1,2,4-triazol-1-yl]-1,3,5-triazin-2-yl |
| 3707 | 6-F, 4-[1,2,4-triazol-1-yl]-1,3,5-triazin-2-yl |
| 3708 | 6-CH₃, 4-[1,2,4-triazol-1-yl]-1,3,5-triazin-2-yl |
| 3709 | 6-CF₃, 4-[1,2,4-triazol-1-yl]-1,3,5-triazin-2-yl |
| 3710 | 4,6-Cl₂-1,3,5-triazin-2-yl |
| 3711 | 4,6-(CH₃)₂-1,3,5-triazin-2-yl |
| 3712 | 4,6-(OCH₃)₂-1,3,5-triazin-2-yl |
| 3713 | 4,6-(OCH₂CH₃)₂-1,3,5-triazin-2-yl |
| 3714 | 4-F, 6-CH₃-1,3,5-triazin-2-yl |
| 3715 | 4-F, 6-OCH₃-1,3,5-triazin-2-yl |
| 3716 | 4-F, 6-OCH₂CH₃-1,3,5-triazin-2-yl |
| 3717 | 4-F, 6-OCH₂CF₃-1,3,5-triazin-2-yl |
| 3718 | 4-F, 6-OCH(CH₃)₂-1,3,5-triazin-2-yl |
| 3719 | 4-Cl, 6-CH₃-1,3,5-triazin-2-yl |
| 3720 | 4-Cl, 6-OCH₃-1,3,5-triazin-2-yl |
| 3721 | 4-Cl, 6-OCH₂CH₃-1,3,5-triazin-2-yl |
| 3722 | 4-Cl, 6-OCH₂CF₃-1,3,5-triazin-2-yl |
| 3723 | 4-Cl, 6-OCH(CH₃)₂-1,3,5-triazin-2-yl |
| 3724 | 4-CH₃, 6-OCH₃-1,3,5-triazin-2-yl |
| 3725 | 4-CH₃, 6-OCH₂CH₃-1,3,5-triazin-2-yl |
| 3726 | 4-CH₃, 6-OCH₂CF₃-1,3,5-triazin-2-yl |
| 3727 | 4-CH₃, 6-OCH(CH₃)₂-1,3,5-triazin-2-yl |
| 3728 | 4-CH₃, 6-OCH₂CH=CH₂-1,3,5-triazin-2-yl |
| 3729 | 4-CH₃, 6-CO₂CH₃-1,3,5-triazin-2-yl |
| 3730 | 4-CH₃, 6-CF₃-1,3,5-triazin-2-yl |
| 3731 | 4-CF₃, 6-CH₂CH₃-1,3,5-triazin-2-yl |
| 3732 | 4-CF₃, 6-OCH₃-1,3,5-triazin-2-yl |
| 3733 | 4-CF₃, 6-OCH₂CH₃-1,3,5-triazin-2-yl |
| 3734 | 4-CF₃, 6-OCH₂CF₃-1,3,5-triazin-2-yl |
| 3735 | 4-OCH₃, 6-OCH₂CH₃-1,3,5-triazin-2-yl |
| 3736 | 4-OCH₃, 6-OCH₂CF₃-1,3,5-triazin-2-yl |
| 3737 | 4-OCH₃, 6-OCH(CH₃)-1,3,5-triazin-2-yl |
| 3738 | 4-OCH₂CH₃, 6-CH₂OCH₂CH₃-1,3,5-triazin-2-yl |
| 3739 | 4-NO₂, 6-CH₃-1,3,5-triazin-2-yl |
| 3740 | 4-NO₂, 6-OCH₃-1,3,5-triazin-2-yl |
| 3741 | 4-NO₂, 6-OCH₂CH₃-1,3,5-triazin-2-yl |
| 3742 | 4-NO₂, 6-OCH(CH₃)₂-1,3,5-triazin-2-yl |
| 3743 | 4-NO₂, 6-OCH₂CF₃-1,3,5-triazin-2-yl |
| 3744 | 4-CN, 6-CH₃-1,3,5-triazin-2-yl |
| 3745 | 4-CN, 6-OCH₃-1,3,5-triazin-2-yl |
| 3746 | 4-CN, 6-OCH₂CH₃-1,3,5-triazin-2-yl |
| 3747 | 4-CN, 6-OCH(CH₃)₂-1,3,5-triazin-2-yl |
| 3748 | 4-CN, 6-OCH₂CF₃-1,3,5-triazin-2-yl |
| 3749 | 1-CH₃, 4-CH₃-indol-2-yl |
| 3750 | 1-CH₃, 4-CH₂CH₃-indol-2-yl |
| 3751 | 1-CH₃, 4-CH(CH₃)₂-indol-2-yl |
| 3752 | 1-CH₃, 4-CH(CH₃)CH₂CH₃-indol-2-yl |
| 3753 | 1-CH₃, 4-CF₃-indol-2-yl |
| 3754 | 1-CH₃, 4-CH=CH₂-indol-2-yl |
| 3755 | 1-CH₃, 4-CH=CHCH₃-indol-2-yl |
| 3756 | 1-CH₃, 4-CH=CHCl-indol-2-yl |
| 3757 | 1-CH₃, 4-C≡CH-indol-2-yl |
| 3758 | 1-CH₃, 4-CH₂C≡CH-indol-2-yl |
| 3759 | 1-CH₃, 4-CH₂C≡CCH₃-indol-2-yl |
| 3760 | 1-CH₃, 4-cyclopropylindol-2-yl |
| 3761 | 1-CH₃, 4-cyclopentylindol-2-yl |
| 3762 | 1-CH₃, 4-OCH₃-indol-2-yl |
| 3763 | 1-CH₃, 4-OCH₂CH₃-indol-2-yl |
| 3764 | 1-CH₃, 4-OCH₂CH₂CH₃-indol-2-yl |
| 3765 | 1-CH₃, 4-OCH(CH₃)₂-indol-2-yl |
| 3766 | 1-CH₃, 4-OCH₂CH₂CH₂CH₃-indol-2-yl |
| 3767 | 1-CH₃, 4-OCH(CH₃)CH₂CH₃-indol-2-yl |
| 3768 | 1-CH₃, 4-OCH₂CH(CH₃)₂-indol-2-yl |
| 3769 | 1-CH₃, 4-OC(CH₃)₄-indol-2-yl |
| 3770 | 1-CH₃, 4-OCH₂CH₂CH₂CH₃-indol-2-yl |
| 3771 | 1-CH₃, 4-OCH₂OCH₃-indol-2-yl |
| 3772 | 1-CH₃, 4-OCH₂OCH₂CH₃-indol-2-yl |
| 3773 | 1-CH₃, 4-OCH(CH₃)OCH₃-indol-2-yl |
| 3774 | 1-CH₃, 4-OCH(CH₃)OCH₂CH₃-indol-2-yl |
| 3775 | 1-CH₃, 4-OCH₂CH₂OCH₃-indol-2-yl |
| 3776 | 1-CH₃, 4-OCH₂CH₂OCH₂CH₃-indol-2-yl |
| 3777 | 1-CH₃, 4-OCH₂CH₂OCH(CH₃)₂-indol-2-yl |
| 3778 | 1-CH₃, 4-OCH₂CH₂SCH₃-indol-2-yl |
| 3779 | 1-CH₃, 4-OCH₂CH₂SO₂CH₃-indol-2-yl |
| 3780 | 1-CH₃, 4-OCH₂CH₂SO(CH₃)₂-indol-2-yl |
| 3781 | 1-CH₃, 4-OCH₂CH₂CN-indol-2-yl |
| 3782 | 1-CH₃, 4-OCH₂CH₂SCH₂CH₂CN-indol-2-yl |
| 3783 | 1-CH₃, 4-OCH₂CH₂OC₆H₅-indol-2-yl |
| 3784 | 1-CH₃, 4-OCH₂CH₂OCH₂C₆H₅-indol-2-yl |
| 3785 | 1-CH₃, 4-OCH₂CH₂N(CH₃)₂-indol-2-yl |
| 3786 | 1-CH₃, 4-OCH₂CH₂CONH₂-indol-2-yl |
| 3787 | 1-CH₃, 4-OCH(CH₃)CO₂CH₂CH₂CH₃-indol-2-yl |
| 3788 | 1-CH₃, 4-OCH(CH₃)CH₂OCH₃-indol-2-yl |
| 3789 | 1-CH₃, 4-OCH(CH₃)CH₂CO₂CH₃-indol-2-yl |
| 3790 | 1-CH₃, 4-OCH(CH₃)CH₂CO₂CH₂CH₃-indol-2-yl |
| 3791 | 1-CH₃, 4-OCH(CH₃)CH(CH₃)CO₂CH₃-indol-2-yl |
| 3792 | 1-CH₃, 4-OCH₂C(=O)CH₃-indol-2-yl |
| 3793 | 1-CH₃, 4-OCH₂C(=O)CH₂CH₃-indol-2-yl |
| 3794 | 1-CH₃, 4-OCH₂CO₂CH₃-indol-2-yl |
| 3795 | 1-CH₃, 4-OCH₂CO₂CH₂CH₃-indol-2-yl |
| 3796 | 1-CH₃, 4-OCH₂C(=O)NH₂-indol-2-yl |
| 3797 | 1-CH₃, 4-OCH₂C(=O)NHCH₃-indol-2-yl |
| 3798 | 1-CH₃, 4-OCH₂C(=O)SCH₃-indol-2-yl |
| 3799 | 1-CH₃, 4-OCH(CH₃)C(=O)NH₂-indol-2-yl |
| 3800 | 1-CH₃, 4-OCH(CH₃)C(=O)NHCH₃-indol-2-yl |
| 3801 | 1-CH₃, 4-OCH(CH₃)C(=O)NHNH₂-indol-2-yl |
| 3802 | 1-CH₃, 4-OCH(CH₃)CO₂CH₃-indol-2-yl |
| 3803 | 1-CH₃, 4-OCH(CH₃)CO₂CH₂CH₃-indol-2-yl |
| 3804 | 1-CH₃, 4-OCH(CH₃)C(=O)CH₃-indol-2-yl |
| 3805 | 1-CH₃, 4-OCH(CH₃)C(=O)CH₂CH₃-indol-2-yl |

TABLE A-continued

| No. | R⁴ |
|---|---|
| 3806 | 1-CH₃, 4-OCH(CH₃)CH₂C(=O)CH₃-indol-2-yl |
| 3807 | 1-CH₃, 4-OCH(CH₃)CH₂OC(CH₃)₄-indol-2-yl |
| 3808 | 1-CH₃, 4-OCH(CH₃)CH₂OCH₂CH₃-indol-2-yl |
| 3809 | 1-CH₃, 4-OCH(CH₃)CH₂O(CH₃)₂CH₃-indol-2-yl |
| 3810 | 1-CH₃, 4-OCH(CH₃)CH₂OCH₂CH=CH₂-indol-2-yl |
| 3811 | 1-CH₃, 4-O(CH₂)₃OCH₃-indol-2-yl |
| 3812 | 1-CH₃, 4-O(CH₂)₃OCH₂CH₃-indol-2-yl |
| 3813 | 1-CH₃, 4-O(CH₂)₃OCH(CH₃)₂-indol-2-yl |
| 3814 | 1-CH₃, 4-O(CH₂)₃OC₆H₅-indol-2-yl |
| 3815 | 1-CH₃, 4-O(CH₂)₃OCH₂C₆H₅-indol-2-yl |
| 3816 | 1-CH₃, 4-OCH(CH₂CH₃)CH₂OCH₃-indol-2-yl |
| 3817 | 1-CH₃, 4-OCH(CH₂CH₃)CH₂CH₂OCH₃-indol-2-yl |
| 3818 | 1-CH₃, 4-OCH(CH₂CH₃)CH₂CH₂OCH₂CH₃-indol-2-yl |
| 3819 | 1-CH₃, 4-O[(CH₂)₃O]₂CH₃-indol-2-yl |
| 3820 | 1-CH₃, 4-OCH₂CH(CH₃)CH₂OCH₃-indol-2-yl |
| 3821 | 1-CH₃, 4-OCH₂CH(CH₃)CH₂OCH₂CH₃-indol-2-yl |
| 3822 | 1-CH₃, 4-OCH(CH₂Cl)CH₂OCH₃-indol-2-yl |
| 3823 | 1-CH₃, 4-OCH(CH₂Cl)CH₂OCH₂CH₃-indol-2-yl |
| 3824 | 1-CH₃, 4-OCH(CH₂Cl)CH₂OCH(CH₃)₂-indol-2-yl |
| 3825 | 1-CH₃, 4-OCH(CH₂Cl)CH₂OCH₂CH=CH₂-indol-2-yl |
| 3826 | 1-CH₃, 4-OCH[CH₂OCH₃]₂-indol-2-yl |
| 3827 | 1-CH₃, 4-OCH[CH₂OCH₂CH₃]₂-indol-2-yl |
| 3828 | 1-CH₃, 4-OCCl₄-indol-2-yl |
| 3829 | 1-CH₃, 4-OCHF₂-indol-2-yl |
| 3830 | 1-CH₃, 4-OCF₃-indol-2-yl |
| 3831 | 1-CH₃, 4-OCF₂CHF₂-indol-2-yl |
| 3832 | 1-CH₃, 4-OCH₂CF₃-indol-2-yl |
| 3833 | 1-CH₃, 4-OCH₂CHF₂-indol-2-yl |
| 3834 | 1-CH₃, 4-O(CH₂)₃F-indol-2-yl |
| 3835 | 1-CH₃, 4-OCH₂CF₃-indol-2-yl |
| 3836 | 1-CH₃, 4-O(CH₂)₄F-indol-2-yl |
| 3837 | 1-CH₃, 4-O(CH₂)₃CF₃-indol-2-yl |
| 3838 | 1-CH₃, 4-OCH(CH₃)CF₂CF₃-indol-2-yl |
| 3839 | 1-CH₃, 4-OCH(CH₃)CF₂CHF₂-indol-2-yl |
| 3840 | 1-CH₃, 4-OCH(CH₃)CF₂CHFCH₃-indol-2-yl |
| 3841 | 1-CH₃, 4-OCH₂(CF₂)₂CF₃-indol-2-yl |
| 3842 | 1-CH₃, 4-O(CF₂)₃CF₃-indol-2-yl |
| 3843 | 1-CH₃, 4-OCH₂CF₂CHF₂-indol-2-yl |
| 3844 | 1-CH₃, 4-CH₂CH=CH₂-indol-2-yl |
| 3845 | 1-CH₃, 4-CH₂C(CH₃)=CH₂-indol-2-yl |
| 3846 | 1-CH₃, 4-OCH₂CH=CHCH₃-indol-2-yl |
| 3847 | 1-CH₃, 4-O(CH₂)₂CH=CH₂-indol-2-yl |
| 3848 | 1-CH₃, 4-OCH₂C(CH₃)=CH₂-indol-2-yl |
| 3849 | 1-CH₃, 4-OCH(CH₃)CH=CH₂-indol-2-yl |
| 3850 | 1-CH₃, 4-OCH₂C≡CH-indol-2-yl |
| 3851 | 1-CH₃, 4-OCH₂C≡CCH₃-indol-2-yl |
| 3852 | 1-CH₃, 4-O(CH₂)₂C≡CH-indol-2-yl |
| 3853 | 1-CH₃, 4-SCH₃-indol-2-yl |
| 3854 | 1-CH₃, 4-SCH₂CH₃-indol-2-yl |
| 3855 | 1-CH₃, 4-OC₆H₅-indol-2-yl |
| 3856 | 1-CH₃, 4-OCH₂C₆H₅-indol-2-yl |
| 3857 | 1-CH₃, 4-NO₂-indol-2-yl |
| 3858 | 1-CH₃, 4-NHCH₃-indol-2-yl |
| 3859 | 1-CH₃, 4-N(CH₃)₂-indol-2-yl |
| 3860 | 1-CH₃, 4-N(CH₃)C₂H₆-indol-2-yl |
| 3861 | 1-CH₃, 4-NHCH₂CF₃-indol-2-yl |
| 3862 | 1-CH₃, 4-F-indol-2-yl |
| 3863 | 1-CH₃, 4-Cl-indol-2-yl |
| 3864 | 1-CH₃, 4-OH-indol-2-yl |
| 3865 | 1-CH₃, 4-CN-indol-2-yl |
| 3866 | 1-CH₃, 4-C(O)NH₂-indol-2-yl |
| 3867 | 1-CH₃, 4-C(S)NH₂-indol-2-yl |
| 3868 | 1-CH₃, 4-CO₂CH₃-indol-2-yl |
| 3869 | 1-CH₃, 4-ON=C(CH₃)₂-indol-2-yl |
| 3870 | 1-CH₃, 4-[O-cyclopropyl]indol-2-yl |
| 3871 | 1-CH₃, 4-[O-cyclobutyl]indol-2-yl |
| 3872 | 1-CH₃, 4-[O-cyclopentyl]indol-2-yl |
| 3873 | 1-CH₃, 4-[O-cyclohexyl]indol-2-yl |
| 3874 | 1-CH₃, 4-[OCH-cyclopropyl]indol-2-yl |
| 3875 | 1-CH₃, 6-F, 4-[OCH₂-cyclopropyl]indol-2-yl |
| 3876 | 1-CH₃, 6-CH₃, 4-[OCH₂-cyclopropyl]indol-2-yl |
| 3877 | 1-CH₃, 6-CF₃, 4-[OCH₂-cyclopropyl]indol-2-yl |
| 3878 | 1-CH₃, 4-[OCH(CH₃)-cyclopropyl]indol-2-yl |
| 3879 | 1-CH₃, 6-F, 4-[OCH(CH₃)-cyclopropyl]indol-2-yl |
| 3880 | 1-CH₃, 6-CH₃, 4-[OCH(CH₃)-cyclopropyl]indol-2-yl |
| 3881 | 1-CH₃, 6-CF₃, 4-[OCH(CH₃)-cyclopropyl]indol-2-yl |
| 3882 | 1-CH₃, 4-[O-(1-CH₃-cyclopropyl)]indol-2-yl |
| 3883 | 1-CH₃, 6-F, 4-[O-(1-CH₃-cyclopropyl)]indol-2-yl |
| 3884 | 1-CH₃, 6-CH₃, 4-[O-(1-CH₃-cyclopropyl)]indol-2-yl |
| 3885 | 1-CH₃, 6-CF₃, 4-[O-(1-CH₃-cyclopropyl)]indol-2-yl |
| 3886 | 1-CH₃, 4-[OCH₂-(1-CH₃-cyclopropyl)]indol-2-yl |
| 3887 | 1-CH₃, 6-F, 4-[OCH₂-(1-CH₃-cyclopropyl)]indol-2-yl |
| 3888 | 1-CH₃, 6-CH₃, 4-[OCH₂-(1-CH₃-cyclopropyl)]indol-2-yl |
| 3889 | 1-CH₃, 6-CF₃, 4-[OCH₂-(1-CH₃-cyclopropyl)]indol-2-yl |
| 3890 | 1-CH₃, 4-[OCH₂-(2-CH₃-cyclopropyl)]indol-2-yl |
| 3891 | 1-CH₃, 6-F, 4-[OCH₂-(2-CH₃-cyclopropyl)]indol-2-yl |
| 3892 | 1-CH₃, 6-CH₃, 4-[OCH₂-(2-CH₃-cyclopropyl)]indol-2-yl |
| 3893 | 1-CH₃, 6-CF₃, 4-[OCH₂-(2-CH₃-cyclopropyl)]indol-2-yl |
| 3894 | 1-CH₃, 4-[OCH₂-(tetrahydropyran-2-yl)]indol-2-yl |
| 3895 | 1-CH₃, 6-F, 4-(OCH₂-(tetrahydropyran-2-yl)]indol-2-yl |
| 3896 | 1-CH₃, 6-CH₃, 4-[OCH₂-(tetrahydropyran-2-yl)]indol-2-yl |
| 3897 | 1-CH₃, 6-CF₃, 4-[OCH₂-(tetrahydropyran-2-yl)]indol-2-yl |
| 3898 | 1-CH₃, 4-[OCH₂-(furan-2-yl)]indol-2-yl |
| 3899 | 1-CH₃, 6-F, 4-[OCH₂-(furan-2-yl)]indol-2-yl |
| 3900 | 1-CH₃, 6-CH₃, 4-[OCH₂-(furan-2-yl)]indol-2-yl |
| 3901 | 1-CH₃, 6-CF₃, 4-[OCH₂-(furan-2-yl)]indol-2-yl |
| 3902 | 1-CH₃, 4-[OCH₂-(furan-4-yl)]indol-2-yl |
| 3903 | 1-CH₃, 6-F, 4-[OCH₂-(furan-4-yl)]indol-2-yl |
| 3904 | 1-CH₃, 6-CH₃, 4-[OCH₂-(furan-4-yl)]indol-2-yl |
| 3905 | 1-CH₃, 6-CF₃, 4-[OCH₂-(furan-4-yl)]indol-2-yl |
| 3906 | 1-CH₃, 4-[OCH₂-(tetrahydrofuran-4-yl)]indol-2-yl |
| 3907 | 1-CH₃, 6-F, 4-[OCH₂-(tetrahydrofuran-4-yl)]indol-2-yl |
| 3908 | 1-CH₃, 6-CH₃, 4-[OCH₂-(tetrahydrofuran-4-yl)]indol-2-yl |
| 3909 | 1-CH₃, 6-CF₃, 4-[OCH₂-(tetrahydrofuran-4-yl)]indol-2-yl |
| 3910 | 1-CH₃, 4-[OCH₂-(tetrahydrofuran-2-yl)]indol-2-yl |
| 3911 | 1-CH₃, 6-F, 4-[OCH₂-(tetrahydrofuran-2-yl)]indol-2-yl |
| 3912 | 1-CH₃, 6-CH₃, 4-[OCH₂-(tetrahydrofuran-2-yl)]indol-2-yl |
| 3913 | 1-CH₃, 6-CF₃, 4-[OCH₂-(tetrahydrofuran-2-yl)]indol-2-yl |
| 3914 | 1-CH₃, 4-[O-(tetrahydropyran-4-yl)]indol-2-yl |
| 3915 | 1-CH₃, 6-F, 4-[O-(tetrahydropyran-4-yl)]indol-2-yl |
| 3916 | 1-CH₃, 6-CH₃, 4-[O-(tetrahydropyran-4-yl)]indol-2-yl |
| 3917 | 1-CH₃, 6-CF₃, 4-[O-(tetrahydropyran-4-yl)]indol-2-yl |
| 3918 | 1-CH₃, 4-[2-Cl—C₅H₄]indol-2-yl |
| 3919 | 1-CH₃, 6-F, 4-[2-Cl—C₅H₄]indol-2-yl |
| 3920 | 1-CH₃, 6-CH₃, 4-[2-Cl—C₅H₄]indol-2-yl |
| 3921 | 1-CH₃, 6-CF₃, 4-[2-Cl—C₅H₄]indol-2-yl |
| 3922 | 1-CH₃, 4-[OCH₂-(pyridin-2-yl)]indol-2-yl |
| 3923 | 1-CH₃, 6-F, 4-[OCH₂-(pyridin-2-yl)]indol-2-yl |
| 3924 | 1-CH₃, 6-CH₃, 4-[OCH₂-(pyridin-2-yl)]indol-2-yl |
| 3925 | 1-CH₃, 6-CF₃, 4-[OCH₂-(pyridin-2-yl)]indol-2-yl |
| 3926 | 1-CH₃, 4-[OCH₂-(pyridin-4-yl)]indol-2-yl |
| 3927 | 1-CH₃, 6-F, 4-[OCH₂-(pyridin-4-yl)]indol-2-yl |
| 3928 | 1-CH₃, 6-CH₃, 4-[OCH₂-(pyridin-4-yl)]indol-2-yl |
| 3929 | 1-CH₃, 6-CF₃, 4-[OCH₂-(pyridin-4-yl)]indol-2-yl |
| 3930 | 1-CH₃, 4-[morpholin-4-yl]indol-2-yl |
| 3931 | 1-CH₃, 4-[1-CH₃-imidazol-2-yl]indol-2-yl |
| 3932 | 1-CH₃, 6-F, 4-[1-CH₃-imidazol-2-yl]indol-2-yl |
| 3933 | 1-CH₃, 6-CH₃, 4-[1-CH₃-imidazol-2-yl]indol-2-yl |
| 3934 | 1-CH₃, 6-CF₃, 4-[1-CH₃-imidazol-2-yl]indo1-2-yl |
| 3935 | 1-CH₃, 4-[1,2,4-triazol-1-yl]indol-2-yl |
| 3936 | 1-CH₃, 6-F, 4-[1,2,4-triazol-1-yl]indol-2-yl |
| 3937 | 1-CH₃, 6-CH₃, 4-[1,2,4-triazol-1-yl]indol-2-yl |
| 3938 | 1-CH₃, 6-CF₃, 4-[1,2,4-triazol-1-yl]indol-2-yl |
| 3939 | 1-CH₃, 4,6-Cl₂-indol-2-yl |
| 3940 | 1-CH₃, 4,6-(CH₃)₂-indol-2-yl |
| 3941 | 1-CH₃, 4,6-(OCH₃)₂-indol-2-yl |
| 3942 | 1-CH₃, 4,6-(OCH₂CH₃)₂-indol-2-yl |
| 3943 | 1-CH₃, 4-F, 6-CH₃-indol-2-yl |
| 3944 | 1-CH₃, 4-F, 6-OCH₃-indol-2-yl |
| 3945 | 1-CH₃, 4-F, 6-OCH₂CH₃-indol-2-yl |
| 3946 | 1-CH₃, 4-F, 6-OCH₂CF₃-indol-2-yl |
| 3947 | 1-CH₃, 4-F, 6-OCH(CH₃)₂-indol-2-yl |
| 3948 | 1-CH₃, 4-Cl, 6-CH₃-indol-2-yl |
| 3949 | 1-CH₃, 4-Cl, 6-OCH₃-indol-2-yl |
| 3950 | 1-CH₃, 4-Cl, 6-OCH₂CH₃-indol-2-yl |
| 3951 | 1-CH₃, 4-Cl, 6-OCH₂CF₃-indol-2-yl |
| 3952 | 1-CH₃, 4-Cl, 6-OCH(CH₃)₂-indol-2-yl |
| 3953 | 1-CH₃, 4-CH₃, 6-OCH₃-indol-2-yl |
| 3954 | 1-CH₃, 4-CH₃, 6-OCH₂CH₃-indol-2-yl |
| 3955 | 1-CH₃, 4-CH₃, 6-OCH₂CF₃-indol-2-yl |
| 3956 | 1-CH₃, 4-CH₃, 6-OCH(CH₃)₂-indol-2-yl |
| 3957 | 1-CH₃, 4-CH₃, 6-OCH₂CH=CH₂-indol-2-yl |
| 3958 | 1-CH₃, 4-CH₃, 6-CO₂CH₃-indol-2-yl |
| 3959 | 1-CH₃, 4-CH₃, 6-CF₃-indol-2-yl |

TABLE A-continued

| No. | R⁴ |
|---|---|
| 3960 | 1-CH₃, 4-CF₃, 6-CH₂CH₃-indol-2-yl |
| 3961 | 1-CH₃, 4-CF₃, 6-OCH₃-indol-2-yl |
| 3962 | 1-CH₃, 4-CF₃, 6-OCH₂CH₃-indol-2-yl |
| 3963 | 1-CH₃, 4-CF₃, 6-OCH₂CF₃-indol-2-yl |
| 3964 | 1-CH₃, 4-OCH₃, 6-OCH₂CH₃-indol-2-yl |
| 3965 | 1-CH₃, 4-OCH₃, 6-OCH₂CF₃-indol-2-yl |
| 3966 | 1-CH₃, 4-OCH₃, 6-OCH(CH₃)-indol-2-yl |
| 3967 | 1-CH₃, 4-OCH₂CH₃, 6-CH₂OCH₂CH₃-indol-2-yl |
| 3968 | 1-CH₃, 4-NO₂, 6-CH₃-indol-2-yl |
| 3969 | 1-CH₃, 4-NO₂, 6-OCH₃-indol-2-yl |
| 3970 | 1-CH₃, 4-NO₂, 6-OCH₂CH₃-indol-2-yl |
| 3971 | 1-CH₃, 4-NO₂, 6-OCH(CH₃)₂-indol-2-yl |
| 3972 | 1-CH₃, 4-NO₂, 6-OCH₂CF₃-indol-2-yl |
| 3973 | 1-CH₃, 4-CN, 6-CH₃-indol-2-yl |
| 3974 | 1-CH₃, 4-CN, 6-OCH₃-indol-2-yl |
| 3975 | 1-CH₃, 4-CN, 6-OCH₂CH₃-indol-2-yl |
| 3976 | 1-CH₃, 4-CN, 6-OCH(CH₃)₂-indol-2-yl |
| 3977 | 1-CH₃, 4-CN, 6-OCH₂CF₃-indol-2-yl |
| 3978 | 1-CH₃, 4-CH₃-indol-3-yl |
| 3979 | 1-CH₃, 4-CH₂CH₃-indol-3-yl |
| 3980 | 1-CH₃, 4-CH(CH₃)₂-indol-3-yl |
| 3981 | 1-CH₃, 4-CH(CH₃)CH₂CH₃-indol-3-yl |
| 3982 | 1-CH₃, 4-CF₃-indol-3-yl |
| 3983 | 1-CH₃, 4-CH=CH₂-indol-3-yl |
| 3984 | 1-CH₃, 4-CH=CHCH₃-indol-3-yl |
| 3985 | 1-CH₃, 4-CH=CHCl-indol-3-yl |
| 3986 | 1-CH₃, 4-C≡CH-indol-3-yl |
| 3987 | 1-CH₃, 4-CH₂C≡CH-indol-3-yl |
| 3988 | 1-CH₃, 4-CH₂C≡CCH₃-indol-3-yl |
| 3989 | 1-CH₃, 4-cyclopropylindol-3-yl |
| 3990 | 1-CH₃, 4-cyclopentylindol-3-yl |
| 3991 | 1-CH₃, 4-OCH₃-indol-3-yl |
| 3992 | 1-CH₃, 4-OCH₂CH₃-indol-3-yl |
| 3993 | 1-CH₃, 4-OCH₂CH₂CH₃-indol-3-yl |
| 3994 | 1-CH₃, 4-OCH(CH₃)₂-indol-3-yl |
| 3995 | 1-CH₃, 4-OCH₂CH₂CH₂CH₃-indol-3-yl |
| 3996 | 1-CH₃, 4-OCH(CH₃)CH₂CH₃-indol-3-yl |
| 3997 | 1-CH₃, 4-OCH₂CH(CH₃)₂-indol-3-yl |
| 3998 | 1-CH₃, 4-OC(CH₃)₄-indol-3-yl |
| 3999 | 1-CH₃, 4-OCH(CH₃)CH₂CH₂CH₃-indol-3-yl |
| 4000 | 1-CH₃, 4-OCH₂OCH₃-indol-3-yl |
| 4001 | 1-CH₃, 4-OCH₂OCH₂CH₃-indol-3-yl |
| 4002 | 1-CH₃, 4-OCH(CH₃)OCH₃-indol-3-yl |
| 4003 | 1-CH₃, 4-OCH(CH₃)OCH₂CH₃-indol-3-yl |
| 4004 | 1-CH₃, 4-OCH₂CH₂OCH₃-indol-3-yl |
| 4005 | 1-CH₃, 4-OCH₂CH₂OCH₂CH₃-indol-3-yl |
| 4006 | 1-CH₃, 4-OCH₂CH₂OCH(CH₃)₂-indol-3-yl |
| 4007 | 1-CH₃, 4-OCH₂CH₂SCH₃-indol-3-yl |
| 4008 | 1-CH₃, 4-OCH₂CH₂SO₂CH₃-indol-3-yl |
| 4009 | 1-CH₃, 4-OCH₂CH₂SCH(CH₃)₂-indol-3-yl |
| 4010 | 1-CH₃, 4-OCH₂CH₂CN-indol-3-yl |
| 4011 | 1-CH₃, 4-OCH₂CH₂SCH₂CH₂CN-indol-3-yl |
| 4012 | 1-CH₃, 4-OCH₂CH₂OC₆H₅-indol-3-yl |
| 4013 | 1-CH₃, 4-OCH₂CH₂OCH₂C₆H₅-indol-3-yl |
| 4014 | 1-CH₃, 4-OCH₂CH₂N(CH₃)₂-indol-3-yl |
| 4015 | 1-CH₃, 4-OCH₂CH₂CONH₂-indol-3-yl |
| 4016 | 1-CH₃, 4-OCH₂CH₂CO₂CH₂CH₂CH₃-indol-3-yl |
| 4017 | 1-CH₃, 4-OCH(CH₃)CH₂OCH₃-indol-3-yl |
| 4018 | 1-CH₃, 4-OCH(CH₃)CH₂OC₂H₅-indol-3-yl |
| 4019 | 1-CH₃, 4-OCH(CH₃)CH₂CO₂CH₂CH₃-indol-3-yl |
| 4020 | 1-CH₃, 4-OCH₂CH(CH₃)CO₂CH₃-indol-3-yl |
| 4021 | 1-CH₃, 4-OCH₂C(=O)CH₃-indol-3-yl |
| 4022 | 1-CH₃, 4-OCH₂C(=O)CH₂CH₃-indol-3-yl |
| 4023 | 1-CH₃, 4-OCH₂CO₂CH₃-indol-3-yl |
| 4024 | 1-CH₃, 4-OCH₂CO₂CH₂CH₃-indol-3-yl |
| 4025 | 1-CH₃, 4-OCH₂C(=O)NH₂-indol-3-yl |
| 4026 | 1-CH₃, 4-OCH₂C(=O)NHCH₃-indol-3-yl |
| 4027 | 1-CH₃, 4-OCH₂C(=O)SCH₃-indol-3-yl |
| 4028 | 1-CH₃, 4-OCH(CH₃)C(=O)NH₂-indol-3-yl |
| 4029 | 1-CH₃, 4-OCH(CH₃)C(=O)NHCH₃-indol-3-yl |
| 4030 | 1-CH₃, 4-OCH(CH₃)C(=O)NHNH₂-indol-3-yl |
| 4031 | 1-CH₃, 4-OCH(CH₃)CO₂CH₃-indol-3-yl |
| 4032 | 1-CH₃, 4-OCH(CH₃)CO₂CH₂CH₃-indol-3-yl |
| 4033 | 1-CH₃, 4-OCH(CH₃)C(=O)CH₃-indol-3-yl |
| 4034 | 1-CH₃, 4-OCH(CH₃)C(=O)CH₂CH₃-indol-3-yl |
| 4035 | 1-CH₃, 4-OCH(CH₃)CH₂C(=O)CH₃-indol-3-yl |
| 4036 | 1-CH₃, 4-OCH(CH₃)CH₂OC(CH₃)₄-indol-3-yl |
| 4037 | 1-CH₃, 4-OCH(CH₃)CH₂OCH₂CH₃-indol-3-yl |
| 4038 | 1-CH₃, 4-OCH(CH₃)CH₂O(CH₂)₂CH₃-indol-3-yl |
| 4039 | 1-CH₃, 4-OCH(CH₃)CH₂OCH₂CH=CH₂-indol-3-yl |
| 4040 | 1-CH₃, 4-O(CH₂)₃OCH₃-indol-3-yl |
| 4041 | 1-CH₃, 4-O(CH₂)₃OCH₂CH₃-indol-3-yl |
| 4042 | 1-CH₃, 4-O(CH₂)₃OCH(CH₃)₂-indol-3-yl |
| 4043 | 1-CH₃, 4-O(CH₂)₃OC₆H₅-indol-3-yl |
| 4044 | 1-CH₃, 4-O(CH₂)₃OCH₂C₆H₅-indol-3-yl |
| 4045 | 1-CH₃, 4-OCH(CH₂CH₃)CH₂OCH₃-indol-3-yl |
| 4046 | 1-CH₃, 4-OCH(CH₂CH₃)CH₂CH₂OCH₃-indol-3-yl |
| 4047 | 1-CH₃, 4-OCH(CH₂CH₃)CH₂CH₂OCH₂CH₃-indol-3-yl |
| 4048 | 1-CH₃, 4-O[(CH₂)₃O]₂CH₃-indol-3-yl |
| 4049 | 1-CH₃, 4-OCH₂CH(CH₃)CH₂OCH₃-indol-3-yl |
| 4050 | 1-CH₃, 4-OCH₂CH(CH₃)CH₂OCH₂CH₃-indol-3-yl |
| 4051 | 1-CH₃, 4-OCH(CH₂Cl)CH₂OCH₃-indol-3-yl |
| 4052 | 1-CH₃, 4-OCH(CH₂Cl)CH₂OCH₂CH₃-indol-3-yl |
| 4053 | 1-CH₃, 4-OCH(CH₂Cl)CH₂OCH₂CH₃-indol-3-yl |
| 4054 | 1-CH₃, 4-OCH(CH₂Cl)CH₂OCH₂CH=CH₂-indol-3-yl |
| 4055 | 1-CH₃, 4-OCH[CH₂OCH₃]₂-indol-3-yl |
| 4056 | 1-CH₃, 4-OCH[CH₂OCH₂CH₃]₂-indol-3-yl |
| 4057 | 1-CH₃, 4-OCCl₄-indol-3-yl |
| 4058 | 1-CH₃, 4-OCHF₂-indol-3-yl |
| 4059 | 1-CH₃, 4-OCF₃-indol-3-yl |
| 4060 | 1-CH₃, 4-OCF₂CHF₂-indol-3-yl |
| 4061 | 1-CH₃, 4-OCH₂CF₃-indol-3-yl |
| 4062 | 1-CH₃, 4-OCH₂CHF₂-indol-3-yl |
| 4063 | 1-CH₃, 4-O(CH₂)₃F-indol-3-yl |
| 4064 | 1-CH₃, 4-OCH(CH₃)CF₃-indol-3-yl |
| 4065 | 1-CH₃, 4-O(CH₂)₄F-indol-3-yl |
| 4066 | 1-CH₃, 4-O(CH₂)₃CF₃-indol-3-yl |
| 4067 | 1-CH₃, 4-OCH(CH₃)CF₂CF₃-indol-3-yl |
| 4068 | 1-CH₃, 4-OCH(CH₃)CF₂CHF₂-indol-3-yl |
| 4069 | 1-CH₃, 4-OCH₂CF₂CHFCH₃-indol-3-yl |
| 4070 | 1-CH₃, 4-OCH₂(CF₂)₂CF₃-indol-3-yl |
| 4071 | 1-CH₃, 4-O(CF₂)₃CF₃-indol-3-yl |
| 4072 | 1-CH₃, 4-OCH₂CF₂CHF₂-indol-3-yl |
| 4073 | 1-CH₃, 4-CH₂CH=CH₂-indol-3-yl |
| 4074 | 1-CH₃, 4-CH₂C(CH₃)=CH₂-indol-3-yl |
| 4075 | 1-CH₃, 4-OCH₂CH=CHCH₃-indol-3-yl |
| 4076 | 1-CH₃, 4-O(CH₂)₂CH=CH₂-indol-3-yl |
| 4077 | 1-CH₃, 4-OCH₂C(CH₃)=CH₂-indol-3-yl |
| 4078 | 1-CH₃, 4-OCH(CH₃)CH=CH₂-indol-3-yl |
| 4079 | 1-CH₃, 4-OCH₂C≡CH-indol-3-yl |
| 4080 | 1-CH₃, 4-OCH₂C≡CCH₃-indol-3-yl |
| 4081 | 1-CH₃, 4-O(CH₂)₂C≡CH-indol-3-yl |
| 4082 | 1-CH₃, 4-SCH₃-indol-3-yl |
| 4083 | 1-CH₃, 4-SCH₂CH₃-indol-3-yl |
| 4084 | 1-CH₃, 4-OC₆H₅-indol-3-yl |
| 4085 | 1-CH₃, 4-OCH₂C₆H₅-indol-3-yl |
| 4086 | 1-CH₃, 4-NO₂-indol-3-yl |
| 4087 | 1-CH₃, 4-NHCH₃-indol-3-yl |
| 4088 | 1-CH₃, 4-N(CH₃)₂-indol-3-yl |
| 4089 | 1-CH₃, 4-N(CH₃)C₂H₆-indol-3-yl |
| 4090 | 1-CH₃, 4-NHCH₂CF₃-indol-3-yl |
| 4091 | 1-CH₃, 4-F-indol-3-yl |
| 4092 | 1-CH₃, 4-Cl-indol-3-yl |
| 4093 | 1-CH₃, 4-OH-indol-3-yl |
| 4094 | 1-CH₃, 4-CN-indol-3-yl |
| 4095 | 1-CH₃, 4-C(O)NH₂-indol-3-yl |
| 4096 | 1-CH₃, 4-C(S)NH₂-indol-3-yl |
| 4097 | 1-CH₃, 4-CO₂CH₃-indol-3-yl |
| 4098 | 1-CH₃, 4-ON=C(CH₃)₂-indol-3-yl |
| 4099 | 1-CH₃, 4-[O-cyclopropyl]indol-3-yl |
| 4100 | 1-CH₃, 4-[O-cyclobutyl]indol-3-yl |
| 4101 | 1-CH₃, 4-[O-cyclopentyl]indol-3-yl |
| 4102 | 1-CH₃, 4-[O-cyclohexyl]indol-3-yl |
| 4103 | 1-CH₃, 4-[OCH₂-cyclopropyl]indol-3-yl |
| 4104 | 1-CH₃, 6-F, 4-[OCH₂-cyclopropyl]indol-3-yl |
| 4105 | 1-CH₃, 6-CH₃, 4-[OCH₂-cyclopropyl]indol-3-yl |
| 4106 | 1-CH₃, 6-CF₃, 4-[OCH₂-cyclopropyl]indol-3-yl |
| 4107 | 1-CH₃, 4-[OCH(CH₃)-cyclopropyl]indol-3-yl |
| 4108 | 1-CH₃, 6-F, 4-[OCH(CH₃)-cyclopropyl]indol-3-yl |
| 4109 | 1-CH₃, 6-CH₃, 4-[OCH(CH₃)-cyclopropyl]indol-3-yl |
| 4110 | 1-CH₃, 6-CF₃, 4-[OCH(CH₃)-cyclopropyl]indol-3-yl |
| 4111 | 1-CH₃, 4-[O-(1-CH₃-cyclopropyl)]indol-3-yl |
| 4112 | 1-CH₃, 6-F, 4-[O-(1-CH₃-cyclopropyl)]indol-3-yl |
| 4113 | 1-CH₃, 6-CH₃, 4-[O-(1-CH₃-cyclopropyl)]indol-3-yl |

TABLE A-continued

| No. | R⁴ |
|---|---|
| 4114 | 1-CH₃, 6-CF₃, 4-[O-(1-CH₃-cyclopropyl)]indol-3-yl |
| 4115 | 1-CH₃, 4-[OCH₂-(1-CH₃-cyclopropyl)]indol-3-yl |
| 4116 | 1-CH₃, 6-F, 4-[OCH₂-(1-CH₃-cyclopropyl)]indol-3-yl |
| 4117 | 1-CH₃, 6-CH₃, 4-[OCH₂-(1-CH₃-cyclopropyl)]indol-3-yl |
| 4118 | 1-CH₃, 6-CF₃, 4-[OCH₂-(1-CH₃-cyclopropyl)]indol-3-yl |
| 4119 | 1-CH₃, 4-[OCH₂-(2-CH₃-cyclopropyl)]indol-3-yl |
| 4120 | 1-CH₃, 6-F, 4-[OCH₂-(2-CH₃-cyclopropyl)]indol-3-yl |
| 4121 | 1-CH₃, 6-CH₃, 4-[OCH₂-(2-CH₃-cyclopropyl)]indol-3-yl |
| 4122 | 1-CH₃, 6-CF₃, 4-[OCH₂-(2-CH₃-cyclopropyl)]indol-3-yl |
| 4123 | 1-CH₃, 4-[OCH₂-(tetrahydropyran-2-yl)]indol-3-yl |
| 4124 | 1-CH₃, 6-F, 4-[OCH₂-(tetrahydropyran-2-yl)]indol-3-yl |
| 4125 | 1-CH₃, 6-CH₃, 4-[OCH₂-(tetrahydropyran-2-yl)]indol-3-yl |
| 4126 | 1-CH₃, 6-CF₃, 4-[OCH₂-(tetrahydropyran-2-yl)]indol-3-yl |
| 4127 | 1-CH₃, 4-[OCH₂-(furan-2-yl)]indol-3-yl |
| 4128 | 1-CH₃, 6-F, 4-[OCH₂-(furan-2-yl)]indol-3-yl |
| 4129 | 1-CH₃, 6-CH₃, 4-[OCH₂-(furan-2-yl)]indol-3-yl |
| 4130 | 1-CH₃, 6-CF₃, 4-[OCH₂-(furan-2-yl)]indol-3-yl |
| 4131 | 1-CH₃, 4-[OCH₂-(furan-4-yl)]indol-3-yl |
| 4132 | 1-CH₃, 6-F, 4-[OCH₂-(furan-4-yl)]indol-3-yl |
| 4133 | 1-CH₃, 6-CH₃, 4-[OCH₂-(furan-4-yl)]indol-3-yl |
| 4134 | 1-CH₃, 6-CF₃, 4-[OCH₂-(furan-4-yl)]indol-3-yl |
| 4135 | 1-CH₃, 4-[OCH₂-(tetrahydrofuran-4-yl)]indol-3-yl |
| 4136 | 1-CH₃, 6-F, 4-[OCH₂-(tetrahydrofuran-4-yl)]indol-3-yl |
| 4137 | 1-CH₃, 6-CH₃, 4-[OCH₂-(tetrahydrofuran-4-yl)]indol-3-yl |
| 4138 | 1-CH₃, 6-CF₃, 4-[OCH₂-(tetrahydrofuran-4-yl)]indol-3-yl |
| 4139 | 1-CH₃, 4-[OCH₂-(tetrahydrofuran-2-yl)]indol-3-yl |
| 4140 | 1-CH₃, 6-F, 4-[OCH₂-(tetrahydrofuran-2-yl)]indol-3-yl |
| 4141 | 1-CH₃, 6-CH₃, 4-[OCH₂-(tetrahydrofuran-2-yl)]indol-3-yl |
| 4142 | 1-CH₃, 6-CF₃, 4-[OCH₂-(tetrahydrofuran-2-yl)]indol-3-yl |
| 4143 | 1-CH₃, 4-[O-(tetrahydropyran-4-yl)]indol-3-yl |
| 4144 | 1-CH₃, 6-F, 4-[O-(tetrahydropyran-4-yl)]indol-3-yl |
| 4145 | 1-CH₃, 6-CH₃, 4-[O-(tetrahydropyran-4-yl)]indol-3-yl |
| 4146 | 1-CH₃, 6-CF₃, 4-[O-(tetrahydropyran-4-yl)]indol-3-yl |
| 4147 | 1-CH₃, 4-[2-Cl—C₅H₄]indol-3-yl |
| 4148 | 1-CH₃, 6-F, 4-[2-Cl—C₅H₄]indol-3-yl |
| 4149 | 1-CH₃, 6-CH₃, 4-[2-Cl—C₅H₄]indol-3-yl |
| 4150 | 1-CH₃, 6-CF₃, 4-[2-Cl—C₅H₄]indol-3-yl |
| 4151 | 1-CH₃, 4-[OCH₂-(pyridin-2-yl)]indol-3-yl |
| 4152 | 1-CH₃, 6-F, 4-[OCH₂-(pyridin-2-yl)]indol-3-yl |
| 4153 | 1-CH₃, 6-CH₃, 4-[OCH₂-(pyridin-2-yl)]indol-3-yl |
| 4154 | 1-CH₃, 6-CF₃, 4-[OCH₂-(pyridin-2-yl)]indol-3-yl |
| 4155 | 1-CH₃, 4-[OCH₂-(pyridin-4-yl)]indol-3-yl |
| 4156 | 1-CH₃, 6-F, 4-[OCH₂-(pyridin-4-yl)]indol-3-yl |
| 4157 | 1-CH₃, 6-CH₃, 4-[OCH₂-(pyridin-4-yl)]indol-3-yl |
| 4158 | 1-CH₃, 6-CF₃, 4-[OCH₂-(pyridin-4-yl)]indol-3-yl |
| 4159 | 1-CH₃, 4-[morpholin-4-yl]indol-3-yl |
| 4160 | 1-CH₃, 4-[1-CH₃-imidazol-2-yl]indol-3-yl |
| 4161 | 1-CH₃, 6-F, 4-[1-CH₃-imidazol-2-yl]indol-3-yl |
| 4162 | 1-CH₃, 6-CH₃, 4-[1-CH₃-imidazol-2-yl]indol-3-yl |
| 4163 | 1-CH₃, 6-CF₃, 4-[1-CH₃-imidazol-2-yl]indol-3-yl |
| 4164 | 1-CH₃, 4-[1,2,4-triazol-1-yl]indol-3-yl |
| 4165 | 1-CH₃, 6-F, 4-[1,2,4-triazol-1-yl]indol-3-yl |
| 4166 | 1-CH₃, 6-CH₃, 4-[1,2,4-triazol-1-yl]indol-3-yl |
| 4167 | 1-CH₃, 6-CF₃, 4-[1,2,4-triazol-1-yl]indol-3-yl |
| 4168 | 1-CH₃, 4,6-Cl₂-indol-3-yl |
| 4169 | 1-CH₃, 4,6-(CH₃)₂-indol-3-yl |
| 4170 | 1-CH₃, 4,6-(OCH₃)₂-indol-3-yl |
| 4171 | 1-CH₃, 4,6-(OCH₂CH₃)₂-indol-3-yl |
| 4172 | 1-CH₃, 4-F, 6-CH₃-indol-3-yl |
| 4173 | 1-CH₃, 4-F, 6-OCH₃-indol-3-yl |
| 4174 | 1-CH₃, 4-F, 6-OCH₂CH₃-indol-3-yl |
| 4175 | 1-CH₃, 4-F, 6-OCH₂CF₃-indol-3-yl |
| 4176 | 1-CH₃, 4-F, 6-OCH(CH₃)₂-indol-3-yl |
| 4177 | 1-CH₃, 4-Cl, 6-CH₃-indol-3-yl |
| 4178 | 1-CH₃, 4-Cl, 6-OCH₃-indol-3-yl |
| 4179 | 1-CH₃, 4-Cl, 6-OCH₂CH₃-indol-3-yl |
| 4180 | 1-CH₃, 4-Cl, 6-OCH₂CF₃-indol-3-yl |
| 4181 | 1-CH₃, 4-Cl, 6-OCH(CH₃)₂-indol-3-yl |
| 4182 | 1-CH₃, 4-CH₃, 6-OCH₃-indol-3-yl |
| 4183 | 1-CH₃, 4-CH₃, 6-OCH₂CH₃-indol-3-yl |
| 4184 | 1-CH₃, 4-CH₃, 6-OCH₂CF₃-indol-3-yl |
| 4185 | 1-CH₃, 4-CH₃, 6-OCH(CH₃)₂-indol-3-yl |
| 4186 | 1-CH₃, 4-CH₃, 6-OCH₂CH=CH₂-indol-3-yl |
| 4187 | 1-CH₃, 4-CH₃, 6-CO₂CH₃-indol-3-yl |
| 4188 | 1-CH₃, 4-CH₃, 6-CF₃-indol-3-yl |
| 4189 | 1-CH₃, 4-CH₃, 6-CH₂CH₃-indol-3-yl |
| 4190 | 1-CH₃, 4-CF₃, 6-OCH₃-indol-3-yl |
| 4191 | 1-CH₃, 4-CF₃, 6-OCH₂CH₃-indol-3-yl |
| 4192 | 1-CH₃, 4-CF₃, 6-OCH₂CF₃-indol-3-yl |
| 4193 | 1-CH₃, 4-OCH₃, 6-OCH₂CH₃-indol-3-yl |
| 4194 | 1-CH₃, 4-OCH₃, 6-OCH₂CF₃-indol-3-yl |
| 4195 | 1-CH₃, 4-OCH₃, 6-OCH(CH₃)-indol-3-yl |
| 4196 | 1-CH₃, 4-OCH₂CH₃, 6-CH₂OCH₂CH₃-indol-3-yl |
| 4197 | 1-CH₃, 4-NO₂, 6-CH₃-indol-3-yl |
| 4198 | 1-CH₃, 4-NO₂, 6-OCH₃-indol-3-yl |
| 4199 | 1-CH₃, 4-NO₂, 6-OCH₂CH₃-indol-3-yl |
| 4200 | 1-CH₃, 4-NO₂, 6-OCH(CH₃)₂-indol-3-yl |
| 4201 | 1-CH₃, 4-NO₂, 6-OCH₂CF₃-indol-3-yl |
| 4202 | 1-CH₃, 4-CN, 6-CH₃-indol-3-yl |
| 4203 | 1-CH₃, 4-CN, 6-OCH₃-indol-3-yl |
| 4204 | 1-CH₃, 4-CN, 6-OCH₂CH₃-indol-3-yl |
| 4205 | 1-CH₃, 4-CN, 6-OCH(CH₃)₂-indol-3-yl |
| 4206 | 1-CH₃, 4-CN, 6-OCH₂CF₃-indol-3-yl |
| 4207 | 4-CH₃-quinolin-2-yl |
| 4208 | 4-CH₂CH₃-quinolin-2-yl |
| 4209 | 4-CH(CH₃)₂-quinolin-2-yl |
| 4210 | 4-CH(CH₃)CH₂CH₃-quinolin-2-yl |
| 4211 | 4-CF₃-quinolin-2-yl |
| 4212 | 4-CH=CH₂-quinolin-2-yl |
| 4213 | 4-CH=CHCH₃-quinolin-2-yl |
| 4214 | 4-CH=CHCl-quinolin-2-yl |
| 4215 | 4-C≡CH-quinolin-2-yl |
| 4216 | 4-CH₂C≡CH-quinolin-2-yl |
| 4217 | 4-CH₂C≡CCH₃-quinolin-2-yl |
| 4218 | 4-cyclopropylquinolin-2-yl |
| 4219 | 4-cyclopentylquinolin-2-yl |
| 4220 | 4-OCH₃-quinolin-2-yl |
| 4221 | 4-OCH₂CH₃-quinolin-2-yl |
| 4222 | 4-OCH₂CH₂CH₃-quinolin-2-yl |
| 4223 | 4-OCH(CH₃)₂-quinolin-2-yl |
| 4224 | 4-OCH₂CH₂CH₂CH₃-quinolin-2-yl |
| 4225 | 4-OCH(CH₃)CH₂CH₃-quinolin-2-yl |
| 4226 | 4-OCH₂CH(CH₃)₂-quinolin-2-yl |
| 4227 | 4-OC(CH₃)₄-quinolin-2-yl |
| 4228 | 4-OCH(CH₃)CH₂CH₂CH₃-quinolin-2-yl |
| 4229 | 4-OCH₂OCH₃-quinolin-2-yl |
| 4230 | 4-OCH₂OCH₂CH₃-quinolin-2-yl |
| 4231 | 4-OCH(CH₃)OCH₃-quinolin-2-yl |
| 4232 | 4-OCH(CH₃)OCH₂CH₃-quinolin-2-yl |
| 4233 | 4-OCH₂CH₂OCH₃-quinolin-2-yl |
| 4234 | 4-OCH₂CH₂OCH₂CH₃-quinolin-2-yl |
| 4235 | 4-OCH₂CH₂OCH(CH₃)₂-quinolin-2-yl |
| 4236 | 4-OCH₂CH₂SCH₃-quinolin-2-yl |
| 4237 | 4-OCH₂CH₂SO₂CH₃-quinolin-2-yl |
| 4238 | 4-OCH₂CH₂SCH(CH₃)₂-quinolin-2-yl |
| 4239 | 4-OCH₂CH₂CN-quinolin-2-yl |
| 4240 | 4-OCH₂CH₂SCH₂CH₂CN-quinolin-2-yl |
| 4241 | 4-OCH₂CH₂OC₆H₅-quinolin-2-yl |
| 4242 | 4-OCH₂CH₂OCH₂C₆H₅-quinolin-2-yl |
| 4243 | 4-OCH₂CH₂N(CH₃)₂-quinolin-2-yl |
| 4244 | 4-OCH₂CH₂CONH₂-quinolin-2-yl |
| 4245 | 4-OCH₂CH₂CO₂CH₂CH₃-quinolin-2-yl |
| 4246 | 4-OCH(CH₃)CH₂OCH₃-quinolin-2-yl |
| 4247 | 4-OCH(CH₃)CH₂CO₂CH₃-quinolin-2-yl |
| 4248 | 4-OCH(CH₃)CH₂CO₂CH₂CH₃-quinolin-2-yl |
| 4249 | 4-OCH(CH₃)CO₂CH₃-quinolin-2-yl |
| 4250 | 4-OCH₂C(=O)CH₃-quinolin-2-yl |
| 4251 | 4-OCH₂C(=O)CH₂CH₃-quinolin-2-yl |
| 4252 | 4-OCH₂CO₂CH₃-quinolin-2-yl |
| 4253 | 4-OCH₂CO₂CH₂CH₃-quinolin-2-yl |
| 4254 | 4-OCH₂C(=O)NH₂-quinolin-2-yl |
| 4255 | 4-OCH₂C(=O)NHCH₃-quinolin-2-yl |
| 4256 | 4-OCH₂C(=O)SCH₃-quinolin-2-yl |
| 4257 | 4-OCH(CH₃)C(=O)NH₂-quinolin-2-yl |
| 4258 | 4-OCH(CH₃)C(=O)NHCH₃-quinolin-2-yl |
| 4259 | 4-OCH(CH₃)C(=O)NHNH₂-quinolin-2-yl |
| 4260 | 4-OCH(CH₃)CO₂CH₃-quinolin-2-yl |
| 4261 | 4-OCH(CH₃)CO₂CH₂CH₃-quinolin-2-yl |
| 4262 | 4-OCH(CH₃)C(=O)CH₃-quinolin-2-yl |
| 4263 | 4-OCH(CH₃)C(=O)CH₂CH₃-quinolin-2-yl |
| 4264 | 4-OCH(CH₃)CH₂C(=O)CH₃-quinolin-2-yl |
| 4265 | 4-OCH(CH₃)CH₂OC(CH₃)₄-quinolin-2-yl |
| 4266 | 4-OCH(CH₃)CH₂OCH₂CH₃-quinolin-2-yl |
| 4267 | 4-OCH(CH₃)CH₂O(CH₃)₂CH₃-quinolin-2-yl |

TABLE A-continued

| No. | R$^4$ |
|---|---|
| 4268 | 4-OCH(CH$_3$)CH$_2$OCH$_2$CH=CH$_2$-quinolin-2-yl |
| 4269 | 4-O(CH$_2$)$_3$OCH$_3$-quinolin-2-yl |
| 4270 | 4-O(CH$_2$)$_3$OCH$_2$CH$_3$-quinolin-2-yl |
| 4271 | 4-O(CH$_2$)$_3$OCH(CH$_3$)$_2$-quinolin-2-yl |
| 4272 | 4-O(CH$_2$)$_3$OC$_6$H$_5$-quinolin-2-yl |
| 4273 | 4-O(CH$_2$)$_3$OCH$_2$C$_6$H$_5$-quinolin-2-yl |
| 4274 | 4-OCH(CH$_2$CH$_3$)CH$_2$OCH$_3$-quinolin-2-yl |
| 4275 | 4-OCH(CH$_2$CH$_3$)CH$_2$CH$_2$OCH$_3$-quinolin-2-yl |
| 4276 | 4-OCH(CH$_2$CH$_3$)CH$_2$CH$_2$OCH$_2$CH$_3$-quinolin-2-yl |
| 4277 | 4-O[(CH$_2$)$_3$O]$_2$CH$_3$-quinolin-2-yl |
| 4278 | 4-OCH$_2$CH(CH$_3$)CH$_2$OCH$_3$-quinolin-2-yl |
| 4279 | 4-OCH$_2$CH(CH$_3$)CH$_2$OCH$_2$CH$_3$-quinolin-2-yl |
| 4280 | 4-OCH(CH$_2$Cl)$_2$-quinolin-2-yl |
| 4281 | 4-OCH(CH$_2$Cl)CH$_2$OCH$_2$CH$_3$-quinolin-2-yl |
| 4282 | 4-OCH(CH$_2$Cl)CH$_2$OCH(CH$_3$)$_2$-quinolin-2-yl |
| 4283 | 4-OCH(CH$_2$Cl)CH$_2$OCH$_2$CH=CH$_2$-quinolin-2-yl |
| 4284 | 4-OCH[CH$_2$Cl]$_2$-quinolin-2-yl |
| 4285 | 4-OCH[CH$_2$OCH$_2$CH$_3$]$_2$-quinolin-2-yl |
| 4286 | 4-OCCl$_4$-quinolin-2-yl |
| 4287 | 4-OCHF$_2$-quinolin-2-yl |
| 4288 | 4-OCF$_3$-quinolin-2-yl |
| 4289 | 4-OCF$_2$CHF$_2$-quinolin-2-yl |
| 4290 | 4-OCH$_2$CF$_3$-quinolin-2-yl |
| 4291 | 4-OCH$_2$CHF$_2$-quinolin-2-yl |
| 4292 | 4-O(CH$_2$)$_3$F-quinolin-2-yl |
| 4293 | 4-OCH(CH$_3$)CF$_3$-quinolin-2-yl |
| 4294 | 4-O(CH$_2$)$_4$F-quinolin-2-yl |
| 4295 | 4-O(CH$_2$)$_3$CF$_3$-quinolin-2-yl |
| 4296 | 4-OCH(CH$_3$)CF$_2$CF$_3$-quinolin-2-yl |
| 4297 | 4-OCH(CH$_3$)CF$_2$CHF$_2$-quinolin-2-yl |
| 4298 | 4-OCH$_2$CF$_2$CHFCH$_3$-quinolin-2-yl |
| 4299 | 4-OCH$_2$(CF$_2$)$_2$CF$_3$-quinolin-2-yl |
| 4300 | 4-O(CF$_2$)$_3$CF$_3$-quinolin-2-yl |
| 4301 | 4-OCH$_2$CF$_2$CHF$_2$-quinolin-2-yl |
| 4302 | 4-CH$_2$CH=CH$_2$-quinolin-2-yl |
| 4303 | 4-CH$_2$C(CH$_3$)=CH$_2$-quinolin-2-yl |
| 4304 | 4-OCH$_2$CH=CHCH$_3$-quinolin-2-yl |
| 4305 | 4-O(CH$_2$)$_2$CH=CH$_2$-quinolin-2-yl |
| 4306 | 4-OCH$_2$C(CH$_3$)=CH$_2$-quinolin-2-yl |
| 4307 | 4-OCH(CH$_3$)CH=CH$_2$-quinolin-2-yl |
| 4308 | 4-OCH$_2$C≡CH-quinolin-2-yl |
| 4309 | 4-OCH$_2$C≡CCH$_3$-quinolin-2-yl |
| 4310 | 4-O(CH$_2$)$_2$C≡CH-quinolin-2-yl |
| 4311 | 4-SCH$_3$-quinolin-2-yl |
| 4312 | 4-SCH$_2$CH$_3$-quinolin-2-yl |
| 4313 | 4-OC$_6$H$_5$-quinolin-2-yl |
| 4314 | 4-OCH$_2$C$_6$H$_5$-quinolin-2-yl |
| 4315 | 4-NO$_2$-quinolin-2-yl |
| 4316 | 4-NHCH$_3$-quinolin-2-yl |
| 4317 | 4-N(CH$_3$)$_2$-quinolin-2-yl |
| 4318 | 4-N(CH$_3$)C$_2$H$_6$-quinolin-2-yl |
| 4319 | 4-NHCH$_2$CF$_3$-quinolin-2-yl |
| 4320 | 4-F-quinolin-2-yl |
| 4321 | 4-Cl-quinolin-2-yl |
| 4322 | 4-OH-quinolin-2-yl |
| 4323 | 4-CN-quinolin-2-yl |
| 4324 | 4-C(O)NH$_2$-quinolin-2-yl |
| 4325 | 4-C(S)NH$_2$-quinolin-2-yl |
| 4326 | 4-CO$_2$CH$_3$-quinolin-2-yl |
| 4327 | 4-ON=C(CH$_3$)$_2$-quinolin-2-yl |
| 4328 | 4-[O-cyclopropyl]quinolin-2-yl |
| 4329 | 4-[O-cyclobutyl]quinolin-2-yl |
| 4330 | 4-[O-cyclopentyl]quinolin-2-yl |
| 4331 | 4-[O-cyclohexyl]quinolin-2-yl |
| 4332 | 4-[OCH$_2$-cyclopropyl]quinolin-2-yl |
| 4333 | 6-F, 4-[OCH$_2$-cyclopropyl]quinolin-2-yl |
| 4334 | 6-CH$_3$, 4-[OCH$_2$-cyclopropyl]quinolin-2-yl |
| 4335 | 6-CF$_3$, 4-[OCH$_2$-cyclopropyl]quinolin-2-yl |
| 4336 | 4-[OCH(CH$_3$)-cyclopropyl]quinolin-2-yl |
| 4337 | 6-F, 4-[OCH(CH$_3$)-cyclopropyl]quinolin-2-yl |
| 4338 | 6-CH$_3$, 4-[OCH(CH$_3$)-cyclopropyl]quinolin-2-yl |
| 4339 | 6-CF$_3$, 4-[OCH(CH$_3$)-cyclopropyl]quinolin-2-yl |
| 4340 | 4-[O-(1-CH$_3$-cyclopropyl)]quinolin-2-yl |
| 4341 | 6-F, 4-[O-(1-CH$_3$-cyclopropyl)]quinolin-2-yl |
| 4342 | 6-CH$_3$, 4-[O-(1-CH$_3$-cyclopropyl)]quinolin-2-yl |
| 4343 | 6-CF$_3$, 4-[O-(1-CH$_3$-cyclopropyl)]quinolin-2-yl |
| 4344 | 4-[OCH$_2$-(1-CH$_3$-cyclopropyl)]quinolin-2-yl |
| 4345 | 6-F, 4-[OCH$_2$-(1-CH$_3$-cyclopropyl)]quinolin-2-yl |
| 4346 | 6-CH$_3$, 4-[OCH$_2$-(1-CH$_3$-cyclopropyl)]quinolin-2-yl |
| 4347 | 6-CF$_3$, 4-[OCH$_2$-(1-CH$_3$-cyclopropyl)]quinolin-2-yl |
| 4348 | 4-[OCH$_2$-(2-CH$_3$-cyclopropyl)]quinolin-2-yl |
| 4349 | 6-F, 4-[OCH$_2$-(2-CH$_3$-cyclopropyl)]quinolin-2-yl |
| 4350 | 6-CH$_3$, 4-[OCH$_2$-(2-CH$_3$-cyclopropyl)]quinolin-2-yl |
| 4351 | 6-CF$_3$, 4-[OCH$_2$-(2-CH$_3$-cyclopropyl)]quinolin-2-yl |
| 4352 | 4-[OCH$_2$-(tetrahydropyran-2-yl)]quinolin-2-yl |
| 4353 | 6-F, 4-[OCH$_2$-(tetrahydropyran-2-yl)]quinolin-2-yl |
| 4354 | 6-CH$_3$, 4-[OCH$_2$-(tetrahydropyran-2-yl)]quinolin-2-yl |
| 4355 | 6-CF$_3$, 4-[OCH$_2$-(tetrahydropyran-2-yl)]quinolin-2-yl |
| 4356 | 4-[OCH$_2$-(furan-2-yl)]quinolin-2-yl |
| 4357 | 6-F, 4-[OCH$_2$-(furan-2-yl)]quinolin-2-yl |
| 4358 | 6-CH$_3$, 4-[OCH$_2$-(furan-2-yl)]quinolin-2-yl |
| 4359 | 6-CF$_3$, 4-[OCH$_2$-(furan-2-yl)]quinolin-2-yl |
| 4360 | 4-[OCH$_2$-(furan-4-yl)]quinolin-2-yl |
| 4361 | 6-F, 4-[OCH$_2$-(furan-4-yl)]quinolin-2-yl |
| 4362 | 6-CH$_3$, 4-[OCH$_2$-(furan-4-yl)]quinolin-2-yl |
| 4363 | 6-CF$_3$, 4-[OCH$_2$-(furan-4-yl)]quinolin-2-yl |
| 4364 | 4-[OCH$_2$-(tetrahydrofuran-4-yl)]quinolin-2-yl |
| 4365 | 6-F, 4-[OCH$_2$-(tetrahydrofuran-4-yl)]quinolin-2-yl |
| 4366 | 6-CH$_3$, 4-[OCH$_2$-(tetrahydrofuran-4-yl)]quinolin-2-yl |
| 4367 | 6-CF$_3$, 4-[OCH$_2$-(tetrahydrofuran-4-yl)]quinolin-2-yl |
| 4368 | 4-[OCH$_2$-(tetrahydrofuran-2-yl)]quinolin-2-yl |
| 4369 | 6-F, 4-[OCH$_2$-(tetrahydrofuran-2-yl)]quinolin-2-yl |
| 4370 | 6-CH$_3$, 4-[OCH$_2$-(tetrahydrofuran-2-yl)]quinolin-2-yl |
| 4371 | 6-CF$_3$, 4-[OCH$_2$-(tetrahydrofuran-2-yl)]quinolin-2-yl |
| 4372 | 4-[O-(tetrahydropyran-4-yl)]quinolin-2-yl |
| 4373 | 6-F, 4-[O-(tetrahydropyran-4-yl)]quinolin-2-yl |
| 4374 | 6-CH$_3$, 4-[O-(tetrahydropyran-4-yl)]quinolin-2-yl |
| 4375 | 6-CF$_3$, 4-[O-(tetrahydropyran-4-yl)]quinolin-2-yl |
| 4376 | 4-[2-Cl—C$_5$H$_4$]quinolin-2-yl |
| 4377 | 6-F, 4-[2-Cl—C$_5$H$_4$]quinolin-2-yl |
| 4378 | 6-CH$_3$, 4-[2-Cl—C$_5$H$_4$]quinolin-2-yl |
| 4379 | 6-CF$_3$, 4-[2-Cl—C$_5$H$_4$]quinolin-2-yl |
| 4380 | 4-[OCH$_2$-(pyridin-2-yl)]quinolin-2-yl |
| 4381 | 6-F, 4-[OCH$_2$-(pyridin-2-yl)]quinolin-2-yl |
| 4382 | 6-CH$_3$, 4-[OCH$_2$-(pyridin-2-yl)]quinolin-2-yl |
| 4383 | 6-CF$_3$, 4-[OCH$_2$-(pyridin-2-yl)]quinolin-2-yl |
| 4384 | 4-[OCH$_2$-(pyridin-4-yl)]quinolin-2-yl |
| 4385 | 6-F, 4-[OCH$_2$-(pyridin-4-yl)]quinolin-2-yl |
| 4386 | 6-CH$_3$, 4-[OCH$_2$-(pyridin-4-yl)]quinolin-2-yl |
| 4387 | 6-CF$_3$, 4-[OCH$_2$-(pyridin-4-yl)]quinolin-2-yl |
| 4388 | 4-[morpholin-4-yl]quinolin-2-yl |
| 4389 | 4-[1-CH$_3$-imidazol-2-yl]quinolin-2-yl |
| 4390 | 6-F, 4-[1-CH$_3$-imidazol-2-yl]quinolin-2-yl |
| 4391 | 6-CH$_3$, 4-[1-CH$_3$-imidazol-2-yl]quinolin-2-yl |
| 4392 | 6-CF$_3$, 4-[1-CH$_3$-imidazol-2-yl]quinolin-2-yl |
| 4393 | 4-[1,2,4-triazol-1-yl]quinolin-2-yl |
| 4394 | 6-F, 4-[1,2,4-triazol-1-yl]quinolin-2-yl |
| 4395 | 6-CH$_3$, 4-[1,2,4-triazol-1-yl]quinolin-2-yl |
| 4396 | 6-CF$_3$, 4-[1,2,4-triazol-1-yl]quinolin-2-yl |
| 4397 | 4,6-Cl$_2$-quinolin-2-yl |
| 4398 | 4,6-(CH$_3$)$_2$-quinolin-2-yl |
| 4399 | 4,6-(OCH$_3$)$_2$-quinolin-2-yl |
| 4400 | 4,6-(OCH$_2$CH$_3$)$_2$-quinolin-2-yl |
| 4401 | 4-F, 6-CH$_3$-quinolin-2-yl |
| 4402 | 4-F, 6-OCH$_3$-quinolin-2-yl |
| 4403 | 4-F, 6-OCH$_2$CH$_3$-quinolin-2-yl |
| 4404 | 4-F, 6-OCH$_2$CF$_3$-quinolin-2-yl |
| 4405 | 4-F, 6-OCH(CH$_3$)$_2$-quinolin-2-yl |
| 4406 | 4-Cl, 6-CH$_3$-quinolin-2-yl |
| 4407 | 4-Cl, 6-OCH$_3$-quinolin-2-yl |
| 4408 | 4-Cl, 6-OCH$_2$CH$_3$-quinolin-2-yl |
| 4409 | 4-Cl, 6-OCH$_2$CF$_3$-quinolin-2-yl |
| 4410 | 4-Cl, 6-OCH(CH$_3$)$_2$-quinolin-2-yl |
| 4411 | 4-CH$_3$, 6-OCH$_3$-quinolin-2-yl |
| 4412 | 4-CH$_3$, 6-OCH$_2$CH$_3$-quinolin-2-yl |
| 4413 | 4-CH$_3$, 6-OCH$_2$CF$_3$-quinolin-2-yl |
| 4414 | 4-CH$_3$, 6-OCH(CH$_3$)$_2$-quinolin-2-yl |
| 4415 | 4-CH$_3$, 6-OCH$_2$CH=CH$_2$-quinolin-2-yl |
| 4416 | 4-CH$_3$, 6-CO$_2$CH$_3$-quinolin-2-yl |
| 4417 | 4-CH$_3$, 6-CF$_3$-quinolin-2-yl |
| 4418 | 4-CF$_3$, 6-CH$_2$CH$_3$-quinolin-2-yl |
| 4419 | 4-CF$_3$, 6-OCH$_3$-quinolin-2-yl |
| 4420 | 4-CF$_3$, 6-OCH$_2$CH$_3$-quinolin-2-yl |
| 4421 | 4-CF$_3$, 6-OCH$_2$CF$_3$-quinolin-2-yl |

TABLE A-continued

| No. | R⁴ |
|---|---|
| 4422 | 4-OCH₃, 6-OCH₂CH₃-quinolin-2-yl |
| 4423 | 4-OCH₃, 6-OCH₂CF₃-quinolin-2-yl |
| 4424 | 4-OCH₃, 6-OCH(CH₃)₂-quinolin-2-yl |
| 4425 | 4-OCH₂CH₃, 6-CH₂OCH₂CH₃-quinolin-2-yl |
| 4426 | 4-NO₂, 6-CH₃-quinolin-2-yl |
| 4427 | 4-NO₂, 6-OCH₃-quinolin-2-yl |
| 4428 | 4-NO₂, 6-OCH₂CH₃-quinolin-2-yl |
| 4429 | 4-NO₂, 6-OCH(CH₃)₂-quinolin-2-yl |
| 4430 | 4-NO₂, 6-OCH₂CF₃-quinolin-2-yl |
| 4431 | 4-CN, 6-CH₃-quinolin-2-yl |
| 4432 | 4-CN, 6-OCH₃-quinolin-2-yl |
| 4433 | 4-CN, 6-OCH₂CH₃-quinolin-2-yl |
| 4434 | 4-CN, 6-OCH(CH₃)₂-quinolin-2-yl |
| 4435 | 4-CN, 6-OCH₂CF₃-quinolin-2-yl |
| 4436 | 4-CH₃-isoquinolin-3-yl |
| 4437 | 4-CH₂CH₃-isoquinolin-3-yl |
| 4438 | 4-CH(CH₃)₂-isoquinolin-3-yl |
| 4439 | 4-CH(CH₃)CH₂CH₃-isoquinolin-3-yl |
| 4440 | 4-CF₃-isoquinolin-3-yl |
| 4441 | 4-CH=CH₂-isoquinolin-3-yl |
| 4442 | 4-CH=CHCH₃-isoquinolin-3-yl |
| 4443 | 4-CH=CHCl-isoquinolin-3-yl |
| 4444 | 4-C≡CH-isoquinolin-3-yl |
| 4445 | 4-CH₂C≡CH-isoquinolin-3-yl |
| 4446 | 4-CH₂C≡CCH₃-isoquinolin-3-yl |
| 4447 | 4-cyclopropylisoquinolin-3-yl |
| 4448 | 4-cyclopentylisoquinolin-3-yl |
| 4449 | 4-OCH₃-isoquinolin-3-yl |
| 4450 | 4-OCH₂CH₃-isoquinolin-3-yl |
| 4451 | 4-OCH₂CH₃-isoquinolin-3-yl |
| 4452 | 4-OCH(CH₃)₂-isoquinolin-3-yl |
| 4453 | 4-OCH₂CH₂CH₃-isoquinolin-3-yl |
| 4454 | 4-OCH(CH₃)CH₂CH₃-isoquinolin-3-yl |
| 4455 | 4-OCH₂CH(CH₃)₂-isoquinolin-3-yl |
| 4456 | 4-OC(CH₃)₄-isoquinolin-3-yl |
| 4457 | 4-OCH(CH₃)CH₂CH₂CH₃-isoquinolin-3-yl |
| 4458 | 4-OCH₂OCH₃-isoquinolin-3-yl |
| 4459 | 4-OCH₂OCH₂CH₃-isoquinolin-3-yl |
| 4460 | 4-OCH(CH₃)OCH₃-isoquinolin-3-yl |
| 4461 | 4-OCH(CH₃)OCH₂CH₃-isoquinolin-3-yl |
| 4462 | 4-OCH₂CH₂OCH₃-isoquinolin-3-yl |
| 4463 | 4-OCH₂CH₂OCH₂CH₃-isoquinolin-3-yl |
| 4464 | 4-OCH₂CH₂OCH(CH₃)₂-isoquinolin-3-yl |
| 4465 | 4-OCH₂CH₂SCH₃-isoquinolin-3-yl |
| 4466 | 4-OCH₂CH₂SO₂CH₃-isoquinolin-3-yl |
| 4467 | 4-OCH₂CH₂SCH(CH₃)₂-isoquinolin-3-yl |
| 4468 | 4-OCH₂CH₂CN-isoquinolin-3-yl |
| 4469 | 4-OCH₂CH₂SCH₂CN-isoquinolin-3-yl |
| 4470 | 4-OCH₂CH₂OC₆H₅-isoquinolin-3-yl |
| 4471 | 4-OCH₂CH₂OCH₂C₆H₅-isoquinolin-3-yl |
| 4472 | 4-OCH₂CH₂N(CH₃)₂-isoquinolin-3-yl |
| 4473 | 4-OCH₂CH₂CONH₂-isoquinolin-3-yl |
| 4474 | 4-OCH₂CH₂CO₂CH₂CH₂CH₃-isoquinolin-3-yl |
| 4475 | 4-OCH(CH₃)CH₂OCH₃-isoquinolin-3-yl |
| 4476 | 4-OCH(CH₃)CO₂CH₃-isoquinolin-3-yl |
| 4477 | 4-OCH(CH₃)CO₂CH₂CH₃-isoquinolin-3-yl |
| 4478 | 4-OCH₂CH(CH₃)CO₂CH₃-isoquinolin-3-yl |
| 4479 | 4-OCH₂C(=O)CH₃-isoquinolin-3-yl |
| 4480 | 4-OCH₂C(=O)CH₂CH₃-isoquinolin-3-yl |
| 4481 | 4-OCH₂CO₂CH₃-isoquinolin-3-yl |
| 4482 | 4-OCH₂CO₂CH₂CH₃-isoquinolin-3-yl |
| 4483 | 4-OCH₂C(=O)NH₂-isoquinolin-3-yl |
| 4484 | 4-OCH₂C(=O)NHCH₃-isoquinolin-3-yl |
| 4485 | 4-OCH₂C(=O)SCH₃-isoquinolin-3-yl |
| 4486 | 4-OCH(CH₃)C(=O)NH₂-isoquinolin-3-yl |
| 4487 | 4-OCH(CH₃)C(=O)NHCH₃-isoquinolin-3-yl |
| 4488 | 4-OCH(CH₃)C(=O)NHNH₂-isoquinolin-3-yl |
| 4489 | 4-OCH(CH₃)CO₂CH₃-isoquinolin-3-yl |
| 4490 | 4-OCH(CH₃)CO₂CH₂CH₃-isoquinolin-3-yl |
| 4491 | 4-OCH(CH₃)C(=O)CH₃-isoquinolin-3-yl |
| 4492 | 4-OCH(CH₃)C(=O)CH₂CH₃-isoquinolin-3-yl |
| 4493 | 4-OCH(CH₃)CH₂C(=O)CH₃-isoquinolin-3-yl |
| 4494 | 4-OCH(CH₃)CH₂OC(CH₃)₄-isoquinolin-3-yl |
| 4495 | 4-OCH(CH₃)CH₂OCH₂CH₃-isoquinolin-3-yl |
| 4496 | 4-OCH(CH₃)CH₂O(CH₃)₂CH₃-isoquinolin-3-yl |
| 4497 | 4-OCH(CH₃)CH₂OCH₂CH=CH₂-isoquinolin-3-yl |
| 4498 | 4-OCH₂)₃OCH₃-isoquinolin-3-yl |
| 4499 | 4-O(CH₂)₃OCH₂CH₃-isoquinolin-3-yl |
| 4500 | 4-O(CH₂)₃OCH(CH₃)₂-isoquinolin-3-yl |
| 4501 | 4-O(CH₂)₃OC₆H₅-isoquinolin-3-yl |
| 4502 | 4-O(CH₂)₃OCH₂C₆H₅-isoquinolin-3-yl |
| 4503 | 4-OCH(CH₂CH₃)CH₂OCH₃-isoquinolin-3-yl |
| 4504 | 4-OCH(CH₂CH₃)CH₂CH₂OCH₃-isoquinolin-3-yl |
| 4505 | 4-OCH(CH₂CH₃)CH₂CH₂OCH₂CH₃-isoquinolin-3-yl |
| 4506 | 4-O[(CH₂)₃O]₂CH₃-isoquinolin-3-yl |
| 4507 | 4-OCH₂CH(CH₃)CH₂OCH₃-isoquinolin-3-yl |
| 4508 | 4-OCH₂CH(CH₃)CH₂OCH₂CH₃-isoquinolin-3-yl |
| 4509 | 4-OCH(CH₂Cl)CH₂OCH₃-isoquinolin-3-yl |
| 4510 | 4-OCH(CH₂Cl)CH₂OCH₂CH₃-isoquinolin-3-yl |
| 4511 | 4-OCH(CH₂Cl)CH₂OCH(CH₃)₂-isoquinolin-3-yl |
| 4512 | 4-OCH(CH₂Cl)CH₂OCH₂CH=CH₂-isoquinolin-3-yl |
| 4513 | 4-OCH[CH₂OCH₃]₂-isoquinolin-3-yl |
| 4514 | 4-OCH[CH₂OCH₂CH₃]₂-isoquinolin-3-yl |
| 4515 | 4-OCCl₄-isoquinolin-3-yl |
| 4516 | 4-OCHF₂-isoquinolin-3-yl |
| 4517 | 4-OCF₃-isoquinolin-3-yl |
| 4518 | 4-OCF₂CHF₂-isoquinolin-3-yl |
| 4519 | 4-OCH₂CF₃-isoquinolin-3-yl |
| 4520 | 4-OCH₂CHF₂-isoquinolin-3-yl |
| 4521 | 4-O(CH₂)₃F-isoquinolin-3-yl |
| 4522 | 4-OCH(CH₃)CF₃-isoquinolin-3-yl |
| 4523 | 4-O(CH₂)₄F-isoquinolin-3-yl |
| 4524 | 4-O(CH₂)₃CF₃-isoquinolin-3-yl |
| 4525 | 4-OCH(CH₃)CF₂CF₃-isoquinolin-3-yl |
| 4526 | 4-OCH(CH₃)CF₂CHF₂-isoquinolin-3-yl |
| 4527 | 4-OCH₂CF₂CHFCH₃-isoquinolin-3-yl |
| 4528 | 4-OCH₂(CF₂)₂CF₃-isoquinolin-3-yl |
| 4529 | 4-O(CF₂)₃CF₃-isoquinolin-3-yl |
| 4530 | 4-OCH₂CF₂CHF₂-isoquinolin-3-yl |
| 4531 | 4-CH₂CH=CH₂-isoquinolin-3-yl |
| 4532 | 4-CH₂C(CH₃)=CH₂-isoquinolin-3-yl |
| 4533 | 4-OCH₂CH=CHCH₃-isoquinolin-3-yl |
| 4534 | 4-O(CH₂)₂CH=CH₂-isoquinolin-3-yl |
| 4535 | 4-OCH₂C(CH₃)=CH₂-isoquinolin-3-yl |
| 4536 | 4-OCH(CH₃)CH=CH₂-isoquinolin-3-yl |
| 4537 | 4-OCH₂C≡CH-isoquinolin-3-yl |
| 4538 | 4-OCH₂C≡CCH₃-isoquinolin-3-yl |
| 4539 | 4-O(CH₂)₂C≡CH-isoquinolin-3-yl |
| 4540 | 4-SCH₃-isoquinolin-3-yl |
| 4541 | 4-SCH₂CH₃-isoquinolin-3-yl |
| 4542 | 4-OC₆H₅-isoquinolin-3-yl |
| 4543 | 4-OCH₂C₆H₅-isoquinolin-3-yl |
| 4544 | 4-NO₂-isoquinolin-3-yl |
| 4545 | 4-NHCH₃-isoquinolin-3-yl |
| 4546 | 4-N(CH₃)₂-isoquinolin-3-yl |
| 4547 | 4-N(CH₃)C₂H₆-isoquinolin-3-yl |
| 4548 | 4-NHCH₂CF₃-isoquinolin-3-yl |
| 4549 | 4-F-isoquinolin-3-yl |
| 4550 | 4-Cl-isoquinolin-3-yl |
| 4551 | 4-OH-isoquinolin-3-yl |
| 4552 | 4-CN-isoquinolin-3-yl |
| 4553 | 4-C(O)NH₂-isoquinolin-3-yl |
| 4554 | 4-C(S)NH₂-isoquinolin-3-yl |
| 4555 | 4-CO₂CH₃-isoquinolin-3-yl |
| 4556 | 4-ON=C(CH₃)₂-isoquinolin-3-yl |
| 4557 | 4-[O-cyclopropyl]isoquinolin-3-yl |
| 4558 | 4-[O-cyclobutyl]isoquinolin-3-yl |
| 4559 | 4-[O-cyclopentyl]isoquinolin-3-yl |
| 4560 | 4-[O-cyclohexyl]isoquinolin-3-yl |
| 4561 | 4-[OCH₂-cyclopropyl]isoquinolin-3-yl |
| 4562 | 6-F, 4-[OCH₂-cyclopropyl]isoquinolin-3-yl |
| 4563 | 6-CH₃, 4-[OCH₂-cyclopropyl]isoquinolin-3-yl |
| 4564 | 6-CF₃, 4-[OCH₂-cyclopropyl]isoquinolin-3-yl |
| 4565 | 4-[OCH(CH₃)-cyclopropyl]isoquinolin-3-yl |
| 4566 | 6-F, 4-[OCH(CH₃)-cyclopropyl]isoquinolin-3-yl |
| 4567 | 6-CH₃, 4-[OCH(CH₃)-cyclopropyl]isoquinolin-3-yl |
| 4568 | 6-CF₃, 4-[OCH(CH₃)-cyclopropyl]isoquinolin-3-yl |
| 4569 | 4-[O-(1-CH₃-cyclopropyl)]isoquinolin-3-yl |
| 4570 | 6-F, 4-[O-(1-CH₃-cyclopropyl)]isoquinolin-3-yl |
| 4571 | 6-CH₃, 4-[O-(1-CH₃-cyclopropyl)]isoquinolin-3-yl |
| 4572 | 6-CF₃, 4-[O-(1-CH₃-cyclopropyl)]isoquinolin-3-yl |
| 4573 | 4-[OCH₂-(1-CH₃-cyclopropyl)]isoquinolin-3-yl |
| 4574 | 6-F, 4-[OCH₂-(1-CH₃-cyclopropyl)]isoquinolin-3-yl |
| 4575 | 6-CH₃, 4-[OCH₂-(1-CH₃-cyclopropyl)]isoquinolin-3-yl |

TABLE A-continued

| No. | R⁴ |
|---|---|
| 4576 | 6-CF₃, 4-[OCH₂-(1-CH₃-cyclopropyl)]isoquinolin-3-yl |
| 4577 | 4-[OCH₂-(2-CH₃-cyclopropyl)]isoquinolin-3-yl |
| 4578 | 6-F, 4-[OCH₂-(2-CH₃-cyclopropyl)]isoquinolin-3-yl |
| 4579 | 6-CH₃, 4-[OCH₂-(2-CH₃-cyclopropyl)]isoquinolin-3-yl |
| 4580 | 6-CF₃, 4-[OCH₂-(2-CH₃-cyclopropyl)]isoquinolin-3-yl |
| 4581 | 4-[OCH₂-(tetrahydropyran-2-yl)]isoquinolin-3-yl |
| 4582 | 6-F, 4-[OCH₂-(tetrahydropyran-2-yl)]isoquinolin-3-yl |
| 4583 | 6-CH₃, 4-[OCH₂-(tetrahydropyran-2-yl)]isoquinolin-3-yl |
| 4584 | 6-CF₃, 4-[OCH₂-(tetrahydropyran-2-yl)]isoquinolin-3-yl |
| 4585 | 4-[OCH₂-(furan-2-yl)]isoquinolin-3-yl |
| 4586 | 6-F, 4-[OCH₂-(furan-2-yl)]isoquinolin-3-yl |
| 4587 | 6-CH₃, 4-[OCH₂-(furan-2-yl)]isoquinolin-3-yl |
| 4588 | 6-CF₃, 4-[OCH₂-(furan-2-yl)]isoquinolin-3-yl |
| 4589 | 4-[OCH₂-(furan-4-yl)]isoquinolin-3-yl |
| 4590 | 6-F, 4-[OCH₂-(furan-4-yl)]isoquinolin-3-yl |
| 4591 | 6-CH₃, 4-[OCH₂-(furan-4-yl)]isoquinolin-3-yl |
| 4592 | 6-CF₃, 4-[OCH₂-(furan-4-yl)]isoquinolin-3-yl |
| 4593 | 4-[OCH₂-(tetrahydrofuran-4-yl)]isoquinolin-3-yl |
| 4594 | 6-F, 4-[OCH₂-(tetrahydrofuran-4-yl)]isoquinolin-3-yl |
| 4595 | 6-CH₃, 4-[OCH₂-(tetrahydrofuran-4-yl)]isoquinolin-3-yl |
| 4596 | 6-CF₃, 4-[OCH₂-(tetrahydrofuran-4-yl)]isoquinolin-3-yl |
| 4597 | 4-[OCH₂-(tetrahydrofuran-2-yl)]isoquinolin-3-yl |
| 4598 | 6-F, 4-[OCH₂-(tetrahydrofuran-2-yl)]isoquinolin-3-yl |
| 4599 | 6-CH₃, 4-[OCH₂-(tetrahydrofuran-2-yl)]isoquinolin-3-yl |
| 4600 | 6-CF₃, 4-[OCH₂-(tetrahydrofuran-2-yl)]isoquinolin-3-yl |
| 4601 | 4-[O-(tetrahydropyran-4-yl)]isoquinolin-3-yl |
| 4602 | 6-F, 4-[O-(tetrahydropyran-4-yl)]isoquinolin-3-yl |
| 4603 | 6-CH₃, 4-[O-(tetrahydropyran-4-yl)]isoquinolin-3-yl |
| 4604 | 6-CF₃, 4-[O-(tetrahydropyran-4-yl)]isoquinolin-3-yl |
| 4605 | 4-[2-Cl—C₅H₄]isoquinolin-3-yl |
| 4606 | 6-F, 4-[2-Cl—C₅H₄]isoquinolin-3-yl |
| 4607 | 6-CH₃, 4-[2-Cl—C₅H₄]isoquinolin-3-yl |
| 4608 | 6-CF₃, 4-[2-Cl—C₅H₄]isoquinolin-3-yl |
| 4609 | 4-[OCH₂-(pyridin-2-yl)]isoquinolin-3-yl |
| 4610 | 6-F, 4-[OCH₂-(pyridin-2-yl)]isoquinolin-3-yl |
| 4611 | 6-CH₃, 4-[OCH₂-(pyridin-2-yl)]isoquinolin-3-yl |
| 4612 | 6-CF₃, 4-[OCH₂-(pyridin-2-yl)]isoquinolin-3-yl |
| 4613 | 4-[OCH₂-(pyridin-4-yl)]isoquinolin-3-yl |
| 4614 | 6-F, 4-[OCH₂-(pyridin-4-yl)]isoquinolin-3-yl |
| 4615 | 6-CH₃, 4-[OCH₂-(pyridin-4-yl)]isoquinolin-3-yl |
| 4616 | 6-CF₃, 4-[OCH₂-(pyridin-4-yl)]isoquinolin-3-yl |
| 4617 | 4-[morpholin-4-yl]isoquinolin-3-yl |
| 4618 | 4-[1-CH₃-imidazol-2-yl]isoquinolin-3-yl |
| 4619 | 6-F, 4-[1-CH₃-imidazol-2-yl]isoquinolin-3-yl |
| 4620 | 6-CH₃, 4-[1-CH₃-imidazol-2-yl]isoquinolin-3-yl |
| 4621 | 6-CF₃, 4-[1-CH₃-imidazol-2-yl]isoquinolin-3-yl |
| 4622 | 4-[1,2,4-triazol-1-yl]isoquinolin-3-yl |
| 4623 | 6-F, 4-[1,2,4-triazol-1-yl]isoquinolin-3-yl |
| 4624 | 6-CH₃, 4-[1,2,4-triazol-1-yl]isoquinolin-3-yl |
| 4625 | 6-CF₃, 4-[1,2,4-triazol-1-yl]isoquinolin-3-yl |
| 4626 | 4,6-Cl₂-isoquinolin-3-yl |
| 4627 | 4,6-(CH₃)₂-isoquinolin-3-yl |
| 4628 | 4,6-(OCH₃)₂-isoquinolin-3-yl |
| 4629 | 4,6-(OCH₂CH₃)₂-isoquinolin-3-yl |
| 4630 | 4-F, 6-CH₃-isoquinolin-3-yl |
| 4631 | 4-F, 6-OCH₃-isoquinolin-3-yl |
| 4632 | 4-F, 6-OCH₂CH₃-isoquinolin-3-yl |
| 4633 | 4-F, 6-OCH₂CF₃-isoquinolin-3-yl |
| 4634 | 4-F, 6-OCH(CH₃)₂-isoquinolin-3-yl |
| 4635 | 4-Cl, 6-CH₃-isoquinolin-3-yl |
| 4636 | 4-Cl, 6-OCH₃-isoquinolin-3-yl |
| 4637 | 4-Cl, 6-OCH₂CH₃-isoquinolin-3-yl |
| 4638 | 4-Cl, 6-OCH₂CF₃-isoquinolin-3-yl |
| 4639 | 4-Cl, 6-OCH(CH₃)₂-isoquinolin-3-yl |
| 4640 | 4-CH₃, 6-OCH₃-isoquinolin-3-yl |
| 4641 | 4-CH₃, 6-OCH₂CH₃-isoquinolin-3-yl |
| 4642 | 4-CH₃, 6-OCH₂CF₃-isoquinolin-3-yl |
| 4643 | 4-CH₃, 6-OCH(CH₃)₂-isoquinolin-3-yl |
| 4644 | 4-CH₃, 6-OCH₂CH=CH₂-isoquinolin-3-yl |
| 4645 | 4-CH₃, 6-CO₂CH₃-isoquinolin-3-yl |
| 4646 | 4-CH₃, 6-CF₃-isoquinolin-3-yl |
| 4647 | 4-CF₃, 6-CH₂CH₃-isoquinolin-3-yl |
| 4648 | 4-CF₃, 6-OCH₃-isoquinolin-3-yl |
| 4649 | 4-CF₃, 6-OCH₂CH₃-isoquinolin-3-yl |
| 4650 | 4-CF₃, 6-OCH₂CF₃-isoquinolin-3-yl |
| 4651 | 4-OCH₃, 6-OCH₂CH₃-isoquinolin-3-yl |
| 4652 | 4-OCH₃, 6-OCH₂CF₃-isoquinolin-3-yl |
| 4653 | 4-OCH₃, 6-OCH(CH₃)-isoquinolin-3-yl |
| 4654 | 4-OCH₂CH₃, 6-CH₂OCH₂CH₃-isoquinolin-3-yl |
| 4655 | 4-NO₂, 6-CH₃-isoquinolin-3-yl |
| 4656 | 4-NO₂, 6-OCH₃-isoquinolin-3-yl |
| 4657 | 4-NO₂, 6-OCH₂CH₃-isoquinolin-3-yl |
| 4658 | 4-NO₂, 6-OCH(CH₃)₂-isoquinolin-3-yl |
| 4659 | 4-NO₂, 6-OCH₂CF₃-isoquinolin-3-yl |
| 4660 | 4-CN, 6-CH₃-isoquinolin-3-yl |
| 4661 | 4-CN, 6-OCH₃-isoquinolin-3-yl |
| 4662 | 4-CN, 6-OCH₂CH₃-isoquinolin-3-yl |
| 4663 | 4-CN, 6-OCH(CH₃)₂-isoquinolin-3-yl |
| 4664 | 4-CN, 6-OCH₂CF₃-isoquinolin-3-yl |
| 4665 | 7-CH₃, 2-CH₃-purin-8-yl |
| 4666 | 7-CH₃, 2-CH₂CH₃-purin-8-yl |
| 4667 | 7-CH₃, 2-CH(CH₃)₂-purin-8-yl |
| 4668 | 7-CH₃, 2-CH(CH₃)CH₂CH₃-purin-8-yl |
| 4669 | 7-CH₃, 2-CF₃-purin-8-yl |
| 4670 | 7-CH₃, 2-CH₂=CH₂-purin-8-yl |
| 4671 | 7-CH₃, 2-CH=CHCH₃-purin-8-yl |
| 4672 | 7-CH₃, 2-CH=CHCl-purin-8-yl |
| 4673 | 7-CH₃, 2-C≡CH-purin-8-yl |
| 4674 | 7-CH₃, 2-CH₂C≡CH-purin-8-yl |
| 4675 | 7-CH₃, 2-CH₂C≡CCH₃-purin-8-yl |
| 4676 | 7-CH₃, 2-cyclopropylpurin-8-yl |
| 4677 | 7-CH₃, 2-cyclopentylpurin-8-yl |
| 4678 | 7-CH₃, 2-OCH₃-purin-8-yl |
| 4679 | 7-CH₃, 2-OCH₂CH₃-purin-8-yl |
| 4680 | 7-CH₃, 2-OCH₂CH₂CH₃-purin-8-yl |
| 4681 | 7-CH₃, 2-OCH(CH₃)₂-purin-8-yl |
| 4682 | 7-CH₃, 2-OCH₂CH₂CH₃-purin-8-yl |
| 4683 | 7-CH₃, 2-OCH(CH₃)CH₂CH₃-purin-8-yl |
| 4684 | 7-CH₃, 2-OCH₂CH(CH₃)₂-purin-8-yl |
| 4685 | 7-CH₃, 2-OC(CH₃)₂-purin-8-yl |
| 4686 | 7-CH₃, 2-OCH₂CH₂CH₂CH₃-purin-8-yl |
| 4687 | 7-CH₃, 2-OCH₂OCH₃-purin-8-yl |
| 4688 | 7-CH₃, 2-OCH₂OCH₂CH₃-purin-8-yl |
| 4689 | 7-CH₃, 2-OCH(CH₃)OCH₃-purin-8-yl |
| 4690 | 7-CH₃, 2-OCH(CH₃)OCH₂CH₃-purin-8-yl |
| 4691 | 7-CH₃, 2-OCH₂CH₂OCH₃-purin-8-yl |
| 4692 | 7-CH₃, 2-OCH₂CH₂OCH₂CH₃-purin-8-yl |
| 4693 | 7-CH₃, 2-OCH₂CH₂OCH(CH₃)₂-purin-8-yl |
| 4694 | 7-CH₃, 2-OCH₂CH₂SCH₃-purin-8-yl |
| 4695 | 7-CH₃, 2-OCH₂CH₂SO₂CH₃-purin-8-yl |
| 4696 | 7-CH₃, 2-OCH₂CH₂SCH(CH₃)₂-purin-8-yl |
| 4697 | 7-CH₃, 2-OCH₂CH₂CN-purin-8-yl |
| 4698 | 7-CH₃, 2-OCH₂CH₂SCH₂CH₂CN-purin-8-yl |
| 4699 | 7-CH₃, 2-OCH₂CH₂OC₆H₅-purin-8-yl |
| 4700 | 7-CH₃, 2-OCH₂CH₂OCH₂C₆H₅-purin-8-yl |
| 4701 | 7-CH₃, 2-OCH₂CH₂N(CH₃)₂-purin-8-yl |
| 4702 | 7-CH₃, 2-OCH₂CH₂CONH₂-purin-8-yl |
| 4703 | 7-CH₃, 2-OCH₂CH₂CO₂CH₂CH₂CH₂CH₃-purin-8-yl |
| 4704 | 7-CH₃, 2-OCH(CH₃)CH₂OCH₃-purin-8-yl |
| 4705 | 7-CH₃, 2-OCH(CH₃)CH₂CO₂CH₃-purin-8-yl |
| 4706 | 7-CH₃, 2-OCH(CH₃)CH₂CO₂CH₂CH₃-purin-8-yl |
| 4707 | 7-CH₃, 2-OCH(CH₃)CH₂CO₂CH₂CH₃-purin-8-yl |
| 4708 | 7-CH₃, 2-OCH₂C(=O)CH₃-purin-8-yl |
| 4709 | 7-CH₃, 2-OCH₂C(=O)CH₂CH₃-purin-8-yl |
| 4710 | 7-CH₃, 2-OCH₂CO₂CH₃-purin-8-yl |
| 4711 | 7-CH₃, 2-OCH₂CO₂CH₂CH₃-purin-8-yl |
| 4712 | 7-CH₃, 2-OCH₂C(=O)NH₂-purin-8-yl |
| 4713 | 7-CH₃, 2-OCH₂C(=O)NHCH₃-purin-8-yl |
| 4714 | 7-CH₃, 2-OCH₂C(=O)SCH₃-purin-8-yl |
| 4715 | 7-CH₃, 2-OCH(CH₃)C(=O)NH₂-purin-8-yl |
| 4716 | 7-CH₃, 2-OCH(CH₃)C(=O)NHCH₃-purin-8-yl |
| 4717 | 7-CH₃, 2-OCH(CH₃)C(=O)NHNH₂-purin-8-yl |
| 4718 | 7-CH₃, 2-OCH(CH₃)CO₂CH₃-purin-8-yl |
| 4719 | 7-CH₃, 2-OCH(CH₃)CO₂CF₃-purin-8-yl |
| 4720 | 7-CH₃, 2-OCH(CH₃)C(=O)CH₃-purin-8-yl |
| 4721 | 7-CH₃, 2-OCH(CH₃)C(=O)CH₂CH₃-purin-8-yl |
| 4722 | 7-CH₃, 2-OCH(CH₃)CH₂C(=O)CH₃-purin-8-yl |
| 4723 | 7-CH₃, 2-OCH(CH₃)CH₂OC(CH₃)₂-purin-8-yl |
| 4724 | 7-CH₃, 2-OCH(CH₃)CH₂OCH₂CH₃-purin-8-yl |
| 4725 | 7-CH₃, 2-OCH(CH₃)CH₂O(CH₃)₂CH₃-purin-8-yl |
| 4726 | 7-CH₃, 2-OCH(CH₃)CH₂OCH₂CH=CH₂-purin-8-yl |
| 4727 | 7-CH₃, 2-O(CH₂)₃OCH₃-purin-8-yl |
| 4728 | 7-CH₃, 2-O(CH₂)₃OCH₂CH₃-purin-8-yl |
| 4729 | 7-CH₃, 2-O(CH₂)₃OCH(CH₃)₂-purin-8-yl |

TABLE A-continued

| No. | R⁴ |
|---|---|
| 4730 | 7-CH₃, 2-O(CH₂)₃OC₆H₅-purin-8-yl |
| 4731 | 7-CH₃, 2-O(CH₂)₃OCH₂C₆H₅-purin-8-yl |
| 4732 | 7-CH₃, 2-OCH(CH₂CH₃)CH₂OCH₃-purin-8-yl |
| 4733 | 7-CH₃, 2-OCH(CH₂CH₃)CH₂CH₂OCH₃-purin-8-yl |
| 4734 | 7-CH₃, 2-OCH(CH₂CH₃)CH₂CH₂OCH₂CH₃-purin-8-yl |
| 4735 | 7-CH₃, 2-O[(CH₂)₃O]₂CH₃-purin-8-yl |
| 4736 | 7-CH₃, 2-OCH₂CH(CH₃)CH₂OCH₃-purin-8-yl |
| 4737 | 7-CH₃, 2-OCH₂CH(CH₃)CH₂OCH₂CH₃-purin-8-yl |
| 4738 | 7-CH₃, 2-OCH(CH₂Cl)CH₂OCH₃-purin-8-yl |
| 4739 | 7-CH₃, 2-OCH(CH₂Cl)CH₂OCH₂CH₃-purin-8-yl |
| 4740 | 7-CH₃, 2-OCH(CH₂Cl)CH₂OCH(CH₃)₂-purin-8-yl |
| 4741 | 7-CH₃, 2-OCH(CH₂Cl)CH₂OCH₂CH=CH₂-purin-8-yl |
| 4742 | 7-CH₃, 2-OCH[CH₂OCH₃]₂-purin-8-yl |
| 4743 | 7-CH₃, 2-OCH[CH₂OCH₂CH₃]₂-purin-8-yl |
| 4744 | 7-CH₃, 2-OCCl₂-purin-8-yl |
| 4745 | 7-CH₃, 2-OCHF₂-purin-8-yl |
| 4746 | 7-CH₃, 2-OCF₃-purin-8-yl |
| 4747 | 7-CH₃, 2-OCF₂CHF₂-purin-8-yl |
| 4748 | 7-CH₃, 2-OCH₂CF₃-purin-8-yl |
| 4749 | 7-CH₃, 2-OCH₂CHF₂-purin-8-yl |
| 4750 | 7-CH₃, 2-O(CH₂)₃F-purin-8-yl |
| 4751 | 7-CH₃, 2-OCH(CH₃)CF₃-purin-8-yl |
| 4752 | 7-CH₃, 2-O(CH₂)₄F-purin-8-yl |
| 4753 | 7-CH₃, 2-O(CH₂)₃CF₃-purin-8-yl |
| 4754 | 7-CH₃, 2-OCH(CH₃)CF₂CF₃-purin-8-yl |
| 4755 | 7-CH₃, 2-OCH(CH₃)CF₂CHF₂-purin-8-yl |
| 4756 | 7-CH₃, 2-OCH₂CF₂CHFCH₂-purin-8-yl |
| 4757 | 7-CH₃, 2-OCH₂(CF₂)₂CF₃-purin-8-yl |
| 4758 | 7-CH₃, 2-O(CF₂)₂CF₃-purin-8-yl |
| 4759 | 7-CH₃, 2-OCF₂CHF₂-purin-8-yl |
| 4760 | 7-CH₃, 2-CH₂CH=CH₂-purin-8-yl |
| 4761 | 7-CH₃, 2-CH₂C(CH₃)=CH₂-purin-8-yl |
| 4762 | 7-CH₃, 2-OCH₂CH=CHCH₃-purin-8-yl |
| 4763 | 7-CH₃, 2-O(CH₂)₂CH=CH₂-purin-8-yl |
| 4764 | 7-CH₃, 2-OCH₂C(CH₃)=CH₂-purin-8-yl |
| 4765 | 7-CH₃, 2-OCH(CH₃)CH=CH₂-purin-8-yl |
| 4766 | 7-CH₃, 2-OCH₂C≡CH-purin-8-yl |
| 4767 | 7-CH₃, 2-OCH₂C≡CCH₃-purin-8-yl |
| 4768 | 7-CH₃, 2-O(CH₂)₂C≡CH-purin-8-yl |
| 4769 | 7-CH₃, 2-SCH₃-purin-8-yl |
| 4770 | 7-CH₃, 2-SCH₂CH₃-purin-8-yl |
| 4771 | 7-CH₃, 2-OC₆H₅-purin-8-yl |
| 4772 | 7-CH₃, 2-OCH₂C₆H₅-purin-8-yl |
| 4773 | 7-CH₃, 2-NO₂-purin-8-yl |
| 4774 | 7-CH₃, 2-NHCH₃-purin-8-yl |
| 4775 | 7-CH₃, 2-N(CH₃)₂-purin-8-yl |
| 4776 | 7-CH₃, 2-N(CH₃)C₂H₆-purin-8-yl |
| 4777 | 7-CH₃, 2-NHCH₂CF₃-purin-8-yl |
| 4778 | 7-CH₃, 2-F-purin-8-yl |
| 4779 | 7-CH₃, 2-Cl-purin-8-yl |
| 4780 | 7-CH₃, 2-OH-purin-8-yl |
| 4781 | 7-CH₃, 2-CN-purin-8-yl |
| 4782 | 7-CH₃, 2-C(O)NH₂-purin-8-yl |
| 4783 | 7-CH₃, 2-C(S)NH₂-purin-8-yl |
| 4784 | 7-CH₃, 2-CO₂CH₃-purin-8-yl |
| 4785 | 7-CH₃, 2-ON=C(CH₃)₂-purin-8-yl |
| 4786 | 7-CH₃, 2-[O-cyclopropyl]purin-8-yl |
| 4787 | 7-CH₃, 2-[O-cyclobutyl]purin-8-yl |
| 4788 | 7-CH₃, 2-[O-cyclopentyl]purin-8-yl |
| 4789 | 7-CH₃, 2-[O-cyclohexyl]purin-8-yl |
| 4790 | 7-CH₃, 2-[OCH₂-cyclopropyl]purin-8-yl |
| 4791 | 7-CH₃, 6-F, 2-[OCH₂-cyclopropyl]purin-8-yl |
| 4792 | 7-CH₃, 6-CH₃, 2-[OCH₂-cyclopropyl]purin-8-yl |
| 4793 | 7-CH₃, 6-CF₃, 2-[OCH₂-cyclopropyl]purin-8-yl |
| 4794 | 7-CH₃, 2-[OCH(CH₃)-cyclopropyl]purin-8-yl |
| 4795 | 7-CH₃, 6-F, 2-[OCH(CH₃)-cyclopropyl]purin-8-yl |
| 4796 | 7-CH₃, 6-CH₃, 2-[OCH(CH₃)-cyclopropyl]purin-8-yl |
| 4797 | 7-CH₃, 6-CF₃, 2-[OCH(CH₃)-cyclopropyl]purin-8-yl |
| 4798 | 7-CH₃, 2-[O-(7-CH₃-cyclopropyl)]purin-8-yl |
| 4799 | 7-CH₃, 6-F, 2-[O-(7-CH₃-cyclopropyl)]purin-8-yl |
| 4800 | 7-CH₃, 6-CH₃, 2-[O-(7-CH₃-cyclopropyl)]purin-8-yl |
| 4801 | 7-CH₃, 6-CF₃, 2-[O-(7-CH₃-cyclopropyl)]purin-8-yl |
| 4802 | 7-CH₃, 2-[OCH₂-(7-CH₃-cyclopropyl)]purin-8-yl |
| 4803 | 7-CH₃, 6-F, 2-[OCH₂-(7-CH₃-cyclopropyl)]purin-8-yl |
| 4804 | 7-CH₃, 6-CH₃, 2-[OCH₂-(7-CH₃-cyclopropyl)]purin-8-yl |
| 4805 | 7-CH₃, 6-CF₃, 2-[OCH₂-(7-CH₃-cyclopropyl)]purin-8-yl |
| 4806 | 7-CH₃, 2-[OCH₂-(2-CH₃-cyclopropyl)]purin-8-yl |
| 4807 | 7-CH₃, 6-F, 2-[OCH₂-(2-CH₃-cyclopropyl)]purin-8-yl |
| 4808 | 7-CH₃, 6-CH₃, 2-[OCH₂-(2-CH₃-cyclopropyl)]purin-8-yl |
| 4809 | 7-CH₃, 6-CF₃, 2-[OCH₂-(2-CH₃-cyclopropyl)]purin-8-yl |
| 4810 | 7-CH₃, 2-[OCH₂-(tetrahydropyran-2-yl)]purin-8-yl |
| 4811 | 7-CH₃, 6-F, 2-[OCH₂-(tetrahydropyran-2-yl)]purin-8-yl |
| 4812 | 7-CH₃, 6-CH₃, 2-[OCH₂-(tetrahydropyran-2-yl)]purin-8-yl |
| 4813 | 7-CH₃, 6-CF₃, 2-[OCH₂-(tetrahydropyran-2-yl)]purin-8-yl |
| 4814 | 7-CH₃, 2-[OCH₂-(furan-2-yl)]purin-8-yl |
| 4815 | 7-CH₃, 6-F, 2-[OCH₂-(furan-2-yl)]purin-8-yl |
| 4816 | 7-CH₃, 6-CH₃, 2-[OCH₂-(furan-2-yl)]purin-8-yl |
| 4817 | 7-CH₃, 6-CF₃, 2-[OCH₂-(furan-2-yl)]purin-8-yl |
| 4818 | 7-CH₃, 2-[OCH₂-(furan-2-yl)]purin-8-yl |
| 4819 | 7-CH₃, 6-F, 2-[OCH₂-(furan-2-yl)]purin-8-yl |
| 4820 | 7-CH₃, 6-CH₃, 2-[OCH₂-(furan-2-yl)]purin-8-yl |
| 4821 | 7-CH₃, 6-CF₃, 2-[OCH₂-(furan-2-yl)]purin-8-yl |
| 4822 | 7-CH₃, 2-[OCH₂-(tetrahydrofuran-2-yl)]purin-8-yl |
| 4823 | 7-CH₃, 6-F, 2-[OCH₂-(tetrahydrofuran-2-yl)]purin-8-yl |
| 4824 | 7-CH₃, 6-CH₃, 2-[OCH₂-(tetrahydrofuran-2-yl)]purin-8-yl |
| 4825 | 7-CH₃, 6-CF₃, 2-[OCH₂-(tetrahydrofuran-2-yl)]purin-8-yl |
| 4826 | 7-CH₃, 2-[OCH₂-(tetrahydrofuran-2-yl)]purin-8-yl |
| 4827 | 7-CH₃, 6-F, 2-[OCH₂-(tetrahydrofuran-2-yl)]purin-8-yl |
| 4828 | 7-CH₃, 6-CH₃, 2-[OCH₂-(tetrahydrofuran-2-yl)]purin-8-yl |
| 4829 | 7-CH₃, 6-CF₃, 2-[OCH₂-(tetrahydrofuran-2-yl)]purin-8-yl |
| 4830 | 7-CH₃, 2-[O-(tetrahydropyran-2-yl)]purin-8-yl |
| 4831 | 7-CH₃, 6-F, 2-[O-(tetrahydropyran-2-yl)]purin-8-yl |
| 4832 | 7-CH₃, 6-CH₃, 2-[O-(tetrahydropyran-2-yl)]purin-8-yl |
| 4833 | 7-CH₃, 6-CF₃, 2-[O-(tetrahydropyran-2-yl)]purin-8-yl |
| 4834 | 7-CH₃, 2-[2-Cl—C₅H₄]purin-8-yl |
| 4835 | 7-CH₃, 6-F, 2-[2-Cl—C₅H₄]purin-8-yl |
| 4836 | 7-CH₃, 6-CH₃, 2-[2-Cl—C₅H₄]purin-8-yl |
| 4837 | 7-CH₃, 6-CF₃, 2-[2-Cl—C₅H₄]purin-8-yl |
| 4838 | 7-CH₃, 2-[OCH₂-(pyridin-2-yl)]purin-8-yl |
| 4839 | 7-CH₃, 6-F, 2-[OCH₂-(pyridin-2-yl)]purin-8-yl |
| 4840 | 7-CH₃, 6-CH₃, 2-[OCH₂-(pyridin-2-yl)]purin-8-yl |
| 4841 | 7-CH₃, 6-CF₃, 2-[OCH₂-(pyridin-2-yl)]purin-8-yl |
| 4842 | 7-CH₃, 2-[OCH₂-(pyridin-2-yl)]purin-8-yl |
| 4843 | 7-CH₃, 6-F, 2-[OCH₂-(pyridin-2-yl)]purin-8-yl |
| 4844 | 7-CH₃, 6-CH₃, 2-[OCH₂-(pyridin-2-yl)]purin-8-yl |
| 4845 | 7-CH₃, 6-CF₃, 2-[OCH₂-(pyridin-2-yl)]purin-8-yl |
| 4846 | 7-CH₃, 2-[morpholin-2-yl]purin-8-yl |
| 4847 | 7-CH₃, 2-[7-CH₃-imidazol-2-yl]purin-8-yl |
| 4848 | 7-CH₃, 6-F, 2-[7-CH₃-imidazol-2-yl]purin-8-yl |
| 4849 | 7-CH₃, 6-CH₃, 2-[7-CH₃-imidazol-2-yl]purin-8-yl |
| 4850 | 7-CH₃, 6-CF₃, 2-[7-CH₃-imidazol-2-yl]purin-8-yl |
| 4851 | 7-CH₃, 2-[1,2,2-triazol-1-yl]purin-8-yl |
| 4852 | 7-CH₃, 6-F, 2-[1,2,2-triazol-1-yl]purin-8-yl |
| 4853 | 7-CH₃, 6-CH₃, 2-[1,2,2-triazol-1-yl]purin-8-yl |
| 4854 | 7-CH₃, 6-CF₃, 2-[1,2,2-triazol-1-yl]purin-8-yl |
| 4855 | 7-CH₃, 4,6-Cl₂-purin-8-yl |
| 4856 | 7-CH₃, 4,6-(CH₃)₂-purin-8-yl |
| 4857 | 7-CH₃, 4,6-(OCH₃)₂-purin-8-yl |
| 4858 | 7-CH₃, 4,6-(OCH₂CH₃)₂-purin-8-yl |
| 4859 | 7-CH₃, 2-F, 6-CH₃-purin-8-yl |
| 4860 | 7-CH₃, 2-F, 6-OCH₃-purin-8-yl |
| 4861 | 7-CH₃, 2-F, 6-OCH₂CH₃-purin-8-yl |
| 4862 | 7-CH₃, 2-F, 6-OCH₂CF₃-purin-8-yl |
| 4863 | 7-CH₃, 2-F, 6-OCH(CH₃)₂-purin-8-yl |
| 4864 | 7-CH₃, 2-Cl, 6-CH₃-purin-8-yl |
| 4865 | 7-CH₃, 2-Cl, 6-OCH₃-purin-8-yl |
| 4866 | 7-CH₃, 2-Cl, 6-OCH₂CH₃-purin-8-yl |
| 4867 | 7-CH₃, 2-Cl, 6-OCH₂CF₃-purin-8-yl |
| 4868 | 7-CH₃, 2-Cl, 6-OCH(CH₃)₂-purin-8-yl |
| 4869 | 7-CH₃, 2-CH₃, 6-CH₃-purin-8-yl |
| 4870 | 7-CH₃, 2-CH₃, 6-OCH₃-purin-8-yl |
| 4871 | 7-CH₃, 2-CH₃, 6-OCH₂CF₃-purin-8-yl |
| 4872 | 7-CH₃, 2-CH₃, 6-OCH(CH₃)₂-purin-8-yl |
| 4873 | 7-CH₃, 2-CH₃, 6-OCH₂CH=CH₂-purin-8-yl |
| 4874 | 7-CH₃, 2-CH₃, 6-CO₂CH₃-purin-8-yl |
| 4875 | 7-CH₃, 2-CH₃, 6-CF₃-purin-8-yl |
| 4876 | 7-CH₃, 2-CF₃, 6-CH₂CH₃-purin-8-yl |
| 4877 | 7-CH₃, 2-CF₃, 6-OCH₃-purin-8-yl |
| 4878 | 7-CH₃, 2-CF₃, 6-OCH₂CH₃-purin-8-yl |
| 4879 | 7-CH₃, 2-CF₃, 6-OCH₂CF₃-purin-8-yl |
| 4880 | 7-CH₃, 2-OCH₃, 6-OCH₂CH₃-purin-8-yl |
| 4881 | 7-CH₃, 2-OCH₃, 6-OCH₂CF₃-purin-8-yl |
| 4882 | 7-CH₃, 2-OCH₃, 6-OCH(CH₃)₂-purin-8-yl |
| 4883 | 7-CH₃, 2-OCH₂CH₃, 6-CH₂OCH₂CH₃-purin-8-yl |

TABLE A-continued

| No. | R⁴ |
|---|---|
| 4884 | 7-CH₃, 2-NO₂, 6-CH₃-purin-8-yl |
| 4885 | 7-CH₃, 2-NO₂, 6-OCH₃-purin-8-yl |
| 4886 | 7-CH₃, 2-NO₂, 6-OCH₂CH₃-purin-8-yl |
| 4887 | 7-CH₃, 2-NO₂, 6-OCH(CH₃)₂-purin-8-yl |
| 4888 | 7-CH₃, 2-NO₂, 6-OCH₂CF₃-purin-8-yl |
| 4889 | 7-CH₃, 2-CN, 6-CH₃-purin-8-yl |
| 4890 | 7-CH₃, 2-CN, 6-OCH₃-purin-8-yl |
| 4891 | 7-CH₃, 2-CN, 6-OCH₂CH₃-purin-8-yl |
| 4892 | 7-CH₃, 2-CN, 6-OCH(CH₃)₂-purin-8-yl |
| 4893 | 7-CH₃, 2-CN, 6-OCH₂CF₃-purin-8-yl |
| 4894 | pyridin-2-yl |
| 4895 | 3-Cl-pyridin-2-yl |
| 4896 | 4-Cl-pyridin-2-yl |
| 4897 | 5-Cl-pyridin-2-yl |
| 4898 | 6-Cl-pyridin-2-yl |
| 4899 | 3-F-pyridin-2-yl |
| 4900 | 4-F-pyridin-2-yl |
| 4901 | 5-F-pyridin-2-yl |
| 4902 | 6-F-pyridin-2-yl |
| 4903 | 3-Br-pyridin-2-yl |
| 4904 | 4-Br-pyridin-2-yl |
| 4905 | 5-Br-pyridin-2-yl |
| 4906 | 6-Br-pyridin-2-yl |
| 4907 | pyridin-3-yl |
| 4908 | pyridin-4-yl |

The compounds of the formula I according to the invention are suitable for controlling harmful fungi and animal pests of the insects, arachnids and nematodes classes. They can be employed as fungicides and pesticides in crop protection and in the hygiene, stored material protection and veterinary sectors.

The harmful insects include:

from the order of the butterflies (Lepidoptera), for example, *Adoxophyes orana, Agrotis ypsilon, Agrotis segetum, Alabama argillacea, Anticarsia gemmatalis, Argyresthia conjugella, Autographa gamma, Cacoecia murinana, Capua reticulana, Choristoneura fumiferana, Chilo partellus, Choristoneura occidentalis, Cirphis unipuncta, Cnaphalocrocis medinalis, Crocidolomia binotalis, Cydia pomonella, Dendrolimus pini, Diaphania nitidalis, Diatraea grandiosella, Earias insulana, Elasmopalpus lignosellus, Eupoecilia ambiguella, Feltia subterranea, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera scitella, Lithocolletis blancardella, Lobesia botrana, Loxostege sticticalis, Lymantria dispar, Lymantria monacha, Lyonetia clerkella, Manduca sexta, Malacosoma neustria, Mamestra brassicae, Mocis repanda, Operophthera brumata, Orgyia pseudotsugata, Ostrinia nubilalis, Pandemis heparana, Panolis flammea, Pectinophora gossypiella, Phthorimaea operculella, Phyllocnistis citrella, Pieris brassicae, Plathypena scabra, Platynota stultana, Plutella xylostella, Prays citri, Prays oleae, Prodenia sunia, Prodenia ornithogalli, Pseudoplusia includens, Rhyacionia frustrana, Scrobipalpula absoluta, Sesamia inferens, Sparganothis pilleriana, Spodoptera frugiperda, Spodoptera littoralis, Spodoptera litura, Syllepta derogata, Synanthedon myopaeformis, Thaumatopoea pityocampa, Tortrix viridana, Trichoplusia ni, Tryporyza incertulas, Zeiraphera canadensis*, further *Galleria mellonella* and *Sitotroga cerealella, Ephestia cautella, Tineola bisselliella*;

from the order of the beetles (Coleoptera), for example, *Agriotes lineatus, Agriotes obscurus, Anthonomus grandis, Anthonomus pomorum, Apion vorax, Atomaria linearis, Blastophagus piniperda, Cassida nebulosa, Cerotoma trifurcata, Ceuthorhynchus assimilis, Ceuthorhynchus napi, Chaetocnema tibialis, Conoderus vespertinus, Crioceris asparagi, Dendroctonus refipennis, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllopertha horticola*, Phyllophaga sp., *Phyllotreta chrysocephala, Phyllotreta nemorum, Phyllotreta striolata, Popillia japonica, Psylliodes napi, Scolytus intricatus, Sitona lineatus*, further *Bruchus rufimanus, Bruchus pisorum, Bruchus lentis, Sitophilus granaria, Lasioderma serricorne, Oryzaephilus surinamensis, Rhyzopertha dominica, Sitophilus oryzae, Tribolium castaneum, Trogoderma granarium, Zabrotes subfasciatus*;

from the order of the dipterous insects (Diptera), for example, *Anastrepha ludens, Ceratitis capitata, Contarinia sorghicola, Dacus cucurbitae, Dacus oleae, Dasineura brassicae, Delia coarctata, Delia radicum, Hydrellia griseola, Hylemyia platura, Liriomyza sativae, Liriomyza trifolii, Mayetiola destructor, Orseolia oryzae, Oscinella frit, Pegomya hyoscyami, Phorbia antiqua, Phorbia brassicae, Phorbia coarctata, Rhagoletis cerasi, Rhagoletis pomonella, Tipula oleracea, Tipula paludosa,* further *Aedes aegypti, Aedes vexans, Anopheles maculipennis, Chrysomya bezziana, Chrysomya hominivorax, Chrysomya macellaria, Cordylobia anthropophaga, Culex pipiens, Fannia canicularis, Gasterophilus intestinalis, Glossina morsitans, Haematobia irritans, Haplodiplosis equestris, Hypoderma lineata, Lucilia cuprina, Lucilia sericata, Musca domestica, Muscina stabulans, Oestrus ovis, Tabanus bovinus, Simulium damnosum;* from the order of the thrips (Thysanoptera), for example, *Frankliniella fusca, Frankliniella occidentalis, Frankliniella tritici, Haplothrips tritici, Scirtothrips citri, Thrips oryzae, Thrips palmi, Thrips tabaci;* from the order of the hymenopterous insects (Hymenoptera), for example, *Athalia rosae, Atta cephalotes, Atta sexdens, Atta texana, Hoplocampa minuta, Hoplocampa testudinea, Iridomyrmes humilis, Iridomyrmex purpureus, Monomorium pharaonis, Solenopsis geminata, Solenopsis invicta, Solenopsis richteri;* from the order of the bugs (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus hesperus, Lygus lineolaris, Lygus pratensis, Nezara viridula, Piesma quadrata, Solubea insularis, Thyanta perditor;* from the order of the plant-sucking insects (Homoptera), for example, *Acyrthosiphon onobrychis, Acyrthosiphon pisum, Adelges laricis, Aonidiella aurantii, Aphidula nasturtii, Aphis fabae, Aphis gossypii, Aphis pomi,*

Aulacorthum solani, Bemisia tabaci, Brachycaudus cardui, Brevicoryne brassicae, Dalbulus maidis, Dreyfusia nordmannianae, Dreyfusia piceae, Dysaphis radicola, Empoasca fabae, Eriosoma lanigerum, Laodelphax striatella, Macrosiphum avenae, Macrosiphum euphorbiae, Macrosiphon rosae, Megoura viciae, Metopolophium dirhodum, Myzus persicae, Myzus cerasi, Nephotettix cincticeps, Nilaparvata lugens, Perkinsiella saccharicida, Phorodon humuli, Planococcus citri, Psylla mali, Psylla piri, Psylla pyricol, Quadraspidiotus perniciosus, Rhopalosiphum maidis, Saissetia oleae, Schizaphis graminum, Selenaspidus articulatus, Sitobion avenae, Sogatella furcifera, Toxoptera citricida, Trialeurodes abutilonea, Trialeurodes vaporariorum, Viteus vitifolii;

from the order of the termites (Isoptera), for example, Calotermes flavicollis, Leucotermes flavipes, Macrotermes subhyalinus, Odontotermes formosanus, Reticulitermes lucifugus, Termes natalensis;

from the order of the orthopterous insects (Orthoptera), for example, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca peregrina, Stauronotus maroccanus, Schistocerca gregaria, further Acheta domestica, Blatta orientalis, Blattella germanica, Periplaneta americana;

from the order of the Arachnoidea, for example, phytophagous mites such as Aculops lycopersicae, Aculops pelekassi, Aculus schlechtendali, Brevipalpus phoenicis, Bryobia praetiosa, Eotetranychus carpini, Eutetranychus banksii, Eriophyes sheldoni, Oligonychus pratensis, Panonychus ulmi, Panonychus citri, Phyllocoptruta oleivora, Polyphagotarsonemus latus, Tarsonemus pallidus, Tetranychus cinnabarinus, Tetranychus kanzawai, Tetranchus pacificus, Tetranychus urticae, ticks such as Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Rhipicephalus appendiculatus and Rhipicephalus evertsi as well as animal-parasitic mites such as Dermanyssus gallinae, Psoroptes ovis and Sarcoptes scabiei;

from the class of the nematodes, for example, root gall nematodes, eg. Meloidogyne hapla, Meloidogyne incognita, Meloidogyne javanica, cyst-forming nematodes, z.B. Globodera pallida, Globodera rostochiensis, Heterodera avenae, Heterodera glycines, Heterodera schachtii, migratory endoparasites and semi-endoparasitic nematodes, eg. Heliocotylenchus multicinctus, Hirschmanniella oryzae, Hoplolaimus spp., Pratylenchus brachyurus, Pratylenchus fallax, Pratylenchus penetrans, Pratylenchus vulnus, Radopholus similis, Rotylenchus reniformis, Scutellonema bradys, Tylenchulus semipenetrans, stem and leaf nematodes eg. Anguina tritici, Aphelenchoides besseyi, Ditylenchus angustus, Ditylenchus dipsaci, virus vectors, eg. Longidorus spp., Trichodorus christei, Trichodorus viruliferus, Xiphinema index, Xiphinema mediterraneum.

The compounds I can be applied as such, in the form of their formulations or the application forms prepared therefrom, eg. in the form of directly sprayable solutions, powders, suspensions or dispersions, emulsions, oil dispersions, pastes, dust compositions, scattering compositions or granules, by spraying, atomizing, dusting, scattering or watering. The application forms depend entirely on the intended uses; in each case they should if possible guarantee the finest dispersion of the active compounds according to the invention.

The compounds of the formula I are in some cases systemically active as fungicides. They can be employed as foliar and soil fungicides against a broad spectrum of phytopathogenic fungi, in particular from the Ascomycetes, Deuteromycetes, Phycomycetes and Basidiomycetes classes.

They are of particular importance for controlling a multiplicity of fungi on various crop plants such as wheat, rye, barley, oats, rice, corn, grass, cotton, soybeans, coffee, sugar cane, grapes, fruit and decorative plants and vegetable plants such as cucumbers, beans and cucurbits, and on the seeds of these plants.

The compounds I are specifically suitable for controlling the following plant diseases:

Erysiphe gralinis (powdery mildew) in cereals,
Erysiphe cichoracearum and Sphaerotheca fuliginea on cucurbits,
Podosphaera leucotricha on apples,
Uncinula necator on vines,
Puccinia species on cereals,
Rhizoctonia species on cotton and grass,
Ustilago species on cereals and sugar cane,
Venturia inaequalis (scab) on apples,
Helminthosporium species on cereals,
Septoria nodorum on wheat,
Botrytis cinerea (gray mold) on strawberries, vines,
Cercospora arachidicola on groundnuts,
Pseudocercosporella herpotrichoides on wheat, barley,
Pyricularia oryzae on rice,
Phytophthora infestans on potatoes and tomatoes,
Fusarium and Verticillium species on various plants,
Plasmopara viticola on vines,
Alternaria species on vegetables and fruit.

The novel compounds can also be employed in the protection of materials, eg. for the protection of wood, paper and textiles eg. against Paecilomyces variotii.

They can be converted into the customary formulations, such as solutions, emulsions, suspensions, dusts, powders, pastes or granules. The use forms here depend on the particular intended use; in each case they should if possible guarantee the finest dispersion of the active compounds.

The formulations are prepared in a known manner, eg. by extending the active compound with solvents and/or carriers, if desired using emulsifiers and dispersants, where if water is used as a diluent other organic solvents can also be used as auxiliary solvents.

Suitable auxiliaries for this purpose are mainly:

solvents such as aromatics (eg. xylene), chlorinated aromatics (eg. chlorobenzenes), paraffins (eg. petroleum fractions), alcohols (eg. methanol, butanol), ketones (eg. cyclohexanone), amines (eg. ethanolamine, dimethylformamide) and water;

carriers such as ground natural minerals (eg. kaolins, argillaceous earths, talc, chalk) and ground synthetic minerals (eg. highly disperse silica, silicates);

emulsifiers such as nonionic and anionic emulsifiers (eg. polyoxyethylene fatty alcohol ethers, alkylsulfonates and arylsulfonates) and dispersants such as lignin-sulfite waste liquors and methylcellulose.

Suitable surface-active substances are the alkali metal, alkaline earth metal and ammonium salts of aromatic sulfonic acids, eg. lignosulfonic, phenolsulfonic, naphthalenesulfonic and dibutylnaphthalenesulfonic acid, and also of fatty acids, alkyl- and alkylarylsulfonates, alkyl, lauryl ether and fatty alcohol sulfates, as well as salts of sulfated hexa-, hepta- and octadecanols, and also of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenol ether, ethoxylated isooctyl-, octyl- or nonylphenol, alkylphenol or tributylphenylpolyglycol ether, alkylaryl polyether alcohols, isotridecyl alcohol, fatty alcohol ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Aqueous use forms can be prepared from emulsion concentrates, dispersions, pastes, wettable powders or water-dispersible granules by addition of water. To prepare emulsions, pastes or oil dispersions, the substances can be homogenized in water as such or dissolved in an oil or solvent, by means of wetting agents, adhesives, dispersants or emulsifiers. However, concentrates consisting of active substance, wetting agent, adhesive, dispersant or emulsifier and possibly solvent or oil can also be prepared which are suitable for dilution with water.

Powder, scattering and dusting compositions can be prepared by mixing or joint grinding of the active substances with a solid carrier.

Granules, eg. coated, impregnated and homogeneous granules, can be prepared by binding the active compounds to solid carriers.

Solid carriers are mineral earths such as silica gel, silicic acids, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products, such as cereal flour, tree bark meal, wood meal and nutshell meal, cellulose powder or other solid carriers. The active compound concentrations in the ready-to-use preparations can be varied within relatively wide ranges.

Very generally, the compositions contain from 0.0001 to 95% by weight of active compound.

Formulations containing more than 95% by weight of active compound can be applied highly successfully in the ultra-low volume process (ULV), it even being possible to use the active compound without additives.

For use as fungicides, concentrations of from 0.01 to 95% by weight, preferably of from 0.5 to 90% by weight, of active compound are recommended. For use as insecticides, formulations containing from 0.0001 to 10% by weight, preferably from 0.01 to 1% by weight, of active compound are suitable.

The active compounds are normally employed in a purity of from 90% to 100%, preferably from 95% to 100% (according to NMR spectrum).

Examples of such preparations are:

I. a solution of 90 parts by weight of a compound I according to the invention and 10 parts by weight of N-methyl-α-pyrrolidone, which is suitable for application in the form of very small drops;

II. a solution of 20 parts by weight of a compound I according to the invention in a mixture of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid, 5 parts by weight of the addition product of 40 mol of ethylene oxide to 1 mol of castor oil; a dispersion is obtained by finely dispersing the formulation in water.

III. a solution of 20 parts by weight of a compound I according to the invention in a mixture of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil; a dispersion is obtained by finely dispersing the formulation in water.

IV. an aqueous dispersion of 20 parts by weight of a compound I according to the invention in a mixture of 25 parts by weight of cyclohexanone, 65 parts by weight of a petroleum fraction of boiling point from 210 to 280° C. and 10 parts by weight of the addition product of 40 mol of ethylene oxide to 1 mol of castor oil; a dispersion is obtained by finely dispersing the formulation in water.

V. a mixture, ground in a hammer mill, of 20 parts by weight of a compound I according to the invention, 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel; a spray mixture is obtained by finely dispersing the mixture in water;

VI. an intimate mixture of 3 parts by weight of a compound I according to the invention and 97 parts by weight of finely divided kaolin; this dusting composition contains 3% by weight of active compound;

VII. an intimate mixture of 30 parts by weight of a compound I according to the invention, 92 parts by weight of powdered silica gel and 8 parts by weight of liquid paraffin which has been sprayed onto the surface of this silica gel; this preparation gives the active compound a good adherence;

VIII. a stable aqueous dispersion of 40 parts by weight of a compound I according to the invention, 10 parts by weight of the sodium salt of a phenolsulfonic acid/urea/formaldehyde condensate, 2 parts by weight of silica gel and 48 parts by weight of water, which can be further diluted;

IX. a stable oily dispersion of 20 parts by weight of a compound I according to the invention, 2 parts by weight of the calcium salt of dodecylbenzenesulfonic acid, 8 parts by weight of fatty alcohol polyglycol ether, 2 parts by weight of the sodium salt of a phenolsulfonic acid/urea/formaldehyde condensate and 68 parts by weight of a paraffinic mineral oil;

X. a mixture, ground in a hammer mill, of 10 parts by weight of a compound I according to the invention, 4 parts by weight of the sodium salt of diisobutylnaphthalene-α-sulfonic acid, 20 parts by weight of the sodium salt of a lignosulfonic acid from a sulfite waste liquor, 38 parts by weight of silica gel and 38 parts by weight of kaolin. By finely dispersing the mixture in 10,000 parts by weight of water, a spray mixture is obtained which contains 0.1% by weight of the active compound.

The compounds I are applied by treating the fungi or the seed, plants, materials or the soil to be protected from fungal attack with a fungicidally active amount of the active compounds.

They are applied before or after the infection of the materials, plants or seed by the fungi.

Depending on the type of effect desired, the application rates are from 0.02 to 3 kg of active compound per ha, preferably from 0.1 to 1 kg/ha.

In seed treatment, amounts of active compound of from 0.001 to 50 g, preferably from 0.01 to 10 g, per kilogram of seed are in general needed.

The application rate of active compound for controlling pests under outdoor conditions is from 0.02 to 10, preferably from 0.1 to 2.0 kg/ha of active compound.

The compounds I, on their own or in combination with herbicides or fungicides, can also be applied jointly mixed with further crop protection agents, for example with growth regulators or with agents for controlling pests or bacteria. Of interest is also the miscibility with fertilizers or with mineral salt solutions which are employed for eliminating nutritional and trace element deficiencies.

The crop protection agents and fertilizers can be added to the compositions according to the invention in a weight ratio of from 1:10 to 10:1, if appropriate even only immediately before use (tank mix). On mixing with fungicides or insecticides, in many cases an increase in the fungicidal spectrum of action is obtained here.

The following list of fungicides with which the compounds according to the invention can be applied jointly is intended to illustrate the combination possibilities, but not restrict them:

sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediamine bisdithiocarbamate, tetramethylthiuram disulfide, ammonia complex of zinc N,N-ethylenebisdithiocarbamate, ammonia complex of zinc N,N'-propylenebisdithiocarbamate, zinc N,N'-propylenebisdithiocarbamate, N,N'-polypropylene-bis (thiocarbamoyl) disulfide; nitro derivatives, such as dinitro-(1-methylheptyl)phenyl crotonate, 2-sec-butyl-4,6-dinitrophenyl 3,3-dimethylacrylate, 2-sec-butyl-4,6-dinitrophenyl isopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-β-[bis(dimethylamino)phosphinyl]-3-phenyl-1,2,4-triazole, 2,3-dicyano-1,4-dithioanthraquinone, 2-thio-1,3-dithiolo-β-[4,5-b]quinoxaline, methyl 1-(butylcarbamoyl)-2-benzimidazolecarbamate, 2-methoxycarbonylaminobenzimidazole, 2-(fur-2-yl)benzimidazole, 2-(thiazol-4-yl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine-1-oxide, 8-hydroxyquinoline or its copper salt, 2,3-dihydro-5-carboxanilido-6-methyl-1,4-oxathiin, 2,3-dihydro-5-carboxanilido-6-methyl-1,4-oxathiin-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis(1-(2,2,2-trichloroethyl))formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and also various fungicides, such as dodecylguanidine acetate, 3-[3-(3,5-dimethyl-2-oxycyclohexyl)-2-hydroxyethyl]glutarimide, hexachlorobenzene, DL-methyl-N-(2,6-dimethylphenyl)-N-2-furoyl alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-ethylaminocarbonyl-2-methoximino]-acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole.

SYNTHESIS EXAMPLES

The procedures described in the synthesis examples below were used with appropriate modification of the starting compounds to obtain further compounds I. The compounds thus obtained are listed with physical data in the following table.

Example 1

Methyl α-(2-(4'-ethoxypyrimidin-2'-ylmethyliminoxymethyl)phenyl)crotonate

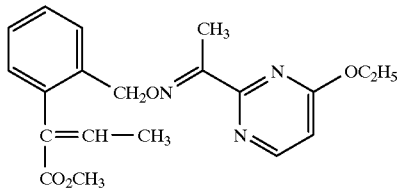

A mixture of 2.0 g (7.4 mmol) of methyl α-(2-bromomethylphenyl)crotonate (DE 41 16 090), 1.35 g (7.4 mmol) of 2-acetyl-4-ethoxypyrimidine oxime (WO 92/18487) and 1.5 g (11 mmol) of $K_2CO_3$ in 10 ml of dimethylformamide is stirred overnight at room temperature. The reaction mixture is then diluted with water and the aqueous phase is extracted three times with methyl t-butyl ether. The combined organic phases are extracted once with water, dried over $MgSO_4$ and concentrated. The residue is purified by column chromatography using cyclohexane/ethyl acetate mixtures. 1.6 g (58%) of the title compound are obtained as a pale yellow oil.

$^1$H-NMR (CDCl$_3$; δ in ppm): 8.5 d, 1H, pyrimidinyl); 7.55 (m, 1H, phenyl); 7.3 (m, 3H, 2×phenyl, =CH—); 7.1 (m, 1H, phenyl); 6.65 (d, 1H, pyrimidinyl); 5.25 (s, broad, OCH$_2$); 4.5 (q, 2H, OCH$_2$); 3.7 (s, 3H, OCH$_3$); 2.3 (s, 3H, CH$_3$); 1.6 (d, 3H, CH$_3$); 1.4 (t, 3H, CH$_3$)

TABLE

| No. | R$^4$ | physical data* |
|---|---|---|
| 01 | pyrimidin-2-yl | 3.7 (s, 3H); 1.65 (d, 3H) |
| 02 | 4-OCH$_2$CH$_3$-pyrimidin-2-yl | 3.7 (s, 3H); 1.6 (d, 3H) |
| 03 | 4-OCH$_2$CF$_3$-pyrimidin-2-yl | 66 |
| 04 | 4-OCH$_3$-pyrimidin-2-yl | 1716, 1574, 1560, 1472, 1435, 1416, 1331, 1295, 1254, 1023 |
| 05 | 4-OCH$_2$CF$_3$, 6-CH$_3$-pyrimidin-2-yl | 7.2 (q, 1H); 1.6 (d, 3H) |
| 06 | pyridin-2-yl | 1.6 (d, 3H) |
| 07 | 6-COCH$_3$-pyridin-2-yl | 1716, 1700, 1365, 1249, 1016 |
| 08 | 6-C(CH$_3$)=NOCH$_3$-pyridin-2-yl | 1717, 1253, 1049, 845 |
| 09 | 6-C(CH$_3$)=NOCH$_2$CH$_3$-pyridin-2-yl | 1718, 1253, 1048, 845 |
| 10 | 6-C(CH$_3$)=NOCH$_2$CH$_2$CH$_3$-pyridin-2-yl | 1718, 1253, 1047, 843 |
| 11 | 6-C(CH$_3$)=NOCH$_2$CH=CH$_2$-pyridin-2-yl | 1717, 1254, 1033, 843 |
| 12 | 6-C(CH$_3$)=NOCH$_2$C≡CH-pyridin-2-yl | 1716, 1254, 1110, 1038, 842 |
| 13 | 6-C(CH$_3$)=NO(CH$_2$)$_3$CH$_3$-pyridin-2-yl | 1718, 1253, 1035, 845 |
| 14 | 6-OCH$_3$-pyrimidin-4-yl | 78 |
| 15 | 6-OCH$_2$CH$_3$-pyrimidin-4-yl | 1.6 (d, 3H) |
| 16 | 4-CH$_3$-pyrimidin-2-yl | 1.63 (d, 3H) |
| 17 | 4-CH$_2$CH(CH$_3$)$_2$-pyrimidin-2-yl | 1.64 (d, 3H) |
| 18 | 4-C(CH$_3$)$_3$-pyrimidin-2-yl | 1.64 (d, 3H) |
| 19 | 4,6-(OCH$_3$)$_2$-pyrimidin-2-yl | 1.63 (d, 3H) |
| 20 | 5-Cl-pyrimidin-2-yl | 73 |
| 21 | 4-OCH$_3$, 6-CF$_3$-pyrimidin-2-yl | 1.63 (d, 3H) |

*$^1$H-NMR (CDCl$_3$, δ in ppm); mp. (° C.); IR (cm$^{-1}$)

Examples of the Action against Harmful Fungi

It was possible to show the fungicidal action of the compounds of the formula I by the following tests:

The active compounds were prepared as a 20% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight Emulphor® EL (Emulan® EL, emulsifier based on ethoxylated fatty alcohols) and diluted with water according to the concentration desired.

*Puccinia recondita* (Brown Rust of Wheat)

Leaves of wheat seedlings (Kanzler variety) were dusted with spores of brown rust (*Puccinia recondita*). The plants treated in this way were incubated for 24 h at 20–22° C. and a relative atmospheric humidity of 90–95% and then treated with the aqueous active compound preparation. After a further 8 days at 20–22° C. and 65–70% relative atmospheric humidity, the extent of fungal development was determined. Assessment was carried out visually.

In this test, the plants treated with the compounds 1, 2, 3 and 4 according to the invention showed 5% or less attack, while the untreated plants were attacked to 70%.

*Pyricularia oryzae* (Rice Blast)

Rice seedlings (Tai Nong 67 variety) were sprayed with the active compound preparation until dripping wet. After 24 hours, the plants were sprayed with an aqueous spore suspension of the fungus *Pyricularia oryzae* and kept at a relative atmospheric humidity of 95–99% at 22–24° C. for 6 days. Assessment was carried out visually.

In this test, the plants treated with the compounds 1, 2, 3 and 4 showed an attack of 15% or less, while the untreated plants were attacked to 60%.

Examples of the Action against Animal Pests

It was possible to show the action of the compounds of the general formula I against animal pests by the following tests:

The active compounds were prepared a) as a 0.1% strength solution in acetone or b) as a 10% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight of Emulphor® EL (Emulan® EL, emulsifier based on ethoxylated fatty alcohols) and diluted with acetone in the case of a) or with water in the case of b) according to the desired concentration.

After conclusion of the tests, the lowest concentration at which the compounds still caused an 80-100% inhibition or mortality in comparison with untreated control tests was determined in each case (activity threshold or minimum concentration).

We claim:

1. An iminobenzylcrotonate ester of the formula I

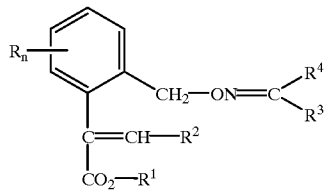

where the index and the substituents have the following meanings:

n is 0 or 1 and when n is 1, $R_n$ is halogen, methyl, trifluoromethyl, methoxy or cyano and is in the 3- or 6- position relative to the crotonic ester, $R^1$ is methyl or ethyl, $R^2$ is hydrogen, methyl or ethyl, $R^3$ is a $C_1$–$C_4$-alkyl, halogen, $C_1$–$C_4$-alkoxy, $C_1$–$C_4$-alkylthio, cyclopropyl or trifluromethyl, $R^4$ is a substituted 2-, 3- or 4-pyridinyl, a substituted 3 or 4-pyridazinyl, a 2-, 4- or 5-pyrimidinyl, or a substituted pyrazinyl or triazinyl, wherein the substituent on $R^4$ is one or more of halogen, methyl, branched chain $C_3$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylcarbonyl, or $CR^{iii}$=$NOR^{iv}$, wherein $R^{iii}$ is hydrogen or $C_1$–$C_4$-alkyl and $R^{iv}$ is $C_1$–$C_4$-alkyl, $C_1$–$C_6$-alkenyl or $C_1$–$C_6$-alkynyl, with the proviso that where $CH_3$— is present as a substituent on the ring, at least one other of the substituents must be present on the ring.

2. An iminobenzylcrotonate ester of claim 1 wherein n is 0 and $R^1$, is $CH_3$—, $R^2$ is $CH_3$—, $R^3$ is $CH_3$—, and $R^4$ is a substituted 2, 3, or 4-pyridinyl, wherein the substituent on $R^4$ is one or more of halogen, methyl, branched chain $C_3$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylcarbonyl, or $CR^{iii}$=$NOR^{iv}$, wherein $R^{iii}$ is hydrogen or $C_1$–$C_4$-alkyl and $R^{iv}$ is $C_1$–$C_4$-alkyl, $C_1$–$C_6$-alkenyl or $C_1$–$C_6$-alkynyl, with the proviso that where $CH_3$— is present as a substituent on the pyridinyl ring, at least one other of the substituents must be present on the pyridinyl ring.

3. An iminobenzylcrotonate ester of claim 2 wherein $R^4$ is 6-$COCH_3$-pyridin-2-yl.

4. An iminobenzylcrotonate ester of claim 2 wherein $R^4$ is 6-$C(CH_3)$=$NOCH_3$-pyridin-2-yl.

5. An iminobenzylcrotonate ester of claim 2 wherein $R^4$ is 6-$C(CH_3)$=$NOCH_2CH$=$CH_2$ pyridin-2-yl.

6. An iminobenzylcrotonate ester of claim 2 wherein $R^4$ is 6-$C(CH_3)$=$NOCH_2$-$C$≡$CH$-pyridin-2-yl.

7. An iminobenzylcrotonate ester of claim 1 wherein n is 0 and $R^1$, is $CH_3$—, $R^2$ is $CH_3$—, $R^3$ is $CH_3$—, and $R^4$ is a substituted 2-, 4, or 5-pyrimidinyl, wherein the substituent on $R^4$ is one or more of halogen, methyl, branched chain $C_3$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylcarbonyl, or $CR^{iii}$=$NOR^{iv}$, wherein $R^{iii}$ is hydrogen or $C_1$–$C_4$-alkyl and $R^{iv}$ is $C_1$–$C_4$-alkyl, $C_1$–$C_6$-alkenyl or $C_1$–$C_6$-alkynyl, with the proviso that where $CH_3$— is present as a substituent on the pyrimidinyl ring, at least one other of the substituents must be present on the pyrimidinyl ring.

8. An iminobenzylcrotonate ester of claim 7 wherein $R^4$ is —$OCH_2CF_3$-pyrimidin-2-yl.

9. An iminobenzylcrotonate ester of claim 7 wherein $R^4$ is 4-$OCH_3$-pyrimidin-2-yl.

10. An iminobenzylcrotonate ester of claim 7 wherein $R^4$ is 4-$OCH_2CF_3$, 6$CH_3$-pyrimidin-2-yl.

11. An iminobenzylcrotonate ester of claim 7 wherein $R^4$ is 6-$OCH_3$-pyrimidin-4-yl.

12. An iminobenzylcrotonate ester of claim 7 wherein $R^4$ is 6-$OCH_2$—$CH_3$-pyrimidin-4yl.

13. An iminobenzylcrotonate ester of claim 7 wherein $R^4$ is 4-$C(CH_3)_3$-pyrimidin-2-yl.

14. An iminobenzylcrotonate ester of claim 7 wherein $R^4$ is 4-$OCH_3$-pyrimidin-2-yl.

15. An iminobenzylcrotonate ester of claim 7 wherein $R^4$ is 4-$OCH_3$, 6-$CF_3$-pyrimidin-2-yl.

16. The compounds of claim 1 wherein $R^4$ substituted 3- or 4-pyridazinyl.

17. The compounds of claim 1 wherein $R^4$ is substituted pyrazinyl or triazinyl.

18. A composition suitable for controlling animal pests or harmful fungi, containing a solid or liquid carrier and a compound of the formula I as claimed in claim 1.

19. A method of controlling harmful fungi, which comprises treating the fungi or the materials, plants, soil or seed to be protected from fungal attack with an active amount of a compound of the formula I as claimed in claim 1.

20. A method of controlling animal pests, which comprises treating the pests or the materials, plants, soil or seed to be protected from them with an active amount of a compound of the formula I as claimed in claim 1.

* * * * *